(12) United States Patent
Crews et al.

(10) Patent No.: US 9,938,264 B2
(45) Date of Patent: Apr. 10, 2018

(54) PROTEOLYSIS TARGETING CHIMERA COMPOUNDS AND METHODS OF PREPARING AND USING SAME

(71) Applicant: YALE UNIVERSITY, New Haven, CT (US)

(72) Inventors: Craig Crews, New Haven, CT (US); Momar Toure, New Haven, CT (US); Eunhwa Ko, Dong-gu (KR); Saul Jaime-Figueroa, Morris Plains, NJ (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 15/341,275

(22) Filed: Nov. 2, 2016

(65) Prior Publication Data

US 2017/0121321 A1    May 4, 2017

Related U.S. Application Data

(60) Provisional application No. 62/249,501, filed on Nov. 2, 2015.

(51) Int. Cl.
    *C07D 417/14* (2006.01)
(52) U.S. Cl.
    CPC .................................. *C07D 417/14* (2013.01)
(58) Field of Classification Search
    CPC .................................................... C07D 417/14
    See application file for complete search history.

(56) References Cited

U.S. PATENT DOCUMENTS

| | | | |
|---|---|---|---|
| 4,522,811 | A | 6/1985 | Eppstein et al. |
| 5,681,858 | A | 10/1997 | Stevens et al. |
| 6,306,663 | B1 | 10/2001 | Kenten et al. |
| 6,559,280 | B2 | 5/2003 | Kenten et al. |
| 7,041,298 | B2 | 5/2006 | Deshaies et al. |
| 7,074,620 | B2 | 7/2006 | Kenten et al. |
| 7,208,157 | B2 | 4/2007 | Sakamoto et al. |
| 7,273,920 | B2 | 9/2007 | Kenten et al. |
| 7,683,160 | B2 | 3/2010 | Eckhardt et al. |
| 7,915,293 | B2 | 3/2011 | Ramesh et al. |
| 2006/0128632 | A1 | 6/2006 | Sharma et al. |
| 2009/0298843 | A1 | 12/2009 | Kloog et al. |
| 2010/0048517 | A1 | 2/2010 | Hu et al. |
| 2012/0270800 | A1 | 10/2012 | Verdine et al. |
| 2014/0356322 | A1 | 12/2014 | Crews et al. |
| 2015/0291562 | A1 | 10/2015 | Crew et al. |
| 2016/0045607 | A1 | 2/2016 | Crew et al. |
| 2016/0136230 | A1 | 5/2016 | Campos et al. |
| 2016/0368911 | A1 | 12/2016 | Campos et al. |

FOREIGN PATENT DOCUMENTS

| | | |
|---|---|---|
| EP | 805147 A1 | 11/1997 |
| WO | 9742216 A1 | 11/1997 |
| WO | 0022110 A2 | 4/2000 |
| WO | 0050445 A1 | 8/2000 |
| WO | 0066119 A1 | 11/2000 |
| WO | 0175145 A2 | 10/2001 |
| WO | 0222577 A2 | 3/2002 |
| WO | 02066512 A1 | 8/2002 |
| WO | 02100845 A1 | 12/2002 |
| WO | 03057820 A2 | 7/2003 |
| WO | 2006113942 A2 | 10/2006 |
| WO | 2007022638 A1 | 3/2007 |
| WO | 2007106670 A2 | 9/2007 |
| WO | 2008011392 A2 | 1/2008 |
| WO | 2008109727 A1 | 9/2008 |
| WO | 2008109731 A2 | 9/2008 |
| WO | 2008115663 A1 | 9/2008 |
| WO | 2009015254 A1 | 1/2009 |
| WO | 2010107485 A1 | 9/2010 |
| WO | 2010141805 A1 | 12/2010 |
| WO | 2011005510 A2 | 1/2011 |
| WO | 2011008260 A2 | 1/2011 |
| WO | 2011082007 A2 | 7/2011 |
| WO | 2011143660 A2 | 11/2011 |
| WO | 2011160016 A2 | 12/2011 |
| WO | 2012003281 A2 | 1/2012 |
| WO | 2012009649 A1 | 1/2012 |
| WO | 2012054110 A2 | 4/2012 |
| WO | 2012078559 A2 | 6/2012 |
| WO | 2012142498 A2 | 10/2012 |
| WO | 2013106643 A2 | 7/2013 |
| WO | 2013106646 A2 | 7/2013 |

(Continued)

OTHER PUBLICATIONS

West, Anthony R., Solid State Chemistry and Its Applications, Wiley, New York, 1988, 358.*
Lai, et al., Modular PROTAC Design for the Degradation of Oncogenic BCR-ABL, Angewandte Chemie, International Edition, 55(2), 807-810 (2016).*
Van Eis, et al., "2,6-Naphthyridines as potent and selective inhibitors of the novel protein kinase C isozymes", Bioorg Med Chem Lett.21(24), Dec. 15, 2011, 7367-7372.
Van Molle, et al., "Dissecting fragment-based lead discovery at the von Hippel-Lindau protein:hypoxia inducible factor 1α protein-protein interface", Chem Biol. 19(10), Oct. 26, 2012, 1300-1312.
Vassilev, et al., "In vivo activation of the p53 pathway by small-molecule antagonists of MDM2", Science 303, Feb. 6, 2004, 844-848.

(Continued)

*Primary Examiner* — Erich A Leeser
(74) *Attorney, Agent, or Firm* — Saul Ewing Arnstein & Lehr LLP; Kathryn Doyle; Domingos J. Silva

(57) ABSTRACT

The present invention includes novel compounds and methods for preventing or treating diseases associated with and/or caused by overexpression and/or uncontrolled activation of a tyrosine kinase in a subject in need thereof. In certain embodiments, the compounds of the present invention comprise a tyrosine kinase inhibitor, a linker and a ubiquitin ligase binder. The methods of the present invention comprise administering to the subject an pharmaceutically effective amount of at least one compound of the invention.

20 Claims, 11 Drawing Sheets

(56) References Cited

FOREIGN PATENT DOCUMENTS

| WO | 2013170147 A1 | 11/2013 |
|---|---|---|
| WO | 2014108452 A1 | 7/2014 |
| WO | 2015000867 A1 | 1/2015 |
| WO | 2015000868 A1 | 1/2015 |

OTHER PUBLICATIONS

Winter, et al., "Drug Development. Phthalimide conjugation as a strategy for in vivo target protein degradation", Science 348(6241), 2015, 1376-1381.
Wright, et al., "Structure-Activity Relationships in Purine-Based Inhibitor Binding to HSP90 Isoforms", Chem Biol. 11(6), Jun. 2004, 775-785.
Zengerle, et al., "Selective Small Molecule Induced Degradation of the BET Bromodomain Protein BRD4", ACS Chem Biol. 10(8), 2015, 1770-1777.
Zhang, et al., "Targeted degradation of proteins by small molecules: a novel tool for functional proteomics", Comb Chem High Throughput Screen. 7(7), 2004, 689-697.
CAS Registry No. 1004933-70-3 entered Feb. 21, 2008.
International Search Report and Written Opinion for PCT International Application No. PCT/US2016/060082 dated Jan. 19, 2017.
National Center for Biotechnology Information. PubChem Compound Database; CID=21042819, http://pubchem.ncbi.nlm.nih.gov/compound/21042819 (accessed Feb. 7, 2016), 2007.
Aghajan, et al., "Chemical genetics screen for enhancers of rapamycin identifies a specific inhibitor of an SCF family E3 ubiquitin ligase", Nat Biotechnol. 28(7), 2010, 738-742.
Aghajanyy, et al., "Chemical genetics screen for enhancers of rapamycin identifies a specific inhibitor of an SCF family E3 ubiquitin ligase", Nature Biotechnology 28(7), Jun. 27, 2010, 738-742.
Ahn, et al., "HIF-1alpha peptide derivatives with modifications at the hydroxyproline residue as activators of HIF-1alpha", Bioorg Med Chem Lett. 19(15), 2009, 4403-4405.
Bargagna-Mohan, et al., "Use of PROTACS as molecular probes of angiogenesis", Bioorg Med Chem Lett. 15(11), 2005, 2724-2727.
Boitano, et al., "Aryl Hydrocarbon Receptor Antagonists Promote the Expansion of Human Hematopoietic Stem Cells", Science 329, Sep. 10, 2010, 1345-1348.
Bondeson, et al., "Catalytic in vivo protein knockdown by small-molecule PROTACs", Nat Chem Biol. 11(8), 2015, 611-617.
Brough, et al., "4,5-Diarylisoxazole HSP90 Chaperone Inhibitors: Potential Therapeutic Agents for the Treatment of Cancer", J Med Chem. 51(2), Jan. 24, 2008, 196-218.
Buckley, et al., "HaloPROTACS: Use of Small Molecule PROTACs to Induce Degradation of HaloTag Fusion Proteins", ACS Chem Biol.10(8), 2015, 1831-1837.
Buckley, et al., "Small-molecule inhibitors of the interaction between the E3 ligase VHL and HIF1α", Angew Chem Int Ed Engl.51(46), Oct. 12, 2012, 11463-11467.
Buckley, et al., "Targeting the von Hippel-Lindau E3 ubiquitin ligase using small molecules to disrupt the VHL/HIF-1α interaction", Journal of the American Chemical Society 134(10), Feb. 27, 2012, 4465-4468.
Carlson, et al., "Selection of small-molecule mediators of the RNA regulation of PKR, the RNA-dependent protein kinase", Chembiochem. 3(9), 2002, 859-865.
Carmony, et al., "PROTAC-induced proteolytic targeting", Methods Mol Biol. 832, 2012, 627-638.
Chang, et al., "Structural basis for G9a-like protein lysine methyltransferase inhibition by BIX-01294", Nat Struct Mol Biol. 16(3), Mar. 2009, 312-317.
Chung, et al., "Discovery and Characterization of Small Molecule Inhibitors of the BET Family Bromodomains", J Med Chem. 54(11), Jun. 9, 2011, 3827-3838.
Cyrus, et al., "Impact of linker length on the activity of PROTACs", Mol Biosyst. 7(2), 2011, 359-364.

Cyrus, et al., "Jostling for position: optimizing linker location in the design of estrogen receptor-targeting PROTACs", ChemMedChem. 5(7), Jul. 5, 2010, 979-985.
Cyrus, et al., "Two-headed PROTAC: an effective new tool for targeted protein degradation", Chembiochem. 11(11), 2010, 1531-1534.
Dawson, et al., "Inhibition of BET recruitment to chromatin as an effective treatment for MLL-fusion leukaemia", Nature 478, Oct. 2, 2011, 529-533.
Filippakopoulos, et al., "Selective inhibition of BET bromodomains", Nature 468, Dec. 23, 2010, 1067-1073.
Finnin, et al., "Structures of a histone deacetylase homologue bound to the TSA and SAHA inhibitors", Nature 401, Sep. 9, 1999, 188-193.
Hanan, et al., "Discovery of selective and noncovalent diaminopyrimidine-based inhibitors of epidermal growth factor receptor containing the T790M resistance mutation", J Med Chem. 57(23), 2014, 10176-10191.
Hewings, et al., "3,5-Dimethylisoxazoles Act As Acetyllysine-mimetic Bromodomain", J Med Chem. 54(19), Oct. 13, 2011, 6761-6770.
Hon, et al., "Structural basis for the recognition of hydroxyproline in HIF-1a by pVHL", Nature 417, Jun. 27, 2002, 975-978.
Jang, et al., "Targeted Degradation of Proteins by PROTACs", Curr Protoc Chem Biol. 2(2), 2010, 71-87.
Jiang, et al., "Synthesis of 7alpha-substituted derivatives of 17beta-estradiol", Steroids 71(5), May 2006, 334-342 (Abstract).
Lee, et al., "Targeted Degradation of the Aryl Hydrocarbon Receptor by the PROTAC Approach: A Useful Chemical Genetic Tool", ChemBioChem. 8(17), Nov. 23, 2007, 2058-2062.
Liu, et al., "Discovery of a 2,4-diamino-7-aminoalkoxyquinazoline as a potent and selective inhibitor of histone lysine methyltransferase G9a", J Med Chem. 52(24), Dec. 24, 2009, 7950-7953.
Llinás-Brunet, et al., "Discovery of a potent and selective noncovalent linear inhibitor of the hepatitis C virus NS3 protease (BI 201335)", J Med Chem. 53(17), Sep. 9, 2010, 6466-6476.
Lountos, et al., "Structural Characterization of Inhibitor Complexes with Checkpoint Kinase 2 (Chk2), a Drug Target for Cancer Therapy", J Struct Biol.176(3), Dec. 11, 2011, 292-301.
Lu, et al., "Hijacking the E3 Ubiquitin Ligase Cereblon to Efficiently Target BRD4", Chem Biol. 22(6), 2015, 755-763.
Mehellou, et al., "Twenty-six years of anti-HIV drug discovery: where do we stand and where do we go?", J Med Chem. 53(2), Jan. 28, 2010, 521-538.
Millan, et al., "Design and Synthesis of Inhaled p38 Inhibitors for the Treatment of Chronic Obstructive Pulmonary Disease", J Med Chem.54(22), Nov. 24, 2011, 7797-7814.
Min, et al., "Structure of an HIV-1-alpha—pVHL complex: hydroxyproline recognition in signaling", Science 296, Jun. 27, 2002, 1886-1889.
Nicodeme, et al., "Suppression of inflammation by a synthetic histone mimic", Nature 468, Dec. 23, 2010, 1119-1123.
Patch, et al., "Identification of diaryl ether-based ligands for estrogen-related receptor α as potential antidiabetic agents", J Med Chem. 54(3), Feb. 10, 2011, 788-808.
Prakash, et al., "Stereoselective Nucleophilic Trifluoromethylation of N-(tert-Butylsulfinyl)imines by Using Trimethyl (trifluoromethyl)silane", Angew Chem Int Ed Engl. 40(3), Feb. 2, 2001, 589-590 (Abstract).
Puppala, et al., "Development of an aryl hydrocarbon receptor antagonist using the proteolysis-targeting chimeric molecules approach: a potential tool for chemoprevention", Mol Pharmacol. 73(4), 2008, 1064-1071.
Rodriguez-Gonzalez, et al., "Targeting steroid hormone receptors for ubiquitination and degradation in breast and prostate cancer", Oncogene. 27(57), Dec. 4, 2008, 7201-7211.
Rotili, et al., "Photoactivable peptides for identifying enzyme-substrate and protein-protein interactions", Chem Commun (Camb). 47(5), 2011, 1488-1490.

(56) References Cited

OTHER PUBLICATIONS

Rusch, et al., "Identification of acyl protein thioesterases 1 and 2 as the cellular targets of the Ras-signaling modulators palmostatin B and M", Angew Chem Int Ed Engl.50(42), Oct. 10, 2011, 9838-9842.

Sakamoto, et al., "Development of Protacs to target cancer-promoting proteins for ubiquitination and degradation", Mol Cell Proteomics. 2(12), Dec. 2003, 1350-1358.

Sakamoto, et al., "Protacs: chimeric molecules that target proteins to the Skp 1—Cullin-F box complex for ubiquitination and degradation", Proc Natl Acad Sci U S A.98(15), Jul. 17, 2001, 8554-8559.

Sargent, et al., "Synthesis of the cyclophane tetramethoxyturriane: a derivative of the phenolic cyclophanes of Grevillea striata R. Br.", J. Chem. Soc., Perkin Trans. 1, 1990, 129-132 (Abstract).

Schenkel, et al., "Discovery of Potent and Highly Selective Thienopyridine Janus Kinase 2 Inhibitors", J Med Chem.54(24), Dec. 22, 2011, 8440-8450.

Schneekloth, et al., "Chemical Genetic Control of Protein Levels: Selective in Vivo Targeted Degradation", J Am Chem Soc. 126(12), Mar. 31, 2004, 3748-3754.

Smith, et al., "Targeted Intracellular Protein Degradation Induced by a Small Molecule: En Route to Ghemical Proteomics", Bioorg Med Chem Lett. 18(22), Nov. 15, 2008, 5904-5908.

Valle, et al., "Tricyclic Series of Heat Shock Protein 90 (HSP90) Inhibitors Part I: Discovery of Tricyclic Imidazo[4,5-c]Pyridines as Potent Inhibitors of the HSP90 Molecular Chaperone", J Med Chem. 54(20), Oct. 27, 2011, 7206-7219.

\* cited by examiner

PROTEOLYSIS TARGETING CHIMERA COMPOUNDS AND METHODS OF PREPARING AND USING SAME

CROSS-REFERENCE TO RELATED APPLICATIONS

The present application claims priority under 35 U.S.C. § 119(e) to U.S. Provisional Application No. 62/249,501, filed Nov. 2, 2015, which application is hereby incorporated by reference in its entirety.

STATEMENT REGARDING FEDERALLY SPONSORED RESEARCH OR DEVELOPMENT

This invention was made with government support under CA197589 and AI084140 awarded by National Institutes of Health. The government has certain rights in the invention.

BACKGROUND OF THE INVENTION

The current inhibitor-based drug paradigm not only limits drug targets to those proteins with a tractable active site, but also requires high dosing in order to achieve adequate $IC_{90}$ concentrations for therapeutic efficacy. To circumvent these issues, alternative therapeutic strategies have been employed to specifically knock down target proteins. While genetic techniques such as RNAi, and CRISPR/Cas9 can significantly reduce protein levels, the pharmacokinetic properties (i.e., metabolic stability and tissue distribution) associated with these approaches have so far limited their development as clinical agents.

The pathologic fusion protein BCR-ABL is a constitutively active tyrosine kinase that drives uncontrolled cell proliferation, resulting in chronic myelogenous leukemia (CML). With the advent of tyrosine kinase inhibitors (TKIs) targeting BCR-ABL, CML has become a chronic but manageable disease. For example, imatinib mesylate, the first TKI developed against BCR-ABL, binds competitively at the ATP-binding site of c-ABL and inhibits both c-ABL and the oncogenic fusion protein BCR-ABL. Second generation TKIs (such as dasatinib and bosutinib) were subsequently developed to treat CML patients with acquired resistance to imatinib. Despite the remarkable success of BCR-ABL TKIs, all CIVIL patients must remain on treatment for life because the TKIs are not curative due to persistent leukemic stem cells (LSCs).

There is thus an unmet need in the art for novel compositions and methods to knock down c-ABL and/or BCR-ABL in a cell. Such methods could be used to treat and/or prevent CML in a mammal. The present invention addresses this need.

BRIEF SUMMARY OF THE INVENTION

The invention provides a compound of formula (I). The invention further provides a pharmaceutical composition comprising at least one compound of formula (I) and at least one pharmaceutically acceptable carrier. The invention further provides a method of treating or preventing a disease or disorder associated with overexpression and/or uncontrolled activation of c-Abl and/or BCR-ABL. The invention further provides a method of preventing or treating a tyrosine kinase-dependent cancer in a subject in need thereof.

In certain embodiments, the compound of formula (I) is TKI-L-$(ULM)_k$ (I), wherein: TKI is a tyrosine kinase inhibitor, L is a linker, each ULM is independently a ubiquitin ligase binder, and k is an integer ranging from 1 to 4, wherein TKI is covalently linked to L and wherein each ULM is covalently linked to L; or a salt, enantiomer, stereoisomer, solvate, polymorph or N-oxide thereof.

In certain embodiments, TKI is capable of binding to c-ABL and/or BCR-ABL. In other embodiments, upon binding of the compound simultaneously to a tyrosine kinase and a ubiquitin ligase, the tyrosine kinase is ubiquitinated by the ubiquitin ligase. In yet other embodiments, at least one ULM binds to an E3 ubiquitin ligase. In yet other embodiments, the E3 ubiquitin ligase comprises a Von Hippel Lindau (VHL) E3 ubiquitin ligase or a Cereblon (CRBN) E3 ligase.

In certain embodiments, the TKI binds to and inhibits c-ABL. In other embodiments, the TKI binds to and inhibits BCR-ABL. In yet other embodiments, the TKI binds to and inhibits both c-ABL and BCR-ABL. In yet other embodiments, the TKI is at least one selected from the group consisting of Dasatinib, Imatinib, Saracatinib, Ponatinib, Nilotinib, Danusertib, AT9283, Degrasyn, Bafetinib, KW-2449, NVP-BHG712, DCC-2036, GZD824, GNF-2, PD173955, GNF-5, Bosutinib, Gefitinib, Erlotinib, Sunitinib, Ruxolitinib, Tofacitinib, Lapatinib, Vandetanib, Sorafenib, Sunitinib, Axitinib, Nintedanib, Regorafenib, Pazopanib, Lenvatinib, Crizotinib, Ceritinib, Cabozantinib, DWF, Afatinib, Ibrutinib, B43, KU004, Foretinib, KRCA-0008, PF-06439015, PF-06463922, Canertinib, GSA-10, GW2974, GW583340, WZ4002, CP-380736, D2667, Mubritinib, PD153035, PD168393, Pelitinib, PF-06459988, PF-06672131, PF-6422899, PKI-166, Reveromycin A, Tyrphostin 1, Tyrphostin 23, Tyrphostin 51, Tyrphostin AG 528, Tyrphostin AG 658, Tyrphostin AG 825, Tyrphostin AG 835, Tyrphostin AG 1478, Tyrphostin RG 13022, Tyrphostin RG 14620, B178, GSK1838705A, PD-161570, PD 173074, SU-5402, Roslin 2, Picropodophyllotoxin, PQ401, I-OMe-Tyrphostin AG 538, GNF 5837, GW441756, Tyrphostin AG 879, DMPQ, JNJ-10198409, PLX647, Trapidil, Tyrphostin A9, Tyrphostin AG 370, Lestaurtinib, DMI-14, Geldanamycin, Genistein, GW2580, Herbimycin A, Lavendustin C, Midostaurin, NVP-BHG712, PD158780, PD-166866, PF-06273340, PP2, RPI, SU 11274, SU5614, Symadex, Tyrphostin AG 34, Tyrphostin AG 974, Tyrphostin AG 1007, UNC2881, Honokiol, SU1498, SKLB1002, CP-547632, JK-P3, KRN633, SC-1, ST638, SU 5416, Sulochrin, Tyrphostin SU 1498, 58567, rociletinib, Dacomitinib, Tivantinib, Neratinib, Masitinib, Vatalanib, Icotinib, XL-184, OSI-930, AB1010, Quizartinib, AZD9291, Tandutinib, HM61713, Brigantinib, Vemurafenib (PLX-4032), Semaxanib, AZD2171, Crenolanib, Damnacanthal, Fostamatinib, Motesanib, Radotinib, OSI-027, Linsitinib, BIX02189, PF-431396, PND-1186, PF-03814735, PF-431396, sirolimus, temsirolimus, everolimus, deforolimus, zotarolimus, BEZ235, INK128, Omipalisib, AZD8055, MHY1485, PI-103, KU-0063794, ETP-46464, GDC-0349, XL388, WYE-354, WYE-132, GSK1059615, WAY-600, PF-04691502, WYE-687, PP121, BGT226, AZD2014, PP242, CH5132799, P529, GDC-0980, GDC-0994, XMD8-92, Ulixertinib, FR180204, SCH772984, Trametinib, PD184352, PD98059, Selumetinib, PD325901, U0126, Pimasertinib, TAK-733, AZD8330, Binimetinib, PD318088, SL-327, Refametinib, GDC-0623, Cobimetinib, BI-847325, Adaphostin, GNF 2, PPY A, AIM-100, ASP 3026, LFM A13, PF 06465469, (−)-Terreic acid, AG-490, BIBU 1361, BIBX 1382, BMS 599626, CGP 52411, GW 583340, HDS 029, HKI 357, JNJ 28871063, WHI-P 154, PF 431396, PF 573228, FIIN 1, PD 166285, SUN 11602, SR 140333, TCS 359, BMS 536924, NVP ADW 742, PQ 401, BMS 509744, CP 690550, NSC 33994, WHI-P 154, KB SRC 4, DDR1-

IN-1, PF 04217903, PHA 665752, SU 16f, A 419259, AZM 475271, PP 1, PP 2, 1-Naphthyl PP1, Src I1, ANA 12, PD 90780, Ki 8751, Ki 20227, ZM 306416, ZM 323881, AEE 788, GTP 14564, PD 180970, R 1530, SU 6668, Toceranib, CEP-32496 (1-(3-((6,7-dimethoxyquinazolin-4-yl)oxy) phenyl)-3-(5-(1,1,1-trifluoro-2-methylpropan-2-yl)isoxazol-3-yl)urea), AZ 628 (4-(2-cyano propan-2-yl)-N-(4-methyl-3-((3-methyl-4-oxo-3,4-dihydroquinazolin-6-yl) amino)phenyl) benzamide), Vemurafenib (PLX-4032), PLX-4720 (N-(3-(5-chloro-1H-pyrrolo[2,3-b]pyridine-3-carbonyl)-2,4-difluorophenyl)propane-1-sulfonamide), SB 590885 ((E)-5-(2-(4-(2-(dimethyl amino)ethoxy)phenyl)-4-(pyridin-4-yl)-1H-imidazol-5-yl)-2,3-dihydro-1H-inden-1-one oxime), GDC-0879 ((E)-5-(2-(2-hydroxyethyl)-4-(pyridin-4-yl)-1H-imidazol-5-yl)-2,3-dihydro-1H-inden-1-one oxime), a compound of formula

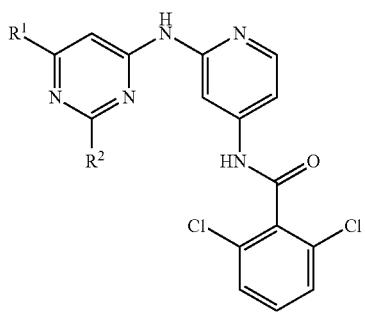

wherein $R^1$ is H or $CH_3$, and $R^2$ is

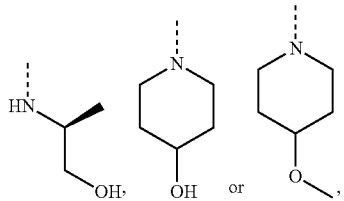

a compound of formula

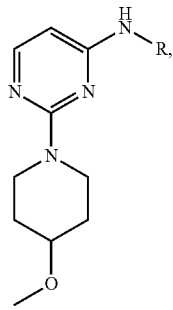

wherein R is

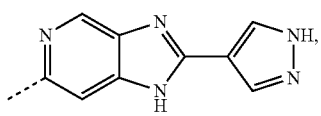

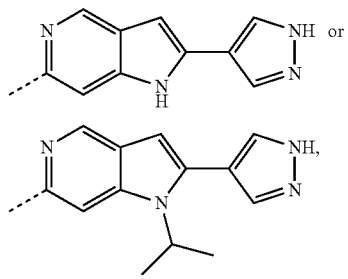

and a compound of formula

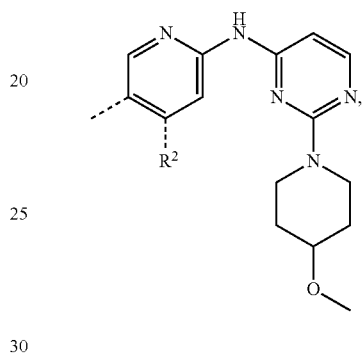

wherein the broken lines correspond to the divalent group

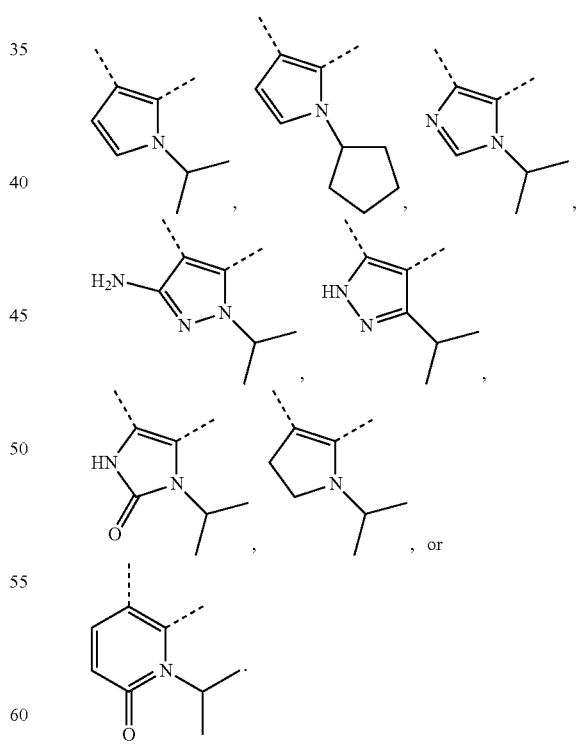

In yet other embodiments, the TKI is Imatinib, Dasatinib or Bosutinib.

In certain embodiments, at least one ULM comprises formula (IX):

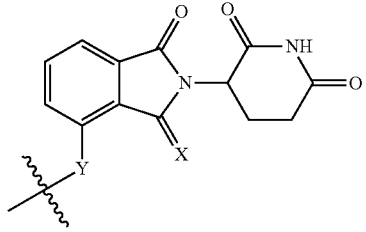

X = H₂, O
Y = N, O, C

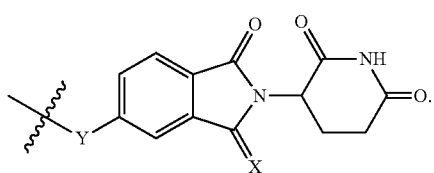

X = H₂, O
Y = N, O, C

In other embodiments, at least one ULM comprises formula (X):

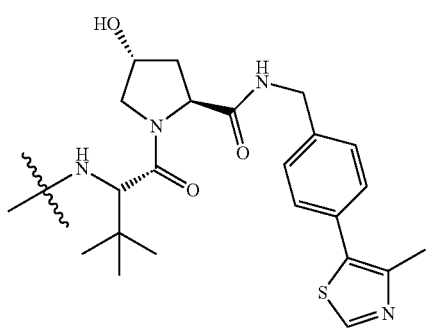

(X)

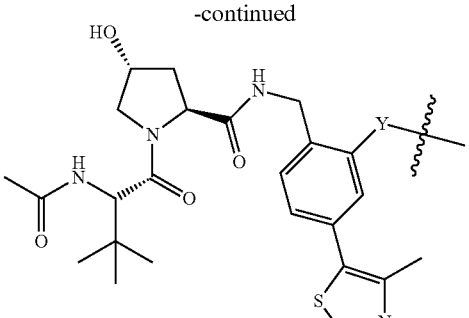

(IX)

Y = N, O, C

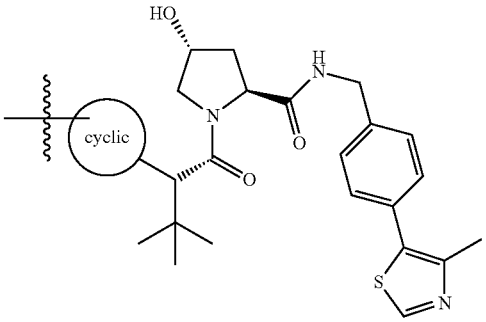

In yet other embodiments, k=1.

In certain embodiments, the linker L corresponds to formula $-(CH_2)_{m1}-X_4-(CH_2-CH_2-X_5)_{m2}-(CH_2)_{m3}-C(X_6)-$, wherein: $-(CH_2)_{m1}$ is covalently bound to the TKI, and $C(X_3)-$ is covalently bound to the ULM; wherein each m1, m2, and m3 is independently 0, 1, 2, 3, 4, 5, 6, 7, 8, 9, or 10; wherein each $X_4$, $X_5$, and $X_6$ is independently absent (a bond), O, S, or $N-R^{20}$, wherein each $R^{20}$ is independently selected from the group consisting of hydrogen, optionally substituted $C_1$-$C_6$ alkyl, optionally substituted aryl, optionally substituted heteroaryl, optionally substituted $C_3$-$C_8$ cycloalkyl, and optionally substituted $C_3$-$C_8$ cycloheteroalkyl. In other embodiments, m1 is 6; m2 is 1 or 2; m3 is 1 or 5; and $X_4$, $X_5$, and $X_6$ are O. In yet other embodiments, m1 is 6; m2 is 5; m3 is 5; $X_4$ and $X_6$ are O; and $X_5$ is absent. In yet other embodiments, m1 is 6; m2 is 5; m3 is 1; $X_4$, $X_5$, and $X_6$ are O.

In certain embodiments, the compound is selected from the group consisting of:
N-(2-chloro-6-methylphenyl)-2-((6-(4-((S)-3-((2S,4R)-4-hydroxy-2-((4-(4-methylthiazol-5-yl)benzyl)carbamoyl)pyrrolidine-1-carbonyl)-2,2-dimethyl-5-oxo-11,14,17-trioxa-4-azatricosan-23-yl)piperazin-1-yl)-2-methylpyrimidin-4-yl)amino)thiazole-5-carboxamide (DAS-6-2-2-6-VHL):

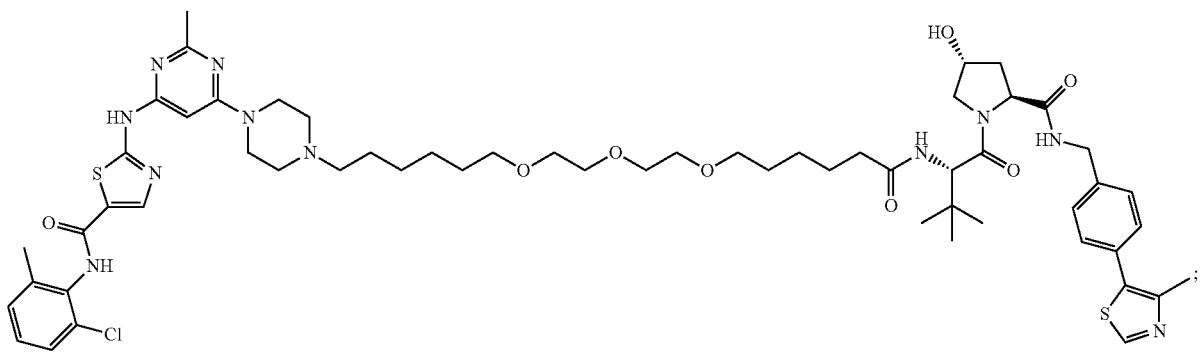

(2S,4R)-1-((S)-2-(tert-butyl)-22-(4-(4-((4-methyl-3-((4-(pyridin-3-yl)pyrimidin-2-yl)amino)phenyl)carbamoyl)benzyl)piperazin-1-yl)-4-oxo-10,13,16-trioxa-3-azadocosanoyl)-4-hydroxy-N-(4-(4-methylthiazol-5-yl)benzyl)pyrrolidine-2-carboxamide (IMA-6-2-2-6-VHL):

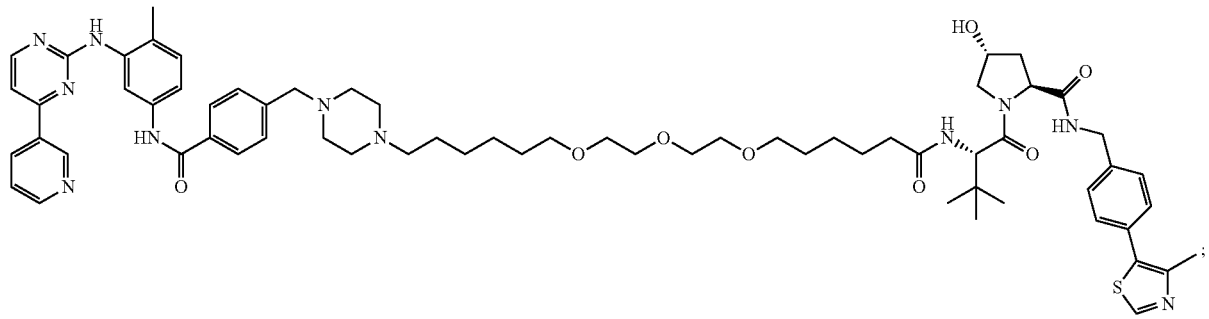 [SMILES: Cc1ccc(NC(=O)c2ccc(CN3CCN(CCCCCCOCCOCCOCCCCCC(=O)N[C@H](C(=O)N4C[C@H](O)C[C@H]4C(=O)NCc4ccc(-c5scnc5C)cc4)C(C)(C)C)CC3)cc2)cc1Nc1nccc(-c2cccnc2)n1]

N-(2-chloro-6-methylphenyl)-2-((6-(4-(6-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)hexyl)piperazin-1-yl)-2-methylpyrimidin-4-yl)amino)thiazole-5-carboxamide (DAS-6-2-2-VHL):

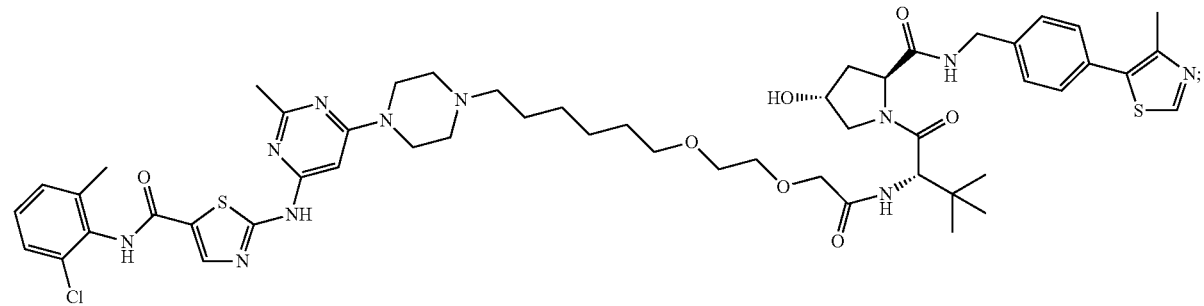 [SMILES: Cc1nc(Nc2ncc(C(=O)Nc3c(C)cccc3Cl)s2)cc(N2CCN(CCCCCCOCCOCC(=O)N[C@H](C(=O)N3C[C@H](O)C[C@H]3C(=O)NCc3ccc(-c4scnc4C)cc3)C(C)(C)C)CC2)n1]

(2S,4R)-1-((S)-3,3-dimethyl-2-(2-(2-((6-(4-(4-((4-methyl-3-((4-(pyridin-3-yl)pyrimidin-2-yl)amino)phenyl)carbamoyl)benzyl)piperazin-1-yl)hexyl)oxy)ethoxy)acetamido)butanoyl)-4-hydroxy-N-(4-(4-methylthiazol-5-yl)benzyl)pyrrolidine-2-carboxamide (IMA-6-2-2-VHL):

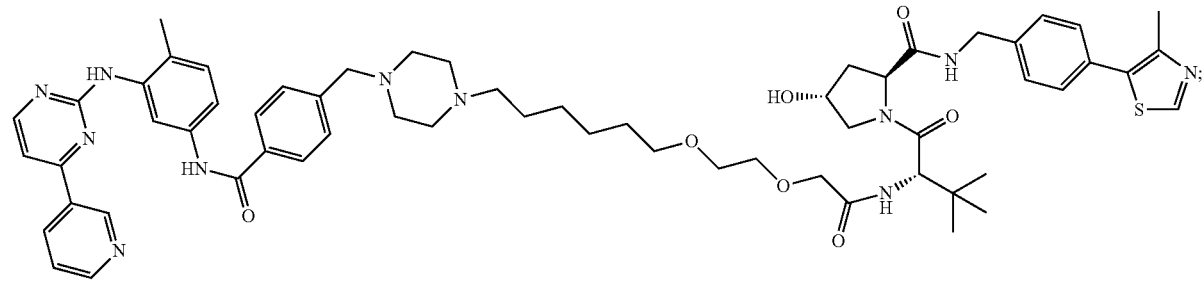 [SMILES: Cc1ccc(NC(=O)c2ccc(CN3CCN(CCCCCCOCCOCC(=O)N[C@H](C(=O)N4C[C@H](O)C[C@H]4C(=O)NCc4ccc(-c5scnc5C)cc4)C(C)(C)C)CC3)cc2)cc1Nc1nccc(-c2cccnc2)n1]

N-(2-chloro-6-methylphenyl)-2-((6-(4-((S)-3-((2S,4R)-4-hydroxy-2-((4-(4-methyl thiazol-5-yl)benzyl)carbamoyl)pyrrolidine-1-carbonyl)-2,2-dimethyl-5-oxo-7,10,13,16,19,22-hexaoxa-4-azaoctacosan-28-yl)piperazin-1-yl)-2-methylpyrimidin-4-yl)amino)thiazole-5-carboxamide (DAS-6-2-2-2-2-2-2-VHL):

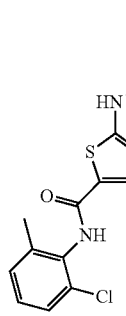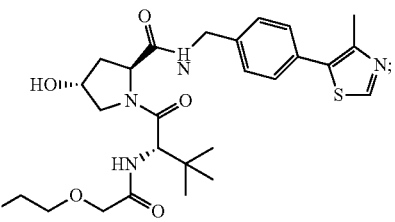

(2S,4R)-1-((S)-2-(tert-butyl)-27-(4-(4-((4-methyl-3-((4-(pyridin-3-yl)pyrimidin-2-yl)amino)phenyl)carbamoyl)benzyl)piperazin-1-yl)-4-oxo-6,9,12,15,18,21-hexaoxa-3-azaheptacosanoyl)-4-hydroxy-N-(4-(4-methylthiazol-5-yl)benzyl)pyrrolidine-2-carboxamide (IMA-6-2-2-2-2-2-2-VHL):

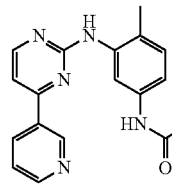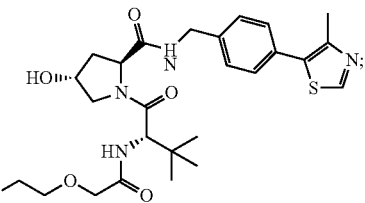

N-(2-chloro-6-methylphenyl)-2-((6-(4-(6-((5-((6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexyl)oxy)pentyl)oxy)hexyl)piperazin-1-yl)-2-methylpyrimidin-4-yl)amino)thiazole-5-carboxamide (DAS-6-5-6-VHL):

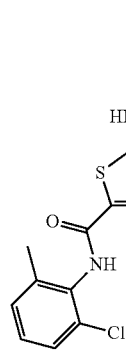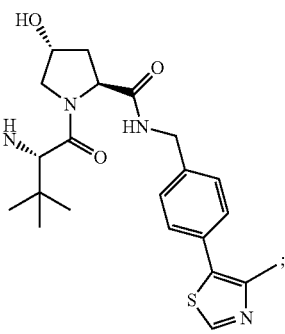

(2S,4R)-1-((S)-3,3-dimethyl-2-(6-((5-((6-(4-(4-((4-methyl-3-((4-(pyridin-3-yl)pyrimidin-2-yl)amino)phenyl)carbamoyl)benzyl)piperazin-1-yl)hexyl)oxy)pentyl)oxy)hexanamido) butanoyl)-4-hydroxy-N-(4-(4-methylthiazol-5-yl)benzyl)pyrrolidine-2-carboxamide (IMA-6-5-6-VHL):

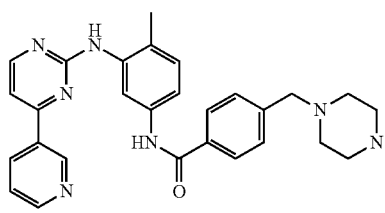
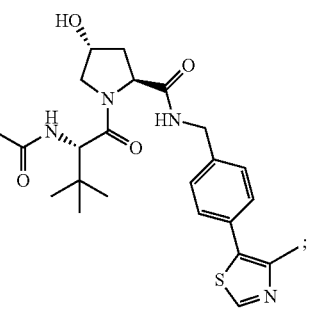

(2S,4R)-1-((S)-2-(tert-butyl)-22-(4-(3-((3-cyano-4-((2,4-dichloro-5-methoxyphenyl)amino)-6-methoxyquinolin-7-yl)oxy)propyl)piperazin-1-yl)-4-oxo-10,13,16-trioxa-3-azadocosanoyl)-4-hydroxy-N-(4-(4-methylthiazol-5-yl)benzyl)pyrrolidine-2-carboxamide (BOS-6-2-2-6-VHL):

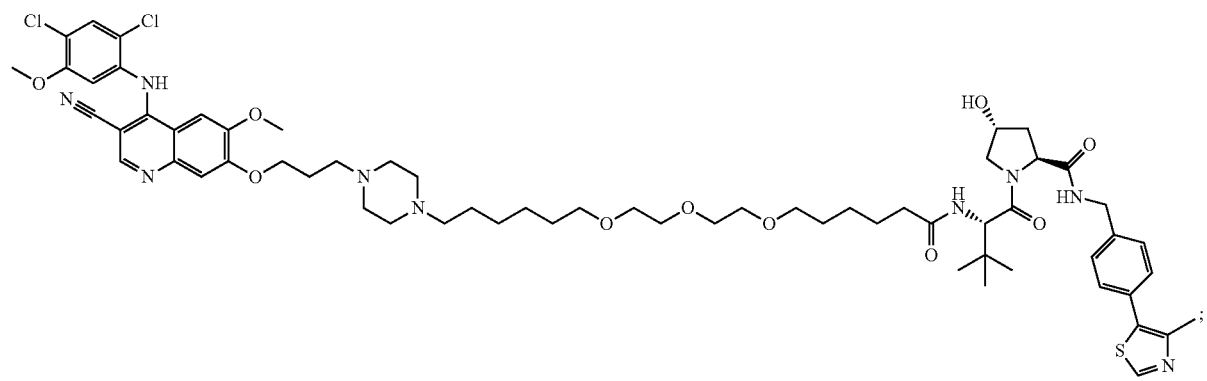

(2S,4R)-1-((S)-2-(2-(2-((6-(4-(3-((3-cyano-4-((2,4-dichloro-5-methoxyphenyl)amino)-6-methoxyquinolin-7-yl)oxy)propyl)piperazin-1-yl)hexyl)oxy)ethoxy)acetamido)-3,3-dimethylbutanoyl)-4-hydroxy-N-(4-(4-methylthiazol-5-yl)benzyl)pyrrolidine-2-carboxamide (BOS-6-2-2-VHL):

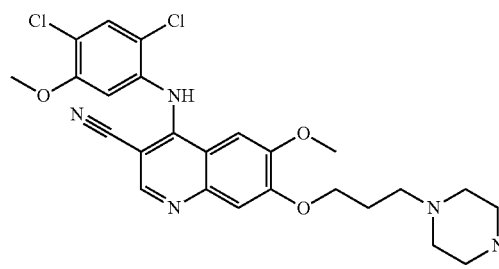
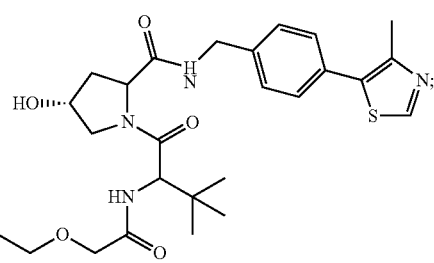

(2S,4R)-1-((S)-2-(tert-butyl)-27-(4-(3-((3-cyano-4-((2,4-dichloro-5-methoxyphenyl)amino)-6-methoxyquinolin-7-yl)oxy)propyl)piperazin-1-yl)-4-oxo-6,9,12,15,18,21-hexaoxa-3-azaheptacosanoyl)-4-hydroxy-N-(4-(4-methylthiazol-5-yl)benzyl)pyrrolidine-2-carboxamide (BOS-6-2-2-2-2-2-2-VHL):

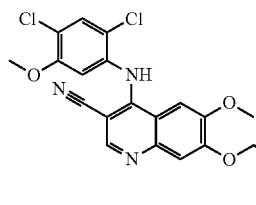 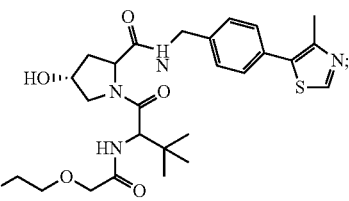

(2S,4R)-1-((S)-2-(6-((5-((6-(4-(3-((3-cyano-4-((2,4-di-chloro-5-methoxyphenyl)amino)-6-methoxyquinolin-7-yl)oxy)propyl)piperazin-1-yl)hexyl)oxy)pentyl)oxy) hexanamido)-3,3-dimethylbutanoyl)-4-hydroxy-N-(4-(4-methylthiazol-5-yl)benzyl)pyrrolidine-2-carboxamide (BOS-6-5-6-VHL):

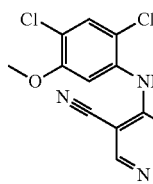 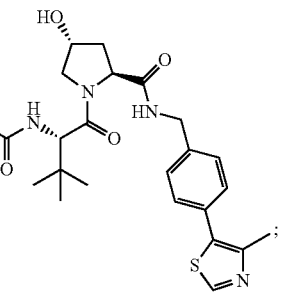

N-(2-chloro-6-methylphenyl)-2-((6-(4-(6-(2-(2-((6-((2-(2, 6-dioxopiperidin-3-yl)-1,3-dioxoisoindolin-4-yl)amino)-6-oxohexyl)oxy)ethoxy)ethoxy)hexyl)piperazin-1-yl)-2-methylpyrimidin-4-yl)amino)thiazole-5-carboxamide (DAS-6-2-2-6-CRBN):

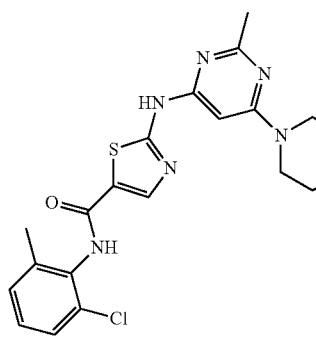 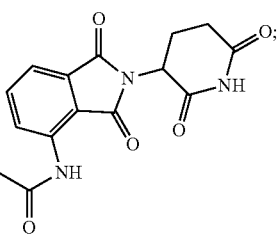

6-(2-(2-((6-(4-(3-((3-cyano-4-((2,4-dichloro-5-methoxy-phenyl)amino)-6-methoxyquinolin-7-yl)oxy)propyl)pip-erazin-1-yl)hexyl)oxy)ethoxy)ethoxy)-N-(2-(2,6-diox-opiperidin-3-yl)-1,3-dioxoisoindolin-4-yl)hexanamide (BOS-6-2-2-6-CRBN):

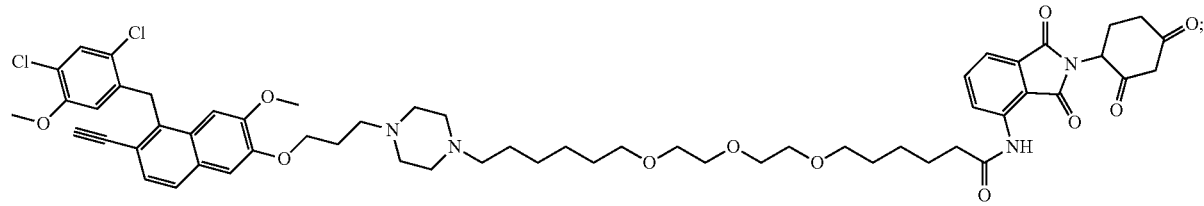

4-((4-(6-(2-(2-((6-((2-(2,6-dioxopiperidin-3-yl)-1,3-diox-oisoindolin-4-yl)amino)-6-oxohexyl) oxy)ethoxy)ethoxy)hexyl)piperazin-1-yl)methyl)-N-(4-methyl-3-((4-(pyridin-3-yl)pyrimidin-2-yl)amino)phenyl)benzamide (IMA-6-2-2-6-CRBN):

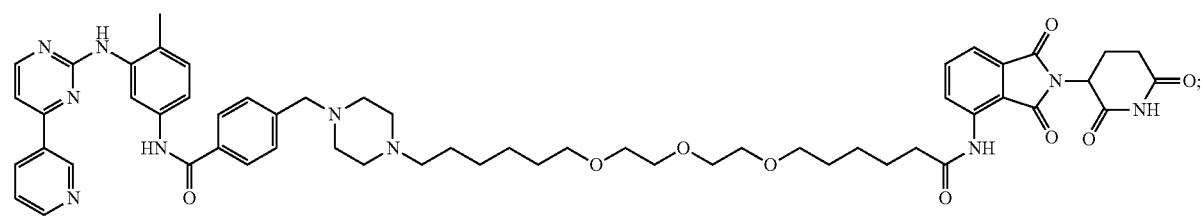

N-(2-chloro-6-methylphenyl)-2-((6-(4-(6-(2-(2-((2-(2,6-di-oxopiperidin-3-yl)-1,3-dioxoisoindolin-4-yl)amino)-2-oxoethoxy)ethoxy)hexyl)piperazin-1-yl)-2-methylpy-rimidin-4-yl)amino)thiazole-5-carboxamide (DAS-6-2-2-CRBN):

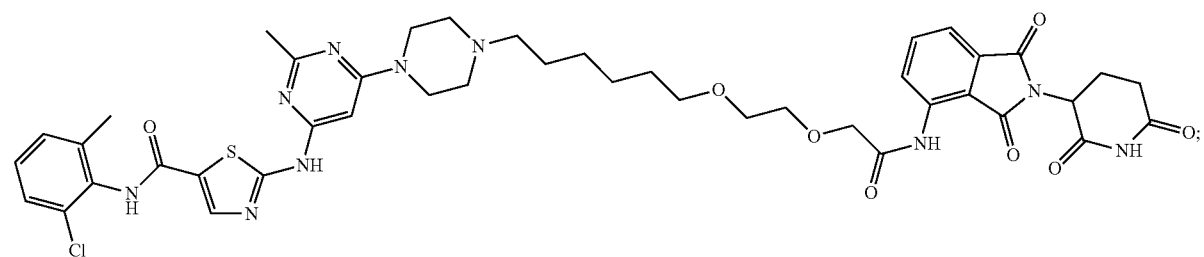 [SMILES: Cc1nc(Nc2ncc(C(=O)Nc3c(C)cccc3Cl)s2)cc(N2CCN(CCCCCCOCCOCC(=O)Nc3cccc4c3C(=O)N(C3CCC(=O)NC3=O)C4=O)CC2)n1]

2-(2-((6-(4-(3-((3-cyano-4-((2,4-dichloro-5-methoxyphe-nyl)amino)-6-methoxyquinolin-7-yl)oxy)propyl)piper-azin-1-yl)hexyl)oxy)ethoxy)-N-(2-(2,6-dioxopiperidin-3-yl)-1,3-dioxoisoindolin-4-yl)acetamide (BOS-6-2-2-CRBN):

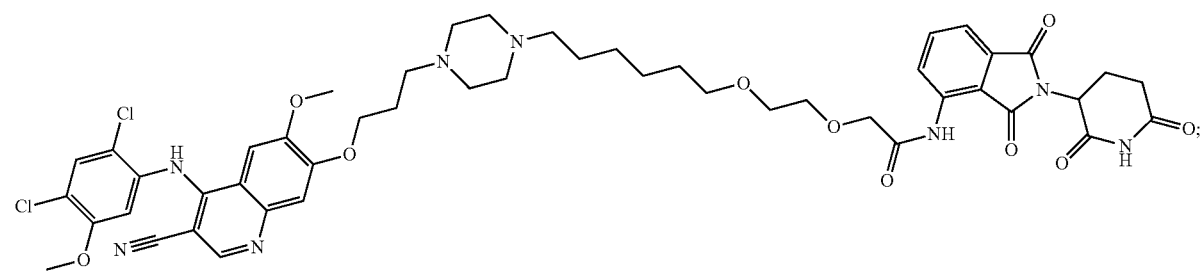 [SMILES: COc1cc(Nc2c(C#N)cnc3cc(OCCCN4CCN(CCCCCCOCCOCC(=O)Nc5cccc6c5C(=O)N(C5CCC(=O)NC5=O)C6=O)CC4)c(OC)cc23)c(Cl)cc1Cl]

4-((4-(6-(2-(2-((2-(2,6-dioxopiperidin-3-yl)-1,3-dioxoisoin-dolin-4-yl)amino)-2-oxoethoxy)ethoxy)hexyl)piperazin-1-yl)methyl)-N-(4-methyl-3-((4-(pyridin-3-yl)pyrimidin-2-yl)amino)phenyl)benzamide (IMA-6-2-2-CRBN):

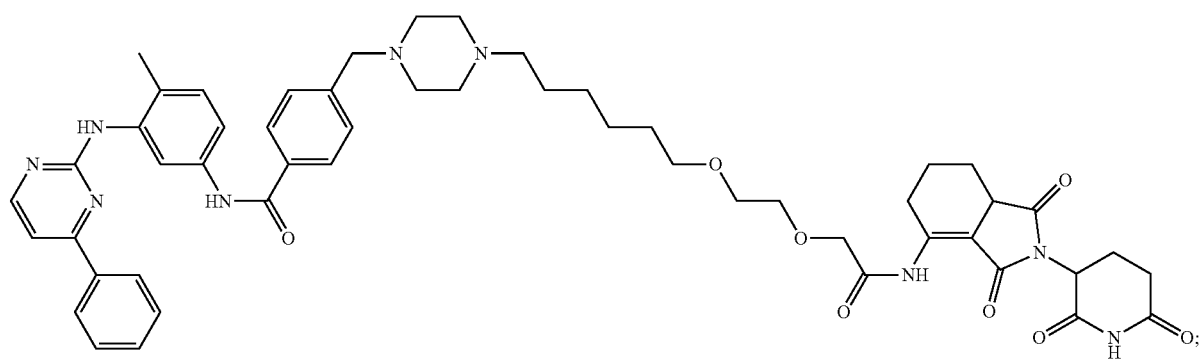 [SMILES: Cc1ccc(NC(=O)c2ccc(CN3CCN(CCCCCCOCCOCC(=O)NC4=C5C(=O)N(C6CCC(=O)NC6=O)C(=O)C5CCC4)CC3)cc2)cc1Nc1nccc(-c2ccccc2)n1]

N-(2-chloro-6-methylphenyl)-2-((6-(4-(1-((2-(2,6-dioxopiperidin-3-yl)-1,3-dioxoisoindolin-4-yl)amino)-1-oxo-3,6,9,12,15,18-hexaoxatetracosan-24-yl)piperazin-1-yl)-2-methylpyrimidin-4-yl)amino)thiazole-5-carboxamide (DAS-6-2-2-2-2-2-2-CRBN):

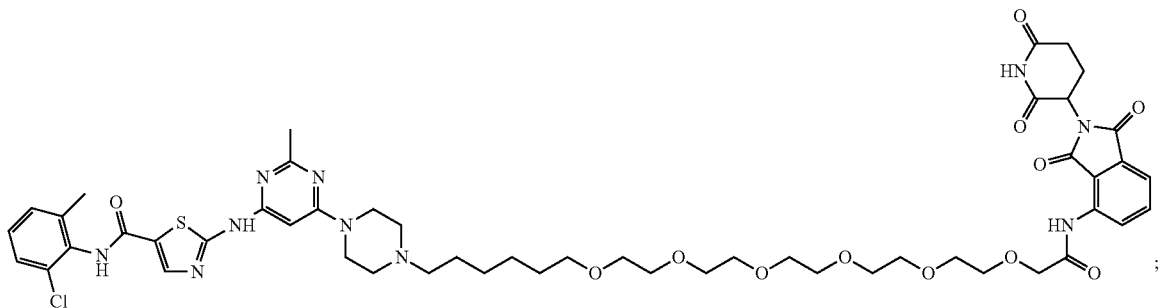 [SMILES: Cc1nc(Nc2ncc(C(=O)Nc3c(C)cccc3Cl)s2)cc(N2CCN(CCCCCCOCCOCCOCCOCCOCCOCC(=O)Nc3cccc4c3C(=O)N(C3CCC(=O)NC3=O)C4=O)CC2)n1]

24-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1,3-dioxoisoindolin-4-yl)-3,6,9,12,15,18-hexaoxatetracosanamide (BOS-6-2-2-2-2-2-2-CRBN):

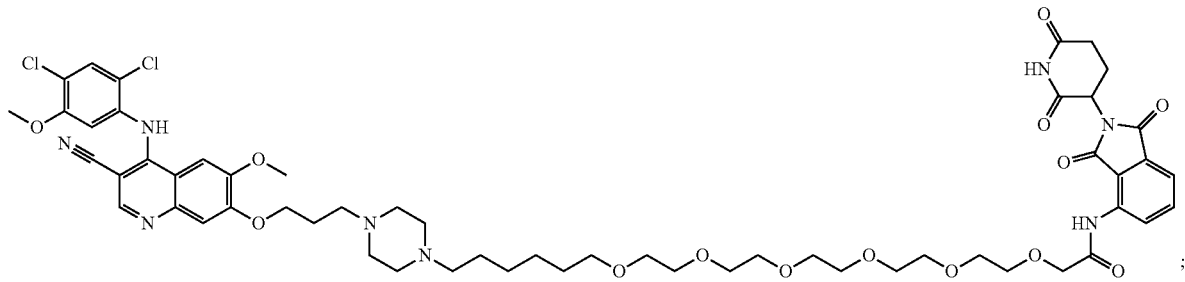 [SMILES: COc1cc(Nc2c(C#N)cnc3cc(OCCCN4CCN(CCCCCCOCCOCCOCCOCCOCCOCC(=O)Nc5cccc6c5C(=O)N(C5CCC(=O)NC5=O)C6=O)CC4)c(OC)cc23)c(Cl)cc1Cl]

N-(2-(2,6-dioxopiperidin-3-yl)-1,3-dioxoisoindolin-4-yl)-24-(4-(4-((4-methyl-3-((4-(pyridin-3-yl)pyrimidin-2-yl)amino)phenyl)carbamoyl)benzyl)piperazin-1-yl)-3,6,9,12,15,18-hexaoxatetracosanamide (IMA-6-2-2-2-2-2-2-CRBN):

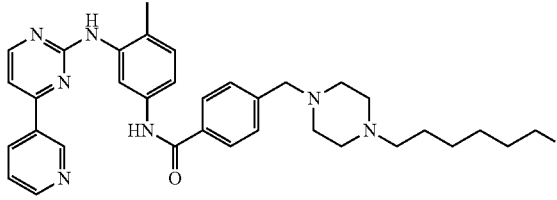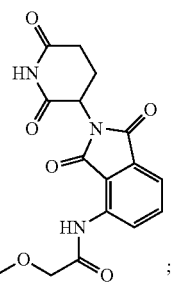

N-(2-chloro-6-methylphenyl)-2-((6-(4-(6-((5-(((6-((2-(2,6-dioxopiperidin-3-yl)-1,3-dioxoisoindolin-4-yl)amino)-6-oxohexyl)oxy)pentyl)oxy)hexyl)piperazin-1-yl)-2-methylpyrimidin-4-yl)amino)thiazole-5-carboxamide (DAS-6-5-6-CRBN):

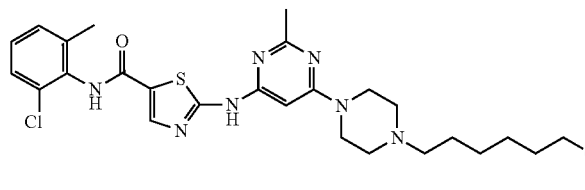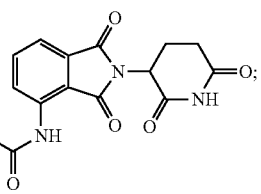

6-((5-(((6-(4-(3-((3-cyano-4-((2,4-dichloro-5-methoxyphenyl)amino)-6-methoxyquinolin-7-yl)oxy)propyl)piperazin-1-yl)hexyl)oxy)pentyl)oxy)-N-(2-(2,6-dioxopiperidin-3-yl)-1,3-dioxoisoindolin-4-yl)hexanamide (BOS-6-5-6-CRBN):

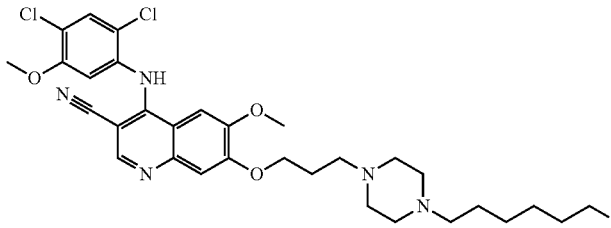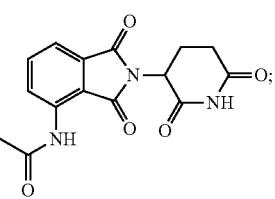

4-((4-(6-((5-(((6-((2-(2,6-dioxopiperidin-3-yl)-1,3-dioxoisoindolin-4-yl)amino)-6-oxohexyl)oxy)pentyl)oxy)hexyl)piperazin-1-yl)methyl)-N-(4-methyl-3-((4-(pyridin-3-yl)pyrimidin-2-yl)amino)phenyl)benzamide (IMA-6-5-6-CRBN):

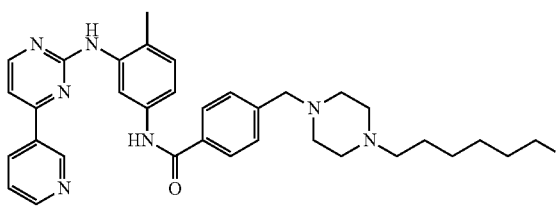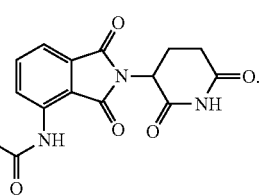

In certain embodiments, the pharmaceutical composition further comprises at least one additional therapeutic compound that treats or prevents cancer.

In certain embodiments, the method comprises administering to the subject a therapeutically effective amount of at least one compound of the invention. In other embodiments, the disease or disorder comprises cancer. In yet other embodiments, the cancer comprises chronic myelogenous leukemia (CML). In yet other embodiments, the compound is administered to the subject by at least one route selected from the group consisting of nasal, inhalational, topical, oral, buccal, rectal, pleural, peritoneal, vaginal, intramuscular, subcutaneous, transdermal, epidural, intrathecal and intravenous routes. In yet other embodiments, the cancer is associated with overexpression and/or uncontrolled activation of the tyrosine kinase. In other embodiments, the tyrosine kinase is oncogenic. In yet other embodiments, the subject is a human.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIG. 1A comprises an image illustrating that PROTACs act through proximity-induced ubiquitination, leading to subsequent degradation by the proteasome. FIG. 1B comprises an image illustrating overlay of the TKIs bosutinib (blue; PDB: 3UE4) and dasatinib (yellow; PDB: 2GQG), in the ABL ATP-binding pocket. Linkers are attached via the solvent exposed site (red circle). FIG. 1C comprises linkers utilized to connect the respective TKI to the E3 recruiting ligand.

DETAILED DESCRIPTION OF THE INVENTION

The present invention relates to the unexpected discovery of bifunctional small compounds that efficiently degrade certain cancer-related tyrosine kinases in a cellular environment. These compounds are based on proteolysis targeting chimera (PROTAC) technology, wherein one end of the compound recruits a ubiquitin ligase while the other end engages the target tyrosine kinase. In certain embodiments, the ubiquitin ligase is an E3 ubiquitin ligase. In other embodiments, the ubiquitin ligase is Von Hippel Lindau (VHL) E3 ubiquitin ligase and/or Cereblon (CRBN) E3 ligase. Ternary complex formation takes place when the compounds of the invention bind to the tyrosine kinase and the ubiquitin ligase, thus bringing the recruited ligase in close proximity with the tyrosine kinase. This leads to the ubiquitination of the tyrosine kinase of interest and its subsequent degradation by proteasome.

In certain embodiments, the compounds of the invention can be used to treat diseases associated with overexpression and/or uncontrolled activation of the tyrosine kinase. In other embodiments, the compounds of the invention can be used to treat a cancer that is associated with and/or caused by an oncogenic tyrosine kinase.

Figure 5:
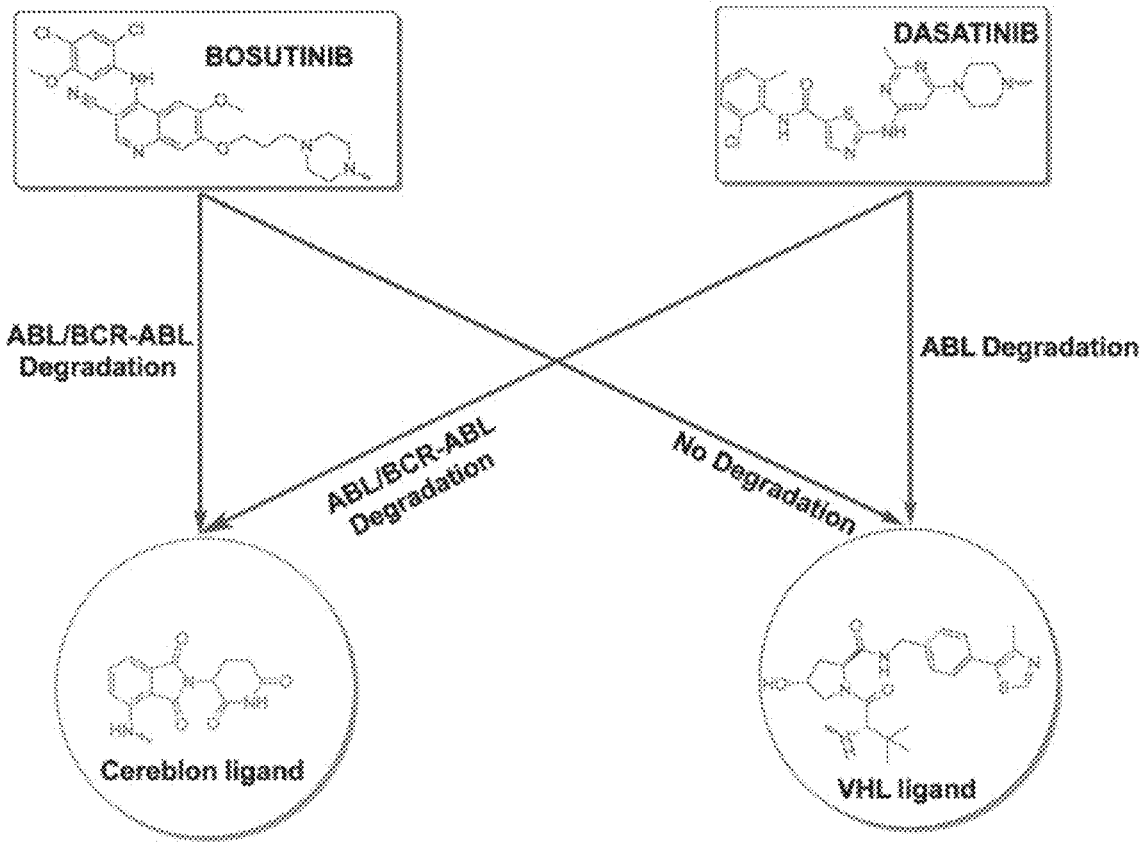
FIG. 5 comprises a schematic illustration of the finding that combination of the inhibitor warhead and the recruited E3 ubiquitin ligase permits targets to be accessed for degradation. IMA-based PROTACs did not induce the degradation of c-ABL or BCR-ABL, despite target engagement.
Figure 6A:
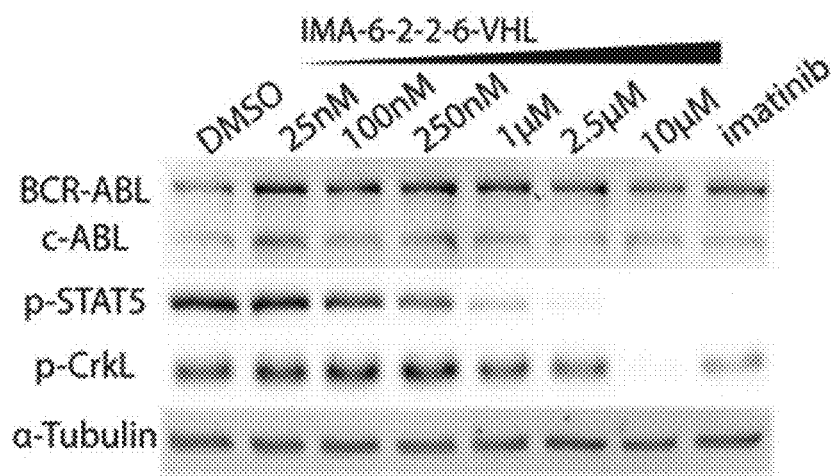
FIGS. 6A-6B illustrate IMA-based PROTACs with linker 6-2-2-6. IMA-6-2-2-6-VHL (FIG. 6A) and IMA-6-2-2-6-CRBN (FIG. 6B) were incubated with K562 human chronic myelogenous leukemia cell line for 24 hrs. The concentration of the parent inhibitors were at 1 µM. As determined by immunoblot, no degradation of c-ABL or BCR-ABL was observed in any of the IMA-based PROTACs.
Figure 6B:
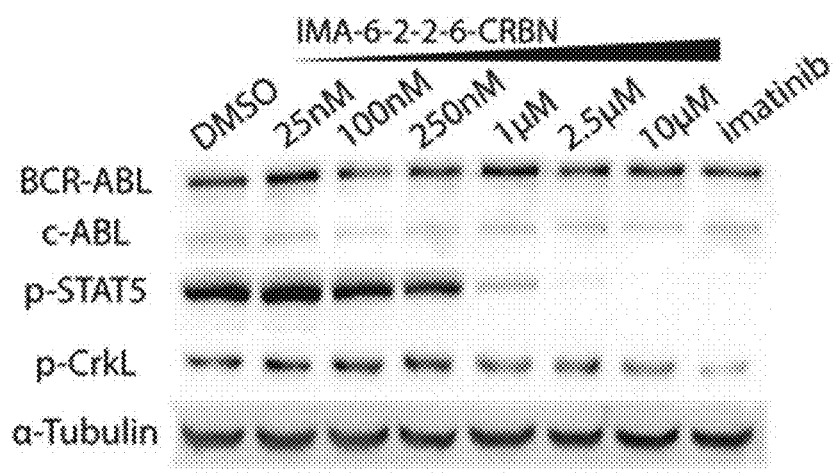
Figure 7A:
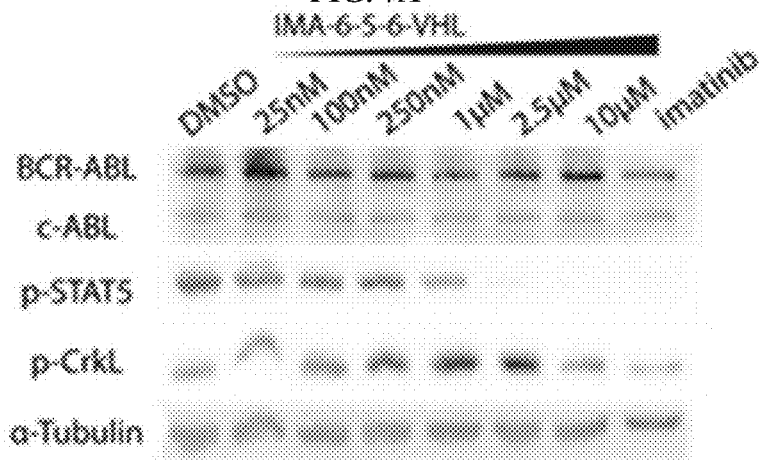
FIGS. 7A-7F illustrate PROTACs with linker 6-5-6. IMA-6-5-6-VHL (FIG. 7A), BOS-6-5-6-VHL (FIG. 7B) and DAS-6-5-6-VHL (FIG. 7C) were incubated with K562 human chronic myelogenous leukemia cell line for 24 hrs. IMA-6-5-6-CRBN (FIG. 7D), BOS-6-5-6-CRBN (FIG. 7E) and DAS-6-5-6-CRBN (FIG. 7F) were incubated with K562 human chronic myelogenous leukemia cell line for 24 hrs. The concentration of the parent inhibitors were at 1 µM. As determined by immunoblot, degradation of c-ABL can be observed with DAS-6-5-6-VHL starting at 1 µM. However, no degradation of BCR-ABL was observed in any of the VHL-based PROTACs.
Figure 7B:
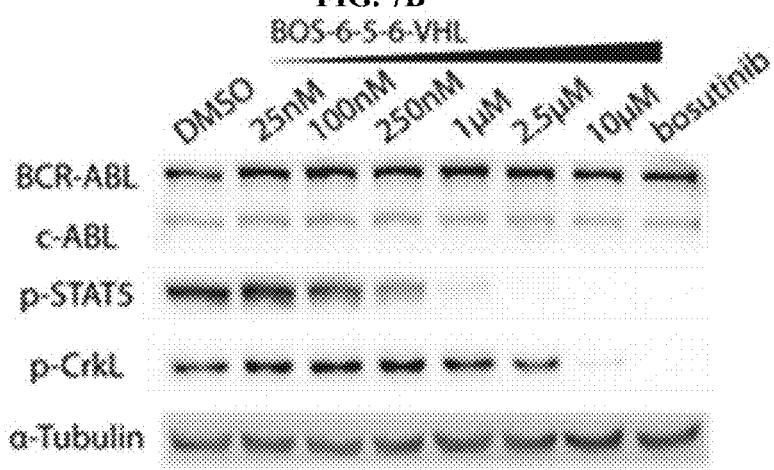
Figure 7C:
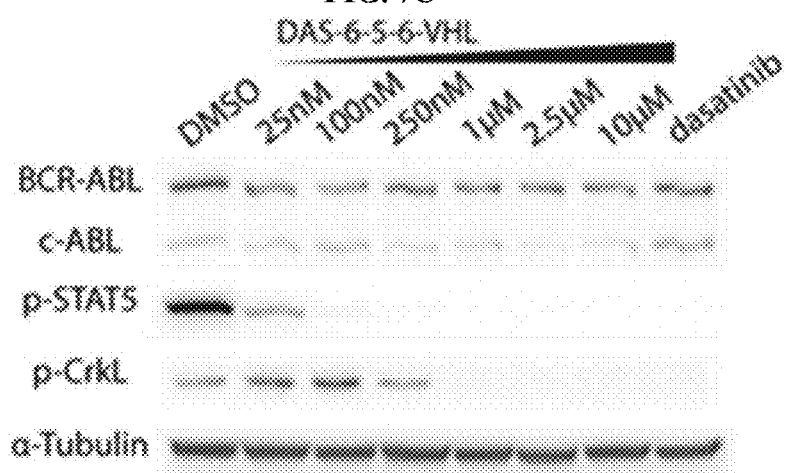
Figure 7D:
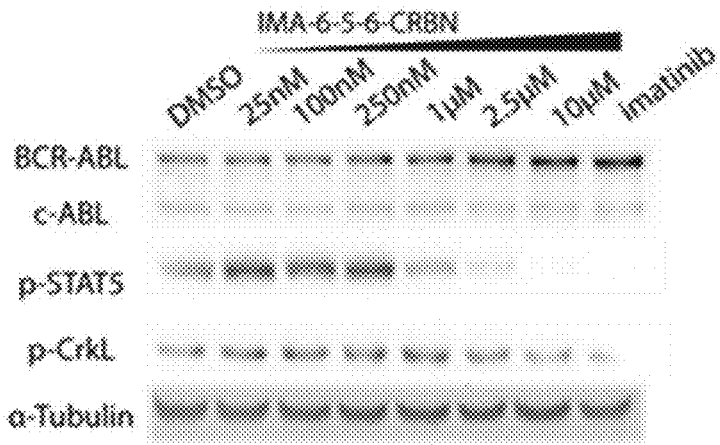
Figure 7E:
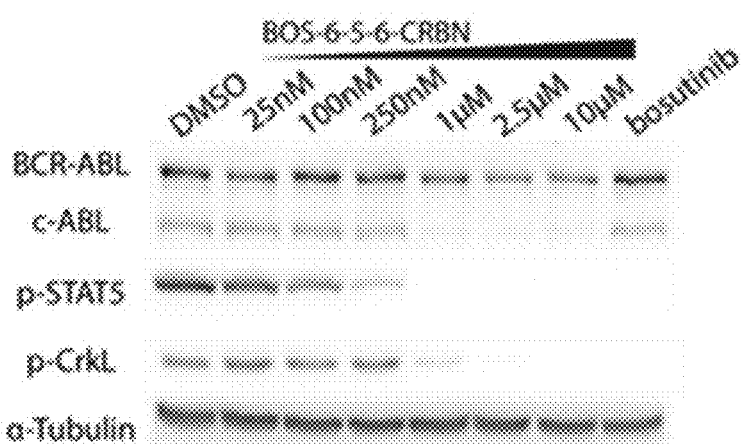
Figure 7F:
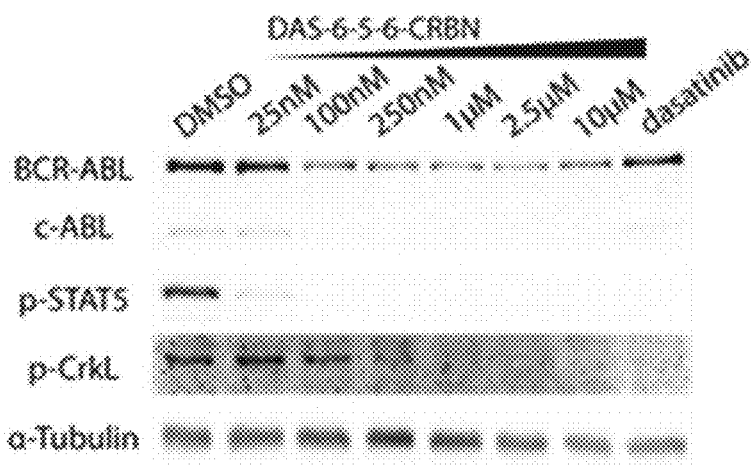
Figure 8A:
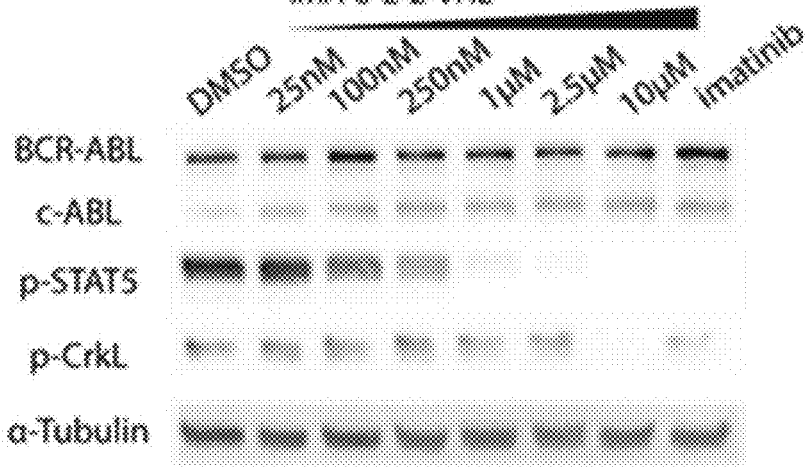
FIGS. 8A-8F illustrates PROTACs with linker 6-2-2. IMA-6-2-2-VHL (FIG. 8A), BOS-6-2-2-VHL (FIG. 8B) and DAS-6-2-2-VHL (FIG. 8C) were incubated with K562 human chronic myelogenous leukemia cell line for 24 hrs. IMA-6-2-2-CRBN (FIG. 8D), BOS-6-2-2-CRBN (FIG. 8E) and DAS-6-2-2-CRBN (FIG. 8F) were incubated with K562 human chronic myelogenous leukemia cell line for 24 hrs. The concentration of the parent inhibitors were at 1 µM. As determined by immunoblot, degradation of c-ABL can be observed with DAS-6-2-2-VHL starting at 1 µM. However, no degradation of BCR-ABL was observed in any of the VHL-based PROTACs.
Figure 8B:
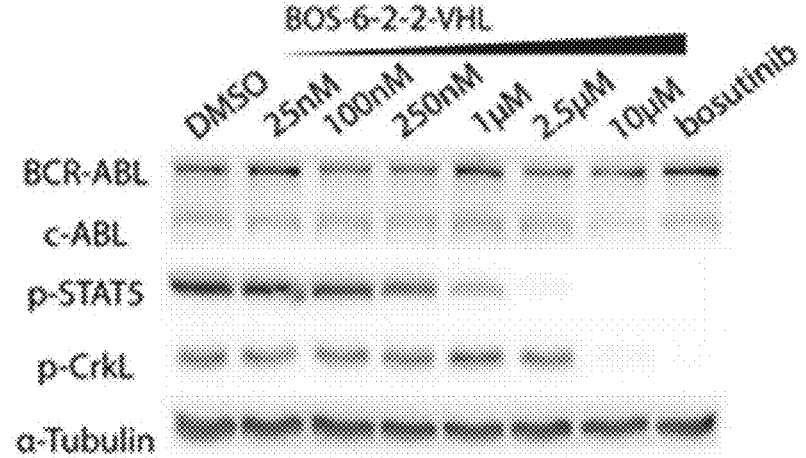
Figure 8C:
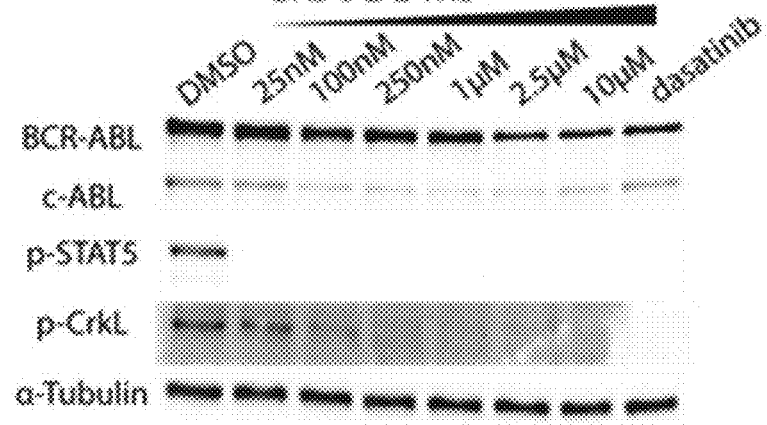
Figure 8D:
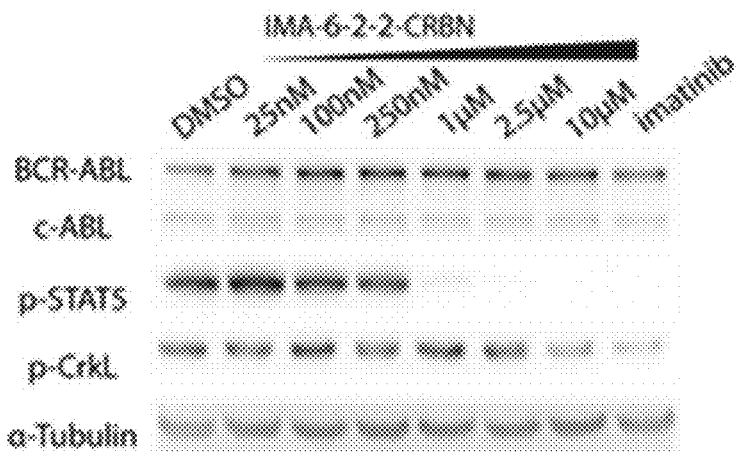
Figure 8E:
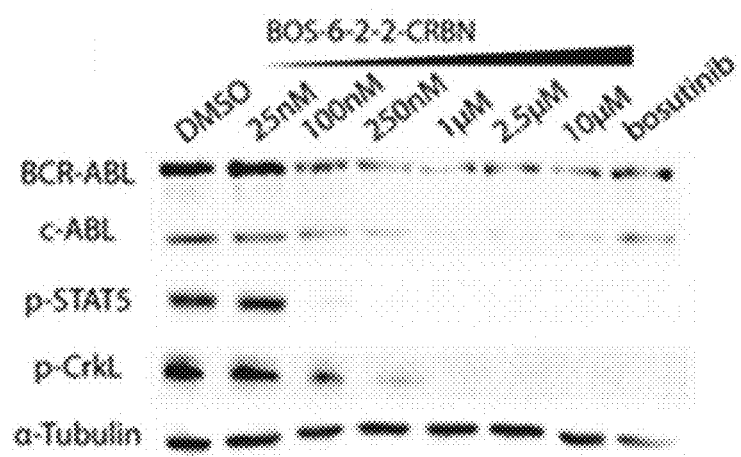
Figure 8F:
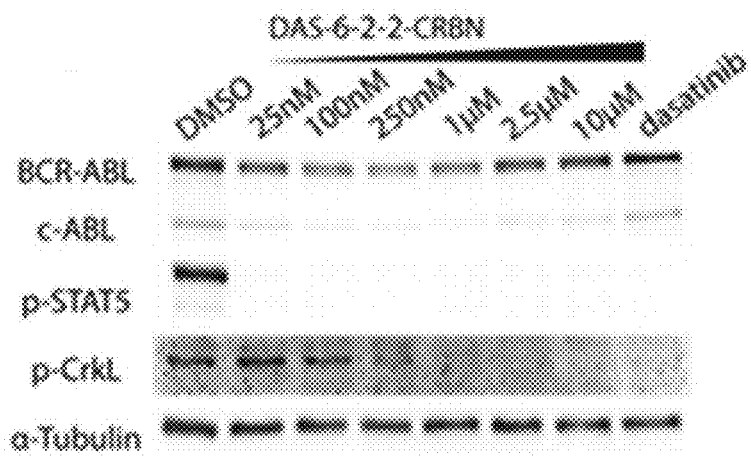
Figure 9A:
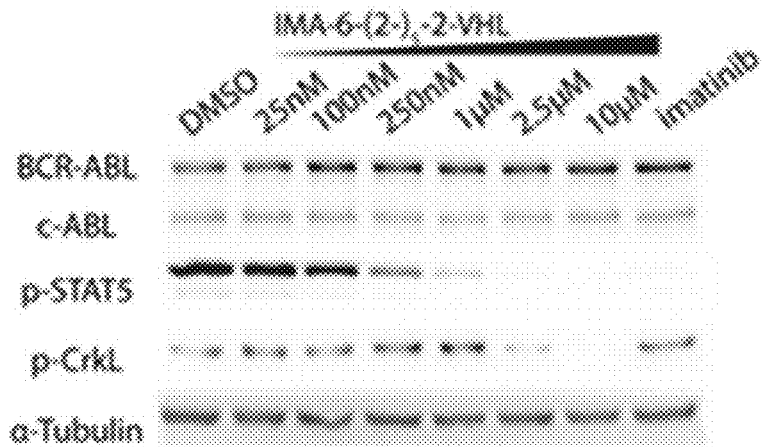
FIGS. 9A-9F illustrates PROTACs with linker 6-(2)$_5$-2. IMA-6-(2)$_5$-2-VHL (FIG. 9A), BOS-6-(2)$_5$-2-VHL (FIG. 9B) and DAS-6-(2)$_5$-2-VHL (FIG. 9C) were incubated with K562 human chronic myelogenous leukemia cell line for 24 hrs. IMA-6-(2)$_5$-2-CRBN (FIG. 9D), BOS-6-(2)$_5$-2-CRBN (FIG. 9E) and DAS-6-(2)$_5$-2-CRBN (FIG. 9F) were incubated with K562 human chronic myelogenous leukemia cell line for 24 hrs. The concentration of the parent inhibitors were at 1 µM. As determined by immunoblot, degradation of c-ABL can be observed with DAS-6-(2)$_5$-2-VHL starting at 1 µM. However, no degradation of BCR-ABL was observed in any of the VHL-based PROTACs.
Figure 9B:
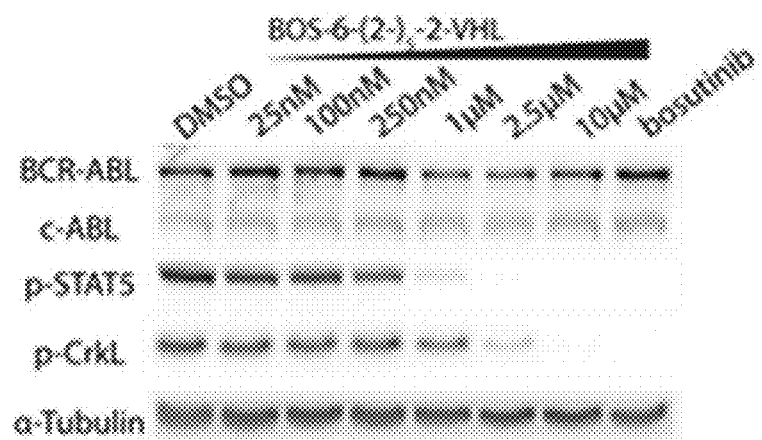
Figure 9C:
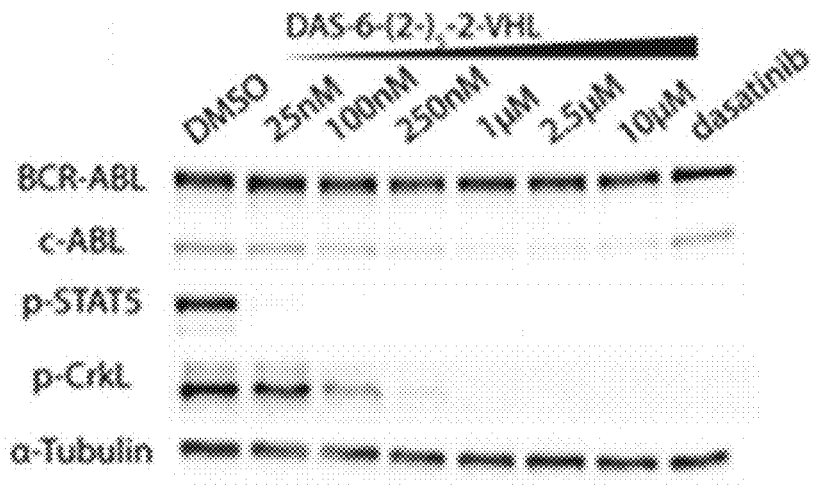
Figure 9D:
Figure 9E:
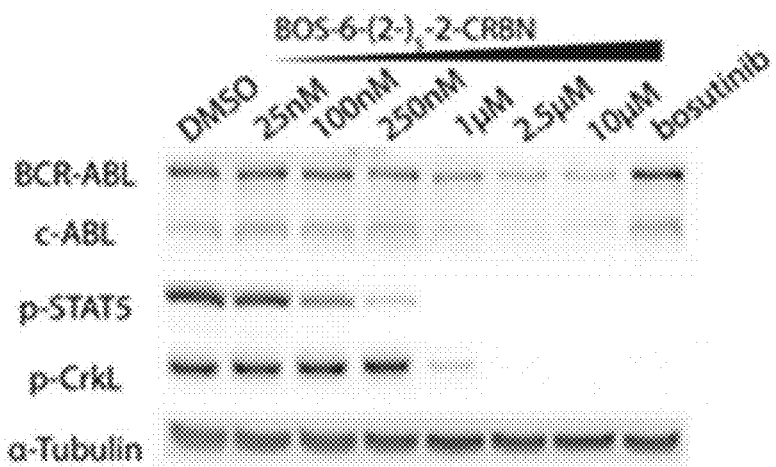
Figure 9F:
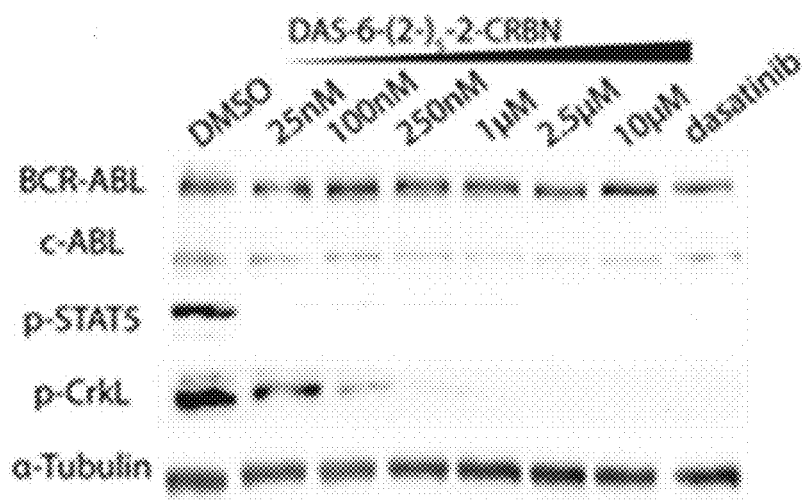

As demonstrated herein, bifunctional small compounds based on two potent TKIs (bosutinib and dasatinib) were synthesized and shown to mediate the degradation of c-ABL and BCR-ABL by hijacking either CRBN or VHL E3 ubiquitin ligase. Furthermore, these novel PROTACs were shown to be selective against the BCR-ABL driven cell line K562. In certain embodiments, changing the inhibitor warhead and the recruited E3 ligase influences which protein targets are susceptible to PROTAC-induced degradation (FIG. 5). By varying the recruited E3 ligase, the substrate spectrum of PROTACs can be significantly altered. In certain embodiments, the selectivity of a promiscuous inhibitor may be narrowed by creating a more selective degrader via the coupling to different E3 ligase recruiting ligands.

The present description provides compounds comprising a ligand, e.g., a small molecule ligand (i.e., having a molecular weight that is lower than about 2,000, 1,000, 500, or 200 Daltons), which is capable of binding to a ubiquitin ligase, such as, but not limited to, VHL or cereblon. The compounds also comprise a moiety that is capable of binding to a target protein, in such a way that the target protein is placed in proximity to the ubiquitin ligase to effect degradation (and/or inhibition) of that protein. In certain embodiments, "small molecule" means, in addition to the above, that the molecule is non-peptidyl, i.e., it is not generally considered a peptide, e.g., comprises fewer than 4, 3, or 2 amino acids. In accordance with the present description, the PTM, ULM and/or PROTAC molecules can be a small molecule.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, specific methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

A disease or disorder is "alleviated" if the severity of a symptom of the disease or disorder, the frequency with which such a symptom is experienced by a patient, or both, is reduced.

The terms "cancer" refers to the physiological condition in a subject typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small cell lung cancer, non-small cell lung cancer ("NSCLC"), vulval cancer, thyroid cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, hepatic carcinoma, anal carcinoma, penile carcinoma, as well as head and neck cancer. In yet other embodiments, the cancer is at least one selected from the group consisting of ALL, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL, Philadelphia chromosome positive CML, lymphoma, leukemia, multiple myeloma myeloproliferative diseases, large B cell lymphoma, and B cell Lymphoma. Without wishing to be limited by any theory, in about 10% of patients with acute lymphocytic leukemia, patients carry a 9;22 translocation cytogenetically indistinguishable from the Philadelphia chromosome of CML.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system.

An appropriate therapeutic amount in any individual case may be determined by one of ordinary skill in the art using routine experimentation.

As used herein, the term "efficacy" refers to the maximal effect ($E_{max}$) achieved within an assay.

As used herein, the term "L" or "Linker" refers to the linker.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids or bases, including inorganic acids or bases, organic acids or bases, solvates, hydrates, or clathrates thereof.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, ammonium salts, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "potency" refers to the dose needed to produce half the maximal response ($ED_{50}$).

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, —NH$_2$, —N(CH$_3$)$_2$, —C(═O)OH, trifluoromethyl, —C≡N, —C(═O)O($C_1$-$C_4$)alkyl, —C(═O)NH$_2$, —SO$_2$NH$_2$, —C(═NH)NH$_2$, and —NO$_2$, preferably containing one or two substituents selected from halogen, —OH, alkoxy, —NH$_2$, trifluoromethyl, —N(CH$_3$)$_2$, and —C(═O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "haloalkyl" means alkyl as defined above, substituted by one, two or three substituents selected from the group consisting of F, Cl, Br, and I.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized or substituted. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—

OH, —CH₂—CH₂—NH—CH₃, —CH₂—S—CH₂—CH₃, —NH—(CH₂)$_m$—OH (m=1-6), —N(CH₃)—(CH₂)$_m$—OH (m=1-6), —NH—(CH₂)$_m$—OCH₃ (m=1-6), and —CH₂CH₂—S(=O)—CH₃. Up to two heteroatoms may be consecutive, such as, for example, —CH₂—NH—OCH₃, or —CH₂—CH₂—S—S—CH₃

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are (C₁-C₃) alkoxy, particularly ethoxy and methoxy.

As used herein, the term "cycloalkyl" refers to a mono cyclic or polycyclic non-aromatic radical, wherein each of the atoms forming the ring (i.e. skeletal atoms) is a carbon atom. In certain embodiments, the cycloalkyl group is saturated or partially unsaturated. In other embodiments, the cycloalkyl group is fused with an aromatic ring. Cycloalkyl groups include groups having from 3 to 10 ring atoms. Illustrative examples of cycloalkyl groups include, but are not limited to, the following moieties:

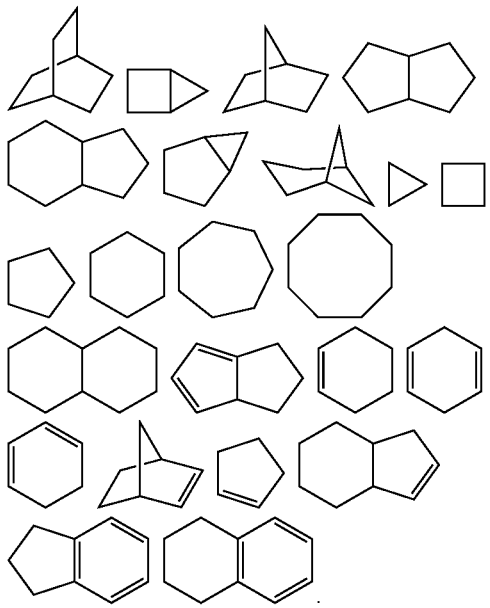

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "aryl-(C₁-C₃)alkyl" means a functional group wherein a one- to three-carbon alkylene chain is attached to an aryl group, e.g., —CH₂CH₂-phenyl. Preferred is aryl-CH₂— and aryl-CH(CH₃)—. The term "substituted aryl-(C₁-C₃)alkyl" means an aryl-(C₁-C₃)alkyl functional group in which the aryl group is substituted. Preferred is substituted aryl(CH₂)—. Similarly, the term "heteroaryl-(C₁-C₃)alkyl" means a functional group wherein a one to three carbon alkylene chain is attached to a heteroaryl group, e.g., —CH₂CH₂-pyridyl. Preferred is heteroaryl-(CH₂)—. The term "substituted heteroaryl-(C₁-C₃) alkyl" means a heteroaryl-(C₁-C₃)alkyl functional group in which the heteroaryl group is substituted. Preferred is substituted heteroaryl-(CH₂)—.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heterocycloalkyl" or "heterocyclyl" refers to a heteroalicyclic group containing one to four ring heteroatoms each selected from O, S and N. In certain embodiments, each heterocycloalkyl group has from 4 to 10 atoms in its ring system, with the proviso that the ring of said group does not contain two adjacent O or S atoms. In other embodiments, the heterocycloalkyl group is fused with an aromatic ring. In certain embodiments, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

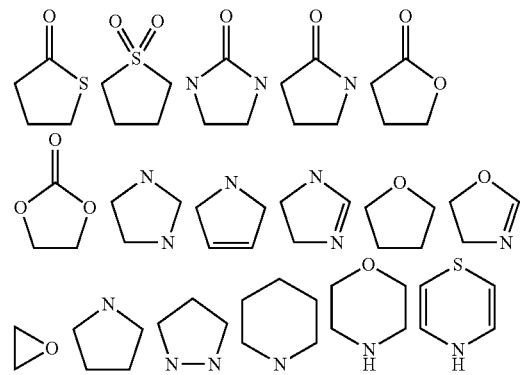

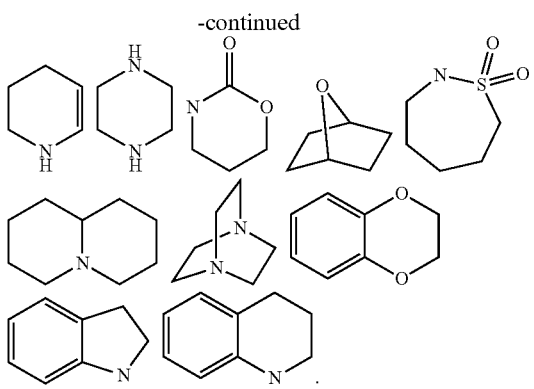

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "heteroaryl" or "heteroaromatic" refers to a heterocycle having aromatic character. A polycyclic heteroaryl may include one or more rings that are partially saturated. Examples include the following moieties:

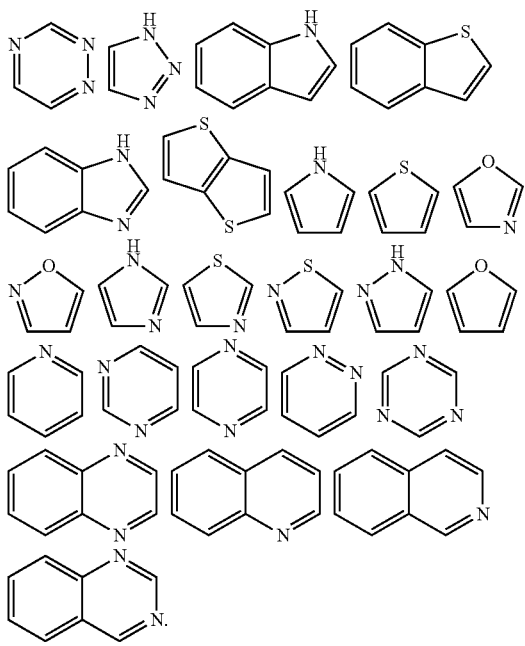

Examples of heteroaryl groups also include pyridyl, pyrazinyl, pyrimidinyl (particularly 2- and 4-pyrimidinyl), pyridazinyl, thienyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two.

As used herein, the term "optionally substituted" means that the referenced group may be substituted or unsubstituted. In certain embodiments, the referenced group is optionally substituted with zero substituents, i.e., the referenced group is unsubstituted. In other embodiments, the referenced group is optionally substituted with one or more additional group(s) individually and independently selected from groups described herein.

In certain embodiments, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$ alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In other embodiments, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet other embodiments, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds

The compounds of the present invention may be synthesized using techniques well-known in the art of organic synthesis. The starting materials and intermediates required for the synthesis may be obtained from commercial sources or synthesized according to methods known to those skilled in the art. General procedure of making certain compounds of the invention is described in U.S. patent application Ser. No. 14/371,956, which is incorporated by reference in its entirety.

The present invention provides a compound of formula (I), or a salt, enantiomer, stereoisomer, solvate, polymorph or N-oxide thereof: TKI-L-(ULM)$_k$ (I), wherein TKI is a tyrosine kinase inhibitor; L is a linker; ULM is a ubiquitin ligase binder; and k is an integer ranging from 1 to 4; wherein TKI is covalently linked to L and ULM is covalently linked to L. In certain embodiments, TKI is capable of binding the tyrosine kinase c-ABL and/or BCR-ABL, wherein, upon binding of the tyrosine kinase to the compound, the tyrosine kinase is ubiquitinated by a ubiquitin ligase.

In any of the aspects or embodiments described herein, the PTM and/or ULM have an affinity ($IC_{50}$) for their respective target protein of less than about 500 µM, 450 µM, 400 µM, 350 µM, 300 µM, 250 µM, 200 µM, 150 µM, 100 µM, 50 µM, 10 µM, 0.10 µM, 0.01 µM, 0.001 µM, 0.1 nM, 0.01 nM, 0.001 nM or less. The determination of the $IC_{50}$ can be performed using methods well known to those of skill in the art in view of the present disclosure.

Tyrosine Kinase Inhibitor (TKI)

A tyrosine kinase inhibitor (TKI) contemplated within the present invention binds to and inhibits a tyrosine kinase, or a subunit thereof. In certain embodiments, the TKI of the present invention binds to and inhibits c-ABL. In other embodiments, the TKI of the present invention binds to and inhibits BCR-ABL. In yet other embodiments, the TKI of the present invention binds to and inhibits c-ABL and BCR-ABL.

In certain embodiments, the TKI of the invention is selected from the group consisting of Dasatinib, Imatinib, Saracatinib, Ponatinib, Nilotinib, Danusertib, AT9283, Degrasyn, Bafetinib, KW-2449, NVP-BHG712, DCC-2036, GZD824, GNF-2, PD173955, GNF-5, Bosutinib, Gefitinib, Erlotinib, and Sunitinib.

In certain embodiments, the TKI of the invention is selected from the group consisting of Ruxolitinib, Tofacitinib, Lapatinib, Vandetanib, Sorafenib, Sunitinib, Axitinib, Nintedanib, Regorafenib, Pazopanib, Lenvatinib, Crizotinib, Ceritinib, Cabozantinib, DWF, Afatinib, Ibrutinib, B43, KU004, Foretinib, KRCA-0008, PF-06439015, PF-06463922, Canertinib, GSA-10, GW2974, GW583340, WZ4002, CP-380736, D2667, Mubritinib, PD153035, PD168393, Pelitinib, PF-06459988, PF-06672131, PF-6422899, PKI-166, Reveromycin A, Tyrphostin 1, Tyrphostin 23, Tyrphostin 51, Tyrphostin AG 528, Tyrphostin AG 658, Tyrphostin AG 825, Tyrphostin AG 835, Tyrphostin AG 1478, Tyrphostin RG 13022, Tyrphostin RG 14620, B178, GSK1838705A, PD-161570, PD 173074, SU-5402, Roslin 2, Picropodophyllotoxin, PQ401, I-OMe-Tyrphostin AG 538, GNF 5837, GW441756, Tyrphostin AG 879, DMPQ, JNJ-10198409, PLX647, Trapidil, Tyrphostin A9, Tyrphostin AG 370, Lestaurtinib, DMH4, Geldanamycin, Genistein, GW2580, Herbimycin A, Lavendustin C, Midostaurin, NVP-BHG712, PD158780, PD-166866, PF-06273340, PP2, RPI, SU 11274, SU5614, Symadex, Tyrphostin AG 34, Tyrphostin AG 974, Tyrphostin AG 1007, UNC2881, Honokiol, SU1498, SKLB1002, CP-547632, JK-P3, KRN633, SC-1, ST638, SU 5416, Sulochrin, Tyrphostin SU 1498, S8567, rociletinib, Dacomitinib, Tivantinib, Neratinib, Masitinib, Vatalanib, Icotinib, XL-184, OSI-930, AB 1010, Quizartinib, AZD9291, Tandutinib, HM61713, Brigantinib, Vemurafenib (PLX-4032), Semaxanib, AZD2171, Crenolanib, Damnacanthal, Fostamatinib, Motesanib, Radotinib, OSI-027, Linsitinib, BIX02189, PF-431396, PND-1186, PF-03814735, PF-431396, sirolimus, temsirolimus, everolimus, deforolimus, zotarolimus, BEZ235, INK128, Omipalisib, AZD8055, MHY1485, PI-103, KU-0063794, ETP-46464, GDC-0349, XL388, WYE-354, WYE-132, GSK1059615, WAY-600, PF-04691502, WYE-687, PP121, BGT226, AZD2014, PP242, CH5132799, P529, GDC-0980, GDC-0994, XMD8-92, Ulixertinib, FR180204, SCH772984, Trametinib, PD184352, PD98059, Selumetinib, PD325901, U0126, Pimasertinib, TAK-733, AZD8330, Binimetinib, PD318088, SL-327, Refametinib, GDC-0623, Cobimetinib, BI-847325, Adaphostin, GNF 2, PPY A, AIM-100, ASP 3026, LFM A13, PF 06465469, (−)-Terreic acid, AG-490, BIBU 1361, BIBX 1382, BMS 599626, CGP 52411, GW 583340, HDS 029, HKI 357, JNJ 28871063, WHI-P 154, PF 431396, PF 573228, FIIN 1, PD 166285, SUN 11602, SR 140333, TCS 359, BMS 536924, NVP ADW 742, PQ 401, BMS 509744, CP 690550, NSC 33994, WHI-P 154, KB SRC 4, DDR1-IN-1, PF 04217903, PHA 665752, SU 16f, A 419259, AZM 475271, PP 1, PP 2, 1-Naphthyl PP1, Src I1, ANA 12, PD 90780, Ki 8751, Ki 20227, ZM 306416, ZM 323881, AEE 788, GTP 14564, PD 180970, R 1530, SU 6668, and Toceranib.

In certain embodiments, the TKI of the invention is selected from the group consisting of CEP-32496 (1-(3-((6,7-dimethoxyquinazolin-4-yl)oxy)phenyl)-3-(5-(1,1,1-trifluoro-2-methylpropan-2-yl)isoxazol-3-yl)urea), AZ 628 (4-(2-cyanopropan-2-yl)-N-(4-methyl-3-((3-methyl-4-oxo-3,4-dihydroquinazolin-6-yl)amino)phenyl)benzamide), Vemurafenib (PLX-4032), PLX-4720 (N-(3-(5-chloro-1H-pyrrolo[2,3-b]pyridine-3-carbonyl)-2,4-difluorophenyl)propane-1-sulfonamide), SB 590885 ((E)-5-(2-(4-(2-(dimethylamino)ethoxy)phenyl)-4-(pyridin-4-yl)-1H-imidazol-5-yl)-2,3-dihydro-1H-inden-1-one oxime), and GDC-0879 ((E)-5-(2-(2-hydroxyethyl)-4-(pyridin-4-yl)-1H-imidazol-5-yl)-2,3-dihydro-1H-inden-1-one oxime).

In certain embodiments, the TKI of the invention is

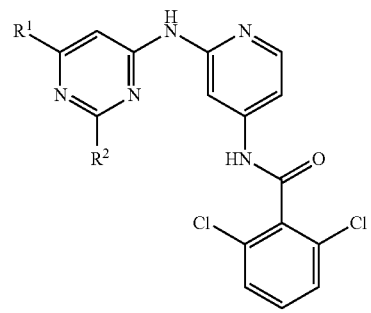

wherein R¹ is H or CH₃, and R² is

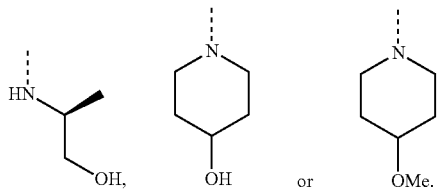

In certain embodiments, the TKI of the invention is

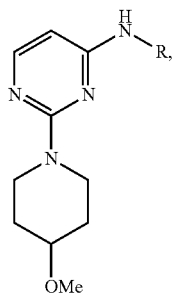

wherein R is

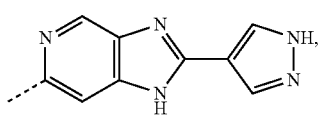

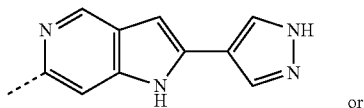

or

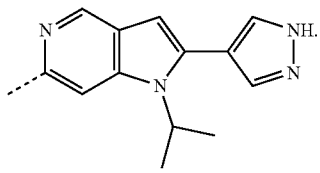

In certain embodiments, the TKI of the invention is

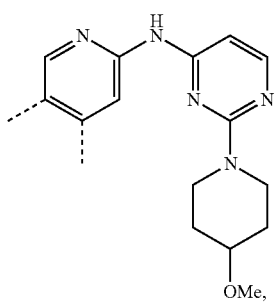

wherein the broken lines correspond to the divalent group

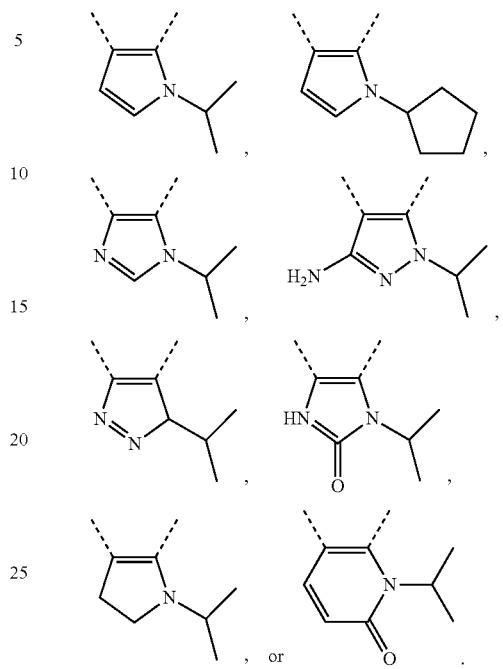

Bosutinib is also known as 4-[(2,4-dichloro-5-methoxyphenyl)amino]-6-methoxy-7-[3-(4-methylpiperazin-1-yl)propoxy]quinoline-3-carbonitrile, and has a formula of:

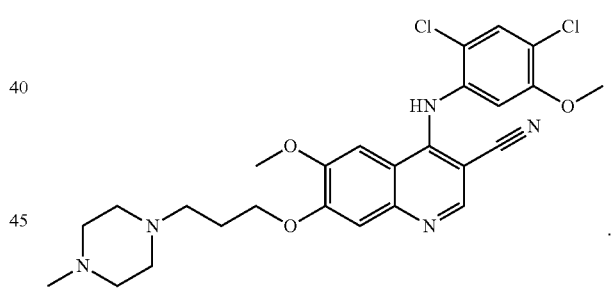

Linker L can be connected, for example, to the piperidine ring of this TKI. In certain embodiments, the N-methyl group is replaced with L. Exemplary positions wherein L may be attached are illustrated below:

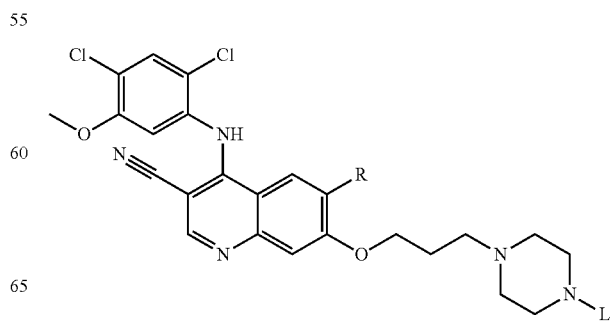

-continued

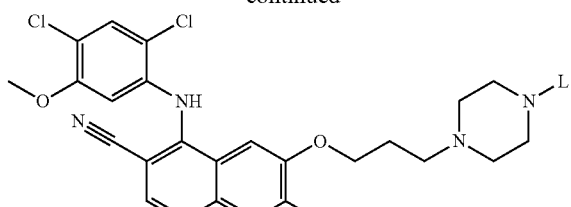

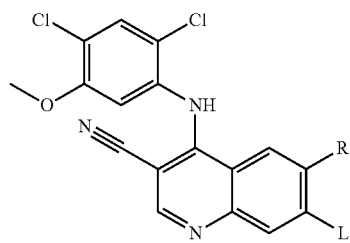

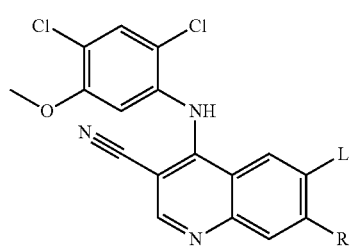

Dasatinib is also known as N-(2-chloro-6-methylphenyl)-2-(6-(4-(2-hydroxyethyl)piperazin-1-yl)-2-methylpyrimidin-4-ylamino)thiazole-5-carboxamide, and has a formula of:

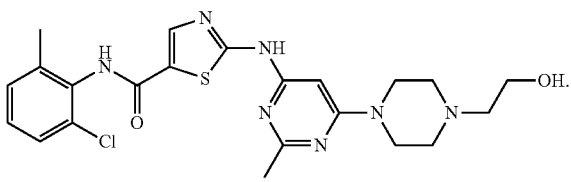 [SMILES: Cc1nc(Nc2ncc(C(=O)Nc3c(C)cccc3Cl)s2)cc(N2CCN(CCO)CC2)n1]

Linker L can be connected, for example, to the piperidine ring of this TKI. In certain embodiments, the N-(2-hydroxyethyl) group is derivatized with and/or replaced with L. Exemplary positions wherein L may be attached are illustrated below:

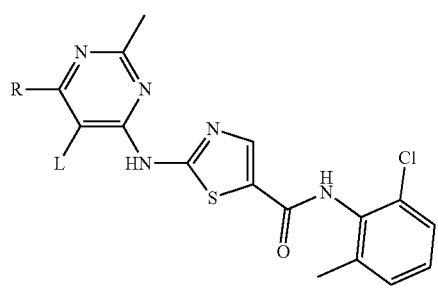

-continued

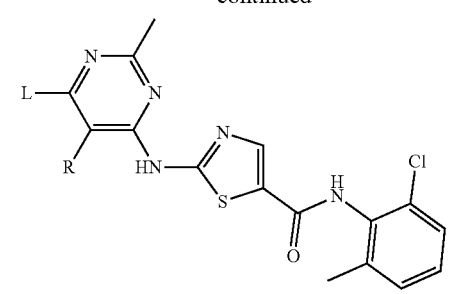

Imatinib is also known as N-(4-methyl-3-(4-(pyridin-3-yl)pyrimidin-2-ylamino)phenyl)-4-((4-methylpiperazin-1-yl)methyl)benzamide, and has a formula of:

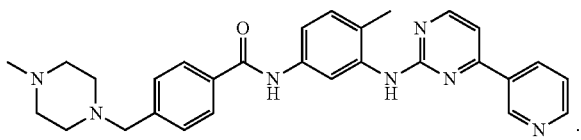 [SMILES: Cc1ccc(NC(=O)c2ccc(CN3CCN(C)CC3)cc2)cc1Nc1nccc(-c2cccnc2)n1]

Linker L can be connected, for example, to the piperidine ring of this TKI. In certain embodiments, the N-methyl group is replaced with L. Exemplary positions wherein L may be attached are illustrated below:

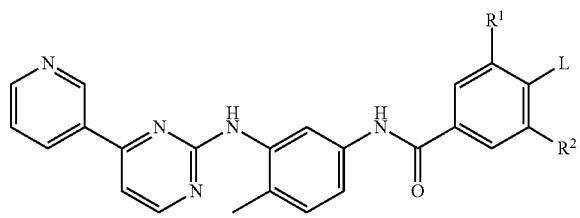

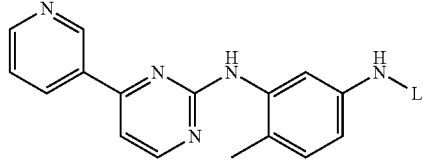

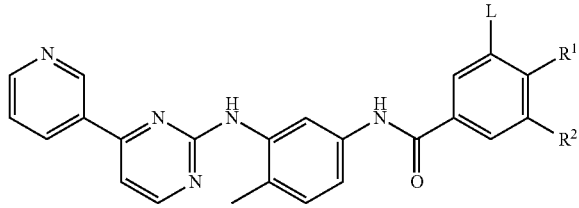

Saracatinib is also known as N-(5-chlorobenzo[d][1,3]dioxol-4-yl)-7-(2-(4-methylpiperazin-1-yl)ethoxy)-5-(tetrahydro-2H-pyran-4-yloxy)quinazolin-4-amine, and has a formula of:

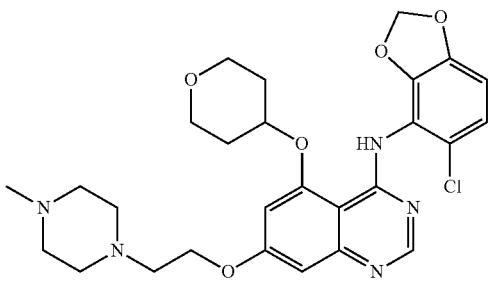

Linker L can be connected, for example, to the piperidine ring of this TKI. In certain embodiments, the N-methyl group is replaced with L. Exemplary positions wherein L may be attached are illustrated below:

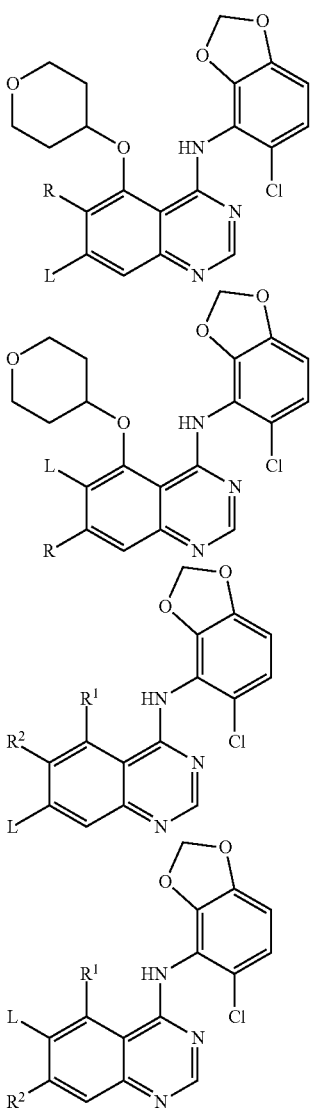

Ponatinib is also known as 3-(2-(imidazo[1,2-b]pyridazin-3-yl)ethynyl)-4-methyl-N-(4-((4-methylpiperazin-1-yl)methyl)-3-(trifluoromethyl)phenyl)benzamide, and has a formula of:

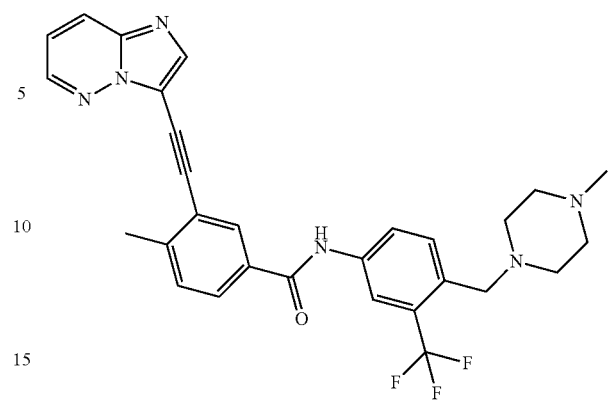

Linker L can be connected, for example, to the piperidine ring of this TKI. In certain embodiments, the N-methyl group is replaced with L. Exemplary positions wherein L may be attached are illustrated below:

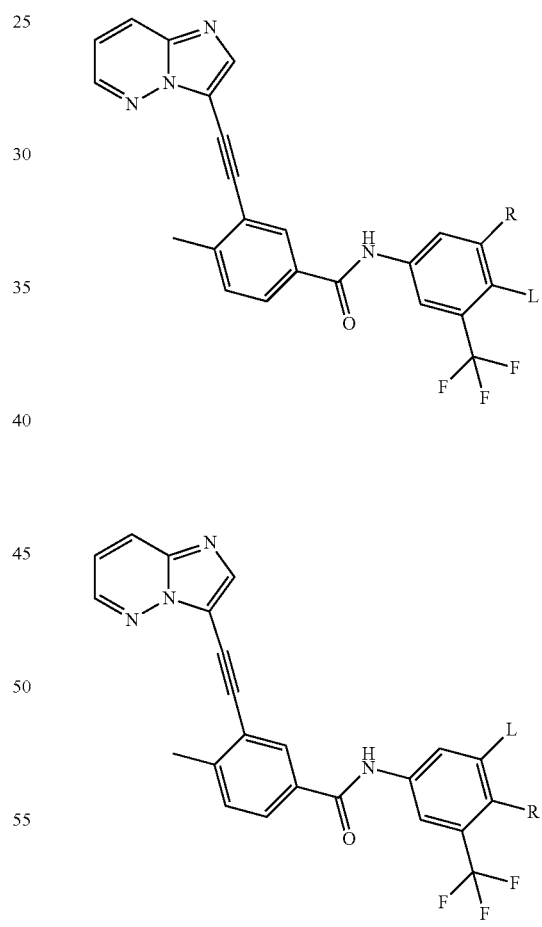

Nilotinib is also known as 4-methyl-N-(3-(4-methyl-1H-imidazol-1-yl)-5-(trifluoromethyl)phenyl)-3-(4-(pyridin-3-yl)pyrimidin-2-ylamino)benzamide, and has a formula of:

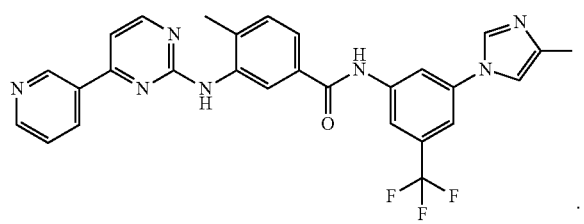 [SMILES: Cc1cn(-c2cc(NC(=O)c3ccc(C)c(Nc4nccc(-c5cccnc5)n4)c3)cc(C(F)(F)F)c2)cn1]

Exemplary positions wherein L may be attached are illustrated below:

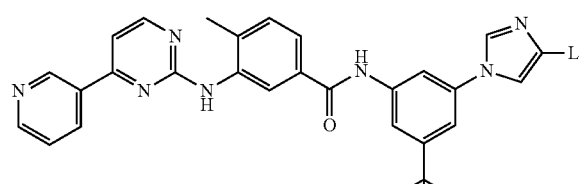

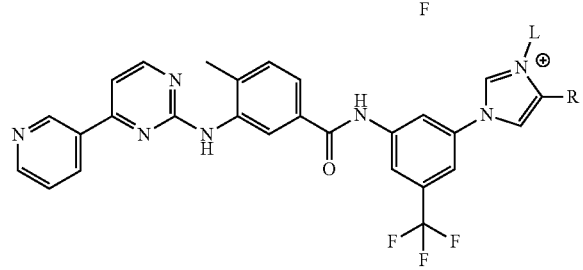

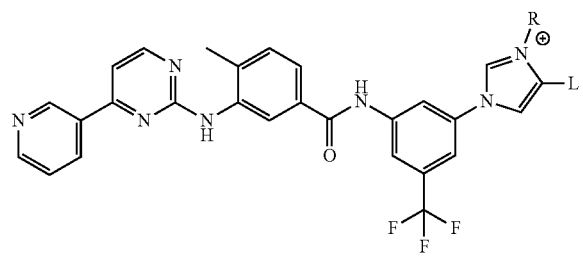

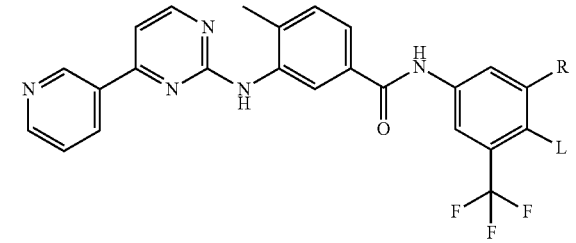

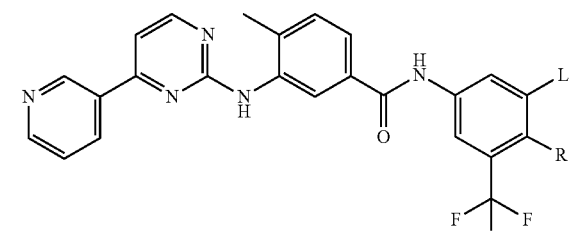

Danusertib is also known as (R)—N-(5-(2-methoxy-2-phenylacetyl)-1,4,5,6-tetrahydropyrrolo[3,4-c]pyrazol-3-yl)-4-(4-methylpiperazin-1-yl)benzamide, and has a formula of:

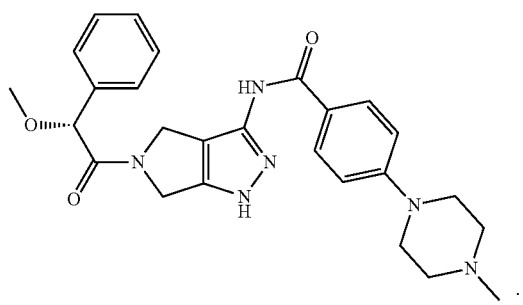

Linker L can be connected, for example, to the piperidine ring of this TKI. In certain embodiments, the N-methyl group is replaced with L. Exemplary positions wherein L may be attached are illustrated below:

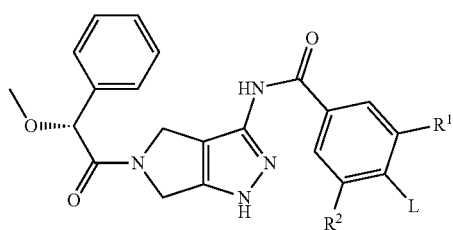

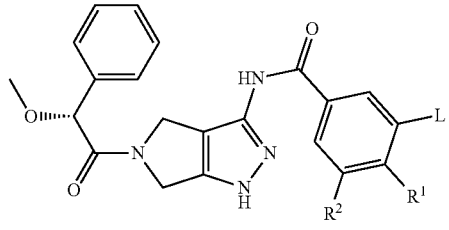

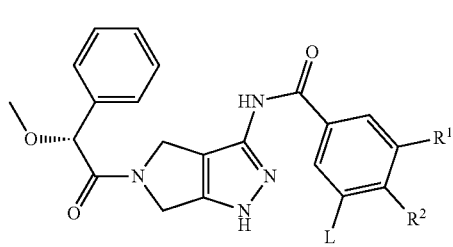

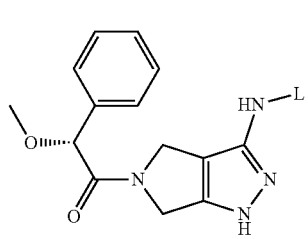

AT9283 is also known as 1-cyclopropyl-3-(3-(5-(morpholinomethyl)-1H-benzo[d]imidazol-2-yl)-1H-pyrazol-4-yl)urea, and has a formula of:

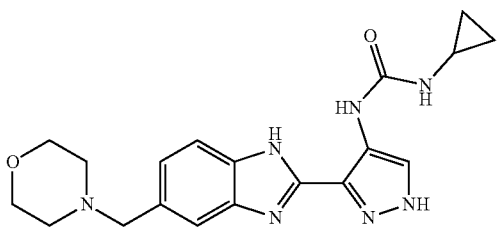

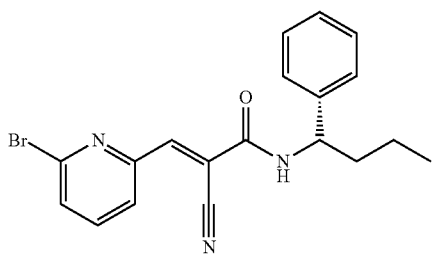

Linker L can be connected, for example, to the morpholino ring of this TKI. Exemplary positions wherein L may be attached are illustrated below:

Exemplary positions wherein L may be attached are illustrated below:

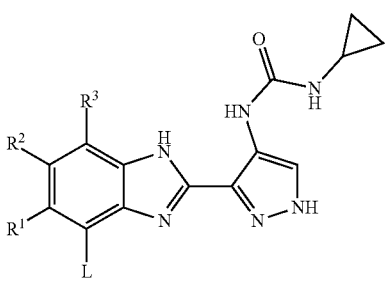

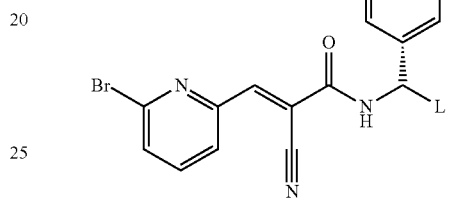

Bafetinib is also known as (S)-4-((3-(dimethylamino) pyrrolidin-1-yl)methyl)-N-(4-methyl-3-(4-(pyrimidin-5-yl) pyrimidin-2-ylamino)phenyl)-3-(trifluoromethyl)benzamide, and has a formula of:

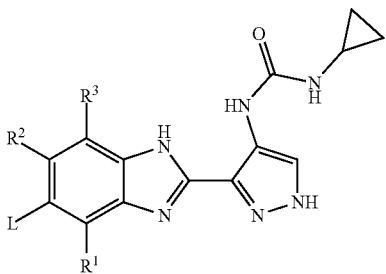

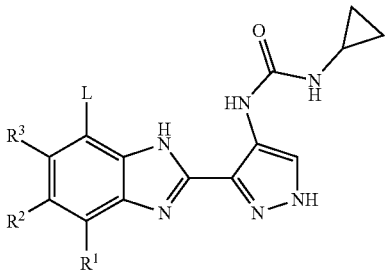

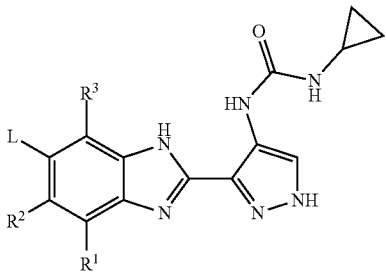

L can be connected, for example, to the pyrrolidine ring of this TKI. In certain embodiments, at least one of the N-methyl groups is replaced with L. Exemplary positions wherein L may be attached are illustrated below:

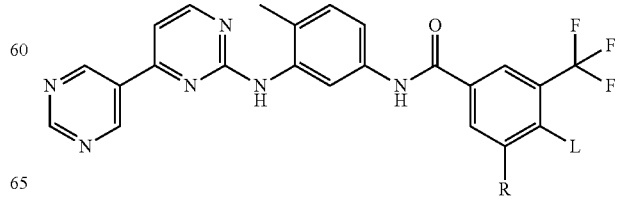

Degrasyn is also known as (S,E)-3-(6-bromopyridin-2-yl)-2-cyano-N-(1-phenyl butyl)acrylamide, and has a formula of:

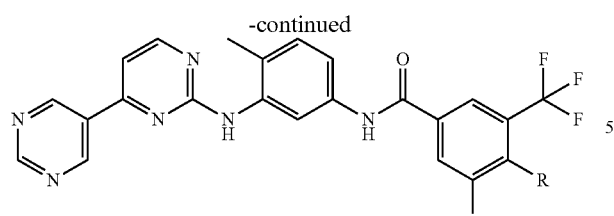

KW-2449 is also known as (E)-(4-(2-(1H-indazol-3-yl)vinyl)phenyl)(piperazin-1-yl)methanone, and has a formula of:

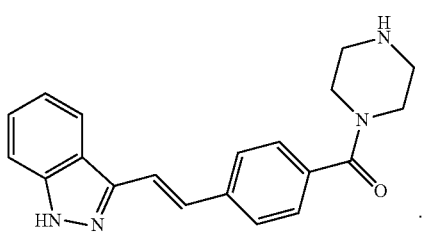 [SMILES: O=C(c1ccc(/C=C/c2n[nH]c3ccccc23)cc1)N1CCNCC1]

Linker L can be connected, for example, to the piperidine ring of this TKI. In certain embodiments, the NH— group of the piperidine group is linked to L. Exemplary positions wherein L may be attached are illustrated below:

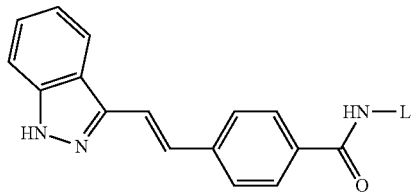

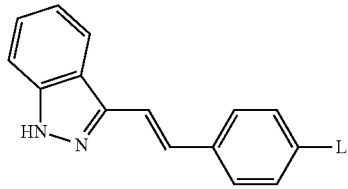

NVP-BHG712 is also known as 4-methyl-3-(1-methyl-6-(pyridin-3-yl)-1H-pyrazolo[3,4-d]pyrimidin-4-ylamino)-N-(3-(trifluoromethyl)phenyl)benzamide, and has a formula of:

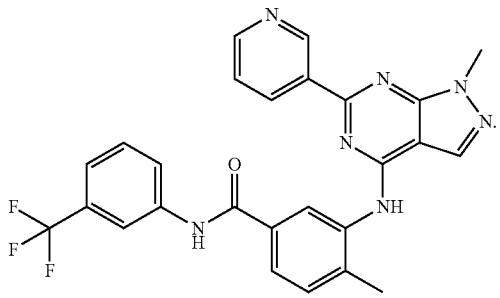 [SMILES: Cc1ccc(C(=O)Nc2cccc(C(F)(F)F)c2)cc1Nc1nc(-c2cccnc2)nc2c1cnn2C]

Exemplary positions wherein L may be attached are illustrated below:

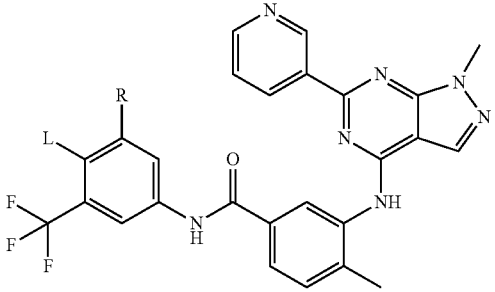

DCC-2036 is also known as 1-(3-tert-butyl-1-(quinolin-6-yl)-1H-pyrazol-5-yl)-3-(2-fluoro-4-(2-(methylcarbamoyl)pyridin-4-yloxy)phenyl)urea, and has a formula of:

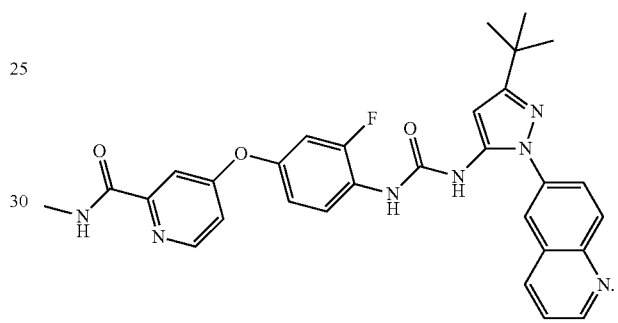

Exemplary positions wherein L may be attached are illustrated below:

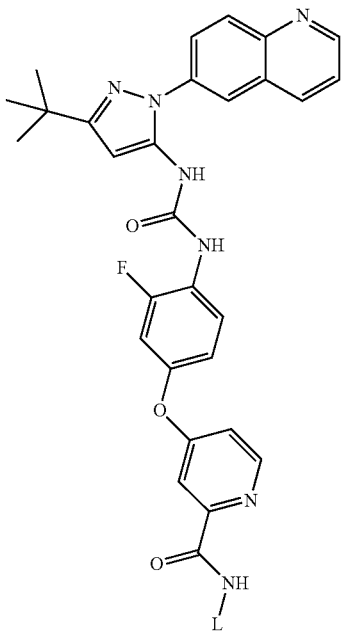

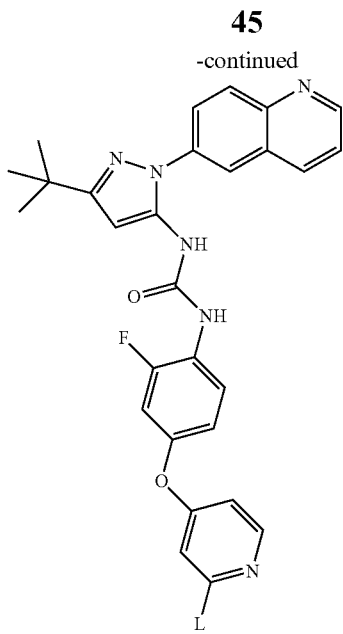

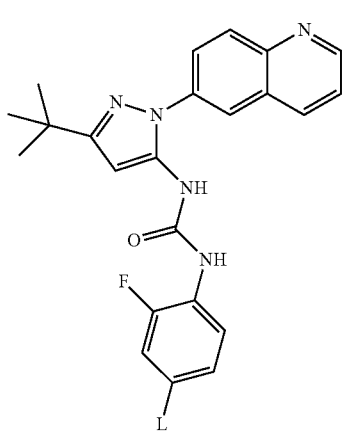

GZD824 is also known as 4-methyl-N-[4-[(4-methyl-1-piperazinyl)methyl]-3-(trifluoromethyl)phenyl]-3-[2-(1H-pyrazolo[3,4-b]pyridin-5-yl)ethynyl]-benzamide, and has a formula of:

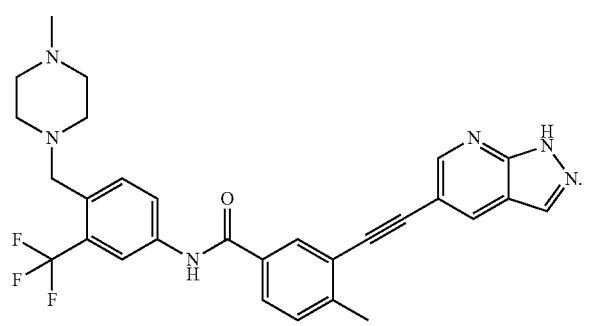 [SMILES: Cc1ccc(C(=O)Nc2ccc(CN3CCN(C)CC3)c(C(F)(F)F)c2)cc1C#Cc1cnc2[nH]ncc2c1]

Linker L can be connected, for example, to the piperidine ring of this TKI. In certain embodiments, the N-methyl group is replaced with L. Exemplary positions wherein L may be attached are illustrated below:

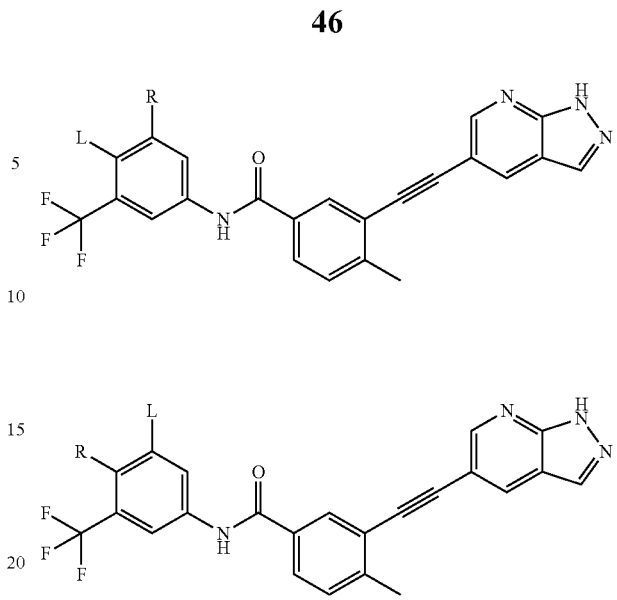

GNF-2 is also known as 3-[6-[[4-(trifluoromethoxy)phenyl]amino]-4-pyrimidinyl]-benzamide, and has a formula of:

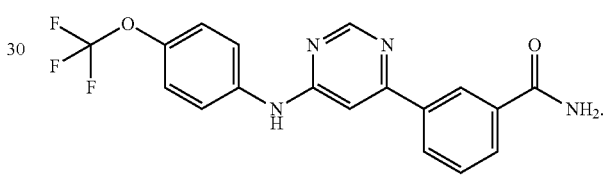

Exemplary positions wherein L may be attached are illustrated below:

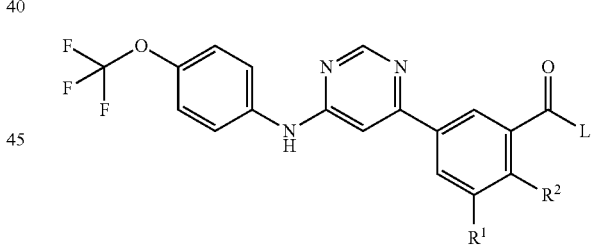

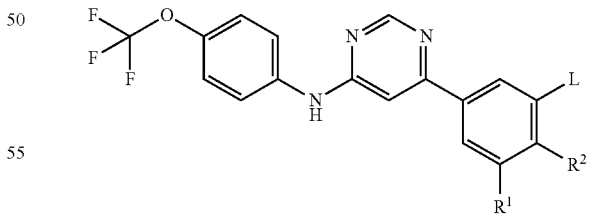

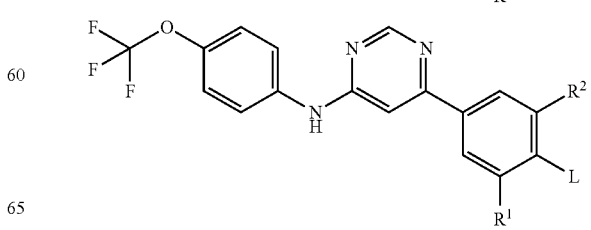

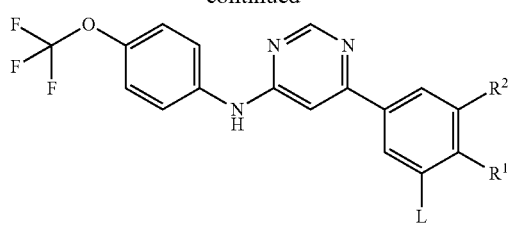

PD173955 is also known as 6-(2,6-dichlorophenyl)-8-methyl-2-((3-(methylthio)phenyl)amino)pyrido[2,3-d]pyrimidin-7(8H)-one, and has a formula of:

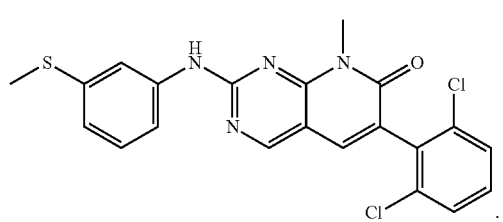 [SMILES: CSc1cccc(Nc2ncc3cc(-c4c(Cl)cccc4Cl)c(=O)n(C)c3n2)c1]

Exemplary positions wherein L may be attached are illustrated below:

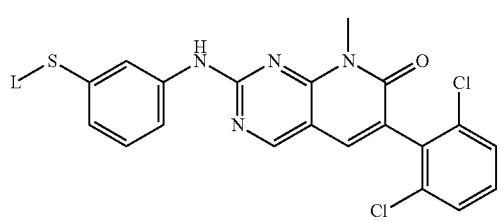

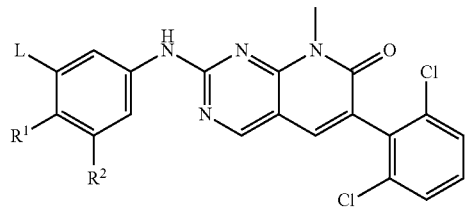

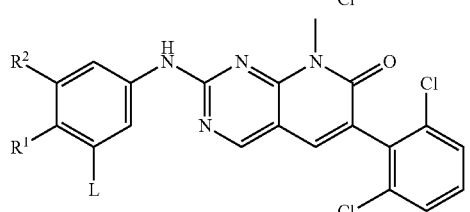

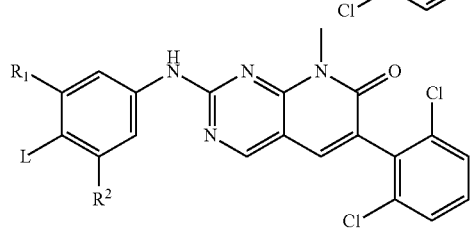

GNF-5 is also known as N-(2-Hydroxyethyl)-3-[6-[[4-(trifluoromethoxy) phenyl]amino]-4-pyrimidinyl]benzamide, and has a formula of:

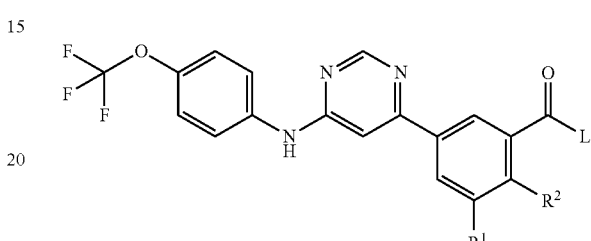

Linker L can be connected, for example, to the terminal amide of this TKI. In certain embodiments, the N-2-hydroxyethyl group is derivatized with and/or replaced with L. Exemplary positions wherein L may be attached are illustrated below:

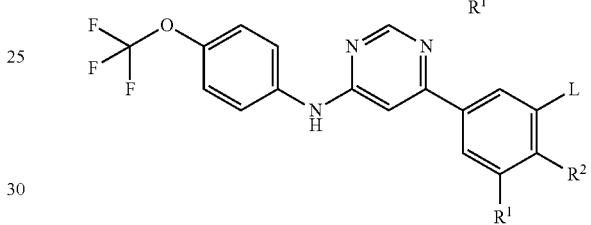

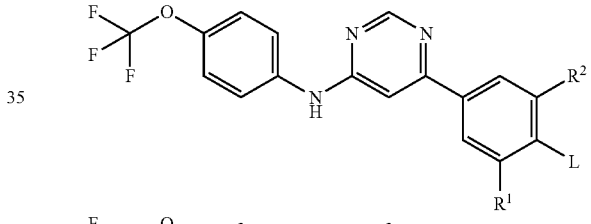

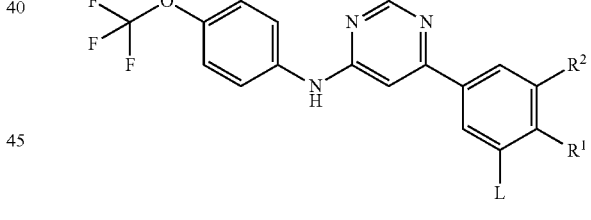

Gefitinib is also known as N-(3-chloro-4-fluoro-phenyl)-7-methoxy-6-(3-morpholin-4-ylpropoxy)quinazolin-4-amine, and has a formula of:

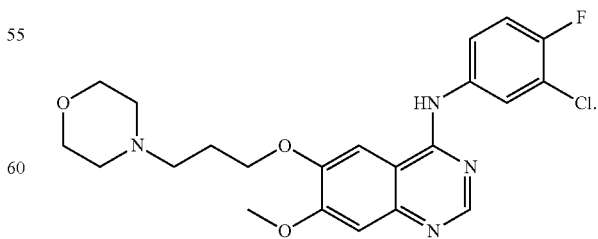

Linker L can be connected, for example, to the morpholino ring of this TKI. Exemplary positions wherein L may be attached are illustrated below:

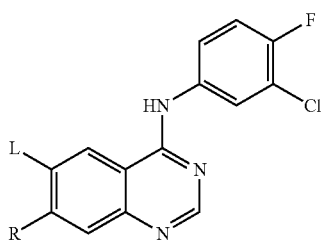

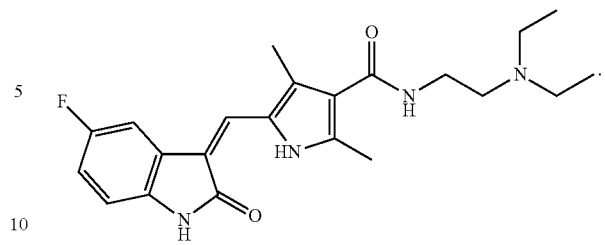

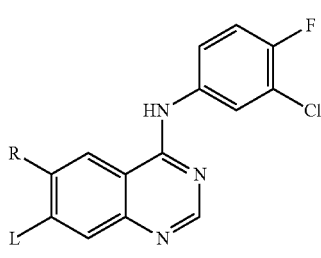

Linker L can be connected, for example, to the amine group of this TKI. In certain embodiments, at least one of the n-ethyl groups is replaced with L. Exemplary positions wherein L may be attached are illustrated below:

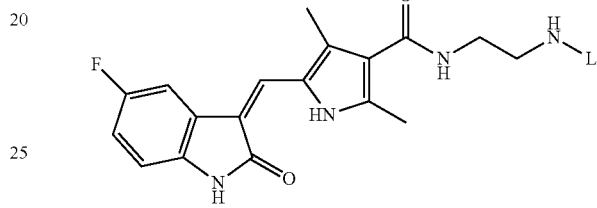

Erlotinib is also known as N-(3-ethynylphenyl)-6,7-bis(2-methoxyethoxy) quinazolin-4-amine, and has a formula of:

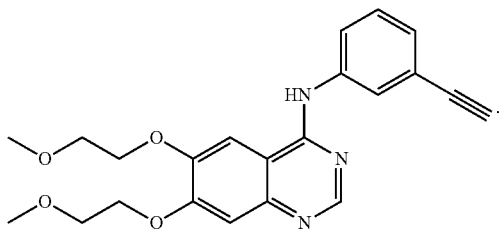 [SMILES: C#Cc1cccc(Nc2ncnc3cc(OCCOC)c(OCCOC)cc23)c1]

Linker L can be connected, for example, to the ether chains of this TKI. In certain embodiments, at least one of the O-methyl groups is replaced with L. Exemplary positions wherein L may be attached are illustrated below:

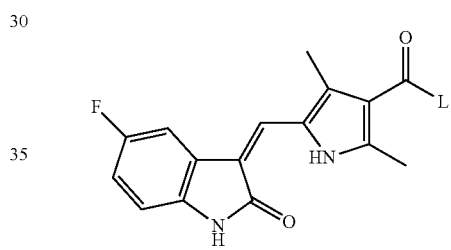

Sunitinib is also known as N-(2-diethylaminoethyl)-5-[(Z)-(5-fluoro-2-oxo-1H-indol-3-ylidene)methyl]-2,4-dimethyl-1H-pyrrole-3-carboxamide, and has a formula of:

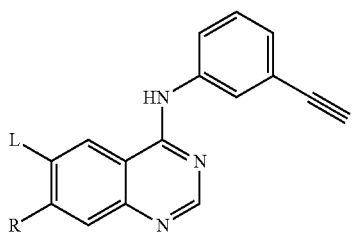

Vemurafenib is also known as N-(3-(5-(4-chlorophenyl)-1H-pyrrolo[2,3-b]pyridine-3-carbonyl)-2,4-difluorophenyl)propane-1-sulfonamide, and has a formula of:

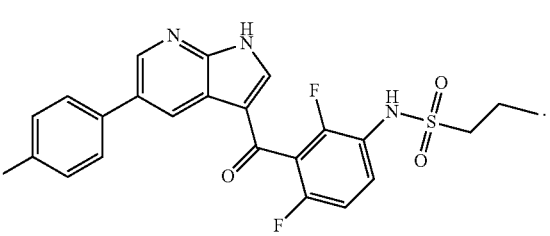

Linker can be connected, for example, to the compound as illustrated herein:

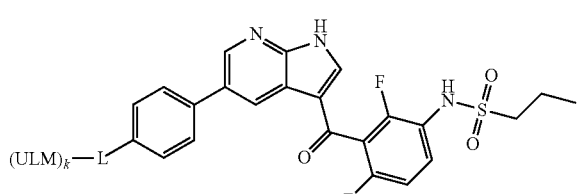

or

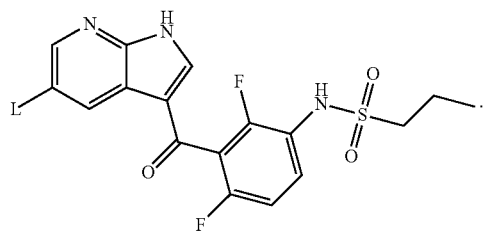

Linker (L)

A suitable linker of the present invention is covalently bonded to the TKI, and is further covalently bonded to at least one ubiquitin ligase binding. In certain embodiment, the ubiquitin ligase is an E3 ubiquitin ligase. In other embodiments, the ubiquitin ligase is Von Hippel Lindau (VHL) E3 ubiquitin ligase and/or Cereblon (CRBN) E3 ligase.

In certain embodiments, the linker of the present invention is a bond.

In certain embodiments, the linker of the present invention corresponds to formula —$(CH_2)_{m1}$—$X_4$—$(CH_2$—$CH_2$—$X_5)_{m2}$—$(CH_2)_{m3}$—$C(X_6)$—, wherein the TKI is covalently bonded to —$(CH_2)_{m1}$, and the ULM is covalently bonded to $C(X_6)$—. Alternatively, —$(CH_2)_{m1}$ is covalently bonded to the ULM, and $C(X_6)$— is covalently bonded to the TKI. Each m1, m2, and m3 is independently 0, 1, 2, 3, 4, 5, 6, 7, 8, 9, or 10; each $X_4$, $X_5$, and $X_6$ is independently absent (a bond), O, S, or N—$R^{20}$, wherein each $R^{20}$ is independently selected from the group consisting of hydrogen, optionally substituted $C_1$-$C_6$ alkyl, optionally substituted aryl, optionally substituted heteroaryl, optionally substituted $C_3$-$C_8$ cycloalkyl, and optionally substituted $C_3$-$C_8$ cycloheteroalkyl.

In other embodiments, the linker of the present invention corresponds to formula —$(CH_2)_{m1}$—O—$(CH_2$—$CH_2$—$O)_{m2}$—$(CH_2)_{m3}$—$C(O)$—, wherein the TKI is covalently bonded to —$(CH_2)_{m1}$, and the ULM is covalently bonded to $C(O)$—. Alternatively, —$(CH_2)m_1$ is covalently bonded to the ULM, and $C(O)$— is covalently bonded to the TKI. Each m1, m2, and m3 is defined elsewhere herein.

In yet other embodiments, the linker of the present invention corresponds to formula —$(CHR_{21})_{m1}$—O—$(CHR_{22}$—$CHR_{23}$—$O)_{m2}$—$(CHR_{24})_{m3}$—$C(O)$—, wherein the TKI is covalently bonded to $(CH_2)_{m1}$, and the ULM is covalently bonded to $C(O)$—. Alternatively, —$(CH_2)m_1$ is covalently bonded to the ULM, and $C(O)$— is covalently bonded to the TKI. Each m1, m2, and m3 is defined elsewhere herein; each $R_{21}$, $R_{22}$, $R_{23}$, and $R_{24}$ is independently selected from the group consisting of hydrogen, optionally substituted $C_1$-$C_6$ alkyl, optionally substituted aryl, optionally substituted heteroaryl, optionally substituted $C_3$-$C_8$ cycloalkyl, and optionally substituted $C_3$-$C_8$ cycloheteroalkyl.

In yet other embodiments, L is a polyethylene glycol chain ranging in size from about 1 to about 12 ethylene glycol units, from about 1 to about 10 ethylene glycol units, from about 2 to about 6 ethylene glycol units, from about 2 to about 5 ethylene glycol units, or from about 2 to about 4 ethylene glycol units.

In yet other embodiments, the linker L corresponds to -(D-CON-D)$_{m1}$- (II), wherein each D is independently a bond (absent), or —$(CH_2)_{m1}$—Y—$C(O)$—Y—$(CH_2)_{m1}$—; wherein m1 is defined elsewhere herein; Y is O, S or N—$R^4$; CON is a bond (absent), an optionally substituted $C_3$-$C_8$ cycloheteroalkyl, piperazinyl or a group selected from the group consisting of the following chemical structures:

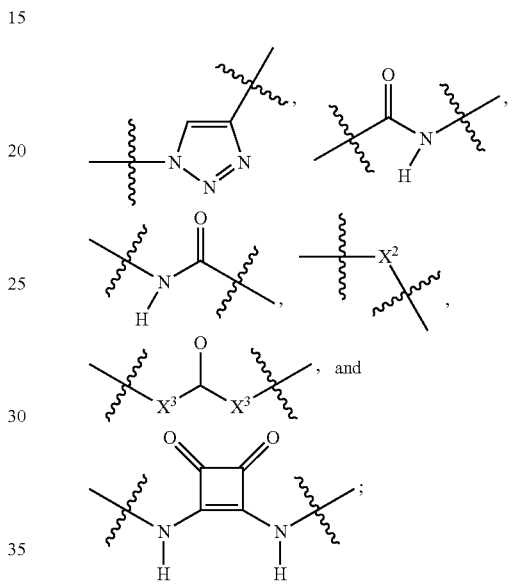

wherein $X^2$ is O, S, $NR^4$, S(O), $S(O)_2$, —$S(O)_2O$, —$OS(O)_2$, or $OS(O)_2O$; $X^3$ is O, S, $CHR^4$, $NR^4$; and $R^4$ is H or a $C_1$-$C_3$ alkyl group optionally substituted with one or two hydroxyl groups.

The linker L of the present invention is covalently bonded to the TKI and ULM, suitable through an amide, ester, thioester, keto group, carbamate (urethane) or ether. The linking position can be anywhere in the TKI and ULM. One of ordinary skill in the art would recognize the suitable linking positions to maximum the binding affinity between the TKI and tyrosine kinase, and between the ULM and the ubiquitin ligase.

Ubiquitin Ligase Moiety (ULM)

A ubiquitin ligase binder (ULM) of a compound of the present invention binds to a ubiquitin ligase. In certain embodiments, the ubiquitin ligase is an E3 ubiquitin ligase.

In certain embodiments, ULM corresponds to formula (III):

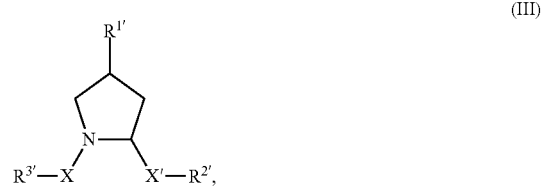

(III)

wherein $R^{1'}$ is a group selected from the group consisting of an optionally substituted $C_1$-$C_6$ alkyl, an optionally substituted —$(CH_2)_n$OH, an optionally substituted —$(CH_2)_n$SH, an optionally substituted $(CH_2)_n$—O—($C_1$-$C_6$)alkyl, an optionally substituted $(CH_2)_n$—$X_7$—($C_1$-$C_6$)alkyl, an optionally substituted —$(CH_2)_n$COOH, an optionally substituted —$(CH_2)_n$C(O)—($C_1$-$C_6$ alkyl), an optionally substituted —$(CH_2)_n$NHC(O)—$R_1$, an optionally substituted —$(CH_2)_n$C(O)—$NR_1R_2$, an optionally substituted —$(CH_2)_n$OC(O)—$NR_1R_2$, —$(CH_2O)_n$H, an optionally substituted —$(CH_2)_n$OC(O)—($C_1$-$C_6$ alkyl), an optionally substituted —$(CH_2)_n$C(O)—O—($C_1$-$C_6$ alkyl), an optionally substituted —$(CH_2O)_n$COOH, an optionally substituted —$(OCH_2)_n$O—($C_1$-$C_6$ alkyl), an optionally substituted —$(CH_2O)_n$C(O)—($C_1$-$C_6$ alkyl), an optionally substituted —$(OCH_2)_n$NHC(O)—$R_1$, an optionally substituted —$(CH_2O)_n$C(O)—$NR_1R_2$, —$(CH_2CH_2O)_n$H, an optionally substituted —$(CH_2CH_2O)_n$COOH, an optionally substituted —$(OCH_2CH_2)_n$O—($C_1$-$C_6$ alkyl), an optionally substituted —$(CH_2CH_2O)_n$C(O)—($C_1$-$C_6$ alkyl), an optionally substituted —$(OCH_2CH_2)_n$NHC(O)—$R_1$, an optionally substituted —$(CH_2CH_2O)_n$C(O)—$NR_1R_2$, an optionally substituted —$SO_2R_S$, $S(O)R_S$, $NO_2$, $CN$, and halogen;

$R_1$ and $R_2$ are each independently H or $C_1$-$C_6$ alkyl which may be optionally substituted with one or two hydroxyl groups or up to three halogen groups;

$R_S$ is $C_1$-$C_6$ alkyl, optionally substituted aryl, optionally substituted heteroaryl or optionally substituted heterocycle or —$(CH_2)_m NR_1R_2$;

X and X' are each independently C=O, C=S, —S(O), $S(O)_2$;

$X_7$ is an optionally substituted epoxide moiety;

$R^{2'}$ is a group selected from the group consisting of optionally substituted —$(CH_2)_n$—(C=O)$_u$(NR$_1$)$_v$(SO$_2$)$_w$—$C_1$-$C_6$ alkyl, an optionally substituted —$(CH_2)_n$—(C=O)$_u$(NR$_1$)$_v$(SO$_2$)$_w$NR$_{1N}$R$_{2N}$, an optionally substituted —$(CH_2)_n$—(C=O)$_u$(NR$_1$)$_v$(SO$_2$)$_w$-Aryl, an optionally substituted —$(CH_2)_n$—(C=O)$_u$(NR$_1$)$_v$(SO$_2$)$_w$-Heteroaryl, an optionally substituted —$(CH_2)_n$—(C=O)$_v$NR$_1$(SO$_2$)$_w$-Heterocycle, an optionally substituted —NR$_{25}$—(CH$_2$)$_n$—C(O)$_u$(NR$_1$)$_v$(SO$_2$)$_w$—$C_1$-$C_6$ alkyl, an optionally substituted —NR$_{25}$—(CH$_2$)$_n$—C(O)$_u$(NR$_1$)$_v$(SO$_2$)$_w$—NR$_{1N}$R$_{2N}$, an optionally substituted —NR$_{25}$—(CH$_2$)$_n$—C(O)$_u$(NR$_1$)$_v$(SO$_2$)$_w$—NR$_1$C(O)R$_{1N}$, an optionally substituted —NR$_{25}$—(CH$_2$)$_n$—(C=O)$_u$(NR$_1$)$_v$(SO$_2$)$_w$-Aryl, an optionally substituted —NR$_{25}$—(CH$_2$)$_n$—(C=O)$_u$(NR$_1$)$_v$(SO$_2$)$_w$-Heteroaryl or an optionally substituted —NR$_{25}$—(CH$_2$)$_n$—(C=O)$_v$NR$_1$(SO$_2$)$_w$-Heterocycle, an optionally substituted —$X^{R2'}$—$C_1$-$C_6$ alkyl; an optionally substituted —$X^{R2'}$-Aryl, an optionally substituted —$X^{R2'}$-Heteroaryl, and an optionally substituted —$X^{R2'}$-Heterocycle;

$R^{3'}$ is a group selected from the group consisting of an optionally substituted $C_1$-$C_6$ alkyl, an optionally substituted —$(CH_2)_n$—C(O)$_u$(NR$_1$)$_v$(SO$_2$)$_w$—$C_1$-$C_6$ alkyl, an optionally substituted —$(CH_2)_n$—C(O)$_u$(NR$_1$)$_v$(SO$_2$)$_w$—NR$_{1N}$R$_{2N}$, an optionally substituted —$(CH_2)_n$—C(O)$_u$(NR$_1$)$_v$(SO$_2$)$_w$—NR$_1$C(O)R$_{1N}$, an optionally substituted —$(CH_2)_n$—C(O)$_u$(NR$_1$)$_v$(SO$_2$)$_w$—C(O)NR$_1$R$_2$, an optionally substituted —$(CH_2)_n$—C(O)$_u$(NR$_1$)$_v$(SO$_2$)$_w$-Aryl, an optionally substituted —$(CH_2)_n$—C(O)$_u$(NR$_1$)$_v$(SO$_2$)$_w$-Heteroaryl, an optionally substituted —$(CH_2)_n$—C(O)$_u$(NR$_1$)$_v$(SO$_2$)$_w$-Heterocycle, an optionally substituted —NR$_{25}$—(CH$_2$)$_n$—C(O)$_u$(NR$_1$)$_v$(SO$_2$)$_w$—$C_1$-$C_6$ alkyl, an optionally substituted —NR$_{25}$—(CH$_2$)$_n$—C(O)$_u$(NR$_1$)$_v$(SO$_2$)$_w$—NR$_{1N}$R$_{2N}$, an optionally substituted —NR$_{25}$—(CH$_2$)$_n$—C(O)$_u$(NR$_1$)$_v$(SO$_2$)$_w$—NR$_1$C(O)R$_{1N}$, an optionally substituted —NR$_{25}$—(CH$_2$)$_n$—C(O)$_u$(NR$_1$)$_v$(SO$_2$)$_w$-Aryl, an optionally substituted —NR$_{25}$—(CH$_2$)$_n$—C(O)$_u$(NR$_1$)$_v$(SO$_2$)$_w$-Heteroaryl, an optionally substituted —NR$_1$—(CH$_2$)$_n$—C(O)$_u$(NR$_1$)$_v$(SO$_2$)$_w$-Heterocycle, an optionally substituted —O—(CH$_2$)n-(C=O)$_u$(NR$_1$)$_v$(SO$_2$)$_w$—$C_1$-$C_6$ alkyl, an optionally substituted —O—(CH$_2$)n-(C=O)$_u$(NR$_1$)$_v$(SO$_2$)$_w$—NR$_{1N}$R$_{2N}$, an optionally substituted —O—(CH$_2$)n-(C=O)$_u$(NR$_1$)$_v$(SO$_2$)$_w$—NR$_1$C(O)R$_{1N}$, an optionally substituted —O—(CH$_2$)n-(C=O)$_u$(NR$_1$)$_v$(SO$_2$)$_w$-Aryl, an optionally substituted —O—(CH$_2$)$_n$—(C=O)$_u$(NR$_1$)$_v$(SO$_2$)$_w$-Heteroaryl, an optionally substituted —O—(CH$_2$)$_n$—(C=O)$_u$(NR$_1$)$_v$(SO$_2$)$_w$-Heterocycle, —(CH$_2$)$_n$—(V)$_{n'}$—(CH$_2$)$_n$—(V)$_{n'}$—$C_1$-$C_6$ alkyl, an optionally substituted —(CH$_2$)$_n$—(V)$_{n'}$—(CH$_2$)$_n$—(V)$_{n'}$-Aryl, an optionally substituted —(CH$_2$)$_n$—(V)$_{n'}$—(CH$_2$)$_n$—(V)$_{n'}$-Heteroaryl, an optionally substituted —(CH$_2$)$_n$—(V)$_{n'}$—(CH$_2$)$_n$—(V)$_{n'}$-Heterocycle, an optionally substituted —(CH$_2$)$_n$—N(R$_1$)(C=O)$_{m'}$—(V)$_{n'}$—$C_1$-$C_6$ alkyl, an optionally substituted —(CH$_2$)$_n$—N(R$_1$)(C=O)$_{m'}$—(V)$_{n'}$-Aryl, an optionally substituted —(CH$_2$)$_n$—N(R$_1$)(C=O)$_{m'}$—(V)$_{n'}$-Heteroaryl, an optionally substituted —(CH$_2$)$_n$—N(R$_1$)(C=O)$_{m'}$—(V)$_{n'}$-Heterocycle, an optionally substituted —$X^{R3'}$—$C_1$-$C_6$ alkyl group; an optionally substituted —$X^{R3'}$-Aryl group; an optionally substituted —$X^{R3'}$-Heteroaryl group; and an optionally substituted —$X^{R3'}$-Heterocycle group;

where $R_{1N}$ and $R_{2N}$ are each independently H, $C_1$-$C_6$ alkyl which is optionally substituted with one or two hydroxyl groups and up to three halogen groups or an optionally substituted —(CH$_2$)$_n$-Aryl, —(CH$_2$)$_n$-Heteroaryl or —(CH$_2$)$_n$-Heterocycle group;

V is O, S or $NR_1$;

each $R_{25}$ is independently H or $C_1$-$C_3$ alkyl;

$X^{R2'}$ and $X^{R3'}$ are each independently an optionally substituted —(CH$_2$)$_n$—, —(CH$_2$)$_n$—CH(X$_v$)=CH(X$_v$)— (cis or trans), —(CH$_2$)$_n$—CH≡CH—, —(CH$_2$CH$_2$O)$_n$— or a $C_3$-$C_6$ cycloalkyl, where $X_v$ is H, a halo or optionally substituted $C_1$-$C_3$ alkyl;

Each m is independently 0, 1, 2, 3, 4, 5, 6;

Each m' is independently 0 or 1;

Each n is independently 0, 1, 2, 3, 4, 5, 6;

Each n' is independently 0 or 1;

Each u is independently 0 or 1;

Each v is independently 0 or 1;

Each w is independently 0 or 1; and wherein any one or more of $R^{1'}$, $R^{2'}$, $R^{3'}$, X and X' of ULM group is modified to be covalently bonded to the TKI group through a linker L.

In other embodiments, the ULM corresponds to formula (IV) or (V):

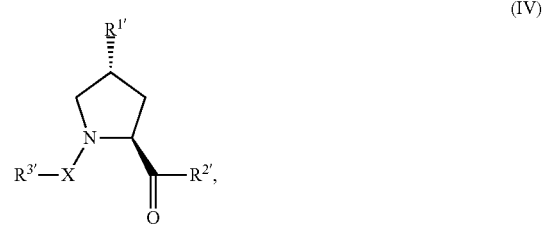

(IV)

-continued

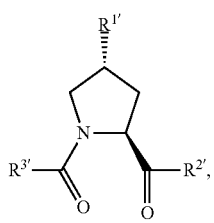

(V)

wherein each of X, $R^{1'}$, $R^{2'}$ and $R^{3'}$ are defined elsewhere herein.

In certain embodiments of the formulas (III), (IV), and (V), $R^{1'}$ is a hydroxyl group or a group which may be metabolized to a hydroxyl or carboxylic group. Exemplary $R^{1'}$ groups include —$(CH_2)_n$OH, —$(CH_2)_n$—O—$(C_1$-$C_6)$ alkyl, —$(CH_2)_n$COOH, —$(CH_2O)_n$H, an optionally substituted —$(CH_2)_n$OC(O)—$(C_1$-$C_6$ alkyl), or an optionally substituted —$(CH_2)_n$C(O)—O—$(C_1$-$C_6$ alkyl), wherein n is defined above.

In yet other embodiments of the formulas (III), (IV), and (V), $R^{2'}$ and $R^{3'}$ are each independently selected from the group consisting of an optionally substituted —$NR_{26}$-T-Aryl, an optionally substituted —$NR_{26}$-T-Heteroaryl or an optionally substituted —$NR_{26}$-T-Heterocycle, wherein $R_{26}$ is H or $CH_3$, and T is a group selected from the group consisting of —$(CH_2)_n$—, —$(CH_2O)_n$—, —$(OCH_2)$—, —$(CH_2CH_2O)$—, and —$(OCH_2CH_2)$—, wherein each one of the methylene groups may be optionally substituted with one or two substituents, selected from the group consisting of halogen, an amino acid, and $C_1$-$C_3$ alkyl; wherein n is defined above.

In yet other embodiments of the formulas (III), (IV), and (V), $R^{2'}$ or $R^{3'}$ is —$NR_{26}$-T-$Ar^1$, wherein the $Ar^1$ is phenyl or naphthyl optionally substituted with a group selected from the group consisting of a linker group L to which is attached a TKI moiety, a halogen, an amine, monoalkyl- or dialkyl amine (preferably, dimethylamine), OH, COOH, $C_1$-$C_6$ alkyl, $CF_3$, OMe, $OCF_3$, $NO_2$, CN, an optionally substituted phenyl, an optionally substituted naphthyl, and an optionally substituted heteroaryl. Suitable heteroaryl includes an optionally substituted isoxazole, an optionally substituted oxazole, an optionally substituted thiazole, an optionally substituted isothiazole, an optionally substituted pyrrole, an optionally substituted imidazole, an optionally substituted benzimidazole, an optionally substituted oximidazole, an optionally substituted diazole, an optionally substituted triazole, an optionally substituted pyridine or an oxapyridine, an optionally substituted furan, an optionally substituted benzofuran, an optionally substituted dihydrobenzofuran, an optionally substituted indole, indolizine, azaindolizine, an optionally substituted quinoline, and an optionally substituted group selected from the group consisting of the chemical structures:

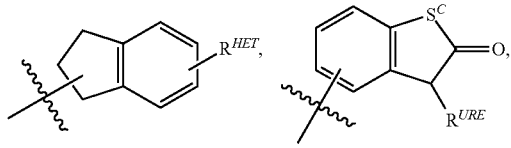

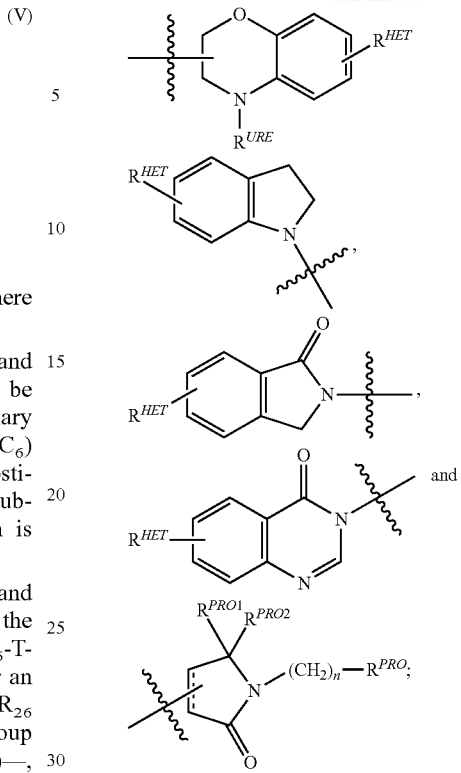

wherein $S^c$ is $CHR^{SS}$, $NR^{URE}$, or O; $R^{HET}$ is H, CN, $NO_2$, halo, optionally substituted $C_1$-$C_6$ alkyl, optionally substituted $O(C_1$-$C_6$ alkyl) or an optionally substituted acetylenic group —C≡C—$R_a$, wherein $R_a$ is H or $C_1$-$C_6$ alkyl; $R^{SS}$ is H, CN, $NO_2$, halo, optionally substituted $C_1$-$C_6$ alkyl, optionally substituted O—$(C_1$-$C_6$ alkyl or optionally substituted —C(O)($C_1$-$C_6$ alkyl); $R^{URE}$ is H, $C_1$-$C_6$ alkyl or —C(O)($C_1$-$C_6$ alkyl), wherein the alky group is optionally substituted with one or two hydroxyl groups, up to three halogens, an optionally substituted phenyl group, an optionally substituted heteroaryl, or an optionally substituted heterocycle, preferably for example piperidine, morpholine, pyrrolidine, tetrahydrofuran; $R^{PRO}$ is H, optionally substituted $C_1$-$C_6$ alkyl, an optionally substituted aryl, an optionally substituted heteroaryl or an optionally substituted heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, and azaindolizine; $R^{PRO1}$ and $R^{PRO2}$ are each independently H, optionally substituted $C_1$-$C_3$ alkyl or together form a keto group; n is defined above.

In yet other embodiments of the formulas (III), (IV), and (V), $R^{2'}$ or $R^{3'}$ is an optionally substituted —$NR_{26}$-T-$Ar^2$ group, wherein the $Ar^2$ group is selected from the group consisting of quinoline, indole, indolizine, azaindolizine, benzofuran, isoxazole, thiazole, isothiazole, thiophene, pyridine, imidazole, pyrrole, diazole, triazole, tetrazole, oximidazole, and a group selected from the group consisting of the following chemical structures:

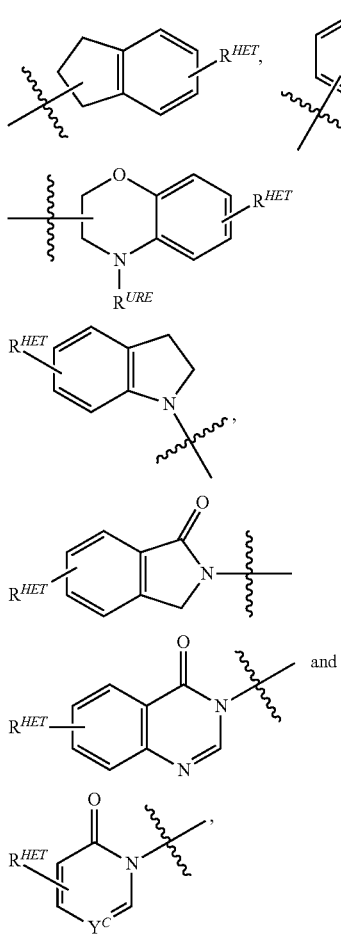

wherein $S^c$, $R^{HET}$, and $R^{URE}$ are defined elsewhere herein; $Y^C$ is N or C—$R^{YC}$; $R^{YC}$ is H, OH, CN, NO$_2$, halo, optionally substituted C$_1$-C$_6$ alkyl, optionally substituted O(C$_1$-C$_6$ alkyl), or an optionally substituted acetylenic group —C≡C—R$_a$; R$_a$ is H or C$_1$-C$_6$ alkyl.

In yet other embodiments of the formulas (III), (IV), and (V), R$^{2'}$ or R$^{3'}$ is an optionally substituted —NR$_{26}$-T-HET$^1$, wherein the HET$^1$ is selected from the group consisting of tetrahydrofuran, tetrahydrothiene, tetrahydroquinoline, piperidine, piperazine, pyrrollidine, morpholine, oxane and thiane. The HET$^1$ is optionally substituted by a group selected from the group consisting of the following chemical structures:

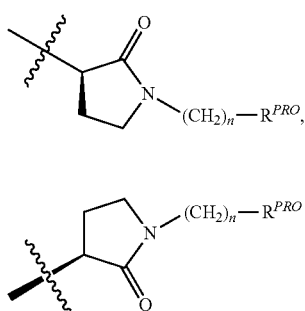

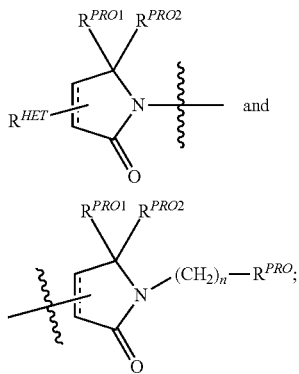

wherein n, $R^{PRO}$, $R^{PRO1}$, $R^{HET}$ and $R^{PRO2}$ are defined elsewhere herein.

In other embodiments, R$^{2'}$ or R$^{3'}$ is optionally substituted —(CH$_2$)$_n$—(V)$_{n'}$—(CH$_2$)$_n$—(V)$_{n'}$—R$^{S3'}$, optionally substituted —(CH$_2$)$_n$—N(R$_{26}$)(C═O)$_m$—(V)$_{n'}$—R$^{S3'}$, optionally substituted —X$^{R3'}$—C$_1$-C$_{10}$ alkyl, optionally substituted —X$^{R3'}$—Ar$^3$, optionally substituted —X$^{R3'}$-HET, optionally substituted —X$^{R3'}$—Ar$^3$-HET or optionally substituted —X$^{R3'}$-HET-Ar$^3$, wherein R$^{S3'}$ is optionally substituted C$_1$-C$_{10}$ alkyl, optionally substituted Ar$^3$ or HET; R$_{26}$ is defined elsewhere herein; V is O, S or NR$_1$; X$^{R3'}$ is —(CH$_2$)$_n$—, —(CH$_2$CH$_2$O)$_n$—, —CH$_2$)$_n$—CH(X$_v$)═CH(X$_v$)— (cis or trans), —CH$_2$)$_n$—CH≡CH—, or a C$_3$-C$_6$ cycloalkyl group, all optionally substituted; wherein X$_v$ is H, a halo or a C$_1$-C$_3$ alkyl group which is optionally substituted with one or two hydroxyl groups or up to three halogen groups; Ar$^3$ is an optionally substituted phenyl or napthyl group; and HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline, or a group selected from the group consisting of the following chemical structures:

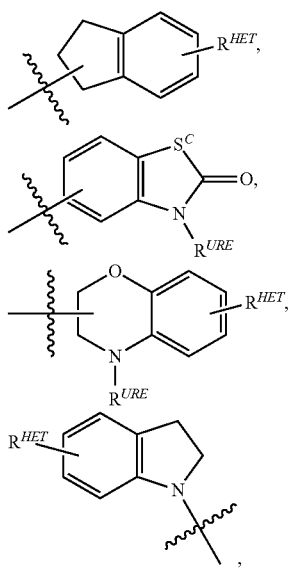

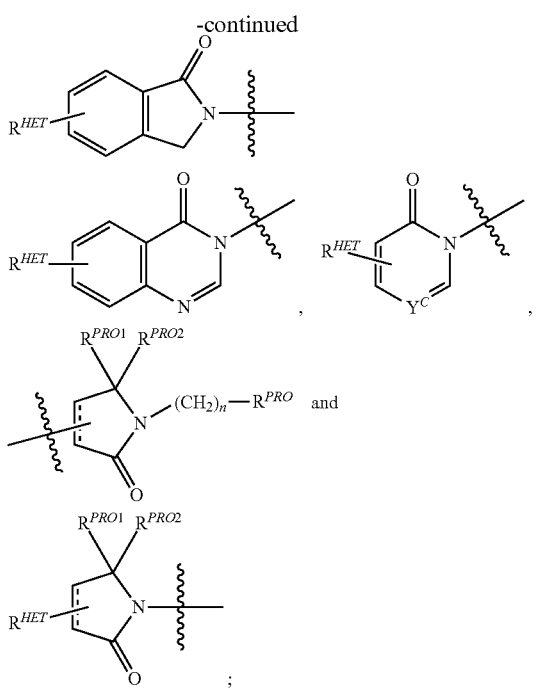

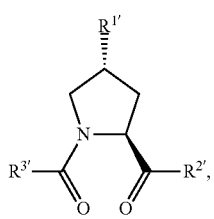

wherein n, v, n', m', $S^c$, $R^{HET}$, $R^{URE}$, $Y^C$, $R^{PRO1}$ and $R^{PRO2}$ are defined elsewhere herein.

In yet other embodiments of the formulas (III), (IV), and (V), $R^{2'}$ or $R^{3'}$ is an optionally substituted —$NR_{26}$—$X^{R2'}$—$C_1$-$C_{10}$ alkyl, —$NR_{26}$—$X^{R2'}$—$Ar^3$, an optionally substituted —$NR_{26}$—$X^{R2'}$-HET, an optionally substituted —$NR_{26}$—$X^{R2'}$—$Ar^3$-HET, or an optionally substituted —$NR_{26}$—$X^{R2'}$-HET-$Ar^3$, $X^{R2'}$ is an optionally substituted —$CH_2)_n$—, —$(CH_2)_n$—$CH(X_v)$=$CH(X_v)$— (cis or trans), —$(CH_2)_n$—CH≡CH—, —$(CH_2CH_2O)_n$— or $C_3$-$C_6$ cycloalkyl; wherein $X_v$ is H, a halo or a $C_1$-$C_3$ alkyl group which is optionally substituted with one or two hydroxyl groups or up to three halogen groups; wherein HET, $Ar^3$, and $R_{26}$ are defined elsewhere herein.

In yet other embodiments, $R^{2'}$ or $R^{3'}$ is —$(CH_2)_n$—$Ar^1$, —$(CH_2CH_2O)_n$—$Ar^1$, —$(CH_2)_n$-HET or —$(CH_2CH_2O)_n$—HET; wherein n, $Ar^1$, and HET are defined elsewhere herein.

In yet other embodiments, ULM corresponds to formula (VI):

(VI)

wherein $R^{1'}$ is OH or a group which is metabolized in a patient or subject to OH; $R^{2'}$ is —NH—$CH_2$—$Ar^4$-$HET^1$; $R^3$ is —$CHR^{CR3'}$—NH—C(O)—$R^{3P1}$ or —$CHR^{CR3'}$—$R^{3P2}$; wherein $R^{CR3'}$ is $C_1$-$C_4$ alkyl, preferably methyl, isopropyl or tert-butyl; $R^{3P1}$ is $C_1$-$C_3$ alkyl, optionally substituted oxetane, —$CH_2OCH_3$, —$CH_2CH_2OCH_3$, morpholino, or $CH_3$—$CH_2$—O—

;

$R^{3P2}$ is a group, wherein $Ar^4$ is phenyl; $HET^1$ is an optionally substituted thiazole or isothiazole; and $R^{HET}$ is H or halo.

In yet other embodiments, ULM corresponds to formula (VII) or (VIII):

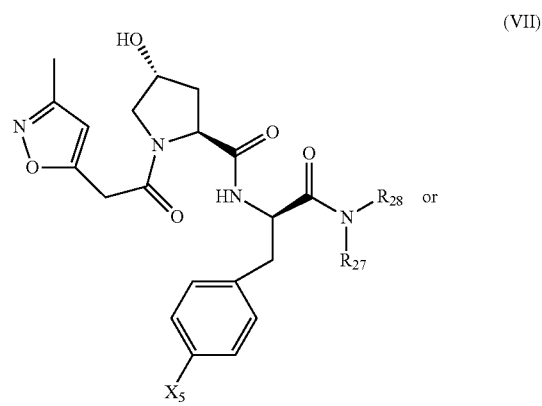

(VII)

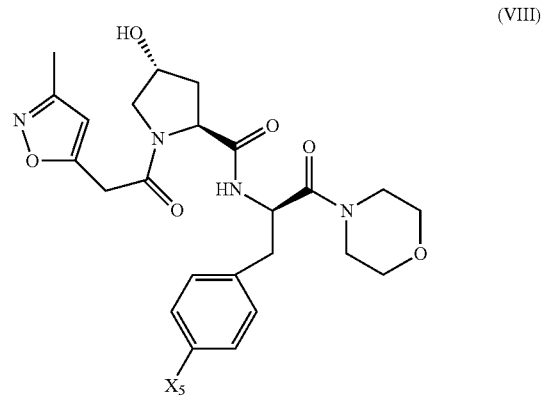

(VIII)

wherein $X_5$ is Cl, F, $C_1$-$C_3$ alkyl or heterocycle; $R_{27}$ and $R_{28}$ are each independently H, $C_1$-$C_3$ alkyl.

In yet other embodiments, ULM is a cereblon ligand of formula (IX) or a VHL ligand of formula (X):

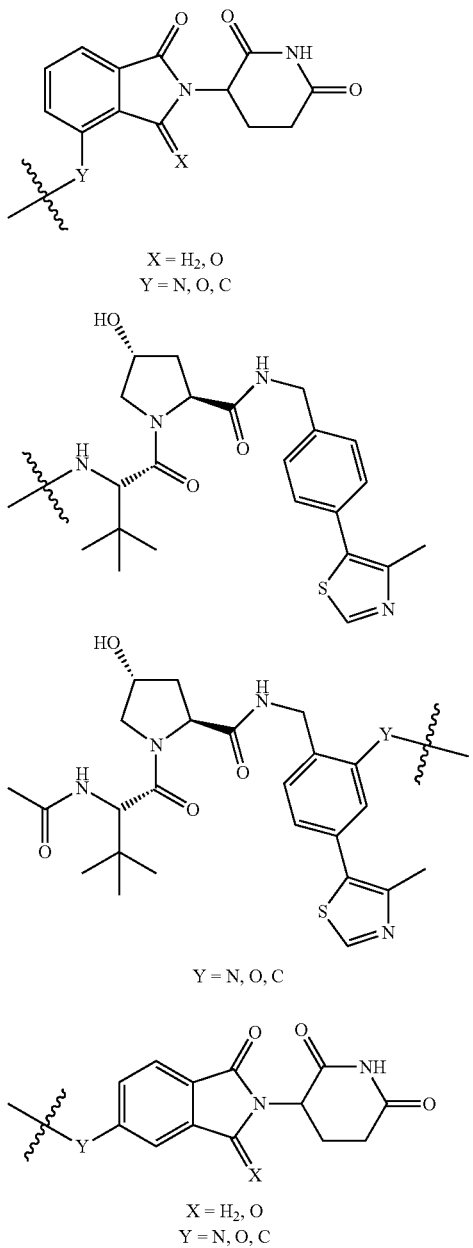

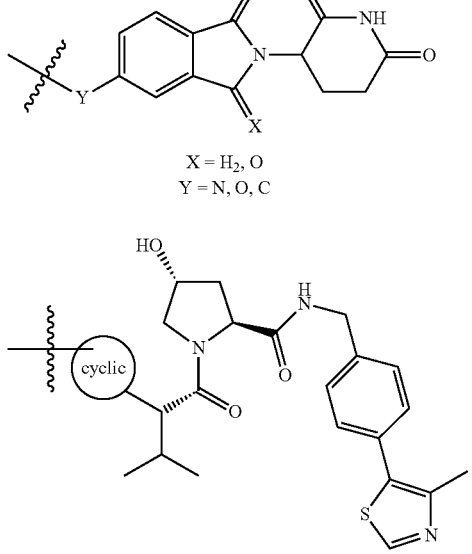

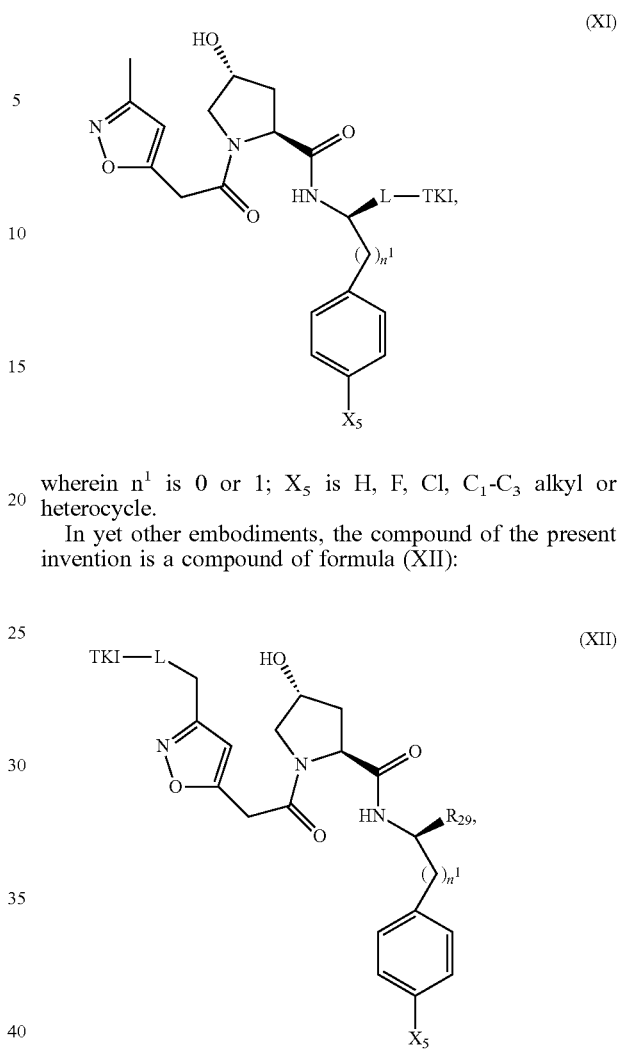

wherein $n^1$ is 0 or 1; $X_5$ is H, F, Cl, $C_1$-$C_3$ alkyl or heterocycle.

In yet other embodiments, the compound of the present invention is a compound of formula (XII):

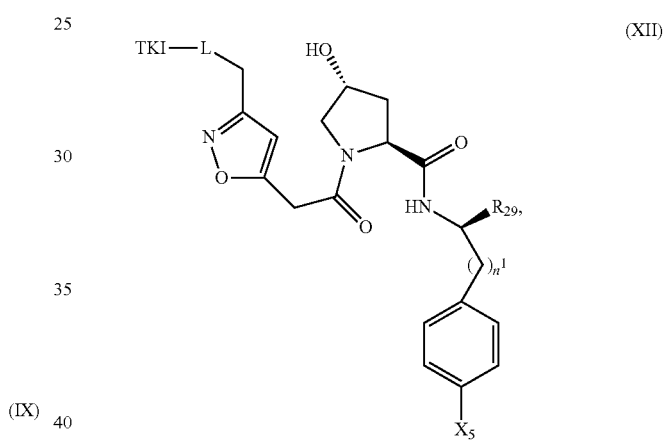

wherein $n^1$ and $X_5$ are defined elsewhere herein; $R_{29}$ is $C_1$-$C_3$ alkyl or —C(O)N$R_{30}R_{31}$ where $R_{30}$ and $R_{31}$ are each independently H, $C_1$-$C_3$ alkyl, phenyl or heterocycle.

In yet other embodiments, the compound of the present invention is a compound of formula (XIII):

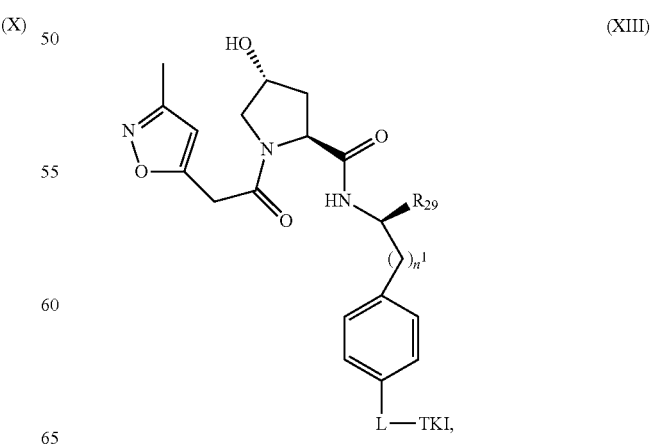

wherein $n^1$ and $R_{29}$ are defined elsewhere herein.

In certain embodiments, the compound of the present invention is a compound of formula (XI):

In yet other embodiments, the compound of the present invention is a compound of formula (XIV):

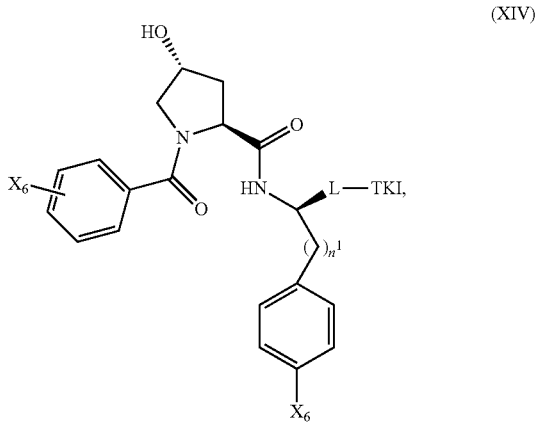

(XIV)

wherein n¹ is defined elsewhere herein; each $X_6$ is independently is H, F, Cl, $C_1$-$C_3$ alkyl, heterocycle, —O—C(O)$NR_{32}R_{33}$ or —C(O)$NR_{32}R_{33}$, wherein each of $R_{32}$ and $R_{33}$ is independently H, $C_1$-$C_3$ alkyl, or phenyl.

In yet other embodiments, the compound of the present invention is a compound of formula (XV):

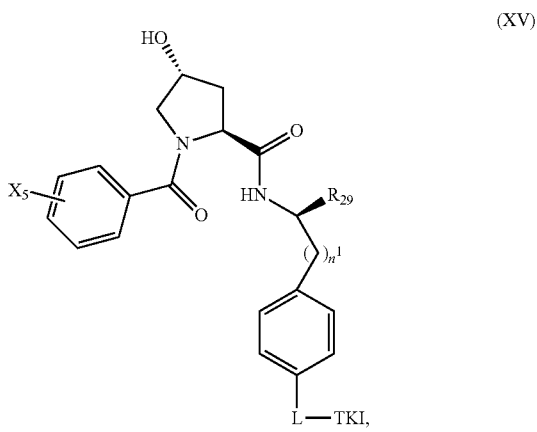

(XV)

wherein n, $R_{29}$, and $X_5$ are defined elsewhere herein.

In yet other embodiments, the compound of the present invention is a compound of formula (XVI):

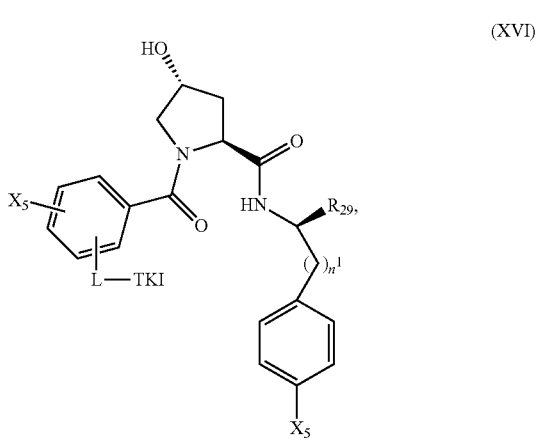

(XVI)

wherein n, $R_{29}$, and $X_5$ are defined elsewhere herein.

In yet other embodiments, the compound of the present invention is a compound of formula (XVII):

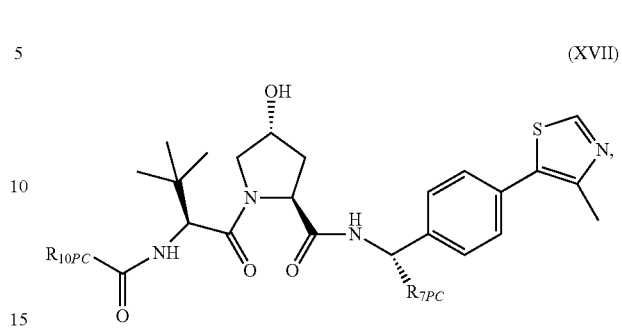

(XVII)

wherein either of $R_{7PC}$ or $R_{10PC}$ is a -L-TKI group and the other $R_{7PC}$ or $R_{10PC}$ is H.

In yet other embodiments, the compound of the present invention is a compound of formula (XVIII):

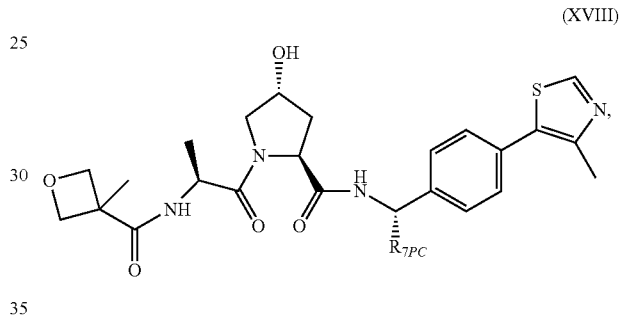

(XVIII)

wherein $R_{7PC}$ is a -L-TKI group.

In yet other embodiments, the compound of the present invention is a compound of formula (XIX):

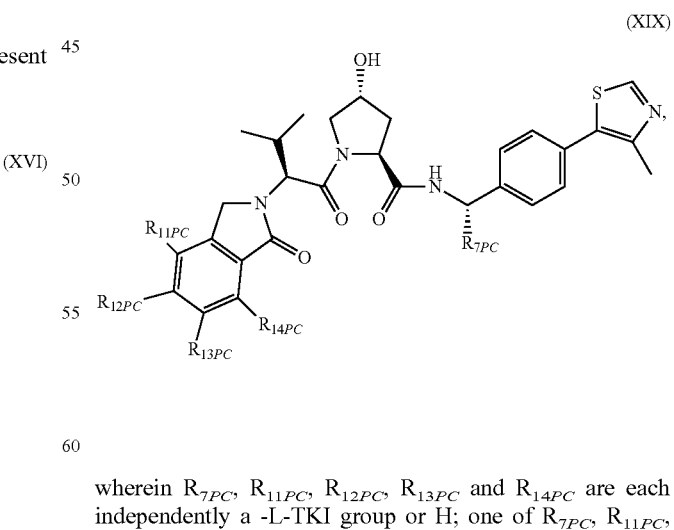

(XIX)

wherein $R_{7PC}$, $R_{11PC}$, $R_{12PC}$, $R_{13PC}$ and $R_{14PC}$ are each independently a -L-TKI group or H; one of $R_{7PC}$, $R_{11PC}$, $R_{12PC}$, $R_{13PC}$ and $R_{14PC}$ is a -L-TKI group and the other groups are H.

In yet other embodiments, the compound of the present invention is a compound of formula (XX):

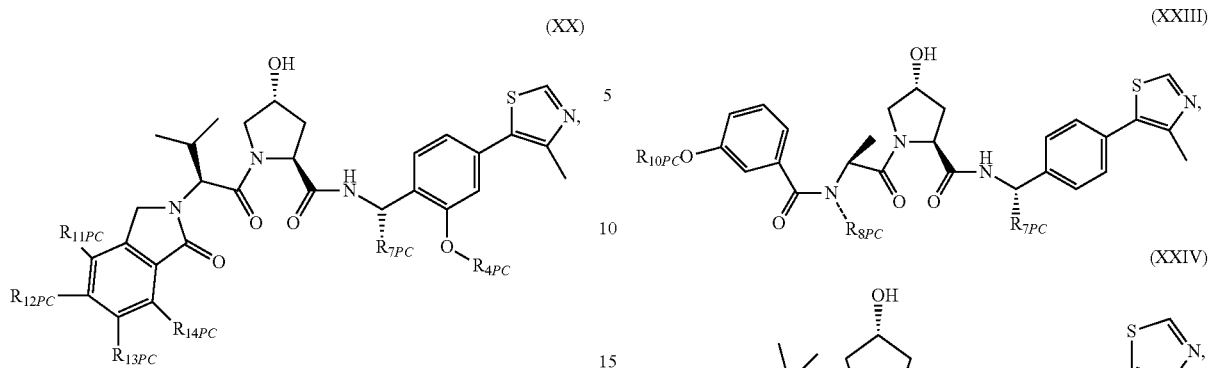

(XX)

wherein $R_{4PC}$, $R_{7PC}$, $R_{11PC}$, $R_{12PC}$, $R_{13PC}$, and $R_{14PC}$ are each independently a -L-TKI group or H; either of $R_{4PC}$, $R_{7PC}$ or one of $R_{11PC}$, $R_{12PC}$, $R_{13PC}$ and $R_{14PC}$ is a -L-TKI group and the other groups are H.

In yet other embodiments, the compound of the present invention is a compound of formula (XXI):

(XXI)

wherein $R_{3PC}$, $R_{7PC}$, $R_{11PC}$, $R_{12PC}$, $R_{13PC}$ and $R_{14PC}$ are each independently a -L-TKI group or H; one of $R_{3PC}$, $R_{7PC}$, $R_{11PC}$, $R_{12PC}$, $R_{13PC}$ and $R_{14PC}$ is a -L-TKI group and the other groups are H.

In yet other embodiments, the compound of the present invention is a compound of formula (XXII):

(XXII)

wherein $R_{7PC}$ and $R_{10PC}$ are each independently a -L-TKI group or H; one of $R_{7PC}$ and $R_{10PC}$ is a -L-TKI group and the other group is H.

In yet other embodiments, the compound of the present invention is a compound of formula (XXIII), (XXIV), (XXV), or (XXVI):

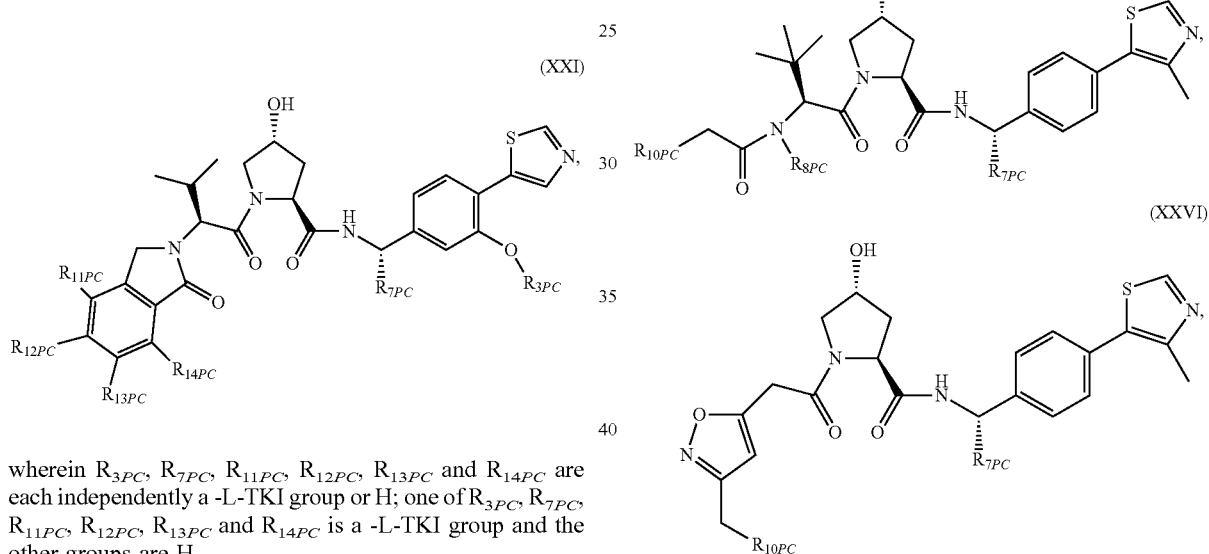

wherein $R_{7PC}$ and $R_{10PC}$ are each independently a -L-TKI group or H and $R_{8PC}$ is H or $CH_3$. In one embodiment, one of $R_{7PC}$ and $R_{10PC}$ is a -L-TKI group and the other group is H and $R_{8PC}$ is H.

In yet other embodiments, the compound of the present invention is a compound of formula of (XXVI):

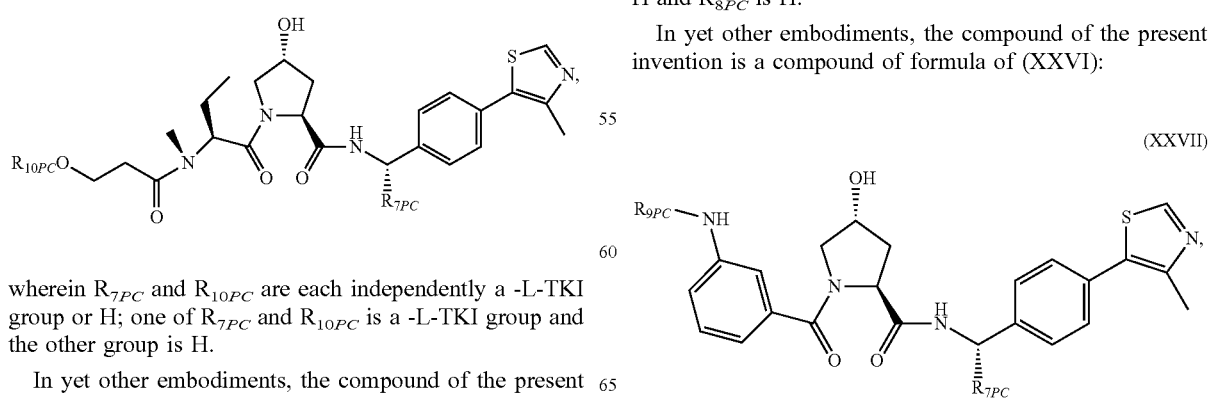

wherein $R_{7PC}$ and $R_{9PC}$ are each independently a -L-TKI group or H. In one embodiment, one of $R_{7PC}$ and $R_{9PC}$ is a -L-TKI group and the other group is H.

In yet other embodiments, the compound of the present invention is a compound of formula (XXVIII):

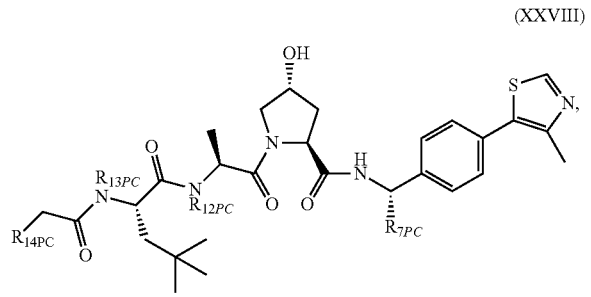

(XXVIII)

wherein $R_{7PC}$ and $R_{14PC}$ are each independently a -L-TKI group or H and each of $R_{12PC}$ and $R_{13PC}$ is H or $CH_3$. In one embodiment, one of $R_{7PC}$ and $R_{14PC}$ is a -L-TKI group and the other of $R_{7PC}$ and $R_{14PC}$ group is H and each of $R_{12PC}$ and $R_{13PC}$ is H.

In yet other embodiments, the compound of the present invention is a compound of formula (XXIX) or (XXX):

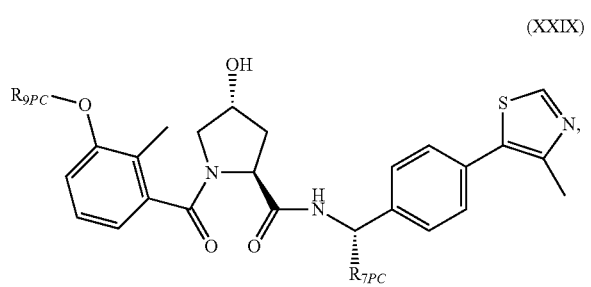

(XXIX)

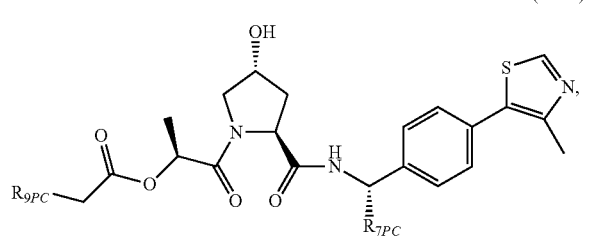

(XXX)

wherein $R_{7PC}$ and $R_{9PC}$ are each independently a -L-TKI group or H. In one embodiment, one of $R_{7PC}$ and $R_{9PC}$ is a -L-TKI group and the other group is H.

In yet other embodiments, the compound of the present invention is a compound of formula (XXXI):

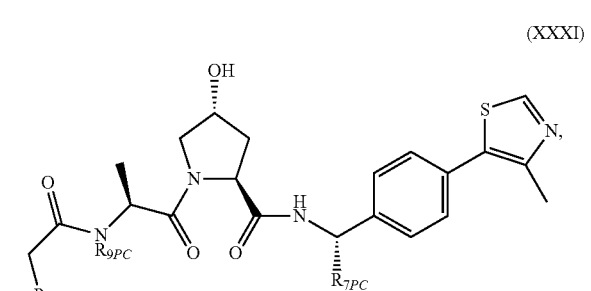

(XXXI)

wherein $R_{7PC}$ and $R_{10PC}$ are each independently a -L-TKI group or H and $R_{9PC}$ is H or $CH_3$. In one embodiment, one of $R_{7PC}$ and $R_{10PC}$ is a -L-TKI group and the other group is H and $R_{9PC}$ is H.

Preparation of Compounds of the Invention

Compounds of formulas (I)-(XXXI) may be prepared by the general schemes described herein, using the synthetic method known by those skilled in the art. The following examples illustrate non-limiting embodiments of the invention.

The compounds of the invention may possess one or more stereocenters, and each stereocenter may exist independently in either the (R) or (S) configuration. In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention may exist as tautomers. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}$H, $^{3}$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

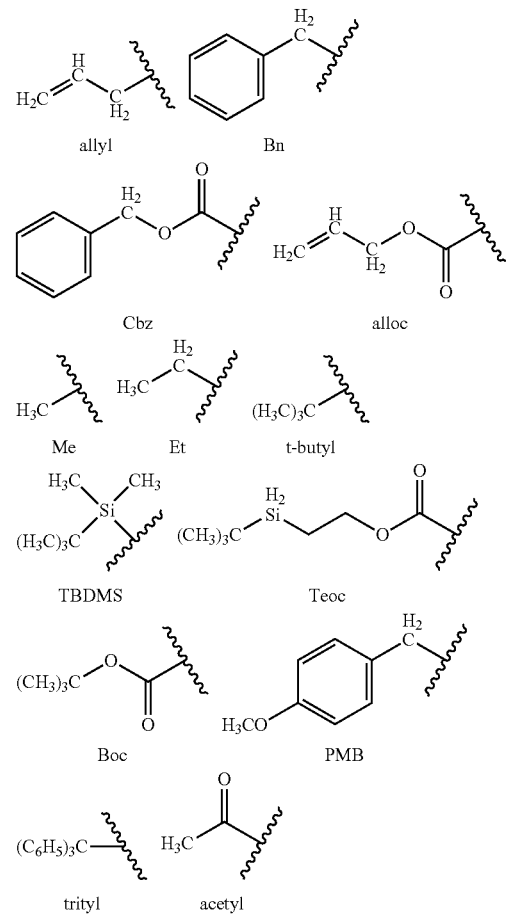

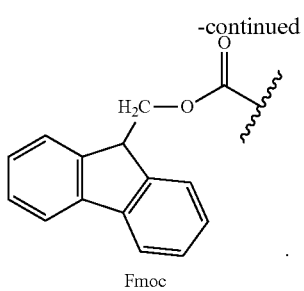

Fmoc

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Compositions

The invention includes a pharmaceutical composition comprising at least one compound of the invention and at least one pharmaceutically acceptable carrier. In certain embodiments, the composition is formulated for an administration route such as oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Methods

The invention includes a method of treating or preventing a disease associated with and/or caused by overexpression and/or uncontrolled activation of a tyrosine kinase in a subject in need thereof. The invention further includes a method of treating or preventing a cancer associated with and/or caused by an oncogenic tyrosine kinase in a subject in need thereof. In certain embodiments, the disease comprises a cancer. In other embodiments, the tyrosine kinase is c-ABL and/or BCR-ABL. In yet other embodiments, the cancer is chronic myelogenous leukemia (CML).

Examples of cancers that can be treated or prevented by the present invention include but are not limited to: squamous cell cancer, lung cancer including small cell lung cancer, non-small cell lung cancer, vulval cancer, thyroid cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, hepatic carcinoma, anal carcinoma, penile carcinoma, and head and neck cancer. In certain embodiments, the cancer is at least one selected from the group consisting of ALL, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL, Philadelphia chromosome positive CML, lymphoma, leukemia, multiple myeloma myeloproliferative diseases, large B cell lymphoma, and B cell Lymphoma.

The methods of the invention comprise administering to the subject a therapeutically effective amount of at least one compound of the invention, which is optionally formulated in a pharmaceutical composition. In certain embodiments, the method further comprises administering to the subject an additional therapeutic agent that treats or prevents cancer.

In certain embodiments, administering the compound of the invention to the subject allows for administering a lower dose of the additional therapeutic agent as compared to the dose of the additional therapeutic agent alone that is required to achieve similar results in treating or preventing a cancer in the subject. For example, in certain embodiments, the compound of the invention enhances the anti-cancer activity of the additional therapeutic compound, thereby allowing for a lower dose of the additional therapeutic compound to provide the same effect.

In certain embodiments, the compound of the invention and the therapeutic agent are co-administered to the subject. In other embodiments, the compound of the invention and the therapeutic agent are coformulated and co-administered to the subject.

In certain embodiments, the subject is a mammal. In other embodiments, the mammal is a human.

Combination Therapies

The compounds useful within the methods of the invention may be used in combination with one or more additional therapeutic agents useful for treating a cancer. These additional therapeutic agents may comprise compounds that are commercially available or synthetically accessible to those skilled in the art. These additional therapeutic agents are known to treat, prevent, or reduce the symptoms, of a cancer.

In non-limiting examples, the compounds useful within the invention may be used in combination with one or more of the following therapeutic agents: Erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum (II), CAS No. 15663-27-1), carboplatin (CAS No. 41575-94-4), paclitaxel (TAXOL®, Bristol-Myers Squibb Oncology, Princeton, N.J.), pemetrexed (ALIMTA®, Eli Lilly), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl) phenoxy]-N,N-dimethylethanamine, NOLVADEX®, ISTUBAL®, VALODEX®), and doxorubicin (ADRIAMYCIN®), Akti-1/2, HPPD, rapamycin, oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®), ALK TKI inhibitors, antibodies such as avastin and cetuximab that target VEGFR and EGFR respectively, other RTK TKIs for PDGFR or RET, immunotherapies such as ipiliumimab and nivolumab, and radiation therapy.

In certain embodiments, the compounds of the present invention are used in combination with radiation therapy. In other embodiments, the combination of administration of the compounds of the present invention and application of radiation therapy is more effective in treating or preventing cancer than application of radiation therapy by itself. In yet other embodiments, the combination of administration of the compounds of the present invention and application of radiation therapy allows for use of lower amount of radiation therapy in treating the subject.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a cancer. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a cancer in the patient. An effective amount of the therapeutic compound necessary to achieve a therapeutic effect may vary according to factors such as the state of the disease or disorder in the patient; the age, sex, and weight of the patient; and the ability of the therapeutic compound to treat a cancer in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/ per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a cancer in a patient.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 g to about 10,000 mg, about 20 g to about 9,500 mg, about 40 g to about 9,000 mg, about 75 g to about 8,500 mg, about 150 g to about 7,500 mg, about 200 g to about 7,000 mg, about 350 g to about 6,000 mg, about 500 g to about 5,000 mg, about 750 g to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a cancer in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropyl methylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as Ph. Helv or similar alcohol.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a cancer in the patient being treated. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Methods and Materials
1. Biology
Cell Lines and Materials

K562 cells were obtained from ATCC and were grown at 37° C., 5% $CO_2$ in Iscove's Modified Dulbecco's Media (IMDM) supplemented with 10% FBS, 100 U/mL penicillin and 100 µg/mL streptomycin. HEK293 and SK-BR-3 cells were obtained from ATCC and were grown at 37° C., 5% $CO_2$ in Dulbecco's Modified Eagle's Media (DMEM) supplemented with 10% FBS, 100 U/mL penicillin and 100 µg/mL streptomycin. Phospho-STAT5 Y694 (#4322) and phospho-CrkL Y207 (#3181) antibodies were obtained from Cell Signaling Technologies. c-ABL (24-11) antibody was obtained from Santa Cruz Biotechnologies. α-Tubulin antibody (T9026) was purchased from Sigma-Aldrich.

Western Blotting

K562 cells (1-1.5×10$^6$) were treated for 24 hours with the indicated compounds solubilized in DMSO. The cells were collected at 300 g for 3 min. The cells were then lysed in lysis buffer (25 mM Tris, 1% Triton, 0.25% deoxycholic acid) with Roche protease inhibitor complete cocktail and phosphatase inhibitors (10 mM sodium fluoride, 10 mM sodium pyrophosphate, 1 mM sodium orthovanadate and 20 mM β-glycerophosphate). The total protein concentrations were determined by Pierce BCA Protein Assay and 30-50 g of protein was loaded onto 10% Tris-Glycine gels. After standard gel electrophoresis, the separated proteins were transferred to nitrocellulose by wet transfer. The immunoblots were then processed by standard procedures and incubated with the respective antibodies. Band intensities were quantified by Bio-Rad's Image Lab software.

In Vitro Kinase Binding Affinity Determination

PROTAC in vitro binding affinities (Kd) to phosphorylated and non-phosphorylated c-ABL kinase domain were determined using the KinomeScan platform (DiscoverRx Corporation). The compounds were solubilized in DMSO and sent to DiscoverRx Corporation as a 10 μM stock solution.

Cell Viability Assay

HEK293T and SK-BR-3 were washed thrice with 1× phosphate-buffered saline (PBS), trypsinized and 6000 cells were plated in triplicates on a tissue cultured treated 96-well plate with 50 μL of DMEM. After 24 hours, PROTAC was added directly on top of cells in 50 μL of DMEM. After 48 hours of PROTAC treatment, a CellTiter-Glo® Luminescent Cell Viability assay (Promega) was performed as detailed in the manufacturer's manual. The data was analyzed using nonlinear regression in GraphPad Prism® 6. Similarly, 6000 cells of K562 suspension cell line were plated in a tissue cultured treated 96-well plate with 50 μL of IMDM. PROTAC was added directly on top of cells in 50 μL of IMDM. After 48 hours of PROTAC treatment, a CellTiter-Glo® Luminescent Cell Viability assay (Promega) was performed as detailed in the manufacturer's manual. The Y-axis of FIG. 4 corresponds to the luminescence of PROTAC-treated samples normalized to the luminescence of DMSO-treated samples.

2. Chemistry

General Methods

All reactions were carried out under an atmosphere of dry nitrogen or argon. Glassware was oven-dried prior to use. Unless otherwise indicated, common reagents or materials were obtained from commercial source and used without further purification. N,N-Diisopropylethylamine (DIPEA) was obtained anhydrous by distillation over potassium hydroxide. Tetrahydrofuran (THF), Dichloromethane ($CH_2Cl_2$), and dimethylformamide (DMF) was dried by a PureSolv™ solvent drying system. Flash column chromatography was performed using silica gel 60 (230-400 mesh). Analytical thin layer chromatography (TLC) was carried out on Merck silica gel plates with QF-254 indicator and visualized by UV or KMnO4. $^1$H and $^{13}$C NMR spectra were recorded on an Agilent DD$_2$ 500 (500 MHz $^1$H; 125 MHz $^{13}$C) or Agilent DD$_2$ 600 (600 MHz $^1$H; 150 MHz $^{13}$C) or Agilent DD$_2$ 400 (400 MHz $^1$H; 100 MHz $^{13}$C) spectrometer at room temperature. Chemical shifts were reported in ppm relative to the residual CDCl$_3$ (δ 7.26 ppm $^1$H; δ 77.0 ppm $^{13}$C), CD$_3$OD (δ 3.31 ppm $^1$H; δ 49.00 ppm $^{13}$C), or d$^6$-DMSO (δ 2.50 ppm $^1$H; δ 39.52 ppm $^{13}$C). NMR chemical shifts were expressed in ppm relative to internal solvent peaks, and coupling constants were measured in Hz. (bs=broad signal). In most cases, only peaks of the major rotamer are reported. Mass spectra were obtained using Agilent 1100 series LC/MSD spectrometers. Analytical HPLC analyses were carried out on 250×4.6 mm C-18 column using gradient conditions (10-100% B, flow rate=1.0 mL/min, 20 min). Preparative HPLC was carried out on 250×21.2 mm C-18 column using gradient conditions (10-100% B, flow rate=10.0 mL/min, 20 min). The eluents used were: solvent A (H$_2$O with 0.1% TFA) and solvent B (CH$_3$CN with 0.1% TFA).

Synthesis of the Linkers

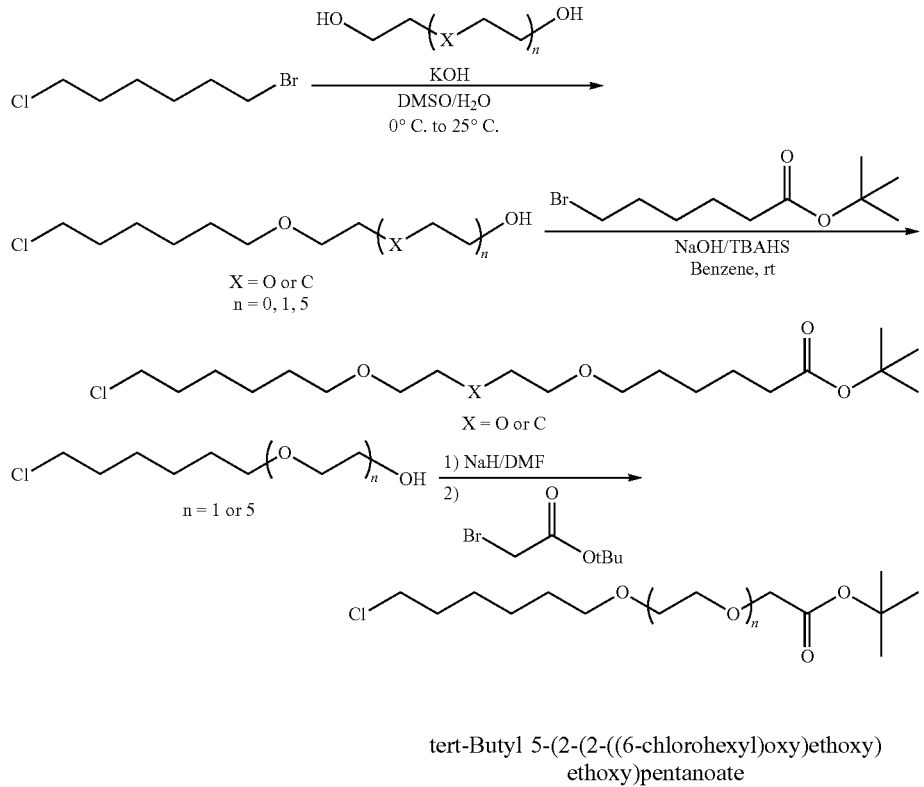

tert-Butyl 5-(2-(2-((6-chlorohexyl)oxy)ethoxy) ethoxy)pentanoate

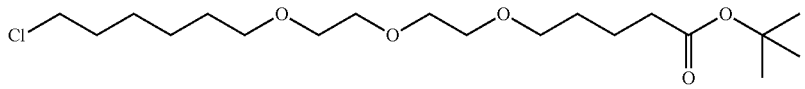 [SMILES: CC(C)(C)OC(=O)CCCCOCCOCCOCCCCCCCl]

To a solution of 2-(2-((6-chlorohexyl)oxy)ethoxy)ethan-1-ol (0.98 ml, 7.32 mmol) and tert-butyl 6-bromohexanoate (1.84 g, 7.32 mmol) in benzene (6 mL) was added aqueous 50% NaOH (4 ml, 50 mmol) and TBAHS (2.49 g, 7.32 mmol). The reaction mixture was stirred vigorously at room temperature for 12 h (overnight). Then the reaction was diluted with ether (50 mL) and water (50 mL), organic layer was separated, washed with water (2×20 mL), dried ($Na_2SO_4$) and evaporated under vacuum. Crude product was purified by column flash chromatography ($SiO_2$-120 g, gradient; Hex 100% to Hex:AcOEt, 95:5) to give the desired product (55% yield) as an oil. $^1$H NMR (400 MHz, Chloroform-d) δ 3.66-3.61 (m, 4H), 3.57 (m, 4H), 3.52 (t, J=6.7 Hz, 2H), 3.45 (td, J=6.6, 2.1 Hz, 4H), 2.20 (t, J=7.5 Hz, 2H), 1.77 (p, J=6.8 Hz, 2H), 1.59 (m, 6H), 1.43 (s, 9H), 1.50-1.29 (m, 12H). $^{13}$C NMR (151 MHz, Chloroform-d) δ 173.28, 80.12, 71.39, 71.35, 70.79, 70.27, 70.26, 45.21, 35.67, 32.71, 29.62, 29.48, 28.27, 26.86, 25.76, 25.59, 25.08. HRMS (ESI); m/z: [M+Na]$^+$ calcd for $C_{20}H_{39}ClO_5Na$: 417.2383, found 417.2376.

tert-Butyl 6-((5-((6-chlorohexyl)oxy)pentyl)oxy)hexanoate

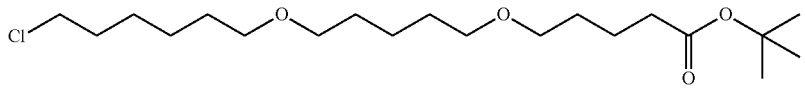 [SMILES: CC(C)(C)OC(=O)CCCCOCCCCCOCCCCCCCl]

Yield (29%); $^1$H NMR (500 MHz, Chloroform-d) δ 3.52 (t, J=6.8, 2H), 3.41-3.36 (m, 8H), 2.20 (t, J=7.8, 2H), 1.80-1.74 (m, 2H), 1.63-1.53 (m, 10H), 1.45-1.34 (m, 17H). $^{13}$C NMR (100 MHz, Chloroform-d) δ 173.14, 79.94, 70.81, 70.78, 70.68, 70.65, 45.05, 35.51, 32.55, 29.58, 29.43, 28.09, 26.71, 25.69, 25.52, 24.94, 22.81. MS (ESI); m/z: [M+Na]$^+$ Calcd. for $C_{21}H_{41}ClO_4Na$, 415.2591. Found 415.2632.

Synthesis of tert-butyl 2-(2-((6-chlorohexyl)oxy)ethoxy)acetate

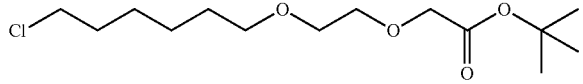 [SMILES: CC(C)(C)OC(=O)COCCOCCCCCCCl]

To a solution of 2-((6-chlorohexyl)oxy)ethan-1-ol (1.6 g, 8.85 mmol) in a mixture of DMF:THF (1:1), 20 mL was added NaH (95%, 268.5 mg, 10.6 mmol) at 0° C., the reaction mixture was stirred for 30 min. at the same temperature. tert-Butyl 2-bromoacetate (2.6 mL, 17.7 mmol) was then added at 0° C. and the reaction mixture was stirred for 12 h. After dilution with ethyl acetate (100 mL) and water (100 mL), the aqueous phase was extracted with ethyl acetate (3×100 mL). The combined organic fractions were washed with brine and dried over $MgSO_4$. After concentration, the crude material was subjected to column chromatography on silica gel (hexane/AcOEt 7/1) to give 1.67 g (64%) of tert-butyl 2-(2-((6-chlorohexyl)oxy)ethoxy)acetate as a colorless oil. $^1$H NMR (400 MHz, Chloroform-d) δ 4.01 (s, 2H), 3.70-3.66 (m, 2H), 3.60-3.59 (m, 2H), 3.54-3.49 (m, 2H), 3.48-3.43 (m, 2H), 1.80-1.73 (m, 2H), 1.61-155 (m, 2H), 1.48-1.40 (m, 11H), 1.38-1.33 (m, 2H). $^{13}$C NMR (151 MHz, Chloroform-d) δ 169.64, 81.45, 71.23, 70.70, 70.11, 69.01, 45.00, 32.51, 29.41, 28.07, 26.66, 25.39. HRMS (ESI); m/z: [M+Na]$^+$ Calcd. for $C_{14}H_{27}ClO_4Na$, 317.1496. Found 317.1536.

tert-Butyl 24-chloro-3,6,9,12,15,18-hexaoxatetracosanoate

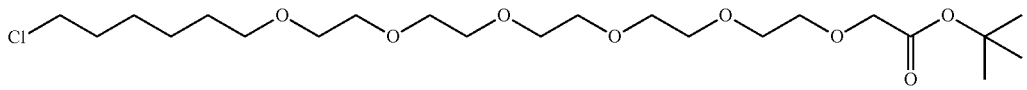 [SMILES: CC(C)(C)OC(=O)COCCOCCOCCOCCOCCOCCCCCCCl]

Yield (68%); ¹H NMR (500 MHz, Chloroform-d) δ 3.99 (s, 2H), 3.70-3.61 (m, 18H), 3.57-3.53 (m, 2H), 3.50 (t, J=6.8 Hz, 2H), 3.42 (t, J=6.8 Hz, 2H), 1.74 (p, J=7.3 Hz, 2H), 1.56 (p, J=7.3 Hz, 2H), 1.47-1.39 (m, 11H), 1.36-1.31 (m, 2H). ¹³C NMR (151 MHz, Chloroform-d) δ 169.64, 81.48, 71.17, 70.67, 70.56, 70.55, 70.53, 70.51, 70.05, 68.98, 45.05, 32.50, 29.41, 28.06, 26.65, 25.37. HRMS (ESI): m/z; [M+Na]⁺ Calcd. for $C_{22}H_{43}ClO_8Na$: 493.2544 Found: 493.2649.
Synthesis of Dasatinib and Imatinib with VHL Ligand
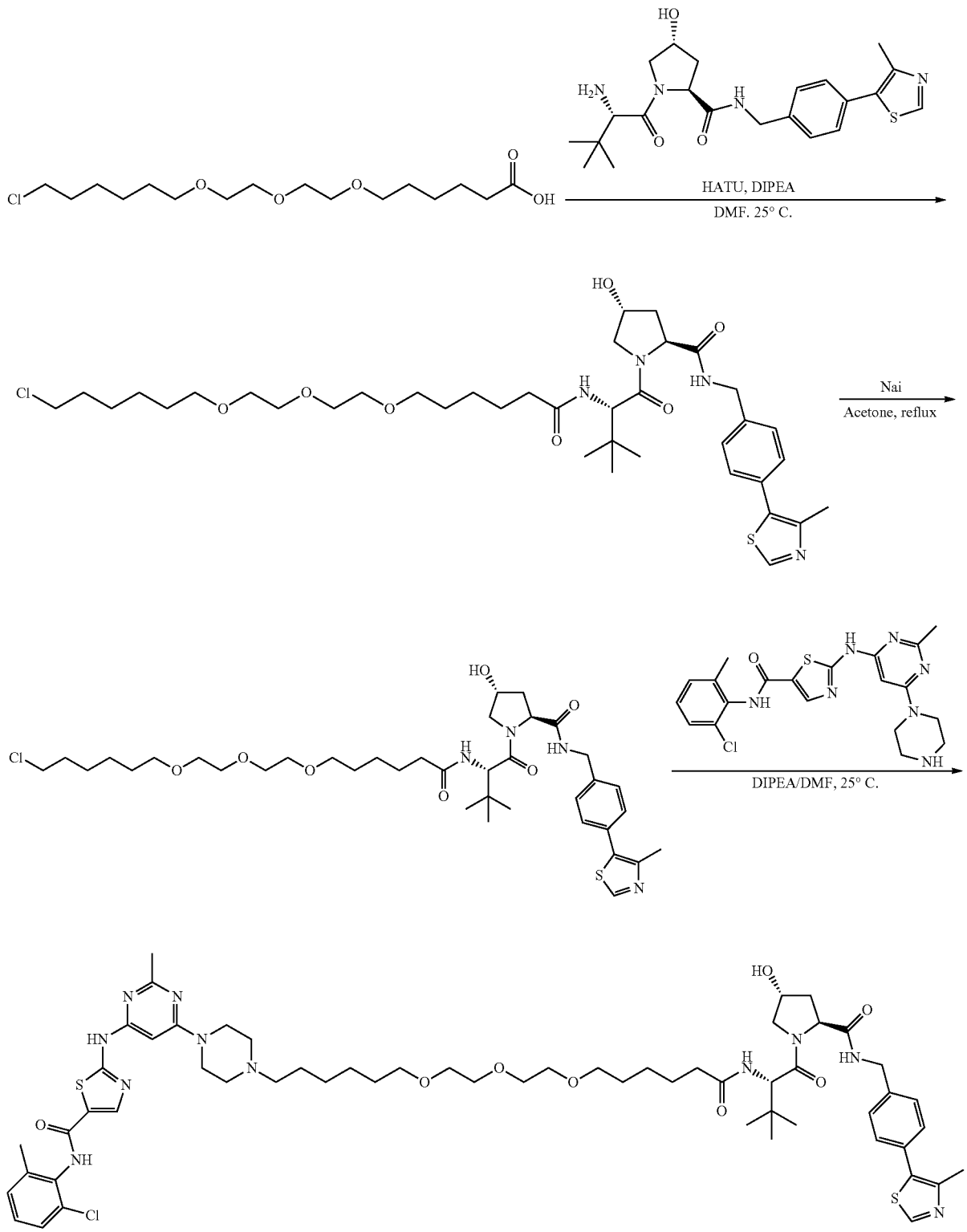

(2S,4R)-1-((S)-2-(tert-butyl)-22-chloro-4-oxo-10,13,16-trioxa-3-azadocosanoyl)-4-hydroxy-N-(4-(4-methylthiazol-5-yl)benzyl)pyrrolidine-2-carboxamide

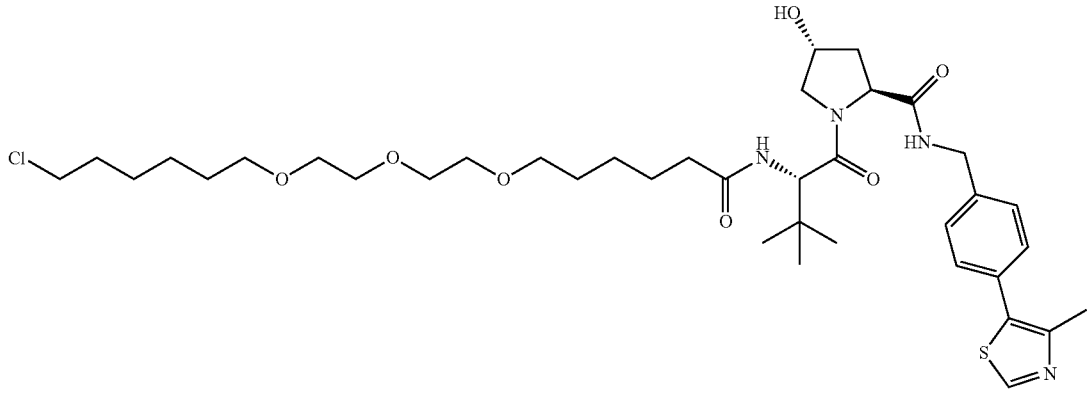 [SMILES: Cc1ncsc1-c1ccc(CNC(=O)[C@@H]2C[C@@H](O)CN2C(=O)[C@@H](NC(=O)CCCCCOCCOCCOCCCCCCCl)C(C)(C)C)cc1]

To a solution of 6-[2-[2-(6-chlorohexoxy)ethoxy]ethoxy]hexanoic acid (80 mg, 0.24 mmol) in DMF (5 mL) was added HATU (179.53 mg, 0.47 mmol) and the resulting solution was stirred for 10 minutes at rt, after which ((2S,4R)-1-[(2S)-2-amino-3,3-dimethyl-butanoyl]-4-hydroxy-N-[[4-(4-methylthiazol-5-yl)phenyl]methyl] pyrrolidine-2-carboxamide; hydrochloride (110.25 mg, 0.24 mmol) and DIEA (0.2 ml, 1.18 mmol) were added respectively. The resulting mixture was stirred at room temperature for 16 h at rt. The product was extracted twice with Ac$_2$O then purified by silica gel DCM/MeOH 95:5 to give 152 mg (85.7%) of the desired product. $^1$H NMR (500 MHz, CD$_3$OD) δ 8.86 (s, 1H), 7.45 (d, J=7.8 Hz, 2H), 7.41 (d, J=7.8 Hz, 2H), 4.69 (bs, 1H), 4.58-4.49 (m, 3H), 4.34 (d, J=15.0 Hz, 1H), 3.89 (d, J=11.0 Hz, 1H), 3.80 (d, J=11.0 Hz, 1H), 3.61-3.53 (m, 10H), 3.47-3.45 (m, 4H), 2.46 (s, 3H), 2.32-2.19 (m, 3H), 2.11-2.06 (m, 1H), 1.78-1.72 (m, 2H), 1.65-1.54 (m, 6H), 1.47-1.35 (m, 6H), 1.03 (s, 9H). $^{13}$C NMR (151 MHz, CD$_3$OD) δ 174.4, 173.0, 170.9, 151.5, 147.5, 138.9, 132.0, 130.0, 128.9, 127.6, 70.74, 70.71, 70.2, 69.8, 69.7, 59.4, 59.3, 57.5, 56.6, 44.3, 42.4, 42.3, 37.5, 35.2, 35.1, 32.4, 29.2, 29.0, 26.3, 25.7, 25.5, 25.4, 25.1, 27.3, 15.9, 14.5. MS (ESI); m/z: [M+H]$^+$ calcd for C$_{38}$H$_{60}$ClN$_4$O$_7$S: 751.4, found 751.1.

(2S,4R)-1-((S)-2-(tert-butyl)-22-iodo-4-oxo-10,13,16-trioxa-3-azadocosanoyl)-4-hydroxy-N-(4-(4-methylthiazol-5-yl)benzyl)pyrrolidine-2-carboxamide

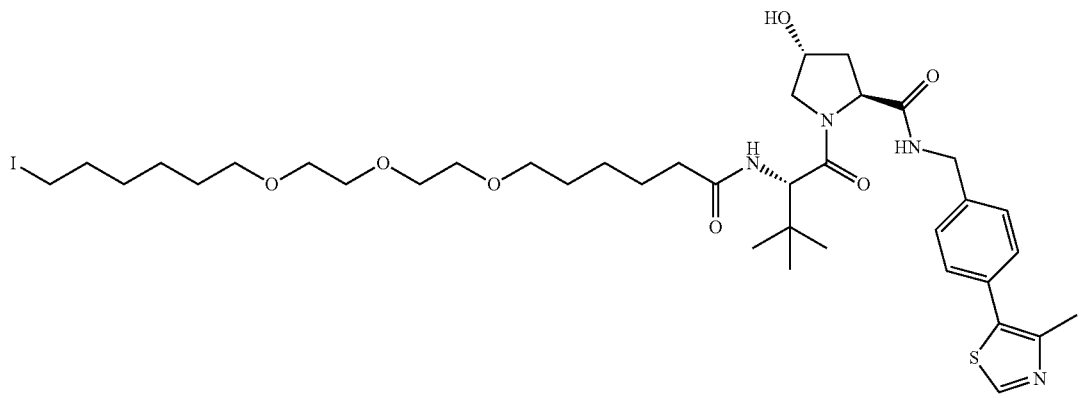 [SMILES: Cc1ncsc1-c1ccc(CNC(=O)[C@@H]2C[C@@H](O)CN2C(=O)[C@@H](NC(=O)CCCCCOCCOCCOCCCCCCI)C(C)(C)C)cc1]

To a solution of (2S,4R)-1-[(2S)-2-[6-[2-[2-(6-chloro-hexoxy)ethoxy] ethoxy]hexanoyl amino]-3,3-dimethyl-butanoyl]-4-hydroxy-N-[[4-(4-methylthiazol-5-yl)phenyl] methyl]pyrrolidine-2-carboxamide (87 mg, 0.12 mmol) in acetone (10 ml) was added NaI (86.77 mg, 0.58 mmol). The reaction mixture was stirred at reflux temperature for 24 h, then the solvent was removed under vacuum and crude product was dissolved in EtOAc (15 mL) and an aqueous solution of $Na_2SO_3$ (10%, 10 mL), organic layer was separated, washed with water (10 mL), dried ($Na_2SO_4$) and evaporated under vacuum. Crude product was pure by NMR (>98% purity), 96 mg (99%) of the desired product. It was used in the next step without any further purification. $^1$H NMR (500 MHz, $CD_3OD$) δ 8.87 (s, 1H), 7.45 (d, J=7.8 Hz, 2H), 7.41 (d, J=7.8 Hz, 2H), 4.65-4.62 (m, 1H), 4.58-4.49 (m, 3H), 4.37-4.32 (m, 1H), 3.89 (d, J=11.0 Hz, 1H), 3.80 (d, J=11.0 Hz, 1H), 3.62-3.58 (m, 4H), 3.57-3.54 (m, 4H), 3.46 (m, 4H), 3.26 (t, J=6.6 Hz, 2H), 2.47 (s, 3H), 2.32-2.19 (m, 3H), 2.11-2.06 (m, 1H), 1.83-1.72 (m, 2H), 1.64-1.54 (m, 6H), 1.44-1.38 (m, 6H), 1.03 (s, 9H). MS (ESI); m/z: [M+H]$^+$ calcd for $C_{38}H_{60}IN_4O_7S$: 843.3, found 843.1.

N-(2-chloro-6-methylphenyl)-2-((6-(4-((S)-3-((2S,4R)-4-hydroxy-2-((4-(4-methylthiazol-5-yl)benzyl) carbamoyl)pyrrolidine-1-carbonyl)-2,2-dimethyl-5-oxo-11,14,17-trioxa-4-azatricosan-23-yl)piperazin-1-yl)-2-methylpyrimidin-4-yl)amino)thiazole-5-carboxamide: DAS-6-2-2-6-VHL

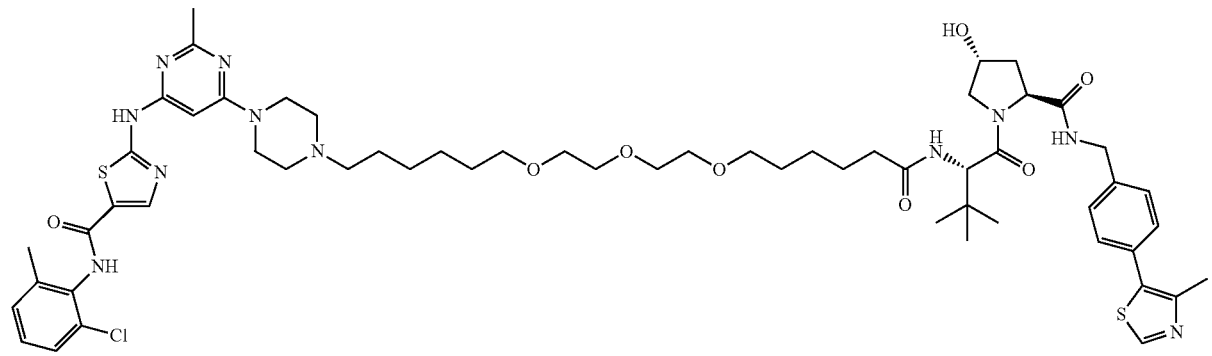 [SMILES: Cc1nc(Nc2ncc(C(=O)Nc3c(C)cccc3Cl)s2)cc(N2CCN(CCCCCCOCCOCCOCCCCCC(=O)N[C@H](C(=O)N3C[C@H](O)C[C@H]3C(=O)NCc3ccc(-c4scnc4C)cc3)C(C)(C)C)CC2)n1]

To a solution of N-(2-chloro-6-methyl-phenyl)-2-[(2-methyl-6-piperazin-1-yl-pyrimidin-4-yl)amino]thiazole-5-carboxamide; 2,2,2-trifluoroacetaldehyde (9.65 mg, 0.02 mmol) and DIEA (5.38 mg, 0.05 mmol) in DMF (1 ml) was added (2S,4R)-4-hydroxy-1-[(2S)-2-[6-[2-[2-(6-iodo-hexoxy)ethoxy]ethoxy]hexanoylamino]-3,3-dimethyl-butanoyl]-N-[[4-(4-methylthiazol-5-yl)phenyl]methyl]pyrrolidine-2-carboxamide (15 mg, 0.02 mmol) and the resulting solution stirred for 16 h at rt. The solvent was evaporated and the residue subjected to Prep TLC purification (ammonia/MeOH/DCM:1/10/60) to give 10.5 mg (50.9%) of the desired product as a foamy brown solid. $^1$H NMR (500 MHz, $CD_3OD$) δ 8.86 (s, 1H), 8.14 (s, 1H), 7.45 (d, J=7.8 Hz, 2H), 7.41 (d, J=7.8 Hz, 2H), 7.35 (d, J=7.6 Hz, 1H), 7.26-7.21 (m, 2H), 6.00 (s, 1H), 4.63 (bs, 1H), 4.58-4.49 (m, 3H), 4.36 (d, J=15.0 Hz, 1H), 3.90 (d, J=11.0 Hz, 1H), 3.80 (dd, J=11.0 Hz, J=3.8 Hz, 1H), 3.64-3.59 (m, 8H), 3.58-3.55 (m, 4H), 3.49-3.45 (m, 4H), 2.55 (bs, 4H), 2.46 (s, 6H), 2.44-2.39 (m, 2H), 2.32 (s, 3H), 2.29-2.19 (m, 3H), 2.10-2.06 (m, 1H), 1.64-1.55 (m, 8H), 1.42-1.34 (m, 6H), 1.03 (s, 9H). $^{13}$C NMR (151 MHz, $CD_3OD$) δ 173.9, 171.9, 171.8, 170.9, 166.1, 163.7, 162.8, 161.1, 156.6, 150.7, 147.6, 140.3, 138.5, 138.1, 132.2, 132.0, 131.8, 130.1, 129.1, 128.8, 127.9, 127.6, 126.8, 125.3, 83.8, 71.1, 70.9, 70.19, 70.18, 69.9, 69.5, 58.96, 58.92, 58.4, 57.2, 56.7, 52.4, 49.4, 43.4, 42.6, 36.6, 36.8, 35.3, 29.2, 28.9, 27.1, 26.1, 25.9, 25.7, 25.6, 25.4, 25.2, 25.0, 18.2, 15.2. MS (ESI); m/z: [M+H]$^+$ calcd for $C_{58}H_{81}ClN_{11}O_8S_2$: 1158.5, found 1158.4.

(2S,4R)-1-((S)-2-(tert-butyl)-22-(4-(4-((4-methyl-3-((4-(pyridin-3-yl)pyrimidin-2-yl)amino)phenyl)carbamoyl)benzyl)piperazin-1-yl)-4-oxo-10,13,16-trioxa-3-azadocosanoyl)-4-hydroxy-N-(4-(4-methylthiazol-5-yl)benzyl)pyrrolidine-2-carboxamide: IMA-6-2-2-6-VHL

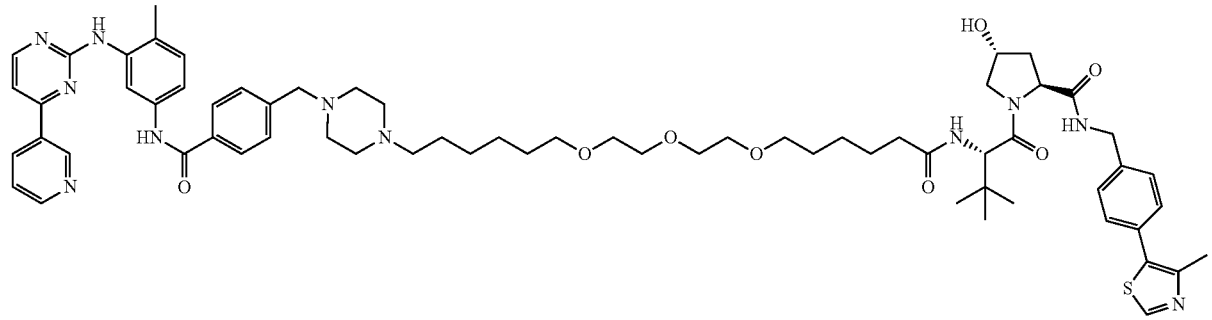 [SMILES: Cc1ccc(NC(=O)c2ccc(CN3CCN(CCCCCCOCCOCCOCCCCCC(=O)N[C@H](C(=O)N4C[C@H](O)C[C@H]4C(=O)NCc4ccc(-c5scnc5C)cc4)C(C)(C)C)CC3)cc2)cc1Nc1nccc(-c2cccnc2)n1]

Yield (61%); $^1$H NMR (500 MHz, CDCl$_3$) δ 9.22 (d, J=2.0 Hz, 1H), 8.69-8.66 (m, 2H), 8.54 (s, 1H), 8.49-8.47 (m, 2H), 8.19 (s, 1H), 7.83 (d, J=8.1 Hz, 2H), 7.42-7.29 (m, 9H), 7.19-7.15 (m, 3H), 6.25 (d, J=9.0 Hz, 1H), 4.69 (t, J=7.9 Hz, 1H), 4.57-4.49 (m, 3H), 4.31 (d, J=14.9 Hz, J=5.1 Hz, 1H), 4.01 (d, J=11.2 Hz, 1H), 3.63-3.53 (m, 10H), 3.47-3.39 (m, 7H), 2.55-2.44 (m, 10H), 2.37-2.34 (m, 2H), 2.32 (s, 3H), 2.20-2.08 (m, 4H), 1.61-1.44 (m, 8H), 1.36-1.34 (m, 6H), 0.91 (s, 9H). $^{13}$C NMR (151 MHz, CDCl$_3$) δ 173.5, 171.8, 170.8, 165.3, 162.7, 160.6, 158.9, 151.4, 150.3, 148.43, 148.40, 142.2, 138.0, 137.7, 136.6, 134.9, 133.9, 132.7, 131.6, 130.9, 130.7, 129.4, 129.3, 128.0, 127.1, 124.7, 123.7, 115.6, 113.7, 108.2, 71.3, 71.1, 70.6, 70.5, 70.0, 69.9, 62.5, 58.6, 57.3, 56.7, 53.1, 52.8, 50.7, 46.3, 43.2, 36.1, 35.9, 35.1, 29.5, 29.2, 27.3, 26.5, 26.4, 25.9, 25.7, 25.3, 17.7, 16.0. MS (ESI); m/z: [M+H]$^+$ calcd for C$_{66}$H$_{88}$N$_{11}$O$_8$S: 1194.6, found 1194.9.

(2S,4R)-1-((S)-2-(2-(2-((6-chlorohexyl)oxy)ethoxy)acetamido)-3,3-dimethylbutanoyl)-4-hydroxy-N-(4-(4-methylthiazol-5-yl)benzyl)pyrrolidine-2-carboxamide

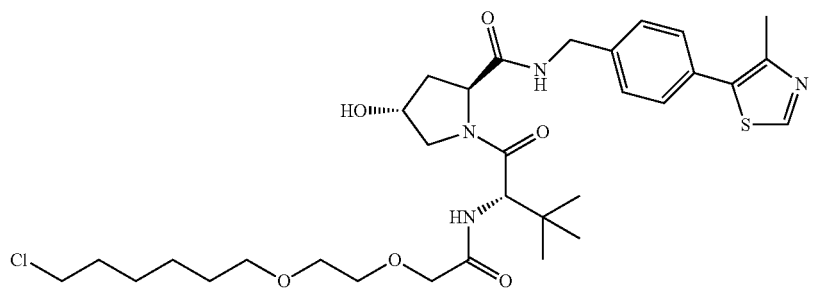 [SMILES: Cc1ncsc1-c1ccc(CNC(=O)[C@@H]2C[C@@H](O)CN2C(=O)[C@@H](NC(=O)COCCOCCCCCCCl)C(C)(C)C)cc1]

Yield (86%); $^1$H NMR (500 MHz, CDCl$_3$) δ 8.70 (s, 1H), 7.45 (s, 1H), 7.40-7.32 (m, 5H), 4.76-4.70 (m, 1H), 4.56-4.51 (m, 2H), 4.37 (d, J=15.0 Hz, 1H), 4.08-3.97 (m, 3H), 3.75-3.60 (m, 6H), 3.55-3.48 (m, 3H), 3.23-3.20 (m, 2H), 2.53 (s, 3H), 2.52-2.48 (m, 1H), 2.16-2.21 (m, 1H), 1.82-1.74 (m, 2H), 1.63-1.59 (m, 2H), 1.51-1.38 (m, 4H), 0.99 (s, 9H). $^{13}$C NMR (151 MHz, CDCl$_3$) δ 171.2, 170.9, 170.5, 150.3, 148.4, 138.1, 131.8, 130.8, 129.4, 128.0, 71.3, 71.2, 70.2, 70.1, 69.7, 58.6, 57.2, 56.6, 55.7, 45.0, 43.6, 43.1, 36.0, 34.9, 32.5, 29.3, 26.6, 26.4, 25.3, 16.0. MS (ESI); m/z: [M+H]$^+$ calcd for C$_{32}$H$_{48}$ClN$_4$O$_6$S: 651.3, found 651.1.

(2S,4R)-4-hydroxy-1-((S)-2-(2-(2-((6-iodohexyl)oxy)ethoxy)acetamido)-3,3-dimethylbutanoyl)-N-(4-(4-methylthiazol-5-yl)benzyl)pyrrolidine-2-carboxamide

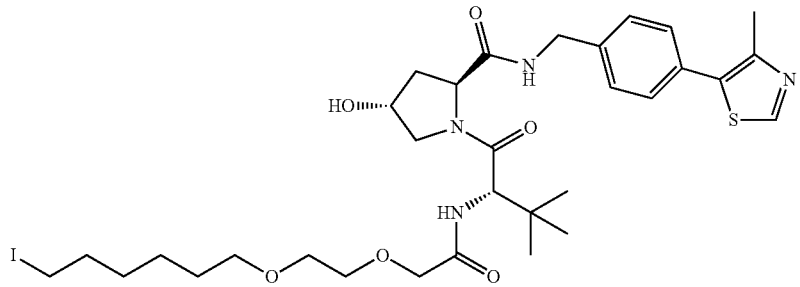 [SMILES: Cc1ncsc1-c1ccc(CNC(=O)[C@@H]2C[C@@H](O)CN2C(=O)[C@@H](NC(=O)COCCOCCCCCCI)C(C)(C)C)cc1]

Yield (89%); $^1$H NMR (500 MHz, CD$_3$OD) δ 8.89 (s, 1H), 7.48-7.45 (m, 2H), 7.43-7.41 (m, 2H), 4.68-4.66 (m, 1H), 4.60-4.55 (m, 2H), 4.37 (d, J=15.5 Hz, 1H), 4.05 (s, 2H), 3.90 (d, J=11.0 Hz, 1H), 3.79 (s, 3H), 3.75-3.70 (m, 2H), 3.65-3.61 (m, 2H), 3.53-3.48 (m, 2H), 3.19 (t, J=6.8 Hz, 1H), 2.47 (s, 3H), 2.26-2.24 (m, 1H), 2.12-2.01 (m, 1H), 1.80-1.74 (m, 2H), 1.61-1.58 (m, 2H), 1.41-1.38 (m, 4H), 1.04 (s, 9H). MS (ESI); m/z: [M+H]$^+$ calcd for C$_{32}$H$_{48}$IN$_4$O$_6$S: 743.2, found 743.0.

N-(2-chloro-6-methylphenyl)-2-((6-(4-(6-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)hexyl)piperazin-1-yl)-2-methylpyrimidin-4-yl)amino)thiazole-5-carboxamide: DAS-6-2-2-VHL

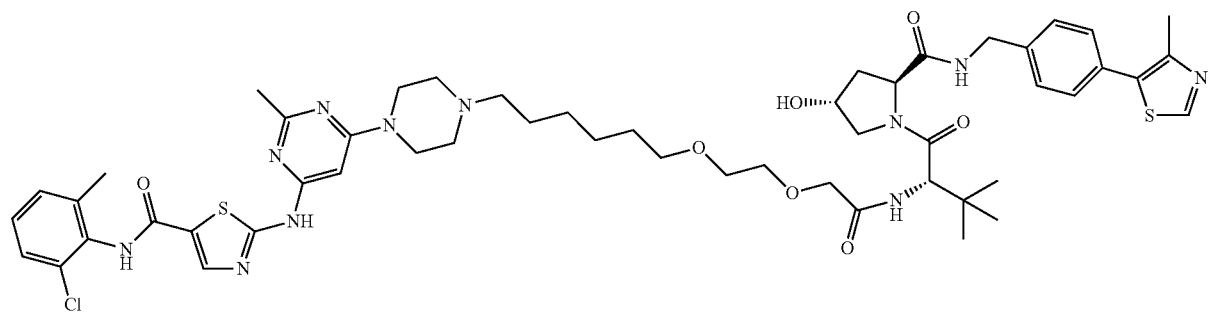 [SMILES: Cc1nc(Nc2ncc(C(=O)Nc3c(C)cccc3Cl)s2)cc(N2CCN(CCCCCCOCCOCC(=O)N[C@H](C(=O)N3C[C@H](O)C[C@H]3C(=O)NCc3ccc(-c4scnc4C)cc3)C(C)(C)C)CC2)n1]

Yield (27%); $^1$H NMR (500 MHz, CD$_3$OD) δ 8.86 (s, 1H), 8.14 (s, 1H), 7.47-7.39 (m, 4H), 7.34 (d, J=7.3 Hz, 1H), 7.27-7.20 (m, 2H), 6.00 (s, 1H), 4.69 (bs, 1H), 4.59-4.56 (m, 1H), 4.52-4.51 (m, 1H), 4.35 (d, J=15.6 Hz, 1H), 4.04 (s, 2H), 3.88 (d, J=11.0 Hz, 1H), 3.80 (dd, J=15.0 Hz, J=3.8 Hz, 1H), 3.76-3.60 (m, 8H), 3.55-3.49 (m, 2H), 3.21-3.17 (m, 1H), 2.56 (bs, 4H), 2.48-2.40 (m, 6H), 2.32 (s, 3H), 2.25-2.21 (m, 1H), 2.12-2.07 (m, 1H), 1.63-1.55 (m, 4H), 1.43-1.28 (m, 6H), 1.05 (s, 9H). $^{13}$C NMR (151 MHz, CD$_3$OD) δ 172.9, 170.7, 170.2, 166.0, 163.8, 162.9, 161.8, 157.2, 151.4, 147.6, 140.7, 138.9, 138.8, 132.9, 132.8, 131.9, 130.0, 129.1, 128.9, 128.7, 128.1, 128.0, 127.5, 126.9, 125.4, 82.5, 70.97, 70.91, 69.66, 69.63, 69.60, 59.4, 58.1, 56.7, 56.7, 52.3, 48.1, 43.2, 42.3, 37.5, 35.6, 29.2, 26.9, 25.8, 25.7, 25.6, 25.5, 24.2, 17.3, 14.4. MS (ESI); m/z: [M+H]$^+$ calcd for C$_{52}$H$_{69}$ClN$_{11}$O$_7$S$_2$: 1058.4, found 1058.2.

(2S,4R)-1-((S)-3,3-dimethyl-2-(2-(2-((6-(4-(4-((4-methyl-3-((4-(pyridin-3-yl)pyrimidin-2-yl)amino)phenyl)carbamoyl)benzyl)piperazin-1-yl)hexyl)oxy)ethoxy)acetamido)butanoyl)-4-hydroxy-N-(4-(4-methylthiazol-5-yl)benzyl)pyrrolidine-2-carboxamide: IMA-6-2-2-VHL

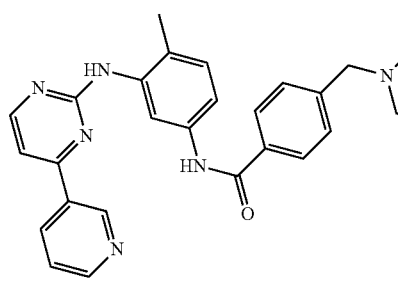
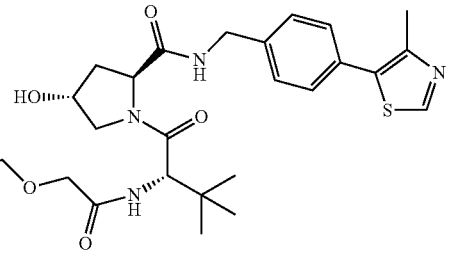

Yield (66%); $^1$H NMR (500 MHz, CDCl$_3$/d$_6$DMSO) δ 9.23 (d, J=2.0 Hz, 1H), 8.69-8.66 (m, 2H), 8.57 (s, 1H), 8.51-8.48 (m, 2H), 8.23 (s, 1H), 7.83 (d, J=8.0 Hz, 2H), 7.47-7.38 (m, 4H), 7.35-7.27 (m, 6H), 7.20-7.16 (m, 2H), 7.08 (s, 1H), 4.69 (t, J=7.9 Hz, 1H), 4.56-4.47 (m, 3H), 4.32 (d, J=15.1 Hz, J=5.3 Hz, 1H), 4.03-3.98 (m, 3H), 3.66-3.5 (m, 8H), 3.43 (t, J=6.5 Hz, 2H), 2.72-2.55 (m, 7H), 2.52-2.45 (m, 6H), 2.33 (s, 3H), 2.14-2.08 (m, 1H), 1.58-1.50 (m, 4H), 1.36-1.25 (m, 6H), 0.94 (s, 9H). $^{13}$C NMR (151 MHz, CDCl$_3$/d$_6$DMSO) δ 171.1, 170.9, 170.4, 165.6, 162.7, 160.5, 159.0, 151.4, 150.3, 148.5, 148.4, 141.7, 138.1, 137.7, 136.6, 134.9, 134.0, 132.7, 131.6, 130.8, 130.7, 129.4, 129.3, 128.0, 127.2, 124.4, 123.8, 115.5, 113.4, 108.3, 71.3, 71.2, 70.3, 69.9, 69.8, 62.2, 58.6, 58.2, 57.1, 56.7, 54.6, 52.8, 51.9, 50.7, 43.1, 36.1, 35.0, 29.2, 27.0, 25.8, 17.7, 16.0. MS (ESI); m/z: [M+H]$^+$ calcd for C$_{60}$H$_{76}$N$_{11}$O$_7$S: 1094.5, found 1094.2.

(2S,4R)-1-((S)-2-(tert-butyl)-27-chloro-4-oxo-6,9,12,15,18,21-hexaoxa-3-azaheptacosanoyl)-4-hydroxy-N-(4-(4-methylthiazol-5-yl)benzyl)pyrrolidine-2-carboxamide

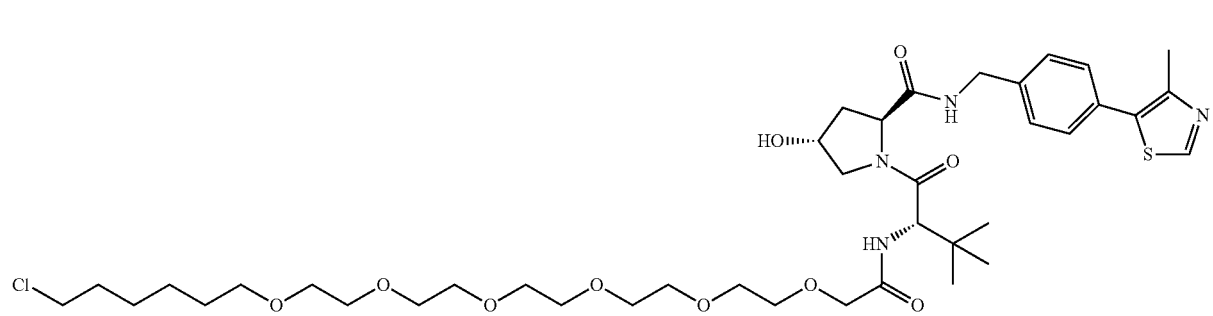 [SMILES: Cc1ncsc1-c1ccc(CNC(=O)[C@@H]2C[C@@H](O)CN2C(=O)[C@@H](NC(=O)COCCOCCOCCOCCOCCOCCCCCCCl)C(C)(C)C)cc1]

Yield (77%); $^1$H NMR (500 MHz, CDCl$_3$) δ 8.69 (s, 1H), 7.47-7.37 (m, 3H), 7.30-7.29 (m, 3H), 4.74-4.69 (m, 1H), 4.58-4.52 (m, 2H), 4.40-4.35 (m, 1H), 4.07-3.98 (m, 3H), 3.72-3.57 (m, 17H), 3.50-3.45 (m, 9H), 3.22-3.18 (m, 1H), 2.55-2.46 (m, 4H), 2.18-2.14 (m, 1H), 1.82-1.76 (m, 2H), 1.64-1.58 (m, 2H), 1.45-1.36 (m, 4H), 0.97 (s, 9H). NMR (151 MHz, CDCl$_3$) δ 171.1, 170.9, 170.4, 150.3, 148.3, 138.2, 131.6, 130.8, 129.4, 128.0, 71.2, 71.0, 70.41, 70.38, 70.32, 70.27, 70.2, 69.98, 69.89, 58.6, 56.9, 56.7, 55.2, 50.6, 45.0, 43.2, 43.1, 36.5, 35.2, 31.4, 29.3, 26.6, 26.3, 25.3, 16.0. MS (ESI); m/z: [M+H]$^+$ calcd for C$_{40}$H$_{64}$ClN$_4$O$_{10}$S: 827.4, found 827.2.

(2S,4R)-1-((S)-2-(tert-butyl)-27-iodo-4-oxo-6,9,12,
15,18,21-hexaoxa-3-azaheptacosanoyl)-4-hydroxy-
N-(4-(4-methylthiazol-5-yl)benzyl)pyrrolidine-2-
carboxamide

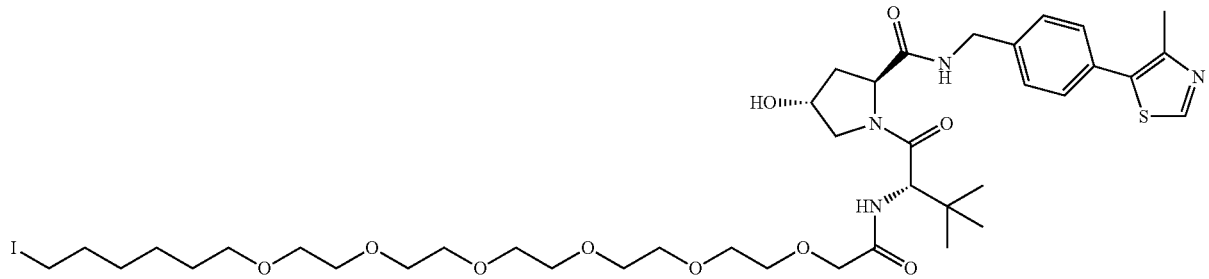 [SMILES: Cc1ncsc1-c1ccc(CNC(=O)[C@@H]2C[C@@H](O)CN2C(=O)[C@@H](NC(=O)COCCOCCOCCOCCOCCOCCCCCCI)C(C)(C)C)cc1]

Yield (96%); $^1$H NMR (500 MHz, CD$_3$OD) δ 8.88 (s, 1H), 7.47 (d, J=8.3 Hz, 2H), 7.42 (d, J=8.3 Hz, 2H), 4.68 (bs, 1H), 4.58-4.51 (m, 3H), 4.36 (d, J=15.4 Hz, 1H), 4.07 (s, 2H), 3.87 (d, J=11.0 Hz, 1H), 3.81 (dd, J=11.0 Hz, J=3.9 Hz, 1H), 3.75-3.61 (m, 18H), 3.58-3.55 (m, 2H), 3.47 (t, J=6.8 Hz, 2H), 3.34 (s, 2H), 3.26-3.21 (m, 3H), 2.48 (s, 3H), 2.25-2.21 (m, 1H), 2.12-2.06 (m, 1H), 1.82-1.77 (m, 2H), 1.60-1.56 (m, 2H), 1.45-1.36 (m, 4H), 1.04 (s, 9H). MS (ESI); m/z: [M+H]$^+$ calcd for C$_{40}$H$_{64}$IN$_4$O$_{10}$S: 919.3, found 919.1.

N-(2-chloro-6-methylphenyl)-2-((6-(4-((S)-3-((2S,4R)-4-hydroxy-2-((4-(4-methyl thiazol-5-yl)benzyl)carbamoyl)pyrrolidine-1-carbonyl)-2,2-dimethyl-5-oxo-7,10,13,16,19,22-hexaoxa-4-azaoctacosan-28-yl)piperazin-1-yl)-2-methylpyrimidin-4-yl)amino)thiazole-5-carboxamide: DAS-6-2-2-2-2-2-2-VHL

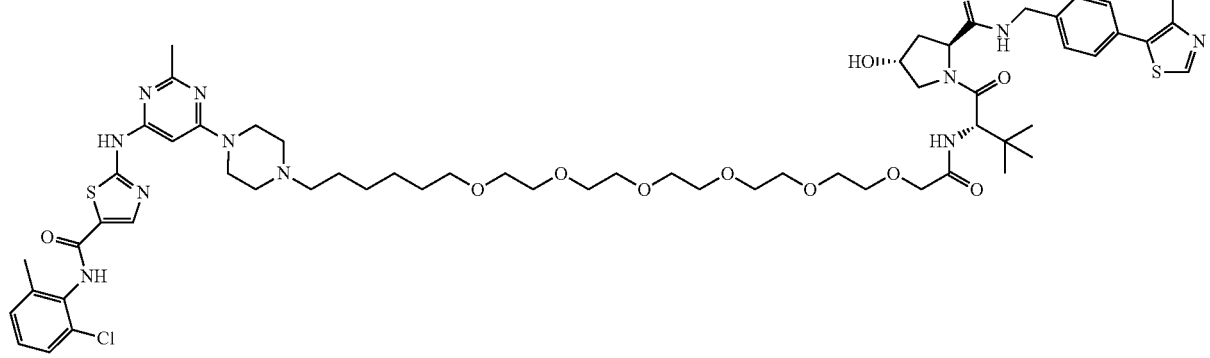

Yield (68%); $^1$H NMR (500 MHz, CD$_3$OD) δ 8.87 (s, 1H), 8.14 (s, 1H), 7.47-7.39 (m, 4H), 7.34 (d, J=7.1 Hz, 1H), 7.26-7.20 (m, 2H), 6.00 (s, 1H), 4.68 (bs, 1H), 4.59-4.50 (m, 3H), 4.37-4.33 (m, 1H), 4.08-4.00 (m, 2H), 3.87 (d, J=11.0 Hz, 1H), 3.80 (dd, J=11.0 Hz, J=3.8 Hz, 1H), 3.70-3.61 (m, 22H), 3.58-3.55 (m, 2H), 3.46 (t, J=6.8 Hz, 2H), 2.58-2.51 (m, 4H), 2.50-2.45 (m, 6H), 2.42-2.39 (m, 2H), 2.32 (s, 3H), 2.25-2.20 (m, 1H), 2.12-2.06 (m, 1H), 1.60-1.53 (m, 4H), 1.42-1.32 (m, 4H), 1.04 (s, 9H). $^{13}$C NMR (151 MHz, CD$_3$OD) δ 173.0, 170.0, 169.8, 168.4, 166.8, 165.9, 163.0, 161.8, 157.1, 152.1, 140.7, 138.9, 136.2, 135.8, 132.9, 132.8, 131.6, 128.7, 128.1, 126.9, 125.4, 124.4, 118.1, 116.4, 82.5, 71.2, 70.8, 70.4, 70.3, 70.2, 70.16, 70.14, 70.12, 69.8, 58.2, 52.4, 49.2, 48.1, 43.3, 30.7, 29.2, 26.9, 25.9, 25.7, 24.2, 22.2, 17.29, 17.28. MS (ESI); m/z: [M+H]$^+$ calcd for C$_{60}$H$_{85}$ClN$_{11}$O$_{11}$S$_2$: 1234.5, found 1234.8.

(2S,4R)-1-((S)-2-(tert-butyl)-27-(4-(4-((4-methyl-3-((4-(pyridin-3-yl)pyrimidin-2-yl)amino)phenyl)carbamoyl)benzyl)piperazin-1-yl)-4-oxo-6,9,12,15,18,21-hexaoxa-3-azaheptacosanoyl)-4-hydroxy-N-(4-(4-methylthiazol-5-yl)benzyl)pyrrolidine-2-carboxamide: IMA-6-2-2-2-2-2-2-2-VHL

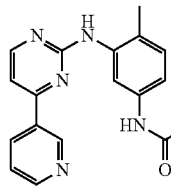
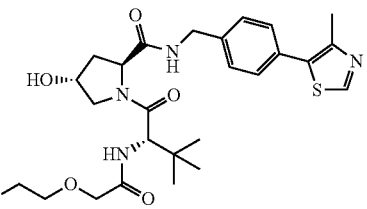

Yield (54%); $^1$H NMR (500 MHz, CDCl$_3$/d$_6$DMSO) δ 9.23 (d, J=2.0 Hz, 1H), 8.69-8.66 (m, 2H), 8.57 (s, 1H), 8.51-8.48 (m, 2H), 8.20 (s, 1H), 7.84 (d, J=8.0 Hz, 2H), 7.42-7.28 (m, 10H), 7.20-7.16 (m, 2H), 7.09 (s, 1H), 4.70 (t, J=7.9 Hz, 1H), 4.56-4.48 (m, 3H), 4.33 (d, J=15.1 Hz, J=5.3 Hz, 1H), 4.03-3.98 (m, 3H), 3.64-3.53 (m, 23H), 3.42 (t, J=6.5 Hz, 2H), 2.72-2.55 (m, 7H), 2.52-2.45 (m, 6H), 2.33 (s, 3H), 2.14-2.08 (m, 1H), 1.58-1.51 (m, 4H), 1.36-1.29 (m, 6H), 0.94 (s, 9H). $^{13}$C NMR (151 MHz, CDCl$_3$/d$_6$DMSO) δ 173.2, 170.8, 170.3, 165.5, 162.7, 160.6, 159.0, 151.4, 150.3, 148.46, 148.41, 141.9, 138.1, 137.7, 136.6, 134.9, 134.0, 132.7, 131.6, 130.9, 130.7, 129.4, 129.3, 128.1, 127.2, 124.5, 123.7, 115.5, 113.4, 108.3, 71.2, 71.1, 70.5, 70.52, 70.51, 70.47, 70.45, 70.38, 70.3, 69.9, 62.2, 58.5, 58.3, 57.0, 56.7, 54.7, 52.9, 52.0, 43.2, 36.0, 35.1, 29.4, 27.1, 25.9, 17.7, 16.0. MS (ESI); m/z: [M+H]$^+$ calcd for C$_{68}$H$_{92}$N$_{11}$O$_{11}$S: 1270.6, found 1270.2.

(2S,4R)-1-((S)-2-(6-((5-((6-chlorohexyl)oxy)pentyl)oxy)hexanamido)-3,3-dimethylbutanoyl)-4-hydroxy-N-(4-(4-methylthiazol-5-yl)benzyl)pyrrolidine-2-carboxamide

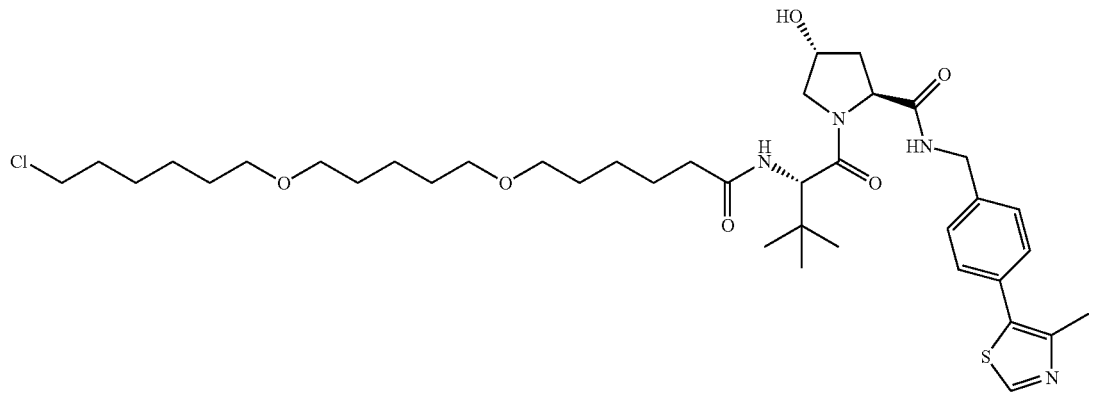 [SMILES: Cc1ncsc1-c1ccc(CNC(=O)[C@@H]2C[C@@H](O)CN2C(=O)[C@@H](NC(=O)CCCCCOCCCCCOCCCCCCCl)C(C)(C)C)cc1]

Yield (72%); $^1$H NMR (500 MHz, CD$_3$OD) δ 8.87 (s, 1H), 7.45 (d, J=7.8 Hz, 2H), 7.41 (d, J=7.8 Hz, 2H), 4.83 (s, 2H), 4.63 (bs, 1H), 4.58-4.49 (m, 3H), 4.37-4.43 (m, 1H), 3.90 (d, J=11.0 Hz, 1H), 3.80 (dd, J=11.0 Hz, J=3.8 Hz, 1H), 3.54 (t, J=6.8 Hz, 2H), 3.43-3.38 (m, 6H), 2.47 (s, 3H), 2.32-2.19 (m, 3H), 2.11-2.06 (m, 1H), 1.78-1.72 (m, 9H), 1.65-1.54 (m, 10H), 1.47-1.35 (m, 8H), 1.03 (s, 9H). $^{13}$C NMR (151 MHz, CD$_3$OD) δ 174.5, 173.1, 170.9, 151.4, 147.6, 138.9, 132.0, 130.0, 128.9, 127.0, 70.43, 70.41, 70.31, 70.29, 69.7, 59.4, 59.3, 57.5, 56.6, 44.3, 42.4, 42.3, 37.5, 35.2, 35.1, 32.3, 29.2, 29.1, 29.0, 26.3, 25.6, 25.5, 25.4, 22.5, 17.3, 14.4. MS (ESI); m/z: [M+H]$^+$ calcd for C$_{39}$H$_{62}$ClN$_4$O$_6$S: 749.4, found 749.2.

(2S,4R)-4-hydroxy-1-((S)-2-(6-((5-(((6-iodohexyl)oxy)pentyl)oxy)hexanamido)-3,3-dimethylbutanoyl)-N-(4-(4-methylthiazol-5-yl)benzyl)pyrrolidine-2-carboxamide

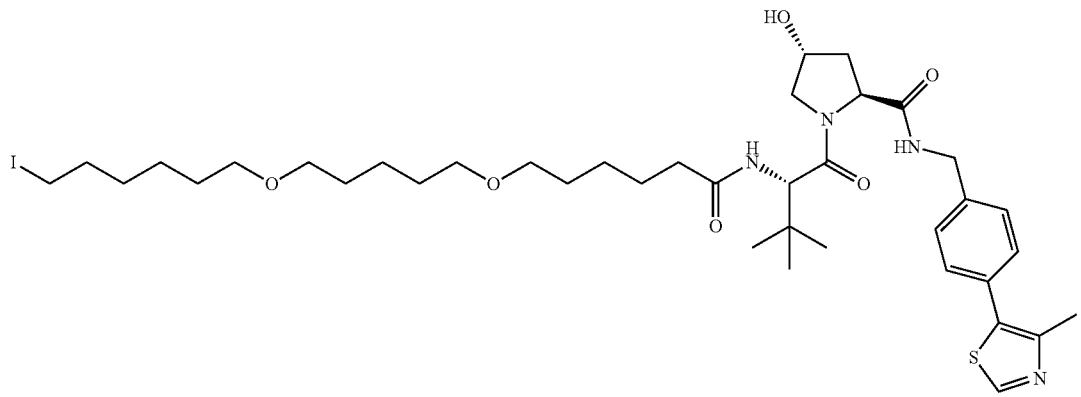 [SMILES: Cc1ncsc1-c1ccc(CNC(=O)[C@@H]2C[C@@H](O)CN2C(=O)[C@@H](NC(=O)CCCCCOCCCCCOCCCCCCI)C(C)(C)C)cc1]

Yield (87%); $^1$H NMR (500 MHz, CD$_3$OD) δ 8.87 (s, 1H), 7.45 (d, J=7.8 Hz, 2H), 7.41 (d, J=7.8 Hz, 2H), 4.84 (s, 2H), 4.65-4.62 (m, 1H), 4.58-4.49 (m, 3H), 4.37-4.43 (m, 1H), 3.90 (d, J=11.0 Hz, 1H), 3.80 (dd, J=11.0 Hz, J=3.8 Hz, 1H), 3.43-3.38 (m, 6H), 3.22 (t, J=7.0 Hz, 2H), 2.47 (s, 3H), 2.32-2.19 (m, 3H), 2.11-2.06 (m, 1H), 1.82-1.77 (m, 2H), 1.65-1.54 (m, 10H), 1.47-1.35 (m, 8H), 1.03 (s, 9H). MS (ESI); m/z: [M+H]$^+$ calcd for C$_{39}$H$_{62}$IN$_4$O$_6$S: 841.3, found 841.0.

N-(2-chloro-6-methylphenyl)-2-((6-(4-(6-((5-((6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexyl)oxy)pentyl)oxy)hexyl)piperazin-1-yl)-2-methylpyrimidin-4-yl)amino)thiazole-5-carboxamide: DAS-6-5-6-VHL

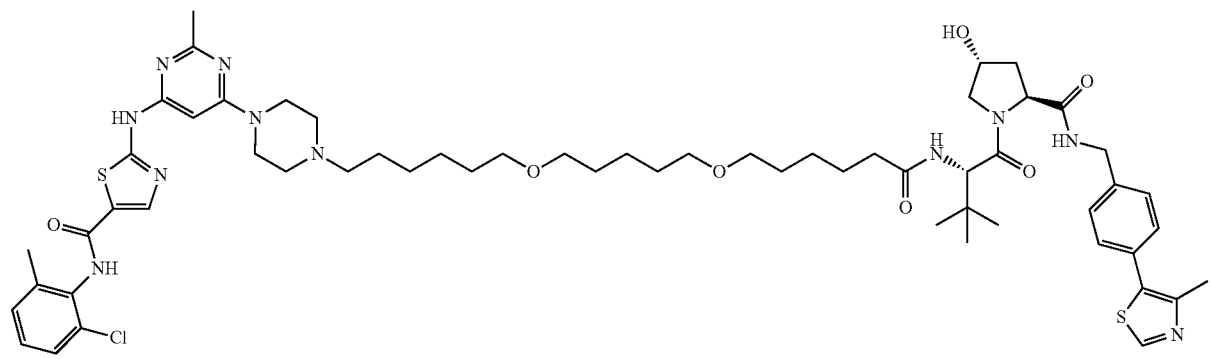

Yield (54%); $^1$H NMR (500 MHz, CD$_3$OD/CDCl$_3$) δ 8.55 (s, 1H), 7.91 (s, 1H), 7.22-7.14 (m, 4H), 7.06-6.99 (m, 2H), 6.91 (d, J=9.3 Hz, 1H), 5.78 (s, 1H), 4.43-4.34 (m, 4H), 4.20 (dd, J=15.0 Hz, J=4.9 Hz, 1H), 3.77 (d, J=11.0 Hz, 1H), 3.55 (dd, J=11.0 Hz, J=3.8 Hz, 1H), 3.47 (bs, 4H), 3.28-3.21 (m, 8H), 2.39 (bs, 4H), 2.33 (bs, 6H), 2.25-2.22 (m, 2H), 2.16 (s, 3H), 2.11-2.02 (m, 4H), 1.49-1.37 (m, 12H), 1.26-1.17 (m, 8H), 0.83 (s, 9H). $^{13}$C NMR (151 MHz, CD$_3$OD/CDCl$_3$) δ 174.2, 174.1, 172.1, 171.1, 166.3, 163.9, 163.0, 161.4, 156.9, 150.9, 147.8, 140.5, 138.7, 138.3, 132.6, 132.5, 132.0, 130.3, 129.3, 128.9, 128.1, 127.7, 127.0, 125.5, 83.0, 70.8, 70.7, 70.6, 69.7, 59.2, 59.6, 57.5, 57.4, 56.9, 52.6, 49.5, 43.6, 42.8, 36.9, 36.0, 35.5, 29.4, 29.3, 29.2, 27.3, 26.3, 26.2, 25.9, 25.7, 25.4, 25.2, 22.6, 18.4, 15.4. MS (ESI); m/z: [M+H]$^+$ calcd for C$_{59}$H$_{83}$ClN$_{11}$O$_7$S$_2$: 1156.5, found 1156.2.

(2S,4R)-1-((S)-3,3-dimethyl-2-(6-((5-(((6-(4-(4-((4-methyl-3-((4-(pyridin-3-yl)pyrimidin-2-yl)amino)phenyl)carbamoyl)benzyl)piperazin-1-yl)hexyl)oxy)pentyl)oxy)hexanamido) butanoyl)-4-hydroxy-N-(4-(4-methylthiazol-5-yl)benzyl)pyrrolidine-2-carboxamide: IMA-6-5-6-VHL

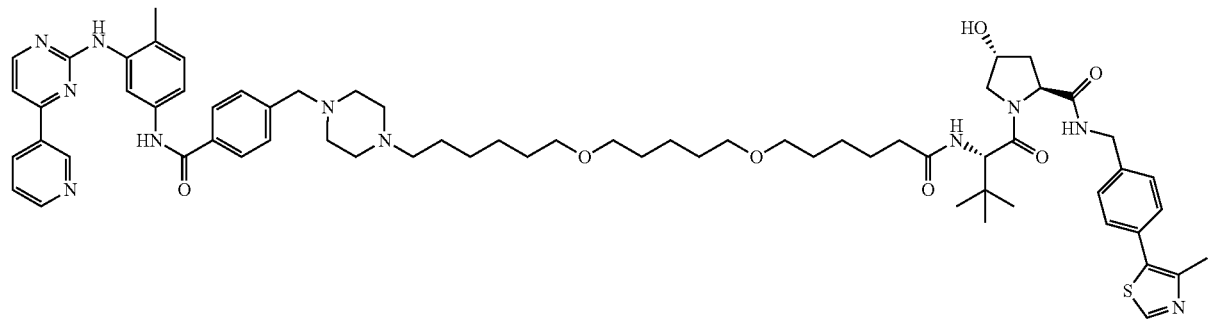 [SMILES: Cc1ccc(NC(=O)c2ccc(CN3CCN(CCCCCCOCCCCCOCCCCCC(=O)N[C@H](C(=O)N4C[C@H](O)C[C@H]4C(=O)NCc4ccc(-c5scnc5C)cc4)C(C)(C)C)CC3)cc2)cc1Nc1nccc(-c2cccnc2)n1]

Yield (47%); $^1$H NMR (500 MHz, CDCl$_3$) δ 9.23 (d, J=2.0 Hz, 1H), 8.69 (d, J=3.4 Hz, 1H), 8.67 (s, 1H), 8.56 (s, 1H), 8.52-8.48 (m, 2H), 8.08 (s, 1H), 7.84 (d, J=8.1 Hz, 2H), 7.45-7.40 (m, 3H), 7.35-7.29 (m, 6H), 7.21-7.17 (m, 2H), 7.14 (s, 1H), 6.17 (d, J=8.6 Hz, 1H), 4.70 (t, J=7.8 Hz, 1H), 4.58-4.49 (m, 3H), 4.31 (d, J=14.9 Hz, J=5.1 Hz, 1H), 4.03 (d, J=11.2 Hz, 1H), 3.59-3.55 (m, 5H), 3.39-3.34 (m, 8H), 2.60-2.44 (m, 10H), 2.40-2.34 (m, 5H), 2.20-2.08 (m, 4H), 1.62-1.43 (m, 12H), 1.40-1.29 (m, 8H), 0.91 (s, 9H). $^{13}$C NMR (151 MHz, CDCl$_3$) δ 173.5, 171.9, 170.7, 165.5, 162.7, 160.6, 159.0, 151.4, 150.3, 148.46, 148.44, 142.3, 138.0, 137.7, 136.6, 134.9, 133.9, 132.7, 131.6, 130.9, 130.8, 129.5, 129.3, 128.1, 127.0, 124.6, 123.7, 115.5, 113.5, 108.3, 70.8, 70.76, 70.71, 70.5, 69.9, 62.5, 58.6, 57.4, 56.7, 53.1, 43.2, 36.4, 35.8, 34.9, 29.6, 29.54, 29.51, 29.3, 27.4, 26.4, 26.1, 25.8, 25.3, 22.8, 17.7, 16.0. MS (ESI); m/z: [M+H]$^+$ calcd for C$_{67}$H$_{90}$N$_{11}$O$_7$S: 1192.6, found 1192.2.

Synthesis of Bosutinib with VHL Ligand

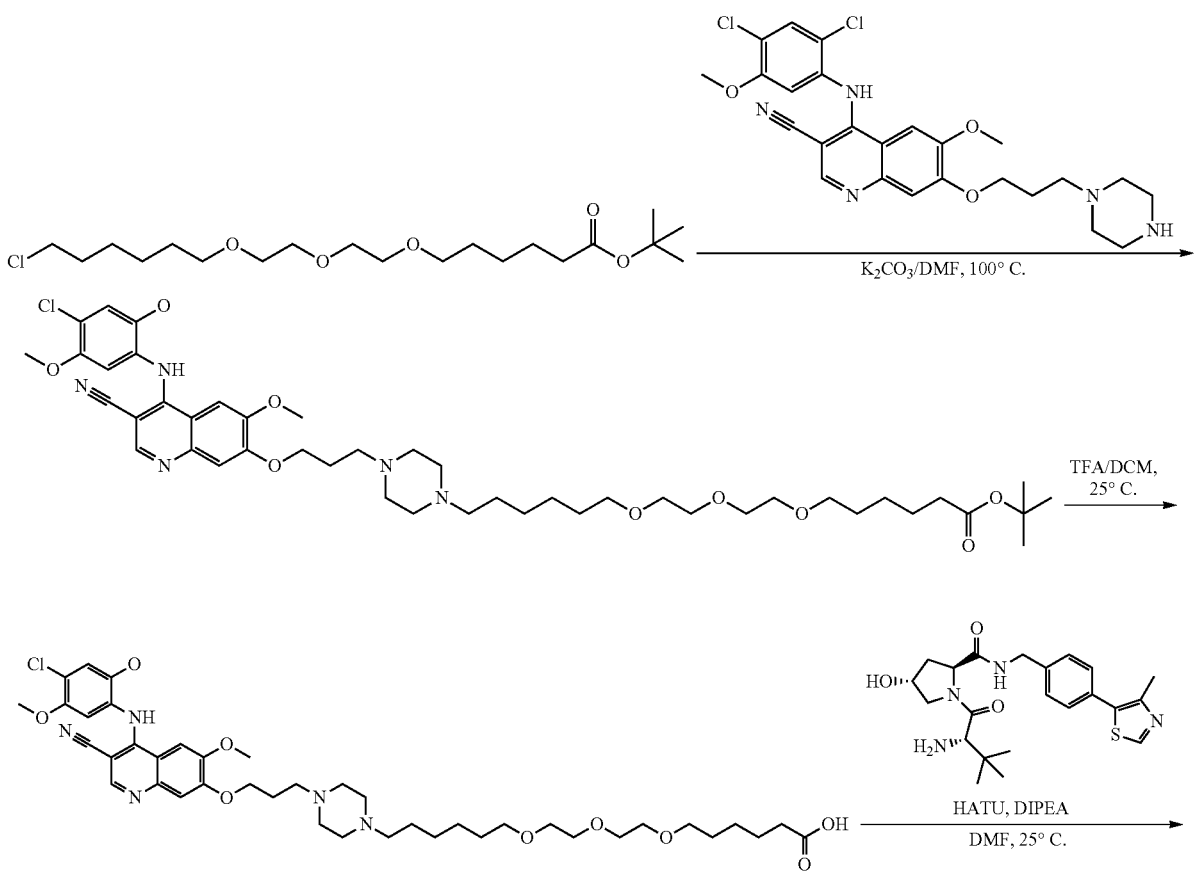

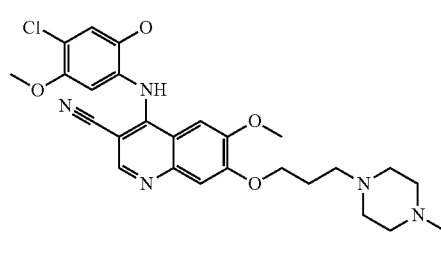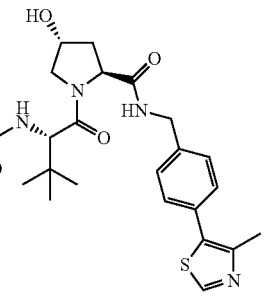

tert-butyl-6-(2-(2-((6-(4-(3-((3-cyano-4-((2, 4-di-chloro-5-methoxyphenyl)amino)-6-methoxyquino-lin-7-yl)oxy)propyl)piperazin-1-yl)hexyl)oxy)ethoxy)ethoxy)hexanoate

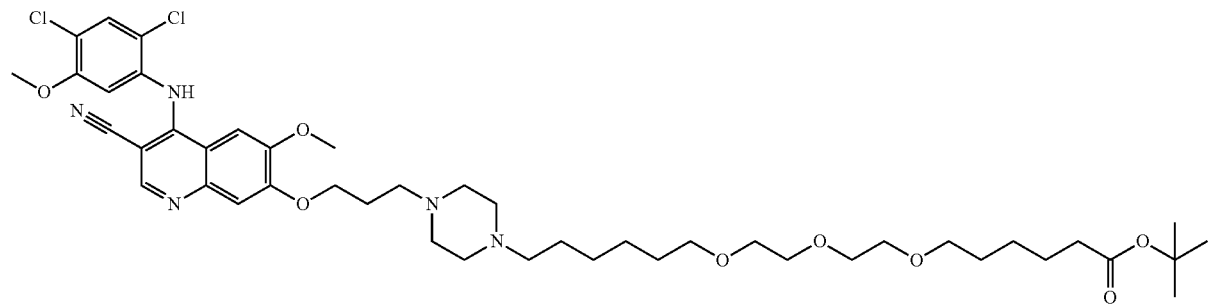 [SMILES: COc1cc(Nc2c(C#N)cnc3cc(OCCCN4CCN(CCCCCCOCCOCCOCCCCCC(=O)OC(C)(C)C)CC4)c(OC)cc23)c(Cl)cc1Cl]

To a solution of 4-(2,4-dichloro-5-methoxy-anilino)-6-methoxy-7-(3-piperazin-1-ylpropoxy)quinoline-3-carbonitrile (40 mg, 0.08 mmol) and K$_2$CO$_3$ (32.11 mg, 0.23 mmol) in DMF (2 ml) was added tert-butyl 6-[2-[2-(6-chloro-hexoxy)ethoxy]ethoxy]hexanoate (36.71 mg, 0.09 mmol) and the resulting solution stirred for 16 h at 100° C. Then the mixture was cooled down to rt. After filtration, the solvent was evaporated and the residue subjected to Prep TLC purification (MeOH/DCM:95/5) to give 11 mg (16.2%) of tert-butyl 6-[2-[2-[6-[4-[3-[[3-cyano-4-(2,4-dichloro-5-methoxy-anilino)-6-methoxy-7-quinolyl]oxy]propyl]piperazin-1-yl]hexoxy]ethoxy]ethoxy]hexanoate as a yellow oil. $^1$H NMR (500 MHz, CDCl$_3$/TMS) δ 8.69 (s, 1H), 7.48 (s, 1H), 7.42 (s, 1H), 6.92 (s, 1H), 6.79 (s, 1H), 6.48 (s, 1H), 4.25 (t, J=6.4 Hz, 2H), 3.77 (s, 3H), 3.66 (s, 3H), 3.65-3.61 (m, 4H), 3.58-3.55 (m, 4H), 346-3.41 (m, 4H), 2.62-2.42 (m, 12H), 2.19 (t, J=7.4 Hz, 2H), 2.13-2.08 (m, 2H), 1.61-1.54 (m, 8H), 1.43 (s, 9H), 1.40-1.28 (m, 6H). $^{13}$C NMR (151 MHz, CDCl$_3$/TMS) δ 173.1, 154.3, 153.9, 150.3, 149.8, 147.7, 147.5, 136.9, 130.5, 118.4, 117.2, 116.4, 114.8, 109.9, 105.4, 101.1, 94.2, 79.9, 71.3, 71.2, 70.61, 70.60, 70.1, 67.6, 58.4, 56.5, 56.1, 54.7, 52.9, 35.5, 29.5, 29.3, 28.1, 27.3, 26.1, 25.9, 25.6, 24.9. MS (ESI); m/z: [M+H]$^+$ calcd for C$_{45}$H$_{66}$C$_{12}$N$_5$O$_8$: 874.4, found 874.2.

6-(2-(2-((6-(4-(3-((3-cyano-4-((2,4-dichloro-5-methoxyphenyl)amino)-6-methoxyquinolin-7-yl)oxy)propyl)piperazin-1-yl)hexyl)oxy)ethoxy)ethoxy)hexanoic acid

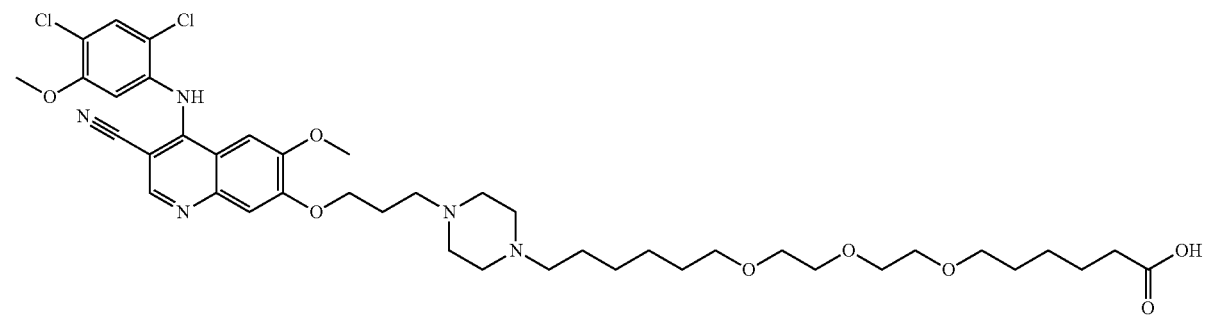 [SMILES: COc1cc(Nc2c(C#N)cnc3cc(OCCCN4CCN(CCCCCCOCCOCCOCCCCCC(=O)O)CC4)c(OC)cc23)c(Cl)cc1Cl]

A solution of tert-butyl-6-(2-(2-((6-(4-(3-((3-cyano-4-((2,4-dichloro-5-methoxyphenyl)amino)-6-methoxyquinolin-7-yl)oxy)propyl)piperazin-1-yl)hexyl)oxy)ethoxy)ethoxy)hexanoate (12 mg, 0.01 mmol) in DCM/TF (1 mL) was stirred at room temperature for 2 h. The solvent was evaporated to give 11.23 mg (100%) of the desired product which was carried to the next step without further purification.

(2S,4R)-1-((S)-2-(tert-butyl)-22-(4-(3-((3-cyano-4-((2,4-dichloro-5-methoxyphenyl)amino)-6-methoxy-quinolin-7-yl)oxy)propyl)piperazin-1-yl)-4-oxo-10,13,16-trioxa-3-azadocosanoyl)-4-hydroxy-N-(4-(4-methylthiazol-5-yl)benzyl)pyrrolidine-2-carboxamide: BOS-6-2-2-6-VHL

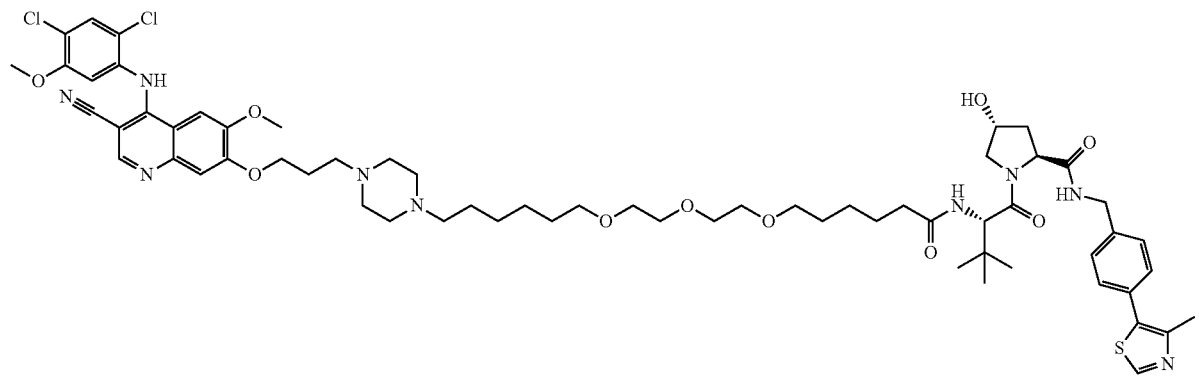

To a solution of 6-[2-[2-[6-[4-[3-[[3-cyano-4-(2,4-dichloro-5-methoxy-anilino)-6-methoxy-7-quinolyl]oxy]propyl]piperazin-1-yl]hexoxy]ethoxy]ethoxy] hexanoic acid (11 mg, 0.01 mmol) in DMF (1 mL) was added HATU (10.22 mg, 0.03 mmol) and the resulting solution stirred for 10 minutes at rt, after which ((2S,4R)-1-[(2S)-2-amino-3,3-dimethyl-butanoyl]-4-hydroxy-N-[[4-(4-methylthiazol-5-yl)phenyl] methyl]pyrrolidine-2-carboxamide; hydrochloride (6.27 mg, 0.01 mmol) and DIEA (0.01 ml, 0.07 mmol) were added respectively. The resulting mixture was stirred at room temperature for 16 h at rt. The product was extracted twice with Ac$_2$O then purified by Prep TLC DCM/(MeOH with 2% ammonia) 95:5 to give 7.9 mg (47.8%) of the desired product as a yellow oil. $^1$H NMR (500 MHz, CDCl$_3$) δ 8.69 (s, 1H), 8.68 (s, 1H), 7.49 (s, 1H), 7.43 (s, 1H), 7.39-7.32 (m, 4H), 7.29 (t, J=6.4 Hz, 1H), 6.95 (s, 1H), 6.86 (s, 1H), 6.52 (s, 1H), 6.10 (d, J=8.3 Hz, 1H), 4.72 (t, J=7.8 Hz, 1H), 4.60-4.49 (m, 3H), 4.34 (dd, J=14.0 Hz, J=4.9 Hz, 1H), 4.26 (t, J=6.4 Hz, 2H), 4.07 (d, J=11.2 Hz, 1H), 3.79 (s, 3H), 3.70-3.55 (m, 22H), 3.45-3.42 (m, 4H), 2.75-2.62 (m, 8H), 2.57-2.53 (m, 2H), 2.51 (s, 3H), 2.21-2.11 (m, 5H), 1.62-1.53 (m, 8H), 1.37-1.29 (m, 6H), 0.92 (s, 9H). $^{13}$C NMR (151 MHz, CDCl$_3$) δ 173.6, 171.9, 170.6, 154.3, 153.8, 150.3, 150.2, 149.8, 148.5, 147.6, 147.5, 138.0, 136.9, 132.9, 131.5, 130.9, 130.5, 129.6, 129.5, 128.3, 128.1, 118.5, 117.8, 116.4, 114.8, 109.8, 105.7, 101.1, 93.9, 71.2, 71.6, 70.6, 70.3, 70.0, 69.9, 67.4, 63.9, 58.4, 58.3, 57.4, 56.7, 56.5, 56.1, 54.6, 52.7, 43.2, 36.4, 35.8, 34.8, 29.5, 29.2, 27.1, 26.4, 25.9, 25.8, 25.7, 25.3, 16.0. MS (ESI); m/z: [M+H]$^+$ calcd for C$_{63}$H$_{86}$Cl$_2$N$_9$O$_{10}$S: 1230.5, found 1230.1.

tert-butyl-2-(2-((6-(4-(3-((3-cyano-4-((2,4-dichloro-5-methoxyphenyl)amino)-6-methoxyquinolin-7-yl)oxy)propyl)piperazin-1-yl)hexyl)oxy) ethoxy)acetate

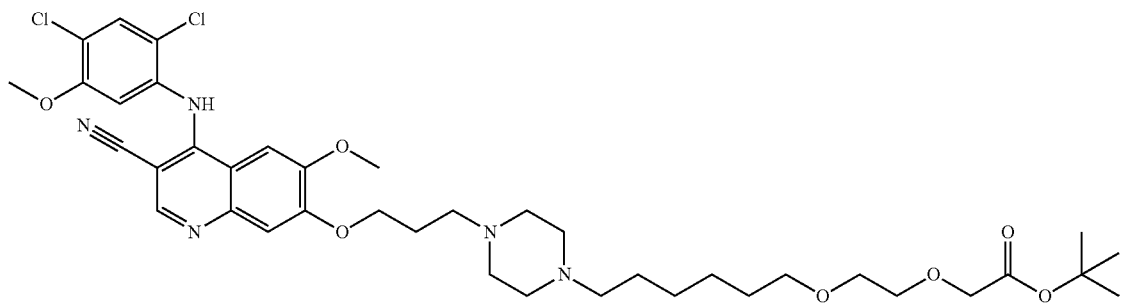 [SMILES: COc1cc(Nc2c(C#N)cnc3cc(OCCCN4CCN(CCCCCCOCCOCC(=O)OC(C)(C)C)CC4)c(OC)cc23)c(Cl)cc1Cl]

Yield (30%); ¹H NMR (500 MHz, CDCl₃) δ 8.70 (s, 1H), 7.49 (s, 1H), 7.42 (s, 1H), 6.90 (s, 1H), 6.75 (s, 1H), 6.46 (s, 1H), 4.25 (t, J=6.8 Hz, 2H), 4.02 (s, 2H), 3.77 (s, 3H), 3.71-3.67 (m, 2H), 3.66 (s, 3H), 3.62-3.58 (m, 2H), 3.45 (t, J=6.8 Hz, 2H), 2.65-2.52 (m, 12H), 2.15-2.08 (m, 2H), 1.61-1.55 (m, 2H), 1.50-1.32 (m, 15H). ¹³C NMR (151 MHz, CDCl₃) δ 169.7, 154.2, 153.9, 150.3, 149.7, 147.7, 147.4, 136.9, 130.5, 118.2, 117.0, 116.4, 114.8, 109.9, 105.2, 101.0, 99.3, 81.5, 71.4, 70.7, 70.0, 69.0, 67.7, 59.4, 56.5, 56.1, 54.8, 53.1, 53.0, 52.9, 52.8, 29.5, 28.1, 28.0, 27.4, 26.2, 26.0. MS (ESI); m/z: [M+H]⁺ calcd for $C_{39}H_{54}Cl_2N_5O_7$: 774.3, found 774.2.

(2S,4R)-1-((S)-2-(2-(2-((6-(4-(3-((3-cyano-4-((2,4-dichloro-5-methoxyphenyl)amino)-6-methoxyquinolin-7-yl)oxy)propyl)piperazin-1-yl)hexyl)oxy)ethoxy)acetamido)-3,3-dimethylbutanoyl)-4-hydroxy-N-(4-(4-methylthiazol-5-yl)benzyl)pyrrolidine-2-carboxamide: BOS-6-2-2-VHL

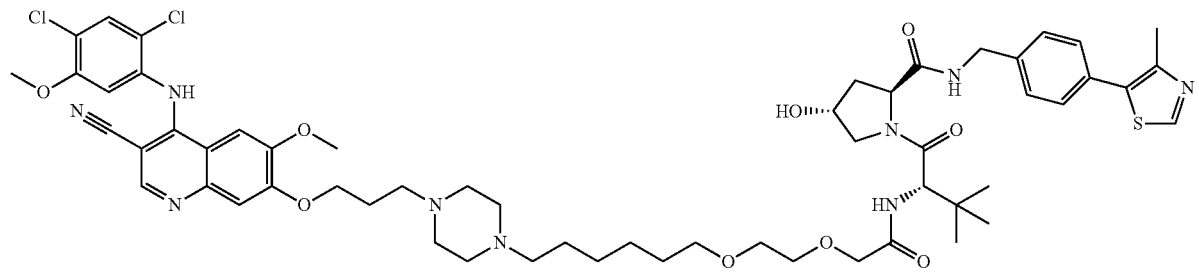 [SMILES: COc1cc(Nc2c(C#N)cnc3cc(OCCCN4CCN(CCCCCCOCCOCC(=O)N[C@H](C(=O)N5C[C@H](O)C[C@H]5C(=O)NCc5ccc(-c6scnc6C)cc5)C(C)(C)C)CC4)c(OC)cc23)c(Cl)cc1Cl]

Yield (55%); ¹H NMR (500 MHz, CD₃OD/CDCl₃) δ 8.67 (bs, 2H), 7.48 (s, 1H), 7.44 (s, 1H), 7.38-7.29 (m, 6H), 6.95 (s, 1H), 6.86 (s, 1H), 6.53 (s, 1H), 4.71 (t, J=7.8 Hz, 1H), 4.56-4.47 (m, 3H), 4.35 (dd, J=14.0 Hz, J=4.1 Hz, 1H), 4.26 (bs, 2H), 4.08-3.94 (m, 3H), 3.79 (s, 3H), 3.74-3.55 (m, 10H), 3.50-3.41 (m, 4H), 3.18-3.12 (m, 2H), 2.77-2.47 (m, 11H), 2.16-2.02 (m, 3H), 1.62-1.51 (m, 4H), 1.48-1.31 (m, 4H), 0.95 (s, 9H). ¹³C NMR (151 MHz, CD₃OD/CDCl₃) δ 171.3, 170.8, 170.5, 154.3, 153.7, 150.3, 150.2, 149.9, 148.4, 147.6, 147.5, 138.0, 136.8, 131.6, 130.9, 130.5, 129.5, 128.1, 120.6, 118.5, 117.5, 116.5, 114.7, 109.8, 105.9, 101.1, 71.3, 71.1, 70.3, 70.1, 69.9, 67.4, 58.5, 58.3, 57.2, 56.6, 56.5, 56.1, 55.5, 54.6, 52.9, 50.8, 43.5, 43.2, 35.9, 34.8, 29.2, 26.4, 25.9, 18.0, 16.1, 12.6. MS (ESI); m/z: [M+H]⁺ calcd for $C_{57}H_{74}Cl_2N_9O_9S$: 1130.4, found 1130.1.

tert-butyl-24-(4-(3-((3-cyano-4-((2, 4-dichloro-5-methoxyphenyl)amino)-6-methoxyquinolin-7-yl)oxy)propyl)piperazin-1-yl)-3,6,9,12,15,18-hexaoxa-tetracosanoate

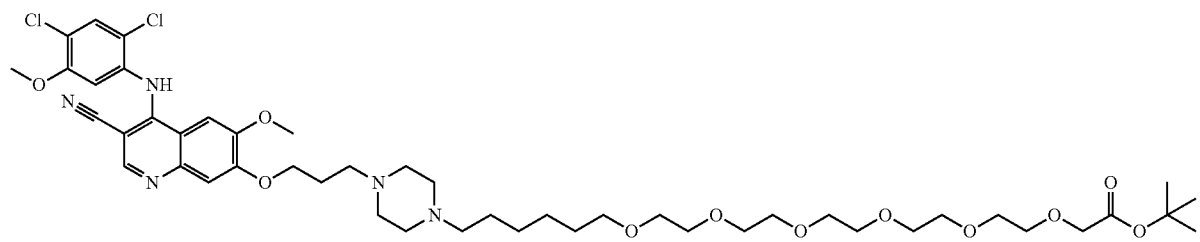 [SMILES: COc1cc(Nc2c(C#N)cnc3cc(OCCCN4CCN(CCCCCCOCCOCCOCCOCCOCCOCC(=O)OC(C)(C)C)CC4)c(OC)cc23)c(Cl)cc1Cl]

Yield (41%); $^1$H NMR (500 MHz, CDCl$_3$) δ 8.67 (s, 1H), 7.47 (s, 1H), 7.41 (s, 1H), 6.95 (s, 1H), 6.88 (s, 1H), 6.51 (s, 1H), 4.24 (t, J=6.8 Hz, 2H), 3.99 (s, 2H), 3.78 (s, 3H), 3.70-3.60 (m, 21H), 3.57-3.54 (m, 2H), 3.42 (t, J=6.8 Hz, 2H), 2.58-2.45 (m, 10H), 2.33-2.30 (m, 2H), 2.12-2.07 (m, 2H), 1.58-1.53 (m, 2H), 1.49-1.43 (m, 11H), 1.35-1.28 (m, 4H). $^{13}$C NMR (151 MHz, CDCl$_3$) δ 169.6, 154.2, 153.9, 150.3, 149.8, 147.6, 136.9, 130.5, 118.5, 117.5, 116.5, 114.7, 109.8, 105.8, 101.1, 93.8, 81.5, 71.4, 70.7, 70.6, 70.54, 70.52, 70.51, 70.0, 68.9, 67.7, 58.7, 56.5, 56.1, 54.8, 53.2, 53.1, 29.5, 28.1, 27.4, 26.7, 26.2, 26.0. MS (ESI); m/z: [M+H]$^+$ calcd for C$_{47}$H$_{70}$Cl$_2$N$_5$O$_{11}$: 950.4, found 950.2.

(2S,4R)-1-((S)-2-(tert-butyl)-27-(4-(3-((3-cyano-4-((2,4-dichloro-5-methoxyphenyl)amino)-6-methoxyquinolin-7-yl)oxy)propyl)piperazin-1-yl)-4-oxo-6,9,12,15,18,21-hexaoxa-3-azaheptacosanoyl)-4-hydroxy-N-(4-(4-methylthiazol-5-yl)benzyl)pyrrolidine-2-carboxamide: BOS-6-2-2-2-2-2-2-VHL

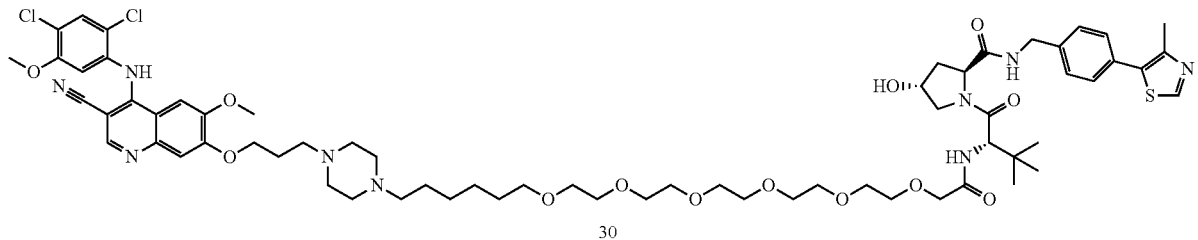

Yield (74%); $^1$H NMR (500 MHz, CD$_3$OD/CDCl$_3$) δ 8.66 (s, 1H), 8.62 (s, 1H), 7.47-7.42 (m, 2H), 7.38 (s, 1H), 7.35-7.30 (m, 4H), 7.01 (s, 1H), 6.57 (s, 1H), 4.68 (t, J=7.8 Hz, 1H), 4.54-4.49 (m, 3H), 4.35 (dd, J=14.0 Hz, J=4.9 Hz, 1H), 4.23 (t, J=5.8 Hz, 2H), 4.03-3.94 (m, 3H), 3.74 (s, 3H), 3.69 (s, 3H), 368-350 (m, 20H), 3.41 (t, J=6.8 Hz, 2H), 3.11-3.07 (m, 1H), 2.62-2.37 (m, 17H), 2.16-2.08 (m, 3H), 1.57-1.49 (m, 4H), 1.40-1.33 (m, 4H), 0.94 (s, 9H). $^{13}$C NMR (151 MHz, CD$_3$OD/CDCl$_3$) δ 171.2, 170.9, 170.5, 154.3, 153.7, 150.4, 150.2, 149.9, 148.3, 147.9, 147.2, 138.2, 136.9, 131.7, 130.7, 130.5, 129.4, 128.0, 118.9, 118.3, 116.5, 114.5, 109.6, 106.7, 101.1, 92.9, 71.3, 70.9, 70.43, 70.40, 70.36, 70.33, 70.30, 70.2, 69.9, 69.8, 67.5, 58.7, 58.4, 57.0, 56.8, 56.6, 56.1, 54.9, 54.7, 52.8, 52.5, 50.6, 43.1, 43.0, 36.3, 35.3, 29.3, 26.3, 25.8, 17.9, 15.9, 12.7. MS (ESI); m/z: [M+H]$^+$ calcd for C$_{65}$H$_{90}$Cl$_2$N$_9$O$_{13}$S: 1306.6, found 1306.4.

tert-butyl-6-((5-((6-(4-(3-((3-cyano-4-((2,4-dichloro-5-methoxyphenyl)amino)-6-methoxyquinolin-7-yl)oxy)propyl)piperazin-1-yl)hexyl)oxy)pentyl)oxy)hexanoate

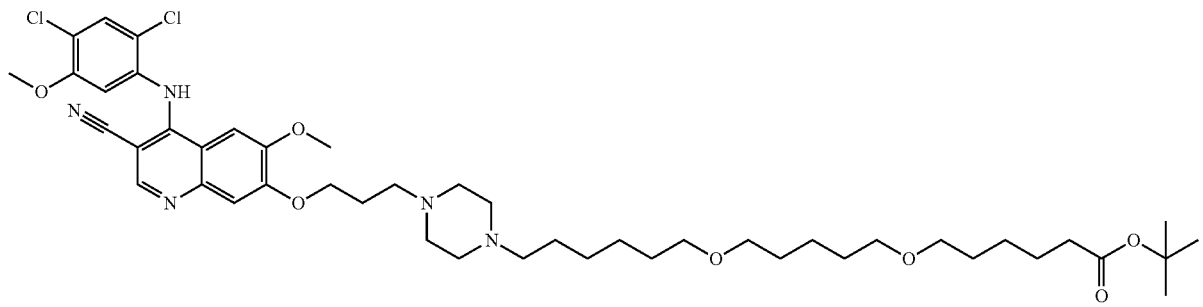 [SMILES: COc1cc(Nc2c(C#N)cnc3cc(OCCCN4CCN(CCCCCCOCCCCCOCCCCCC(=O)OC(C)(C)C)CC4)c(OC)cc23)c(Cl)cc1Cl]

113

Yield (68%); $^1$H NMR (500 MHz, CDCl$_3$) δ 8.66 (s, 1H), 7.48 (s, 1H), 7.41 (s, 1H), 6.97 (bs, 2H), 6.52 (s, 1H), 4.24 (t, J=5.8 Hz, 2H), 3.78 (s, 3H), 3.68 (s, 3H), 3.40-3.35 (m, 8H), 2.82-2.66 (m, 12H), 2.20 (t, J=7.8 Hz, 2H), 2.11 (bs, 2H), 1.71-1.50 (m, 12H), 1.43 (s, 9H), 1.40-1.30 (m, 8H). $^{13}$C NMR (151 MHz, CDCl$_3$) δ 173.2, 154.3, 153.6, 150.2, 149.9, 147.7, 147.4, 136.8, 130.5, 118.7, 117.7, 116.4, 114.7, 109.8, 106.1, 101.1, 93.7, 79.9, 70.8, 70.7, 70.6, 70.5, 68.9, 57.4, 56.5, 56.1, 54.1, 51.9, 50.6, 35.5, 29.6, 29.5, 29.48, 29.4, 28.1, 26.7, 25.8, 25.6, 24.9, 22.8. MS (ESI); m/z: [M+H]$^+$ calcd for C$_{46}$H$_{68}$Cl$_2$N$_5$O$_7$: 872.4, found 872.2.

114

(2S,4R)-1-((S)-2-(6-((5-((6-(4-(3-((3-cyano-4-((2,4-dichloro-5-methoxyphenyl)amino)-6-methoxyquinolin-7-yl)oxy)propyl)piperazin-1-yl)hexyl)oxy)pentyl)oxy)hexanamido)-3,3-dimethylbutanoyl)-4-hydroxy-N-(4-(4-methylthiazol-5-yl)benzyl)pyrrolidine-2-carboxamide: BOS-6-5-6-VHL

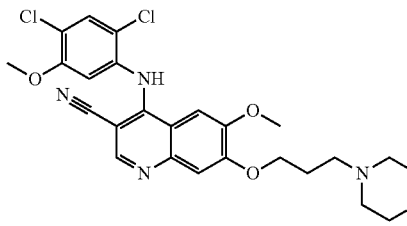

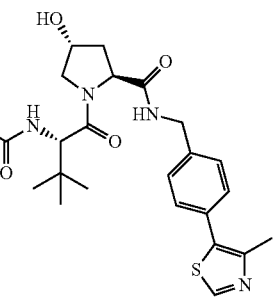

Yield (38%); $^1$H NMR (500 MHz, CDCl$_3$/TMS) δ 8.69 (s, 1H), 8.68 (s, 1H), 7.49 (s, 1H), 7.42 (s, 1H), 7.39-7.32 (m, 4H), 7.29 (t, J=6.4 Hz, 1H), 6.95 (s, 1H), 6.87 (s, 1H), 6.51 (s, 1H), 6.09 (d, J=8.8 Hz, 1H), 4.72 (t, J=7.8 Hz, 1H), 4.59-4.49 (m, 3H), 4.33 (dd, J=14.0 Hz, J=4.9 Hz, 1H), 4.26 (t, J=7.4 Hz, 2H), 4.07 (d, J=11.2 Hz, 1H), 3.79 (s, 3H), 3.74-3.59 (m, 12H), 3.40-3.36 (m, 6H), 2.75-2.67 (m, 8H), 2.57-2.53 (m, 2H), 2.51 (s, 3H), 2.21-2.18 (m, 2H), 2.16-2.08 (m, 3H), 1.62-1.52 (m, 12H), 1.41-1.32 (m, 8H), 0.92 (s, 9H). $^{13}$C NMR (151 MHz, CDCl$_3$/TMS) δ 171.6, 171.9, 170.6, 154.3, 153.7, 150.3, 150.2, 149.8, 148.5, 147.6, 147.5, 138.0, 136.9, 131.6, 130.9, 130.5, 129.5, 128.1, 118.6, 117.5, 116.4, 114.8, 109.8, 105.8, 101.1, 93.9, 70.78, 70.76, 70.7, 70.5, 69.9, 67.4, 58.4, 58.2, 57.4, 56.6, 56.5, 56.1, 54.5, 52.7, 43.2, 36.4, 35.8, 34.8, 29.7, 29.6, 29.53, 29.51, 29.3, 27.1, 26.4, 25.9, 25.8, 25.3, 22.8, 16.0. MS (ESI); m/z: [M+H]$^+$ calcd for C$_{64}$H$_{88}$Cl$_2$N$_9$O$_9$S: 1228.6, found 1229.0.

Synthesis of Dasatinib/Bosutinib/Imatinib with Pomalidomide

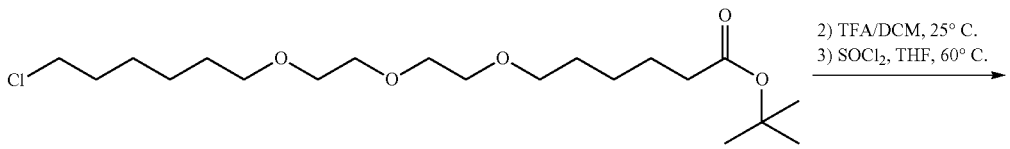

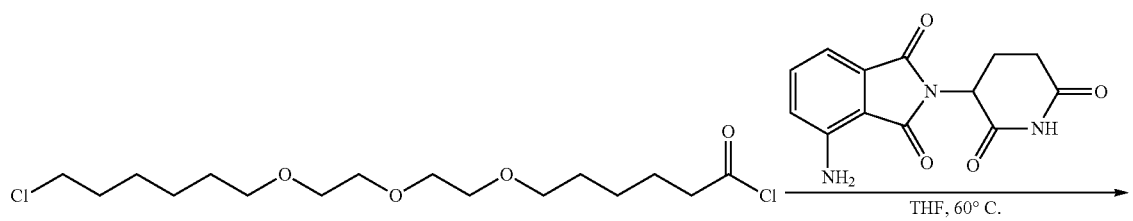

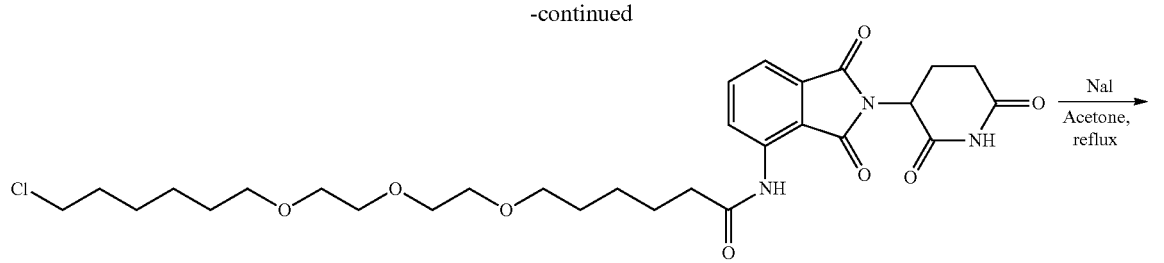

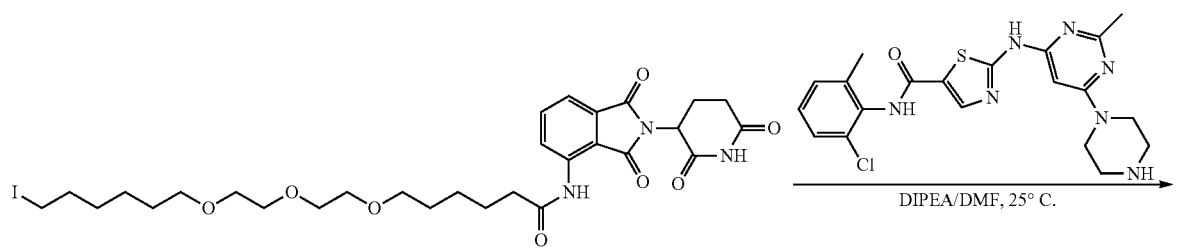

40

6-(2-(2-((6-chlorohexyl)oxy)ethoxy)ethoxy)-N-(2-(2,6-dioxopiperidin-3-yl)-1,3-dioxoisoindolin-4-yl)hexanamide

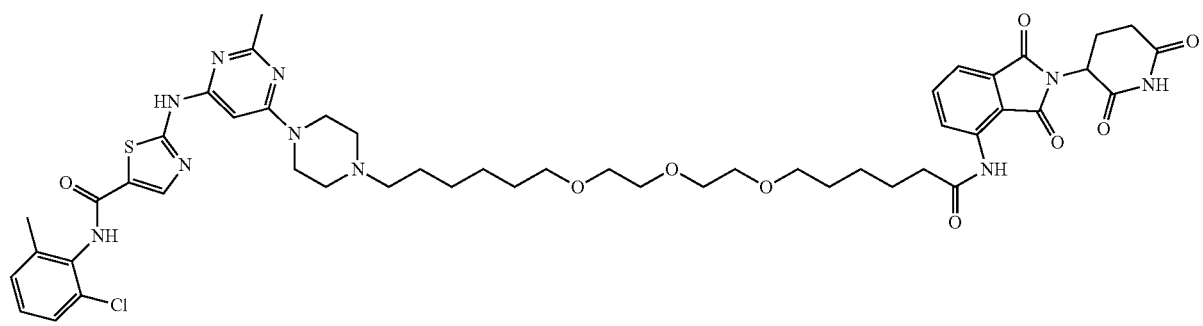

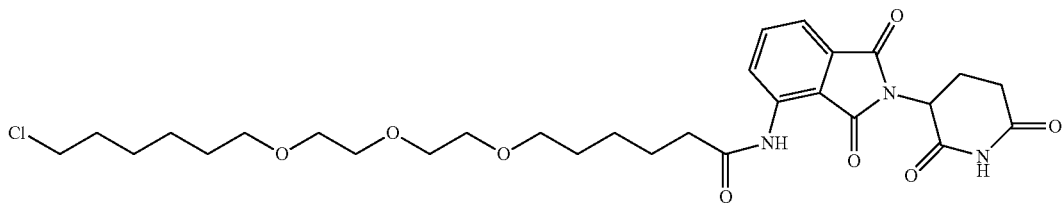 [SMILES: O=C1CCC(N2C(=O)c3cccc(NC(=O)CCCCCOCCOCCOCCCCCCCl)c3C2=O)C(=O)N1]

6-[2-[2-(6-chlorohexoxy)ethoxy]ethoxy]hexanoyl chloride (110 mg, 0.31 mmol) was dissolved in THF (2 ml). To this solution was added 4-amino-2-(2,6-dioxo-3-piperidyl)isoindoline-1,3-dione (84.12 mg, 0.31 mmol). The resulting suspension was heated to reflux for 4 hours. The solvent was evaporated in vacuo and the resulting solid was purified by flash chromatography (50/50 to 0/100 hexane/ethyl acetate) to give a light yellow solid 157 mg (85.8%) of the desired product. $^1$H NMR (500 MHz, Chloroform-d) δ 9.41 (s, 1H), 8.82 (d, J=7.8 Hz, 1H), 8.45 (s, 1H), 7.70 (t, J=7.8 Hz, 1H), 7.54 (d, J=7.8 Hz, 1H), 4.96 (dd, J=12.0 Hz, J=6.5 Hz, 1H), 3.66-3.61 (m, 4H), 3.60-3.57 (m, 4H), 3.52 (t, J=6.3 Hz, 2H), 3.50-3.43 (m, 4H), 2.91 (d, J=13.6 Hz, 1H), 2.85-2.72 (m, 2H), 2.46 (t, J=7.3 Hz, 2H), 2.21-2.12 (m, 1H), 1.80-1.73 (m, 4H), 1.67-1.55 (m, 4H), 1.50-1.34 (m, 6H). $^{13}$C NMR (151 MHz, Chloroform-d) δ 172.2, 170.9, 169.1, 167.9, 166.7, 137.8, 136.4, 131.1, 125.2, 118.4, 115.2, 71.2, 71.0, 70.6, 70.0, 49.2, 45.0, 37.9, 32.5, 31.4, 29.4, 29.3, 26.7, 25.7, 25.4, 25.0, 22.6. MS (ESI); m/z: [M+H]$^+$ calcd for C$_{29}$H$_{41}$ClN$_3$O$_8$: 594.2, found 594.1.

N-(2-(2,6-dioxopiperidin-3-yl)-1,3-dioxoisoindolin-4-yl)-6-(2-(2-((6-iodohexyl)oxy)ethoxy) ethoxy) hexanamide

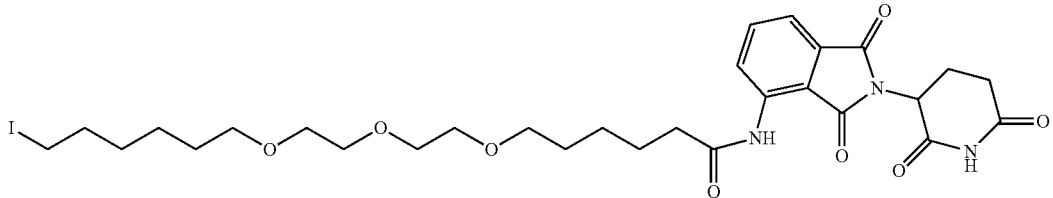 [SMILES: O=C1CCC(N2C(=O)c3cccc(NC(=O)CCCCCOCCOCCOCCCCCCI)c3C2=O)C(=O)N1]

To a solution of 6-[2-[2-(6-chlorohexoxy)ethoxy]ethoxy]-N-[2-(2,6-dioxo-3-piperidyl)-1,3-dioxo-isoindolin-4-yl] hexanamide (130 mg, 0.22 mmol) in Acetone (10 ml) was added NaI (164 mg, 1.09 mmol). The reaction mixture was stirred at reflux temperature for 24 h, then the solvent was removed under vacuum and crude product was dissolved in EtOAc (15 mL) and an aqueous solution of $Na_2SO_3$ (10%, 10 mL), the organic layer was separated, washed with water (10 mL), dried ($Na_2SO_4$) and evaporated under vacuum. The crude product was pure by NMR (>98% purity), 127 mg (83.8%) of the desired product. It was used in the next step without any further purification. $^1$H NMR (400 MHz, Chloroform-d) δ 9.41 (s, 1H), 8.82 (d, J=7.8 Hz, 1H), 8.10 (s, 1H), 7.70 (t, J=7.8 Hz, 1H), 7.55 (d, J=7.8 Hz, 1H), 4.95 (dd, J=12.0 Hz, J=6.5 Hz, 1H), 3.66-3.61 (m, 4H), 3.60-3.56 (m, 4H), 3.50-3.42 (m, 4H), 3.17 (t, J=7.0 Hz, 2H), 2.95-2.70 (m, 3H), 2.46 (t, J=7.3 Hz, 2H), 2.21-2.12 (m, 1H), 1.86-1.73 (m, 4H), 1.67-1.55 (m, 4H), 1.50-1.34 (m, 6H). MS (ESI); m/z: [M+H]$^+$ calcd for $C_{29}H_{41}IN_3O_8$: 686.2, found 686.0.

N-(2-chloro-6-methylphenyl)-2-((6-(4-(6-(2-(2-((6-((2-(2,6-dioxopiperidin-3-yl)-1,3-dioxoisoindolin-4-yl)amino)-6-oxohexyl)oxy)ethoxy)ethoxy) hexyl) piperazin-1-yl)-2-methylpyrimidin-4-yl)amino) thiazole-5-carboxamide: DAS-6-2-2-6-CRBN

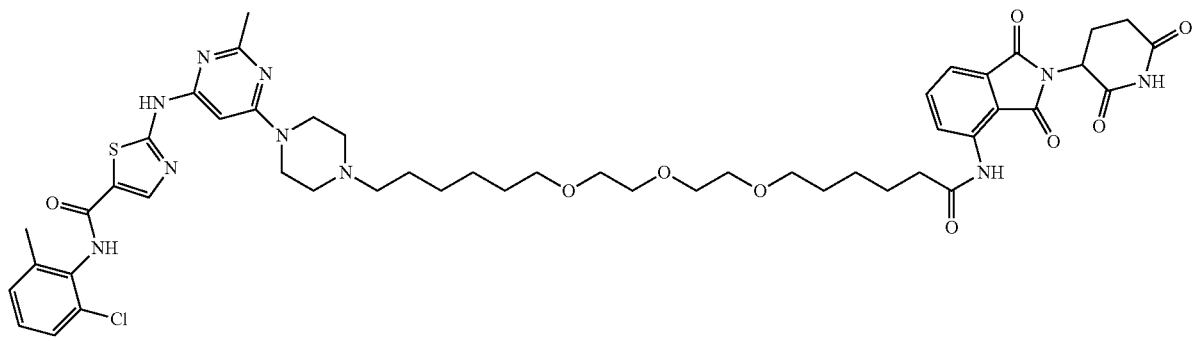 [SMILES: Cc1nc(Nc2ncc(C(=O)Nc3c(C)cccc3Cl)s2)cc(N2CCN(CCCCCCOCCOCCOCCCCCC(=O)Nc3cccc4c3C(=O)N(C3CCC(=O)NC3=O)C4=O)CC2)n1]

To a solution of N-(2-chloro-6-methyl-phenyl)-2-[(2-methyl-6-piperazin-1-yl-pyrimidin-4-yl)amino]thiazole-5-carboxamide; hydrochloride (21.02 mg, 0.04 mmol) and DIEA (99.71 µl, 0.57 mmol) in DMF (1 ml) was added N-[2-(2,6-dioxo-3-piperidyl)-1,3-dioxo-isoindolin-4-yl]-6-[2-[2-(6-iodohexoxy)ethoxy]ethoxy]hexanamide (15 mg, 0.02 mmol) and the resulting solution stirred for 16 h at 80° C. Then the mixture was cooled down to rt. The solvent was evaporated and the residue subjected to Prep TLC purification (2% ammonia in MeOH/DCM: 10/90) to give 7.4 mg (33.8%) of the desired product as a foamy yellow solid. $^1$H NMR (500 MHz, CD$_3$OD) δ 8.63 (d, J=8.3 Hz, 1H), 8.13 (s, 1H), 7.74 (t, J=8.3 Hz, 1H), 7.53 (d, J=7.3 Hz, 1H), 7.35 (d, J=7.3 Hz, 1H), 7.27-7.20 (m, 2H), 5.97 (s, 1H), 5.11 (dd, J=12.0 Hz, J=6.5 Hz, 1H), 3.66-3.53 (m, 10H), 3.51-3.45 (m, 4H), 2.90-2.83 (m, 4H), 2.78-2.68 (m, 2H), 2.58 (bs, 2H), 2.50 (t, J=7.3 Hz, 2H), 2.45 (s, 3H), 2.42 (m, 2H), 2.32 (s, 3H), 2.19-2.12 (m, 1H), 1.76 (quint, J=7.3 Hz, 2H), 1.66-1.55 (m, 6H), 1.50-1.34 (m, 7H). $^{13}$C NMR (151 MHz, CD$_3$OD) δ 173.0, 172.9, 169.9, 168.5, 166.8, 166.0, 163.7, 163.0, 161.8, 157.1, 140.7, 138.9, 136.8, 135.7, 132.9, 132.8, 131.5, 128.7, 128.1, 126.9, 125.9, 125.4, 125.2, 117.9, 116.5, 82.5, 70.7, 71.6, 70.2, 69.8, 58.2, 52.4, 49.1, 48.1, 43.3, 36.9, 30.7, 29.2, 28.9, 26.9, 25.9, 25.7, 25.4, 24.4, 24.2, 22.2, 17.3. MS (ESI); m/z: [M+H]$^+$ calcd for $C_{49}H_{62}ClN_{10}O_9S$: 1001.4, found 1001.1.

6-(2-(2-((6-(4-(3-((3-cyano-4-((2,4-dichloro-5-methoxyphenyl)amino)-6-methoxyquinolin-7-yl)oxy)propyl)piperazin-1-yl) hexyl)oxy)ethoxy)ethoxy)-N-(2-(2, 6-dioxopiperidin-3-yl)-1,3-dioxoisoindolin-4-yl)hexanamide: BOS-6-2-2-6-CRBN

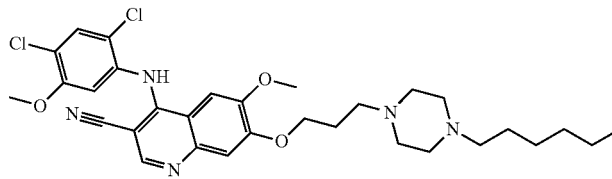

Yield (55%); ¹H NMR (500 MHz, CDCl₃) δ 9.41 (s, 1H), 8.81 (d, J=8.8 Hz, 1H), 8.71 (s, 1H), 7.70 (t, J=7.8 Hz, 1H), 7.73 (d, J=7.3 Hz, 1H), 7.48 (s, 1H), 7.45 (s, 1H), 6.93 (s, 1H), 6.82 (s, 1H), 6.49 (s, 1H), 4.92 (dd, J=12.0 Hz, J=6.5 Hz, 1H), 4.25 (t, J=6.8 Hz, 2H), 3.78 (s, 3H), 3.67 (s, 3H), 3.65-3.61 (m, 4H), 3.59-3.55 (m, 4H), 3.50-3.42 (m, 4H), 2.96-2.40 (m, 16H), 2.21-2.08 (m, 3H), 1.77 (quint, J=7.3 Hz, 2H), 1.66-1.42 (m, 9H), 1.40-1.27 (m, 4H). ¹³C NMR (151 MHz, CDCl₃) δ 172.2, 171.1, 169.2, 168.2, 166.7, 154.3, 153.9, 150.3, 149.8, 147.6, 147.5, 137.8, 136.9, 136.4, 131.1, 130.6, 125.2, 118.4, 118.3, 117.2, 116.4, 115.2, 114.8, 109.8, 105.5, 101.1, 99.1, 71.3, 70.9, 70.6, 70.1, 70.0, 67.5, 58.4, 56.5, 56.1, 54.6, 52.8, 49.3, 37.9, 31.5, 29.5, 29.3, 27.3, 26.0, 25.9, 25.7, 25.0, 22.7. MS (ESI); m/z: [M+H]⁺ calcd for $C_{54}H_{67}Cl_2N_8O_{11}$: 1073.4, found 1073.1.

4-((4-(6-(2-(2-((6-(((2-(2, 6-dioxopiperidin-3-yl)-1,3-dioxoisoindolin-4-yl)amino)-6-oxohexyl) oxy)ethoxy)ethoxy)hexyl)piperazin-1-yl)methyl)-N-(4-methyl-3-((4-(pyridin-3-yl)pyrimidin-2-yl)amino)phenyl)benzamide: IMA-6-2-2-6-CRBN

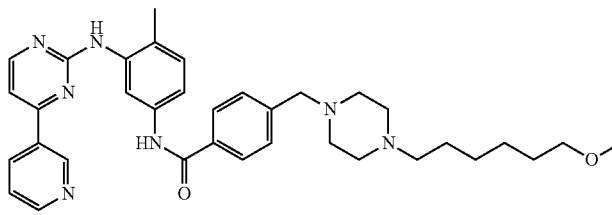

Yield (63%); ¹H NMR (500 MHz, CDCl₃) δ 9.40 (s, 1H), 9.24 (s, 1H), 8.80 (d, J=8.1 Hz, 1H), 6.69 (dd, J=4.6 Hz, J=1.5 Hz, 1H), 8.53 (s, 1H), 8.51-8.48 (m, 2H), 8.07 (s, 1H), 7.83 (d, J=8.1 Hz, 2H), 7.68 (t, J=8.3 Hz, 1H), 7.51 (d, J=7.3 Hz, 1H), 7.42-7.39 (m, 3H), 7.32 (dd, J=7.3 Hz, J=1.5 Hz, 1H), 7.20-7.15 (m, 3H), 4.92 (dd, J=12.5 Hz, J=5.4 Hz, 1H), 3.63-3.62 (m, 4H), 3.58-3.55 (m, 6H), 3.47-3.42 (m, 6H), 2.89-2.68 (m, 4H), 2.59 (bs, 4H), 2.44 (t, J=7.8 Hz, 2H), 2.41-2.37 (m, 2H), 2.33 (s, 3H), 2.16-2.12 (m, 1H), 1.76 (quint, J=7.3 Hz, 2H), 1.65-1.14 (m, 9H), 1.37-1.25 (m, 4H). ¹³C NMR (151 MHz, CDCl₃) δ 172.1, 171.3, 169.1, 168.3, 166.8, 165.4, 162.7, 160.5, 158.9, 151.4, 148.4, 142.0, 137.8, 137.7, 136.6, 136.4, 135.0, 133.9, 132.6, 131.1, 130.7, 129.4, 127.1, 125.2, 124.5, 123.7, 118.4, 115.5, 115.2, 113.4, 108.3, 71.3, 71.0, 70.6, 70.1, 70.0, 62.4, 58.4, 52.9, 52.5, 50.8, 49.3, 37.9, 31.5, 29.5, 29.3, 27.3, 26.2, 25.9, 25.7, 25.0, 22.7, 17.7. MS (ESI); m/z: [M+H]⁺ calcd for $C_{57}H_{69}N_{10}O_9$: 1037.5, found 1037.4.

2-(2-((6-chlorohexyl)oxy)ethoxy)-N-(2-(2,6-dioxopiperidin-3-yl)-1,3-dioxoisoindolin-4-yl)acetamide

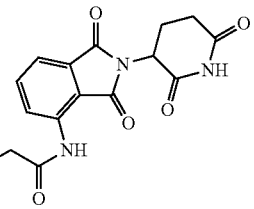

Yield (63%); ¹H NMR (500 MHz, Chloroform-d) δ 10.46 (s, 1H), 8.87 (d, J=8.3 Hz, 1H), 8.23 (s, 1H), 7.72 (t, J=8.3 Hz, 1H), 7.58 (d, J=8.3 Hz, 1H), 4.96 (dd, J=12.0 Hz, J=6.5 Hz, 1H), 4.22 (s, 2H), 3.84-3.81 (m, 2H), 3.74-3.70 (m, 2H), 3.54-3.46 (m, 4H), 2.95-2.71 (m, 3H), 2.19-2.13 (m, 1H), 1.74 (quint, J=7.3 Hz, 2H), 1.58 (quint, J=7.3 Hz, 2H), 1.46-1.32 (m, 4H). ¹³C NMR (151 MHz, Chloroform-d) δ 170.8, 169.6, 168.3, 167.8, 166.7, 136.8, 136.3, 131.1, 125.3, 118.9, 116.1, 71.6, 71.4, 71.1, 70.2, 49.2, 45.0, 32.4, 31.9, 29.4, 26.6, 25.4, 22.6. MS (ESI); m/z: [M+H]⁺ calcd for $C_{23}H_{29}ClN_3O_7$: 494.2, found 494.0.

N-(2-(2, 6-dioxopiperidin-3-yl)-1,3-dioxoisoindolin-4-yl)-2-(2-((6-iodohexyl)oxy)ethoxy) acetamide

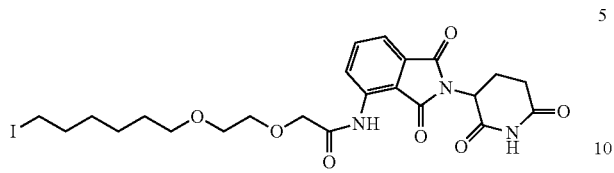

Yield (85%); $^1$H NMR (500 MHz, Chloroform-d) δ 10.45 (s, 1H), 8.86 (d, J=7.8 Hz, 1H), 8.36 (s, 1H), 7.72 (t, J=7.8 Hz, 1H), 7.57 (d, J=7.8 Hz, 1H), 4.95 (dd, J=12.0 Hz, J=6.5 Hz, 1H), 4.22 (s, 2H), 3.84-3.82 (m, 2H), 3.73-3.70 (m, 2H), 3.47 (t, J=6.3 Hz, 2H), 3.15 (t, J=6.8 Hz, 2H), 2.94-2.70 (m, 3H), 2.20-2.11 (m, 1H), 1.78 (quint, J=6.8 Hz, 2H), 1.57 (quint, J=6.8 Hz, 2H), 1.43-1.30 (m, 4H). MS (ESI); m/z: [M+H]$^+$ calcd for $C_{23}H_{29}IN_3O_7$: 586.1, found 586.0.

N-(2-chloro-6-methylphenyl)-2-((6-(4-(6-(2-(2-((2-(2, 6-dioxopiperidin-3-yl)-1,3-dioxoisoindolin-4-yl)amino)-2-oxoethoxy)ethoxy)hexyl)piperazin-1-yl)-2-methylpyrimidin-4-yl)amino)thiazole-5-carboxamide: DAS-6-2-2-CRBN

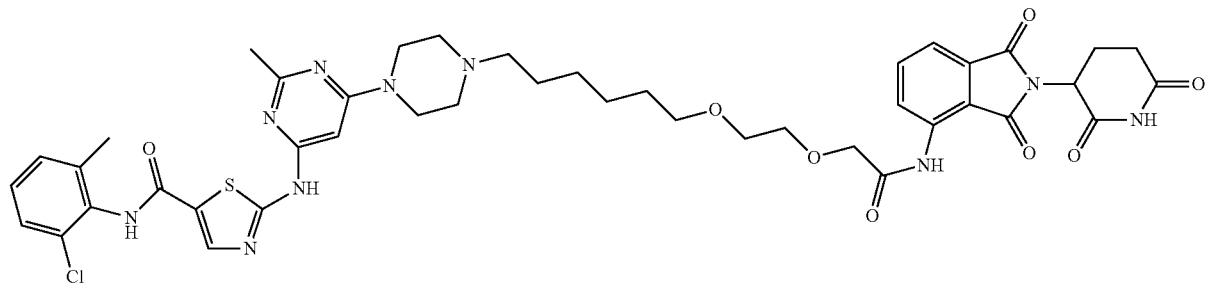 [SMILES: Cc1nc(Nc2ncc(C(=O)Nc3c(C)cccc3Cl)s2)cc(N2CCN(CCCCCCOCCOCC(=O)Nc3cccc4c3C(=O)N(C3CCC(=O)NC3=O)C4=O)CC2)n1]

Yield (57%); $^1$H NMR (500 MHz, CD$_3$OD) δ 8.88 (d, J=8.3 Hz, 1H), 8.14 (s, 1H), 7.78 (t, J=8.3 Hz, 1H), 7.57 (d, J=7.3 Hz, 1H), 7.35 (d, J=7.3 Hz, 1H), 7.27-7.20 (m, 2H), 5.98 (s, 1H), 5.12 (dd, J=12.0 Hz, J=6.5 Hz, 1H), 4.21 (s, 2H), 3.84-3.80 (m, 2H), 3.75-3.71 (m, 2H), 3.64-3.59 (m, 4H), 3.50 (t, J=6.4 Hz, 2H), 2.92-2.86 (m, 1H), 2.79-2.70 (m, 2H), 2.52-2.48 (m, 4H), 2.46 (s, 3H), 2.36-2.31 (m, 5H), 2.20-2.13 (m, 1H), 1.58-1.46 (m, 4H), 1.40-1.26 (m, 4H). $^{13}$C NMR (151 MHz, CD$_3$OD) δ 173.1, 170.2, 169.8, 168.4, 166.8, 166.0, 163.8, 163.0, 161.9, 157.1, 140.7, 138.9, 136.2, 135.8, 132.9, 132.8, 131.6, 128.7, 128.1, 126.9, 125.4, 124.5, 118.1, 116.5, 82.4, 71.3, 70.9, 70.6, 69.9, 58.1, 52.4, 49.2, 48.4, 43.3, 30.8, 29.2, 26.9, 25.9, 25.7, 24.2, 22.2, 17.3. MS (ESI); m/z: [M+H]$^+$ calcd for $C_{43}H_{50}ClN_{10}O_8S$: 901.3, found 901.1.

2-(2-((6-(4-(3-((3-cyano-4-((2,4-dichloro-5-methoxyphenyl)amino)-6-methoxyquinolin-7-yl)oxy)propyl)piperazin-1-yl) hexyl)oxy)ethoxy)-N-(2-(2, 6-dioxopiperidin-3-yl)-1,3-dioxoisoindolin-4-yl) acetamide: BOS-6-2-2-CRBN

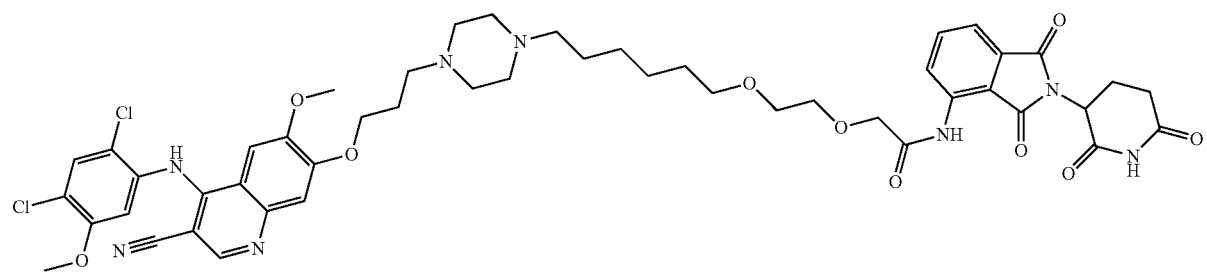 [SMILES: COc1cc(Nc2c(C#N)cnc3cc(OCCCN4CCN(CCCCCCOCCOCC(=O)Nc5cccc6c5C(=O)N(C5CCC(=O)NC5=O)C6=O)CC4)c(OC)cc23)c(Cl)cc1Cl]

123

Yield (62%); ¹H NMR (500 MHz, CDCl₃) δ 9.41 (s, 1H), 8.84 (d, J=8.3 Hz, 1H), 8.71 (s, 1H), 7.71 (t, J=7.8 Hz, 1H), 7.57 (d, J=7.3 Hz, 1H), 7.48 (s, 1H), 7.44 (s, 1H), 6.90 (s, 1H), 6.76 (s, 1H), 6.46 (s, 1H), 4.92 (dd, J=12.0 Hz, J=6.5 Hz, 1H), 4.29-4.13 (m, 4H), 3.81-3.71 (m, 7H), 3.66 (s, 3H), 3.53 (t, J=6.4 Hz, 2H), 2.96-2.84 (m, 2H), 2.76-2.44 (m, 13H), 2.17-2.04 (m, 3H), 1.64-1.42 (m, 4H), 1.40-1.26 (m, 4H). ¹³C NMR (151 MHz, CDCl₃) δ 171.8, 169.3, 168.6, 168.4, 167.0, 154.3, 153.9, 150.3, 149.7, 147.7, 147.5, 137.0, 136.7, 136.1, 131.9, 130.6, 125.3, 118.7, 118.3, 117.0, 116.4, 116.2, 114.8, 109.9, 105.4, 101.1, 94.4, 71.7, 71.5, 70.9, 69.8, 67.6, 67.3, 58.0, 56.5, 56.1, 54.6, 52.7, 49.6, 45.6, 39.4, 31.9, 29.2, 27.1, 26.1, 25.9, 22.5. MS (ESI); m/z: [M+H]⁺ calcd for $C_{48}H_{55}Cl_2N_{80}O_{10}$: 973.3, found 1073.5.

124

4-((4-(6-(2-(2-((2-(2, 6-dioxopiperidin-3-yl)-1,3-dioxoisoindolin-4-yl)amino)-2-oxoethoxy)ethoxy)hexyl)piperazin-1-yl)methyl)-N-(4-methyl-3-((4-(pyridin-3-yl)pyrimidin-2-yl)amino)phenyl)benzamide: IMA-6-2-2-CRBN

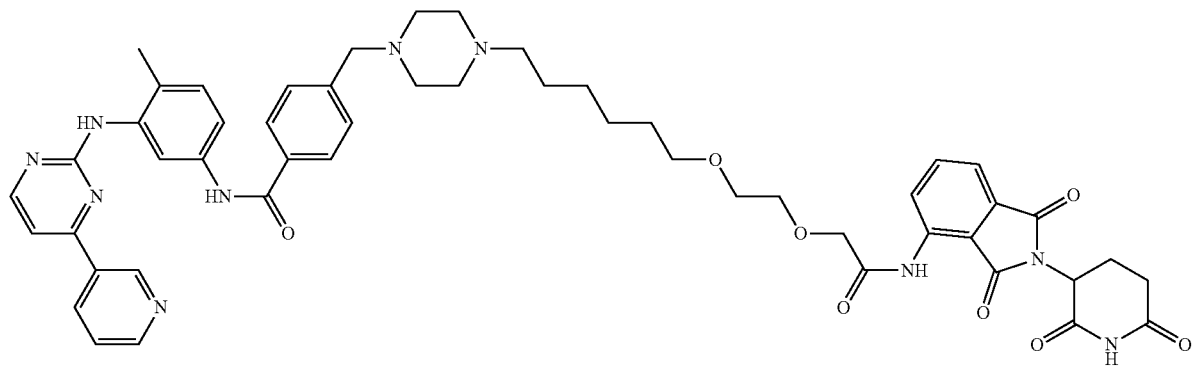 [SMILES: Cc1ccc(NC(=O)c2ccc(CN3CCN(CCCCCCOCCOCC(=O)Nc4cccc5c4C(=O)N(C4CCC(=O)NC4=O)C5=O)CC3)cc2)cc1Nc1nccc(-c2cccnc2)n1]

Yield (50%); ¹H NMR (500 MHz, CDCl₃) δ 10.41 (s, 1H), 9.23 (s, 1H), 8.85 (d, J=8.6 Hz, 1H), 8.70 (dd, J=4.6 Hz, J=1.5 Hz, 1H), 8.57 (s, 1H), 8.53-8.50 (m, 2H), 8.04 (s, 1H), 7.83 (d, J=8.1 Hz, 2H), 7.68 (t, J=8.3 Hz, 1H), 7.53 (d, J=7.3 Hz, 1H), 7.43-7.39 (m, 3H), 7.32 (d, J=8.1 Hz, 1H), 7.21-7.15 (m, 2H), 7.06 (s, 1H), 4.88 (dd, J=13.0 Hz, J=5.1 Hz, 1H), 4.21-4.12 (m, 2H), 3.81-3.66 (m, 4H), 3.57 (s, 2H), 3.53-3.48 (m, 2H), 2.92-2.81 (m, 2H), 2.72-2.65 (m, 2H), 2.49 (bs, 4H), 2.41-2.30 (m, 7H), 2.13-2.09 (m, 1H), 1.71-1.42 (m, 5H), 1.37-1.25 (m, 4H). ¹³C NMR (151 MHz, CDCl₃) δ 171.9, 169.3, 168.6, 168.4, 167.1, 165.4, 162.7, 160.5, 159.0, 151.5, 148.4, 141.9, 137.7, 136.7, 136.6, 136.1, 134.9, 133.9, 132.6, 131.4, 130.7, 129.5, 126.9, 125.4, 124.3, 123.7, 118.7, 116.2, 115.3, 113.2, 108.3, 71.7, 71.6, 70.9, 69.5, 62.3, 58.0, 52.7, 52.3, 49.6, 31.8, 29.2, 27.2, 25.8, 22.5, 17.7. MS (ESI); m/z: [M+H]⁺ calcd for $C_{51}H_{57}N_{10}O_8$: 937.4, found 937.1.

24-chloro-N-(2-(2, 6-dioxopiperidin-3-yl)-1,3-dioxoisoindolin-4-yl)-3,6,9,12,15,18-hexaoxatetracosanamide

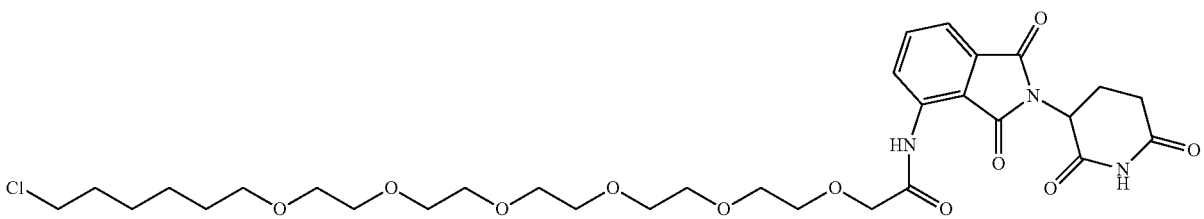 [SMILES: O=C1CCC(N2C(=O)c3cccc(NC(=O)COCCOCCOCCOCCOCCOCCCCCCCl)c3C2=O)C(=O)N1]

Yield (91%); $^1$H NMR (500 MHz, Chloroform-d) δ 10.47 (s, 1H), 8.85 (s, 1H), 8.83 (d, J=8.8 Hz, 1H), 7.70 (t, J=8.3 Hz, 1H), 7.53 (d, J=7.3 Hz, 1H), 4.92 (dd, J=12.0 Hz, J=6.5 Hz, 1H), 4.17 (s, 2H), 3.72-3.62 (m, 16H), 3.56-3.49 (m, 4H), 3.45-3.40 (m, 4H), 2.90-2.69 (m, 3H), 2.16-2.10 (m, 1H), 1.78-1.71 (m, 2H), 1.60-1.53 (m, 2H), 1.45-1.32 (m, 4H). $^{13}$C NMR (151 MHz, Chloroform-d) δ 171.0, 169.3, 168.4, 167.9, 166.8, 136.7, 136.2, 131.3, 125.1, 118.7, 116.1, 71.6, 71.2, 71.1, 70.9, 70.8, 70.64, 70.60, 70.55, 70.51, 70.49, 70.44, 70.42, 70.1, 70.0, 68.6, 49.2, 45.0, 32.5, 31.4, 29.4, 26.6, 25.4, 22.6. MS (ESI); m/z: [M+H]$^+$ calcd for $C_{31}H_{45}ClN_3O_{11}$: 670.3, found 670.1.

N-(2-(2, 6-dioxopiperidin-3-yl)-1,3-dioxoisoindolin-4-yl)-24-iodo-3, 6,9,12,15,18-hexaoxatetracosanamide

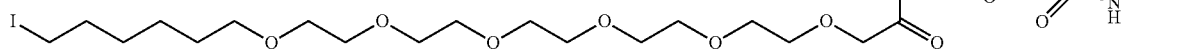

Yield (80%); $^1$H NMR (500 MHz, Chloroform-d) δ 10.48 (s, 1H), 8.84 (d, J=8.3 Hz, 1H), 8.76 (s, 1H), 7.71 (t, J=7.8 Hz, 1H), 7.56 (d, J=7.3 Hz, 1H), 4.92 (dd, J=12.0 Hz, J=6.5 Hz, 1H), 4.18 (s, 2H), 3.72-3.56 (m, 20H), 3.48-3.41 (m, 2H), 3.16 (t, J=6.8 Hz, 2H), 2.90-2.69 (m, 3H), 2.15-2.11 (m, 1H), 1.80-1.72 (m, 2H), 1.60-1.53 (m, 2H), 1.43-1.34 (m, 4H). MS (ESI); m/z: [M+H]$^+$ calcd for $C_{31}H_{45}IN_3O_{11}$: 762.2, found 762.0.

N-(2-chloro-6-methylphenyl)-2-((6-(4-(1-((2-(2, 6-dioxopiperidin-3-yl)-1,3-dioxoisoindolin-4-yl) amino)-1-oxo-3, 6,9,12,15,18-hexaoxatetracosan-24-yl)piperazin-1-yl)-2-methylpyrimidin-4-yl)amino) thiazole-5-carboxamide: DAS-6-2-2-2-2-2-2-CRBN

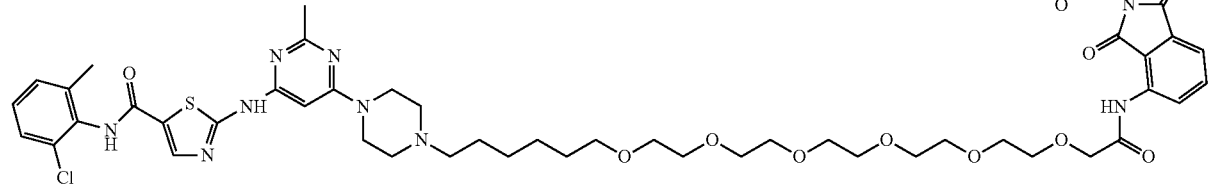

Yield (25%); $^1$H NMR (500 MHz, CD$_3$OD) δ 8.78 (d, J=8.3 Hz, 1H), 8.13 (s, 1H), 7.77 (t, J=8.3 Hz, 1H), 7.57 (d, J=7.3 Hz, 1H), 7.35 (d, J=7.3 Hz, 1H), 7.27-7.20 (m, 2H), 5.98 (s, 1H), 5.13 (dd, J=12.0 Hz, J=6.5 Hz, 1H), 4.20 (s, 2H), 3.83-3.77 (m, 4H), 3.68-3.54 (m, 20H), 3.46 (t, J=6.4 Hz, 2H), 2.92-2.85 (m, 1H), 279-2.70 (m, 2H), 2.61-2.54 (m, 4H), 2.49-2.42 (m, 5H), 2.32 (s, 3H), 2.20-2.13 (m, 1H), 1.61-1.53 (m, 4H), 1.43-1.32 (m, 4H). $^{13}$C NMR (151 MHz, CD$_3$OD) δ 173.1, 170.0, 169.8, 168.4, 166.8, 166.0, 163.8, 161.8, 157.1, 140.7, 138.9, 136.2, 135.8, 132.9, 132.8, 131.6, 128.7, 128.1, 126.9, 125.4, 124.4, 118.1, 116.4, 82.5, 71.2, 70.8, 70.4, 70.3, 70.2, 70.16, 70.14, 70.12, 69.8, 58.2, 52.4, 49.2, 48.1, 43.3, 30.7, 29.2, 26.9, 25.9, 25.7, 24.2, 22.2, 17.3. MS (ESI); m/z: [M+H]$^+$ calcd for $C_{51}H_{66}ClN_{10}O_{12}S$: 1077.4, found 1077.8.

24-(4-(3-((3-cyano-4-((2,4-dichloro-5-methoxyphenyl)amino)-6-methoxyquinolin-7-yl)oxy) propyl)piperazin-1-yl)-N-(2-(2,6-dioxopiperidin-3-yl)-1,3-dioxoisoindolin-4-yl)-3, 6,9,12,15,18-hexaoxatetracosanamide: BOS-6-2-2-2-2-2-2-CRBN

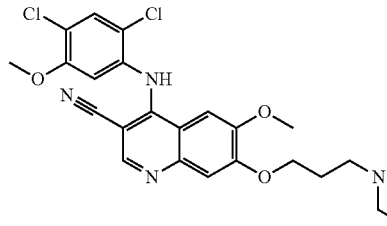 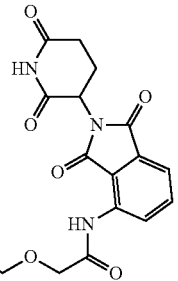

Yield (75%); $^1$H NMR (500 MHz, CDCl$_3$) δ 9.48 (s, 1H), 8.83 (d, J=8.3 Hz, 1H), 8.70 (s, 1H), 7.71 (t, J=8.3 Hz, 1H), 7.55 (d, J=7.3 Hz, 1H), 7.48 (s, 1H), 7.44 (s, 1H), 6.92 (s, 1H), 6.81 (s, 1H), 6.49 (s, 1H), 4.93 (dd, J=12.0 Hz, J=6.5 Hz, 1H), 4.25 (t, J=6.8 Hz, 2H), 4.19 (s, 2H), 3.80 (s, 3H), 3.78 (s, 3H), 3.71-3.51 (m, 20H), 3.43 (t, J=6.8 Hz, 2H), 2.96-2.70 (m, 4H), 2.62-2.35 (m, 12H), 2.17-2.06 (m, 3H), 1.58-1.54 (m, 4H), 1.35-1.28 (m, 4H). $^{13}$C NMR (151 MHz, CDCl$_3$) δ 171.1, 169.3, 168.4, 168.1, 167.8, 154.3, 153.9, 150.3, 149.8, 147.6, 147.5, 136.9, 136.7, 136.2, 131.4, 130.5, 125.2, 118.7, 118.4, 117.2, 116.4, 116.1, 114.8, 109.8, 105.5, 101.1, 94.1, 71.6, 71.3, 70.9, 70.7, 70.6, 70.56, 70.54, 70.52, 70.48, 70.47, 67.6, 56.5, 56.1, 54.7, 52.9, 50.8, 49.3, 31.5, 29.5, 27.4, 26.1, 25.9, 22.7. MS (ESI); m/z: [M+H]$^+$ calcd for C$_{56}$H$_{71}$Cl$_2$N$_8$O$_{14}$: 1149.4, found 1149.7.

N-(2-(2, 6-dioxopiperidin-3-yl)-1,3-dioxoisoindolin-4-yl)-24-(4-(4-((4-methyl-3-((4-(pyridin-3-yl)pyrimidin-2-yl)amino)phenyl)carbamoyl)benzyl)piperazin-1-yl)-3,6,9,12,15,18-hexaoxatetracosanamide: IMA-6-2-2-2-2-2-2-CRBN

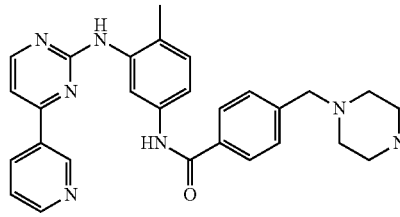 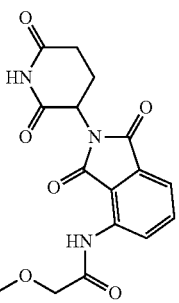

Yield (43%); $^1$H NMR (500 MHz, CDCl$_3$) δ 10.47 (s, 1H), 9.24 (s, 1H), 8.83 (d, J=8.6 Hz, 1H), 8.70 (d, J=4.4 Hz, 1H), 8.55 (s, 1H), 8.51 (d, J=4.4 Hz, 2H), 7.98 (s, 1H), 7.83 (d, J=8.1 Hz, 2H), 7.70 (t, J=7.8 Hz, 1H), 7.54 (d, J=7.1 Hz, 1H), 7.45-7.39 (m, 3H), 7.32 (d, J=7.6 Hz, 1H), 7.21-7.16 (m, 2H), 7.10 (s, 1H), 4.92 (dd, J=12.0 Hz, J=5.1 Hz, 1H), 4.21-4.16 (m, 2H), 3.79 (s, 4H), 3.74-3.55 (m, 18H), 3.42 (t, J=6.4 Hz, 2H), 2.95-2.68 (m, 4H), 2.51 (bs, 8H), 2.34 (s, 3H), 2.13-2.10 (m, 1H), 1.58-1.42 (m, 5H), 1.40-1.25 (m, 4H). $^{13}$C NMR (151 MHz, CDCl$_3$) δ 171.2, 169.3, 168.4, 168.2, 166.8, 165.4, 162.7, 160.5, 159.0, 151.4, 148.5, 142.3, 137.7, 136.7, 136.6, 136.2, 134.9, 133.9, 132.7, 131.3, 130.7, 129.4, 127.0, 125.2, 124.3, 123.7, 118.7, 116.1, 115.3, 113.2, 108.3, 71.6, 71.3, 70.9, 70.6, 70.57, 70.53, 70.48, 70.46, 70.0, 62.5, 58.5, 53.0, 52.8, 49.3, 31.5, 29.5, 27.4, 25.9, 22.7, 17.7. MS (ESI); m/z: [M+H]$^+$ calcd for C$_{59}$H$_{73}$N$_{10}$O$_{12}$: 1113.5, found 1113.4.

6-((5-((6-chlorohexyl)oxy)pentyl)oxy)-N-(2-(2, 6-dioxopiperidin-3-yl)-1,3-dioxoisoindolin-4-yl) hexanamide

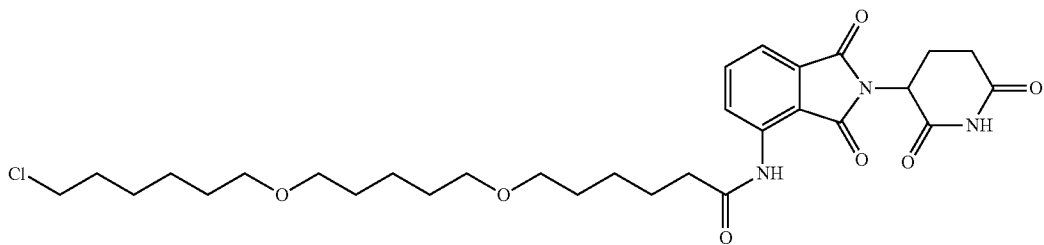 [SMILES: O=C1CCC(N2C(=O)c3cccc(NC(=O)CCCCCOCCCCCOCCCCCCCl)c3C2=O)C(=O)N1]

Yield (58%); ¹H NMR (500 MHz, Chloroform-d) δ 9.40 (s, 1H), 8.82 (d, J=8.5 Hz, 1H), 8.31 (s, 1H), 7.70 (t, J=7.8 Hz, 1H), 7.54 (d, J=7.3 Hz, 1H), 4.95 (dd, J=12.0 Hz, J=6.5 Hz, 1H), 3.52 (t, J=6.4 Hz, 2H), 3.44-3.37 (m, 8H), 2.93-2.72 (m, 3H), 2.46 (t, J=7.6 Hz, 2H), 2.20-2.12 (m, 1H), 1.88-1.73 (m, 4H), 1.67-1.53 (m, 8H), 1.50-1.34 (m, 8H). ¹³C NMR (151 MHz, Chloroform-d) δ 172.2, 170.7, 169.1, 167.8, 166.7, 137.9, 136.4, 131.1, 125.3, 118.4, 115.2, 70.8, 70.7, 70.6, 70.5, 49.2, 45.1, 37.9, 32.5, 31.4, 29.5, 29.4, 26.7, 25.8, 25.5, 25.0, 22.8, 22.7. MS (ESI); m/z: [M+H]⁺ calcd for $C_{30}H_{43}ClN_3O_7$: 592.3, found 592.1.

N-(2-(2, 6-dioxopiperidin-3-yl)-1,3-dioxoisoindolin-4-yl)-6-((5-((6-iodohexyl)oxy)pentyl)oxy) hexanamide

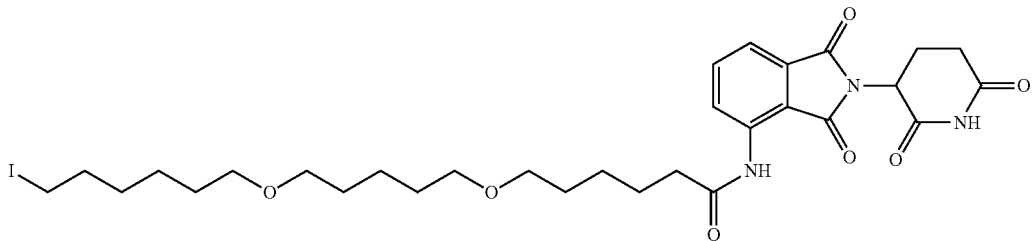 [SMILES: O=C1CCC(N2C(=O)c3cccc(NC(=O)CCCCCOCCCCCOCCCCCCI)c3C2=O)C(=O)N1]

Yield (93%); ¹H NMR (500 MHz, Chloroform-d) δ 9.41 (s, 1H), 8.82 (d, J=8.0 Hz, 1H), 8.30 (s, 1H), 7.71 (t, J=7.8 Hz, 1H), 7.55 (d, J=7.3 Hz, 1H), 4.95 (dd, J=12.0 Hz, J=6.5 Hz, 1H), 3.46-3.31 (m, 8H), 3.18 (t, J=6.4 Hz, 2H), 2.94-2.72 (m, 3H), 2.47 (t, J=6.8 Hz, 2H), 2.20-2.12 (m, 1H), 1.86-1.72 (m, 4H), 1.66-1.53 (m, 8H), 1.51-1.34 (m, 8H). MS (ESI); m/z: [M+H]⁺ calcd for $C_{30}H_{43}IN_3O_7$: 684, found 684.0.

N-(2-chloro-6-methylphenyl)-2-((6-(4-(6-((5-((6-((2-(2, 6-dioxopiperidin-3-yl)-1,3-dioxoisoindolin-4-yl) amino)-6-oxohexyl)oxy)pentyl)oxy)hexyl)piperazin-1-yl)-2-methylpyrimidin-4-yl)amino)thiazole-5-carboxamide: DAS-6-5-6-CRBN

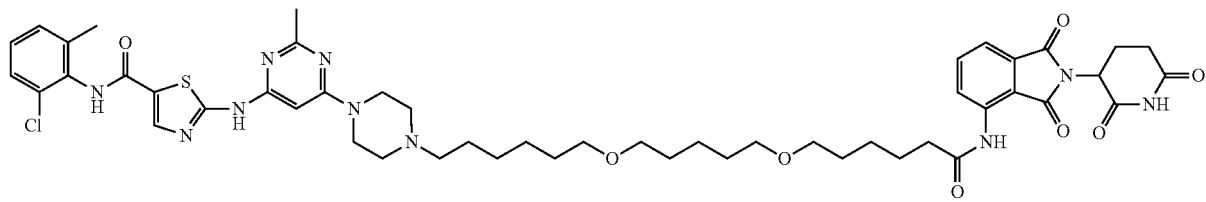 [SMILES: Cc1nc(Nc2ncc(C(=O)Nc3c(C)cccc3Cl)s2)cc(N2CCN(CCCCCCOCCCCCOCCCCCC(=O)Nc3cccc4c3C(=O)N(C3CCC(=O)NC3=O)C4=O)CC2)n1]

Yield (59%); ¹H NMR (500 MHz, CD₃OD/CDCl₃) δ 8.22 (d, J=8.3 Hz, 1H), 7.67 (s, 1H), 7.27 (t, J=8.3 Hz, 1H), 7.08 (d, J=7.3 Hz, 1H), 6.86 (d, J=7.3 Hz, 1H), 6.78-6.70 (m, 2H), 5.52 (s, 1H), 4.63 (dd, J=12.0 Hz, J=6.5 Hz, 1H), 3.19 (bs, 4H), 3.00-2.94 (m, 8H), 2.40-2.28 (m, 3H), 2.14 (bs, 4H), 2.06-1.98 (m, 7H), 1.86 (s, 3H), 1.74-1.68 (m, 1H), 1.34-1.28 (m, 2H), 1.19-1.09 (m, 10H), 1.04-0.85 (m, 8H). ¹³C NMR (151 MHz, CD₃OD/CDCl₃) δ 172.9, 169.7, 168.7, 166.8, 166.1, 162.9, 161.9, 157.1, 140.7, 138.9, 137.0, 135.9, 132.8, 131.4, 128.7, 128.1, 126.9, 125.4, 125.2, 118.1, 116.2, 82.8, 70.6, 70.52, 70.50, 70.3, 58.3, 52.5, 49.2, 43.3, 37.2, 30.9, 29.3, 29.2, 29.0, 27.0, 25.9, 25.8, 25.5, 24.8, 24.6, 22.6, 22.4, 17.7. MS (ESI); m/z: [M+H]⁺ calcd for C₅₀H₆₄ClN₁₀O₈S: 999.4, found 999.2.

Yield (56%); ¹H NMR (500 MHz, CDCl₃) δ 9.40 (s, 1H), 9.24 (s, 1H), 8.81 (d, J=8.1 Hz, 1H), 6.70 (dd, J=4.6 Hz, J=1.5 Hz, 1H), 8.55 (s, 1H), 8.53-8.49 (m, 2H), 7.97 (s, 1H), 7.84 (d, J=8.1 Hz, 2H), 7.69 (t, J=8.3 Hz, 1H), 7.52 (d, J=7.3 Hz, 1H), 7.45-7.40 (m, 3H), 7.32 (dd, J=7.3 Hz, J=1.5 Hz, 1H), 7.21-7.17 (m, 2H), 7.12 (s, 1H), 4.92 (dd, J=12.5 Hz, J=5.4 Hz, 1H), 3.57 (bs, 2H), 3.48 (s, 2H), 3.42-3.36 (m, 8H), 2.91-2.69 (m, 4H), 2.52 (bs, 4H), 2.45 (t, J=7.8 Hz, 2H), 2.41-2.35 (m, 2H), 2.34 (s, 3H), 2.17-2.12 (m, 1H), 1.76 (quint, J=7.3 Hz, 2H), 1.64-1.43 (m, 13H), 1.42-1.27 (m, 6H). ¹³C NMR (151 MHz, CDCl₃) δ 172.2, 171.1, 169.1, 168.2, 166.8, 165.4, 162.7, 160.5, 158.9, 151.4, 148.4, 142.0, 137.8, 137.7, 136.6, 136.4, 135.0, 133.9, 132.7, 131.1, 130.8, 129.4, 127.0, 125.2, 124.4, 123.7, 118.4, 115.4, 115.2, 113.2, 108.3, 70.8, 70.77, 70.74, 70.4, 62.4, 58.5, 52.9, 52.8, 50.8, 49.3, 37.9, 31.5, 29.6, 29.5, 29.4, 27.4, 26.1, 25.8, 25.0, 22.8, 22.7, 17.7. MS (ESI); m/z: [M+H]⁺ calcd for C₅₈H₇₁N₁₀O₈: 1035.5, found 1035.1.

6-((5-((6-(4-(3-((3-cyano-4-((2,4-dichloro-5-methoxyphenyl)amino)-6-methoxyquinolin-7-yl)oxy)propyl)piperazin-1-yl) hexyl)oxy)pentyl)oxy)-N-(2-(2, 6-dioxopiperidin-3-yl)-1,3-dioxoisoindolin-4-yl)hexanamide: BOS-6-5-6-CRBN

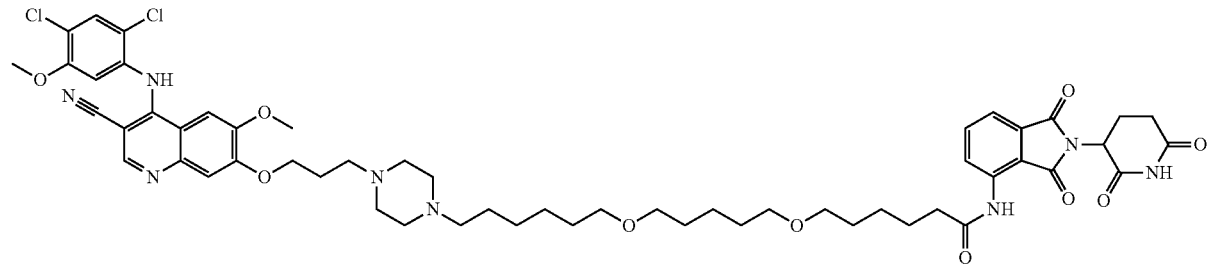 [SMILES: COc1cc(Nc2c(C#N)cnc3cc(OCCCN4CCN(CCCCCCOCCCCCOCCCCCC(=O)Nc5cccc6c5C(=O)N(C5CCC(=O)NC5=O)C6=O)CC4)c(OC)cc23)c(Cl)cc1Cl]

Yield (80%); ¹H NMR (500 MHz, CD3OD/CDCl₃) δ 9.41 (s, 1H), 8.80 (d, J=8.5 Hz, 1H), 8.68 (s, 1H), 7.69 (t, J=8.3 Hz, 1H), 7.51 (d, J=7.3 Hz, 1H), 7.48 (s, 1H), 7.43 (s, 1H), 6.92 (s, 1H), 6.88 (s, 1H), 6.49 (s, 1H), 4.91 (dd, J=12.0 Hz, J=6.5 Hz, 1H), 4.22 (t, J=6.4 Hz, 2H), 3.77 (s, 3H), 3.67 (s, 3H), 3.53-2.46 (m, 14H), 3.41-3.36 (m, 4H), 2.94-2.72 (m, 3H), 2.55-2.44 (m, 4H), 2.35-2.32 (m, 1H), 2.17-2.08 (m, 2H), 1.79-1.73 (m, 2H), 1.64-1.25 (m, 18H). ¹³C NMR (151 MHz, CDCl₃) δ 168.4, 167.3, 165.2, 164.3, 162.8, 150.3, 149.9, 146.3, 145.8, 143.8, 143.5, 133.8, 132.9, 132.4, 127.1, 126.6, 121.3, 114.6, 114.4, 113.5, 112.5, 111.3, 110.8, 105.7, 101.8, 97.1, 89.9, 68.9, 68.84, 68.81, 66.5, 63.7, 54.6, 52.6, 50.8, 49.0, 48.9, 46.8, 45.3, 33.9, 27.5, 25.7, 25.5, 25.4, 23.5, 22.6, 22.1, 21.9, 21.0, 18.8, 18.7. MS (ESI); m/z: [M+H]⁺ calcd for C₅₅H₆₉Cl₂N₈O₁₀: 1071.4, found 1071.2.

4-((4-(6-((5-((6-((2-(2, 6-dioxopiperidin-3-yl)-1,3-dioxoisoindolin-4-yl)amino)-6-oxohexyl)oxy)pentyl)oxy)hexyl)piperazin-1-yl)methyl)-N-(4-methyl-3-((4-(pyridin-3-yl)pyrimidin-2-yl)amino)phenyl)benzamide: IMA-6-5-6-CRBN

EXAMPLE

As demonstrated herein, small molecule PROTACs were found to induce the degradation of BCR-ABL kinase. By varying the target binding ligand (warhead) and the E3 ligase being recruited, BCR-ABL PROTACs can enter cells and bind their target, achieving degradation of the protein.

Figure 1A:
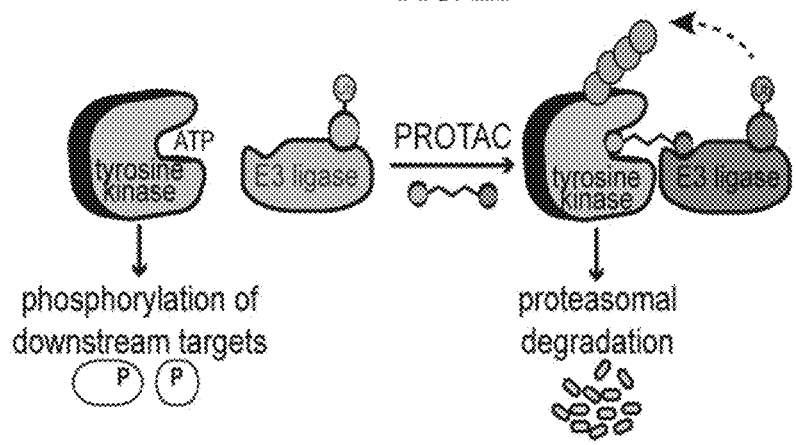
FIGS. 1A-1C comprise illustrations of a non-limiting approach to proteolysis targeting chimera (PROTAC) development.
Figure 1B:
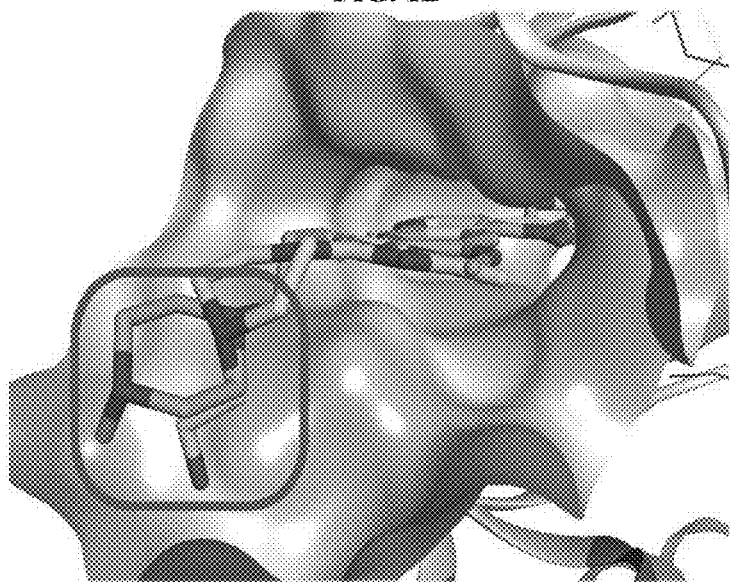
Figure 1C:
Figure 1C:
Figure 1C:
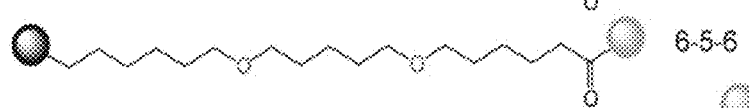
Figure 1C:
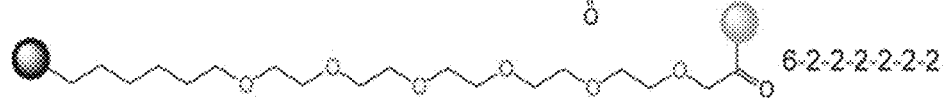

To produce BCR-ABL degrader compounds, BCR-ABL TKIs (imatinib, bosutinib and dasatinib) that bind the c-ABL kinase domain were conjugated to a Von Hippel Lindau (VHL) E3 ubiquitin ligase ligand or to the thalidomide derivative, pomalidomide, to recruit Cereblon (CRBN) E3 ligase. Without wishing to be limited by any theory, the resulting bifunctional compounds may bind BCR-ABL via the TKI moiety, and bind to VHL or CRBN via its recruiting ligand. Using the crystal structures of the c-ABL kinase domain in complex with the TKIs (imatinib, dasatinib and bosutinib), positions to attach the linkers to the respective TKIs were selected such that critical binding interactions were not disrupted (FIG. 1B). Four different linkers with varying composition and length were evaluated (FIG. 1C).

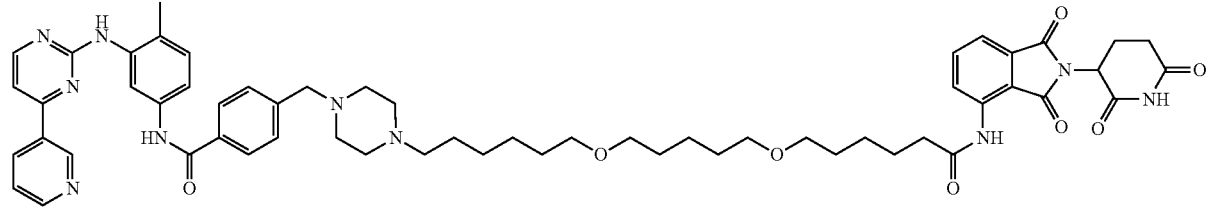 [SMILES: Cc1ccc(NC(=O)c2ccc(CN3CCN(CCCCCCOCCCCCOCCCCCC(=O)Nc4cccc5c4C(=O)N(C4CCC(=O)NC4=O)C5=O)CC3)cc2)cc1Nc1nccc(-c2cccnc2)n1]

These linkers contain a mixture of hydrophobic and hydrophilic moieties to balance the hydrophobicity/hydrophilicity of the resulting hybrid compounds. The panel of hybrid compounds was then assayed for retention of binding to c-ABL kinase domain through KinomeScan (Table 1). All compounds lost affinity for the phosphorylated and non-phosphorylated form of ABL compared to the parent compound. Within each warhead series, the 1,5-bis(hexyloxy) pentane linker (hereby designated 6-5-6) yielded compounds with the most significant loss (maximum 86-fold) in binding affinity (Table 2). All hybrid compounds bound non-phosphorylated c-ABL in the low nanomolar range (0.28 nM-24 nM). The bosutinib- and dasatinib-based PROTACs bound phosphorylated c-ABL in the high picomolar range (88 pM-1500 pM).

All PROTACs were then tested for c-ABL and BCR-ABL degradation in cell culture. No degradation of BCR-ABL or c-ABL was observed in K562 CML cells when treated with imatinib-VHL (IMA-VHL) or imatinib-CRBN (IMA-CRBN) PROTACs despite the fact that the PROTACs bound their targets as evidenced by the reduced phosphorylation of CrkL and STAT5 at higher concentrations (FIGS. 6A-6B, 7A-7F, 8A-8F, 9A-9F).

Figure 2A:
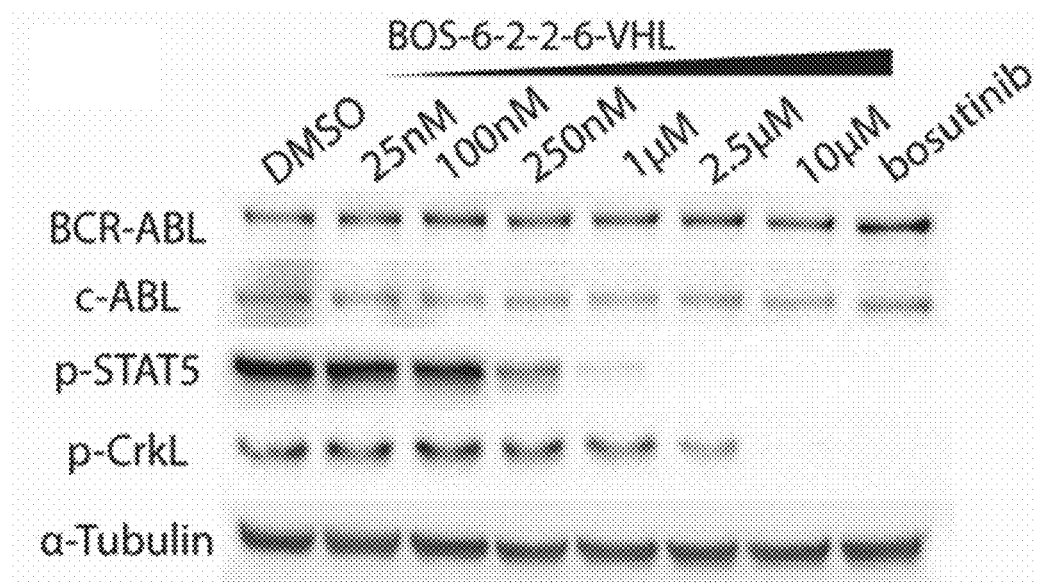
FIGS. 2A-2B illustrate biological effects of VHL-based PROTACs. BOS-6-2-2-6-VHL (FIG. 2A) and DAS-6-2-2-6-VHL (FIG. 2B) were incubated with K562 human chronic myelogenous leukemia cells for 24 hrs. The concentrations of the parent inhibitors were 1 µM. As determined by immunoblot, degradation of c-ABL was observed with DAS-VHL starting at 1 µM; however, no degradation of BCR-ABL was observed in any of the VHL-based PROTACs.

A more potent inhibitor warhead (bosutinib or dasatinib) was then selected for a follow-on PROTAC series. Through a similar synthetic route, bosutinib was conjugated to the VHL recruiting ligand, producing bosutinib-VHL (BOS-VHL) PROTACs. Despite target engagement as determined by inhibition of downstream signaling, the BOS-VHL PROTACs also did not induce degradation of BCR-ABL or c-ABL (FIG. 2A). This finding was consistent across several different linkers connecting the bosutinib inhibitor and the VHL recruiting ligand (FIGS. 7A-7F, 8A-8F, 9A-9F). The representative blot shown in FIG. 2A is of BOS-VHL with the linker 1-(2-(2-(hexyloxy)ethoxy)ethoxy)hexane hereby designated as 6-2-2-6, which refers to the alkyl/ether composition.

Figure 2B:
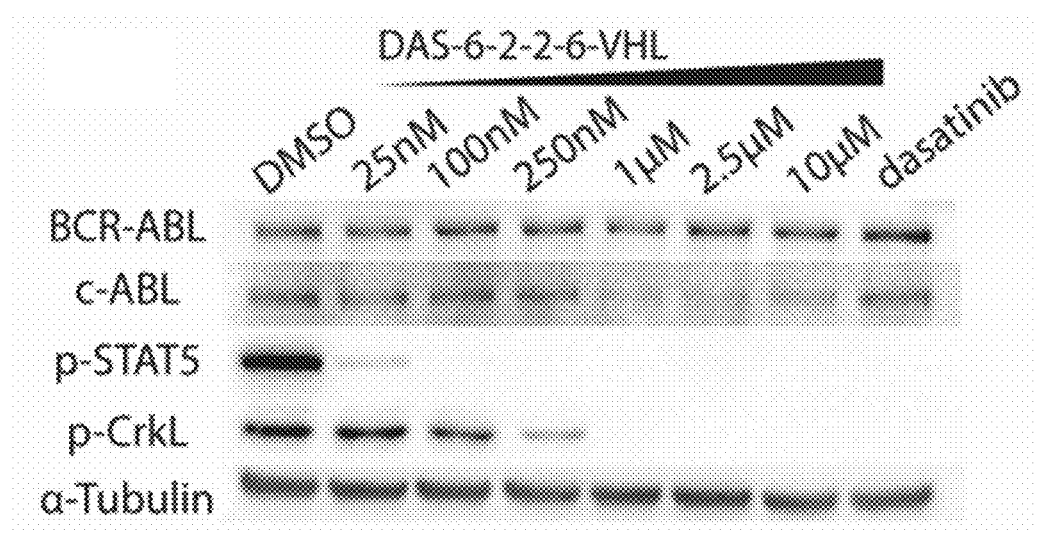

In addition to the BOS-VHL series, dasatinib was also incorporated as the ligand binding warhead. In contrast to the IMA-VHL and BOS-VHL PROTACs, dasatinib-based PROTAC (DAS-VHL) induced a clear (>65%) decrease of c-ABL at 1 µM PROTAC concentration (FIG. 2B). The apparent decrease of protein degradation seen at higher PROTAC concentrations (10 µM) was observed with other PROTACs and, without wishing to be limited by any theory, may be attributed to the formation of separate c-ABL-PROTAC and VHL-PROTAC dimers rather than the c-ABL-PROTAC-VHL trimeric complex required for productive ubiquitination. The c-ABL degradation seen with the prototype DAS-VHL PROTAC was consistently observed with PROTACs possessing different linkers (FIGS. 7A-7F, 8A-8F, 9A-9F). Thus, independent of simple target binding, the inhibitor warhead (imatinib, bosutinib or dasatinib) largely determines the capability of a PROTAC to induce c-ABL degradation.

Despite the success of DAS-VHL with the c-ABL degradation, no degradation of BCR-ABL was seen with any of the VHL-based PROTACs. This lack of degradation cannot be attributed to loss of binding affinity since these VHL-based PROTACs still bind and inhibit both c-ABL and BCR-ABL in cell culture (FIGS. 2A-2B). Since E3 ligase presentation to the target is important for ubiquitination of an available lysine residue, a differently oriented E3 ligase, such as CRBN E3 ligase, may be required for adequate ubiquitination and degradation of BCR-ABL.

Figure 3A:
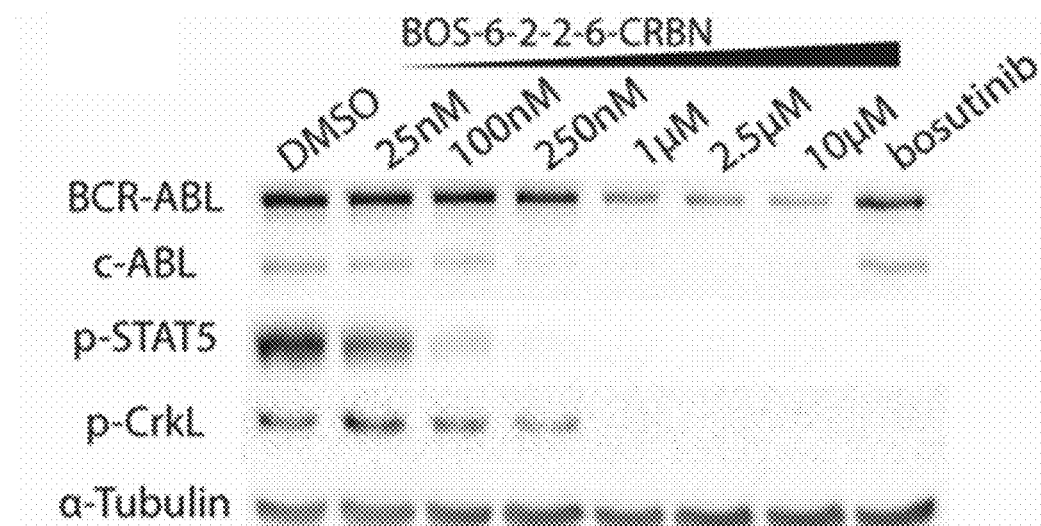
FIGS. 3A-3B illustrate biological effects of CRBN-based PROTACs. BOS-6-2-2-6-CRBN (FIG. 3A) and DAS-6-2-2-6-CRBN (FIG. 3B) were incubated with K562 cells for 24 hrs. The concentrations of the parent inhibitors were 1 µM. As determined by immunoblot, degradation of BCR-ABL and c-ABL was observed in the DAS-CRBN and BOS-CRBN series.
Figure 3B:
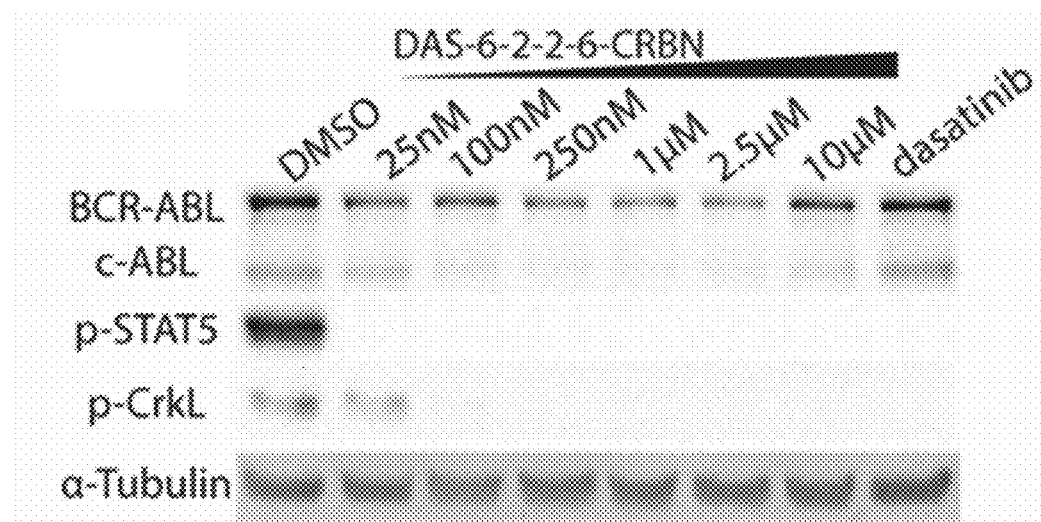

When dasatinib was conjugated to pomalidomide to recruit CRBN, the dasatinib-CRBN (DAS-CRBN) PROTAC not only retained its ability to induce degradation of c-ABL (>85% at 1 µM) but also induced BCR-ABL degradation (>60% at 1 µM), demonstrating the first PROTAC-induced degradation of an oncogenic tyrosine kinase (FIGS. 3A-3B).

This result was consistent across the several different linkers used previously in the series of VHL-based PROTACs (FIGS. 6A-6B, 7A-7F, 8A-8F, 9A-9F). When the VHL recruiting ligand in the bosutinib PROTAC series was exchanged for the CRBN ligand, c-ABL (>90%) and BCR-ABL (>80%) degradation were observed at 2.5 µM (FIG. 3A). The accessibility of BCR-ABL and c-ABL for degradation with the BOS-CRBN series stands in contrast with the BOS-VHL series where, despite target engagement, no degradation of c-ABL or BCR-ABL was observed. Thus, the inactive BOS-VHL compounds were converted to active BCR-ABL and c-ABL degrader compounds by switching to the CRBN E3 ligase. As demonstrated by these two inhibitor warhead series, the oncogenic fusion protein BCR-ABL was differentially susceptible to PROTAC-mediated degradation, depending on the E3 ligase (VHL or CRBN) recruited to the target.

Figure 4:
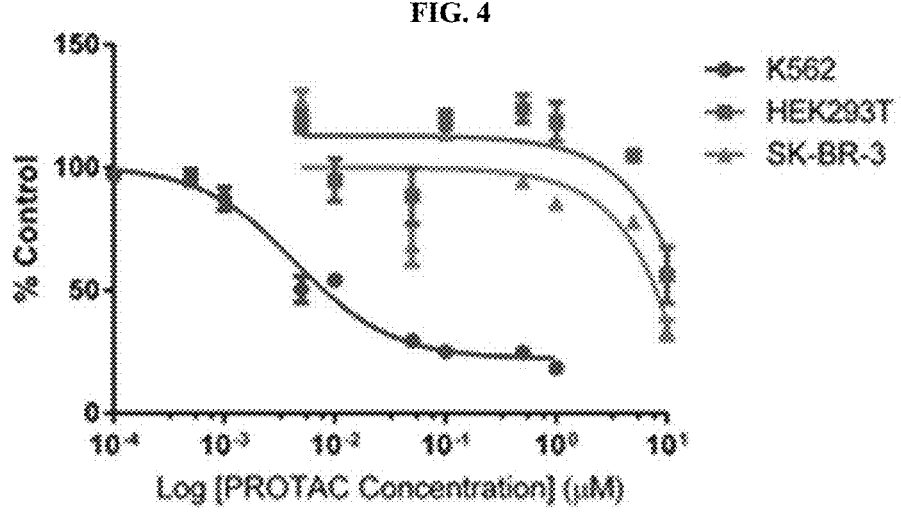
FIG. 4 comprises a graph illustrating cell viability with DAS-6-2-2-6-CRBN. This PROTAC was greater than a thousand-fold more effective against the BCR-ABL driven cell line K562 over non-BCR-ABL driven cell lines, as determined by CellTiter-Glo® Luminescent Cell Viability assay after a 48 hr treatment. Error bars displayed are S.E.M (n=3). Data was normalized to DMSO-treated controls.

Since BCR-ABL degradation was observed at 25 nM with the DAS-6-2-2-6-CRBN PROTAC, the cellular effects of the PROTAC were evaluated (FIG. 3B). In a cell viability assay, DAS-6-2-2-6-CRBN was active against BCR-ABL driven K562 with a half-maximal response concentration ($EC_{50}$) of 4.4±2.1 nM (FIG. 4). Furthermore, the PROTAC compound was more than $10^3$-fold less active against the non-BCR-ABL driven cell lines, HEK293T and SK-BR-3 breast carcinoma. Thus, this PROTAC compound retained selective activity against the BCR-ABL driven cell line K562.

TABLE 1

Selected PROTAC Affinities for the ABL Kinase Domain

| Compound | ABL (non-phosphorylated) | ABL (phosphorylated) |
| --- | --- | --- |
| Imatinib | 0.86 nM | 36 nM |
| IMA-6-2-2-6-VHL | 4.3 nM | 93 nM |
| IMA-6-2-2-6-CRBN | 6.2 nM | 110 nM |
| Bosutinib | 0.063 nM | 0.023 nM |
| BOS-6-2-2-6-VHL | 1.4 nM | 0.63 nM |
| BOS-6-2-2-6-CRBN | 0.91 nM | 0.55 nM |
| Dasatinib | 0.03 nM | 0.02 nM |
| DAS-6-2-2-6-VHL | 0.92 nM | 0.47 nM |
| DAS-6-2-2-6-CRBN | 0.60 nM | 0.32 nM |

TABLE 2

| Compound | ABL (non-phosphorylated) | ABL (phosphorylated) |
| --- | --- | --- |
| Imatinib | 0.86 nM | 36 nM |
| IMA-6-2-2-6-VHL | 4.3 nM | 93 nM |
| IMA-6-2-2-VHL | 5.8 nM | 98 nM |
| IMA-6-(2-)$_5$-2-VHL | 1.7 nM | 35 nM |
| IMA-6-5-6-VHL | 19 nM | 46 nM |
| IMA-6-2-2-6-CRBN | 6.2 nM | 110 nM |
| IMA-6-2-2-CRBN | 4.7 nM | 72 nM |
| IMA-6-(2-)$_5$-2-CRBN | 3.0 nM | 84 nM |
| IMA-6-5-6-CRBN | 24 nM | 360 nM |
| Bosutinib | 0.063 nM | 0.023 nM |
| BOS-6-2-2-6-VHL | 1.4 nM | 0.63 nM |
| BOS-6-2-2-VHL | 1.3 nM | 0.67 nM |
| BOS-6-(2-)$_5$-2-VHL | 0.57 nM | 0.30 nM |
| BOS-6-5-6-VHL | 4.6 nM | 1.5 nM |
| BOS-6-2-2-6-CRBN | 0.91 nM | 0.55 nM |
| BOS-6-2-2-CRBN | 0.28 nM | 0.11 nM |

TABLE 2-continued

| Compound | ABL (non-phosphorylated) | ABL (phosphorylated) |
|---|---|---|
| BOS-6-(2-)₅-2-CRBN | 0.38 nM | 0.13 nM |
| BOS-6-5-6-CRBN | 2.8 nM | 1.1 nM |
| Dasatinib | 0.030 nM | 0.020 nM |
| DAS-6-2-2-6-VHL | 0.92 nM | 0.47 nM |
| DAS-6-2-2-VHL | 0.36 nM | 0.21 nM |
| DAS-6-(2-)₅-2-VHL | 0.28 nM | 0.088 nM |
| DAS-6-5-6-VHL | 2.6 nM | 1.3 nM |
| DAS-6-2-2-6-CRBN | 0.60 nM | 0.32 nM |
| DAS-6-2-2-CRBN | 0.28 nM | 0.19 nM |
| DAS-6-(2-)₅-2-CRBN | 0.26 nM | 0.23 nM |
| DAS-6-5-6-CRBN | 1.3 nM | 1.4 nM |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (I):

TKI-L-(ULM)$_k$      (I), wherein:

TKI is a tyrosine kinase inhibitor,
L is a linker,
each ULM is independently a ubiquitin ligase binder, and
k is an integer ranging from 1 to 4,
wherein the TKI is covalently linked to the L and wherein each ULM is covalently linked to the L;
or a salt, enantiomer, stereoisomer, polymorph, or N-oxide thereof.

2. The compound of claim 1, wherein the TKI is capable of binding to at least one selected from the group consisting of c-ABL and BCR-ABL.

3. The compound of claim 1, wherein, upon binding of the compound simultaneously to a tyrosine kinase and a ubiquitin ligase, the tyrosine kinase is ubiquitinated by the ubiquitin ligase.

4. The compound of claim 1, wherein at least one ULM binds to an E3 ubiquitin ligase.

5. The compound of claim 4, wherein the E3 ubiquitin ligase comprises a Von Hippel Lindau (VHL) E3 ubiquitin ligase or a Cereblon (CRBN) E3 ligase.

6. The compound of claim 2, wherein the TKI binds to and inhibits c-ABL.

7. The compound of claim 2, wherein the TKI binds to and inhibits BCR-ABL.

8. The compound of claim 2, wherein the TKI binds to and inhibits both c-ABL and BCR-ABL.

9. The compound of claim 1, wherein the TKI is at least one selected from the group consisting of Dasatinib, Imatinib, Saracatinib, Ponatinib, Nilotinib, Danusertib, AT9283, Degrasyn, Bafetinib, KW-2449, NVP-BHG712, DCC-2036, GZD824, GNF-2, PD173955, GNF-5, Bosutinib, Gefitinib, Erlotinib, Sunitinib, Ruxolitinib, Tofacitinib, Lapatinib, Vandetanib, Sorafenib, Sunitinib, Axitinib, Nintedanib, Regorafenib, Pazopanib, Lenvatinib, Crizotinib, Ceritinib, Cabozantinib, DWF, Afatinib, Ibrutinib, B43, KU004, Foretinib, KRCA-0008, PF-06439015, PF-06463922, Canertinib, GSA-10, GW2974, GW583340, WZ4002, CP-380736, D2667, Mubritinib, PD153035, PD168393, Pelitinib, PF-06459988, PF-06672131, PF-6422899, PKI-166, Reveromycin A, Tyrphostin 1, Tyrphostin 23, Tyrphostin 51, Tyrphostin AG 528, Tyrphostin AG 658, Tyrphostin AG 825, Tyrphostin AG 835, Tyrphostin AG 1478, Tyrphostin RG 13022, Tyrphostin RG 14620, B178, GSK1838705A, PD-161570, PD 173074, SU-5402, Roslin 2, Picropodophyllotoxin, PQ401, I-OMe-Tyrphostin AG 538, GNF 5837, GW441756, Tyrphostin AG 879, DMPQ, JNJ-10198409, PLX647, Trapidil, Tyrphostin A9, Tyrphostin AG 370, Lestaurtinib, DMH4, Geldanamycin, Genistein, GW2580, Herbimycin A, Lavendustin C, Midostaurin, NVP-BHG712, PD158780, PD-166866, PF-06273340, PP2, RPI, SU 11274, SU5614, Symadex, Tyrphostin AG 34, Tyrphostin AG 974, Tyrphostin AG 1007, UNC2881, Honokiol, SU1498, SKLB1002, CP-547632, JK-P3, KRN633, SC-1, ST638, SU 5416, Sulochrin, Tyrphostin SU 1498, 58567, rociletinib, Dacomitinib, Tivantinib, Neratinib, Masitinib, Vatalanib, Icotinib, XL-184, OSI-930, AB1010, Quizartinib, AZD9291, Tandutinib, HM61713, Brigantinib, Vemurafenib (PLX-4032), Semaxanib, AZD2171, Crenolanib, Damnacanthal, Fostamatinib, Motesanib, Radotinib, OSI-027, Linsitinib, BIX02189, PF-431396, PND-1186, PF-03814735, PF-431396, sirolimus, temsirolimus, everolimus, deforolimus, zotarolimus, BEZ235, INK128, Omipalisib, AZD8055, MHY1485, PI-103, KU-0063794, ETP-46464, GDC-0349, XL388, WYE-354, WYE-132, GSK1059615, WAY-600, PF-04691502, WYE-687, PP121, BGT226, AZD2014, PP242, CH5132799, P529, GDC-0980, GDC-0994, XMD8-92, Ulixertinib, FR180204, SCH772984, Trametinib, PD184352, PD98059, Selumetinib, PD325901, U0126, Pimasertinib, TAK-733, AZD8330, Binimetinib, PD318088, SL-327, Refametinib, GDC-0623, Cobimetinib, BI-847325, Adaphostin, GNF 2, PPY A, AIM-100, ASP 3026, LFM A13, PF 06465469, (−)-Terreic acid, AG-490, BIBU 1361, BIBX 1382, BMS 599626, CGP 52411, GW 583340, HDS 029, HKI 357, JNJ 28871063, WHI-P 154, PF 431396, PF 573228, FIIN 1, PD 166285, SUN 11602, SR 140333, TCS 359, BMS 536924, NVP ADW 742, PQ 401, BMS 509744, CP 690550, NSC 33994, WHI-P 154, KB SRC 4, DDR1-IN-1, PF 04217903, PHA 665752, SU 16f, A 419259, AZM 475271, PP 1, PP 2, 1-Naphthyl PP1, Src I1, ANA 12, PD 90780, Ki 8751, Ki 20227, ZM 306416, ZM 323881, AEE 788, GTP 14564, PD 180970, R 1530, SU 6668, Toceranib, CEP-32496 (1-(3-((6,7-dimethoxyquinazolin-4-yl)oxy)phenyl)-3-(5-(1,1,1-trifluoro-2-methylpropan-2-yl)isoxazol-3-yl)urea), AZ 628 (4-(2-cyanopropan-2-yl)-N-(4-methyl-3-((3-methyl-4-oxo-3,4-dihydroquinazolin-6-yl)amino) phenyl) benzamide), Vemurafenib (PLX-4032), PLX-4720 (N-(3-(5-chloro-1H-pyrrolo[2,3-b]pyridine-3-carbonyl)-2,4-difluorophenyl)propane-1-sulfonamide), SB 590885 ((E)-5-(2-(4-(2-(dimethylamino)ethoxy)phenyl)-4-(pyridin-4-yl)-1H-imidazol-5-yl)-2,3-dihydro-1H-inden-1-one oxime), GDC-0879 ((E)-5-(2-(2-hydroxyethyl)-4-(pyridin-4-yl)-1H-imidazol-5-yl)-2,3-dihydro-1H-inden-1-one oxime), a compound of formula

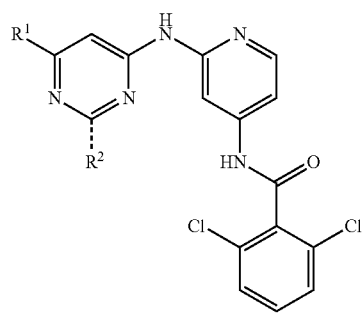

wherein $R^1$ is H or $CH_3$, and $R^2$ is

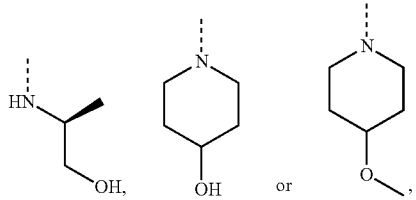

a compound of formula

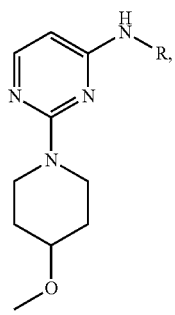

wherein R is

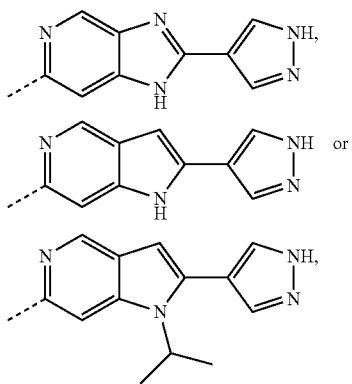

and a compound of formula

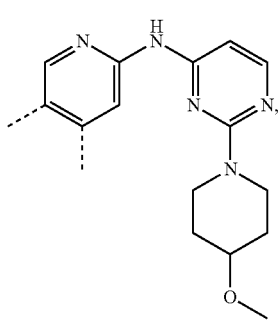

wherein the broken lines correspond to the divalent group

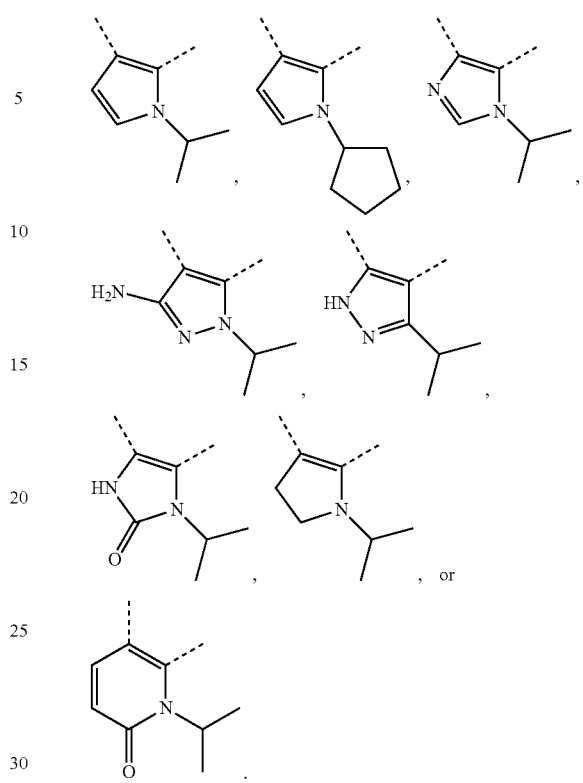

10. The compound of claim 1, wherein the TKI is Imatinib, Dasatinib or Bosutinib.

11. The compound of claim 1, wherein at least one ULM comprises formula (IX):

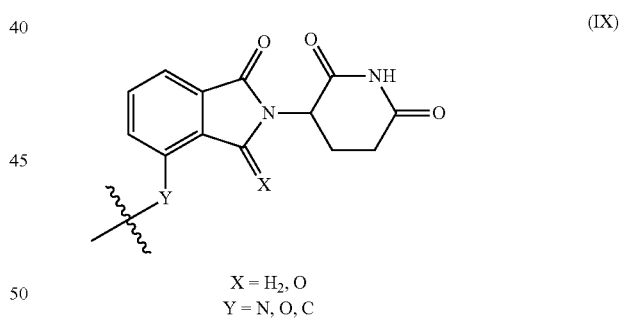

$X = H_2, O$
$Y = N, O, C$

12. The compound of claim 1, wherein at least one ULM comprises formula (X):

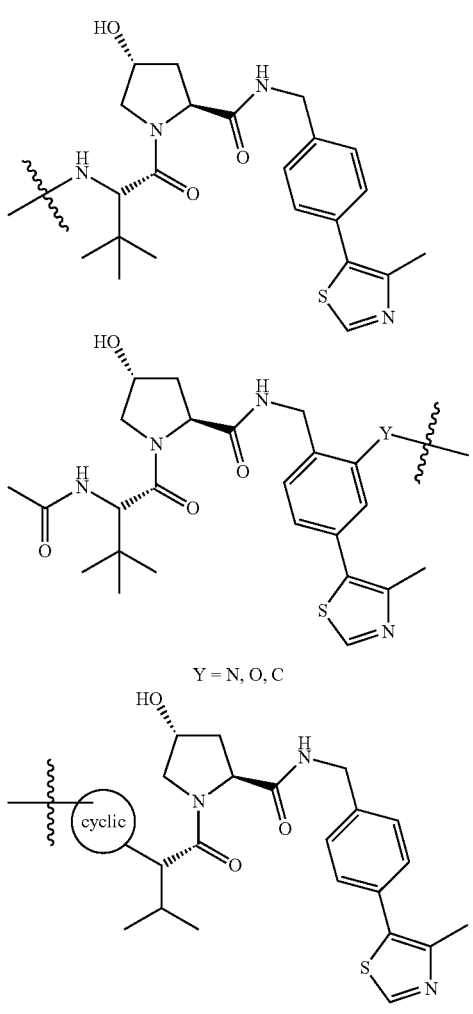

(X)

Y = N, O, C

13. The compound of claim 1, wherein k is 1.

14. The compound of claim 1, wherein the linker L corresponds to formula —(CH$_2$)$_{m1}$—X$_4$—(CH$_2$—CH$_2$—X$_5$)$_{m2}$—(CH$_2$)$_{m3}$—C(X$_6$)—, wherein:

—(CH$_2$)$_{m1}$ is covalently bound to the TKI, and C(X$_6$)— is covalently bound to the ULM;

each m1, m2, and m3 is independently 0, 1, 2, 3, 4, 5, 6, 7, 8, 9, or 10;

each X$_4$, X$_5$, and X$_6$ is independently absent (a bond), O, S, or N—R$^{20}$, wherein each R$^{20}$ is independently selected from the group consisting of hydrogen, optionally substituted C$_1$-C$_6$ alkyl, optionally substituted aryl, optionally substituted heteroaryl, optionally substituted C$_3$-C$_8$ cycloalkyl, and optionally substituted C$_3$-C$_8$ cycloheteroalkyl.

15. The compound of claim 14, wherein m1 is 6; m2 is 1 or 2; m3 is 1 or 5; and X$_4$, X$_5$, and X$_6$ are O.

16. The compound of claim 14, wherein m1 is 6; m2 is 5; m3 is 5; X$_4$ and X$_6$ are O; and X$_5$ is absent.

17. The compound of claim 14, wherein m1 is 6; m2 is 5; m3 is 1; X$_4$, X$_5$, and X$_6$ are O.

18. The compound of claim 1, which is selected from the group consisting of:

N-(2-chloro-6-methylphenyl)-2-((6-(4-((S)-3-((2S,4R)-4-hydroxy-2-((4-(4-methylthiazol-5-yl)benzyl)carbamoyl)pyrrolidine-1-carbonyl)-2,2-dimethyl-5-oxo-11,14,17-trioxa-4-azatricosan-23-yl)piperazin-1-yl)-2-methylpyrimidin-4-yl)amino)thiazole-5-carboxamide (DAS-6-2-2-6-VHL):

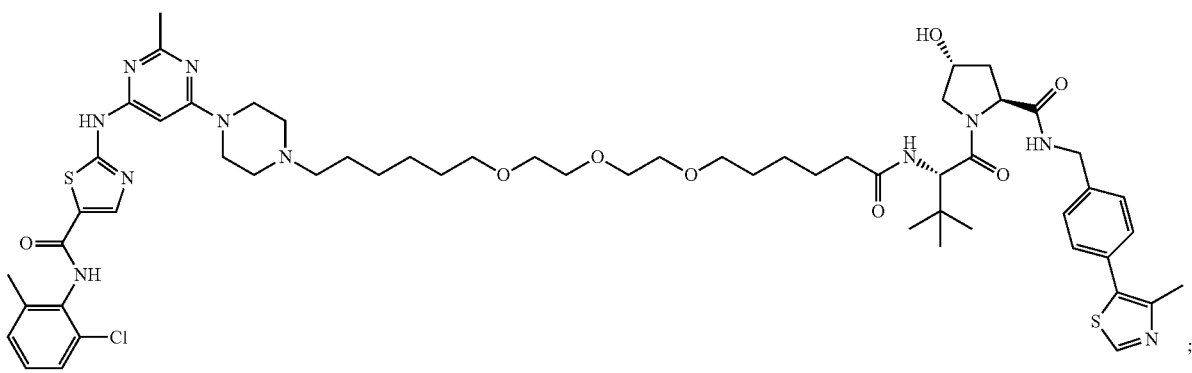 [SMILES: Cc1nc(Nc2ncc(C(=O)Nc3c(C)cccc3Cl)s2)cc(N2CCN(CCCCCCOCCOCCOCCCCCC(=O)N[C@H](C(=O)N3C[C@H](O)C[C@H]3C(=O)NCc3ccc(-c4scnc4C)cc3)C(C)(C)C)CC2)n1]

(2S,4R)-1-((S)-2-(tert-butyl)-22-(4-(4-((4-methyl-3-((4-(pyridin-3-yl)pyrimidin-2-yl)amino) phenyl)carbamoyl)benzyl)piperazin-1-yl)-4-oxo-10,13,16-trioxa-3-azadocosanoyl)-4-hydroxy-N-(4-(4-methylthiazol-5-yl)benzyl)pyrrolidine-2-carboxamide (IMA-6-2-2-6-VHL):

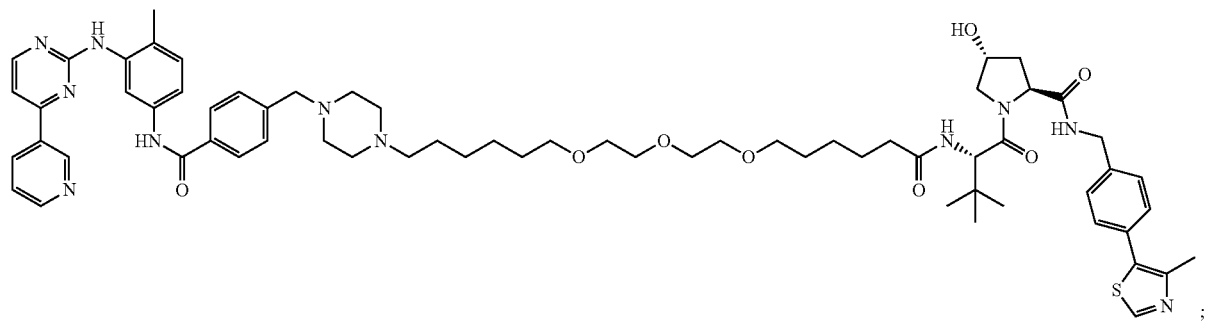 [SMILES: Cc1ccc(NC(=O)c2ccc(CN3CCN(CCCCCCOCCOCCOCCCCCC(=O)N[C@H](C(=O)N4C[C@H](O)C[C@H]4C(=O)NCc4ccc(-c5scnc5C)cc4)C(C)(C)C)CC3)cc2)cc1Nc1nccc(-c2cccnc2)n1]

N-(2-chloro-6-methylphenyl)-2-((6-(4-(6-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)hexyl)piperazin-1-yl)-2-methylpyrimidin-4-yl)amino)thiazole-5-carboxamide (DAS-6-2-2-VHL):

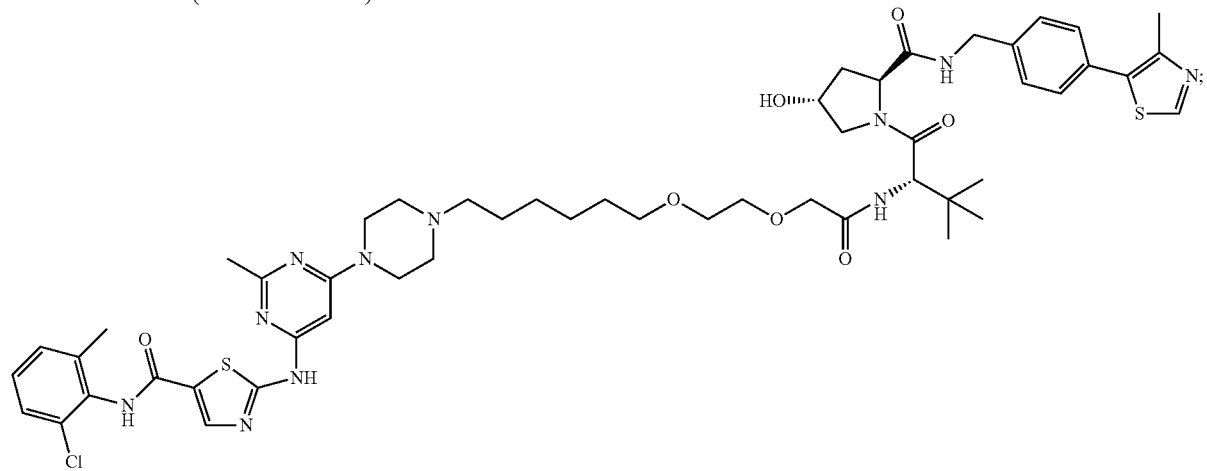

(2S,4R)-1-((S)-3,3-dimethyl-2-(2-(2-((6-(4-(4-((4-methyl-3-((4-(pyridin-3-yl)pyrimidin-2-yl)amino)phenyl)carbamoyl)benzyl)piperazin-1-yl)hexyl)oxy)ethoxy)acetamido)butanoyl)-4-hydroxy-N-(4-(4-methylthiazol-5-yl)benzyl)pyrrolidine-2-carboxamide (IMA-6-2-2-VHL):

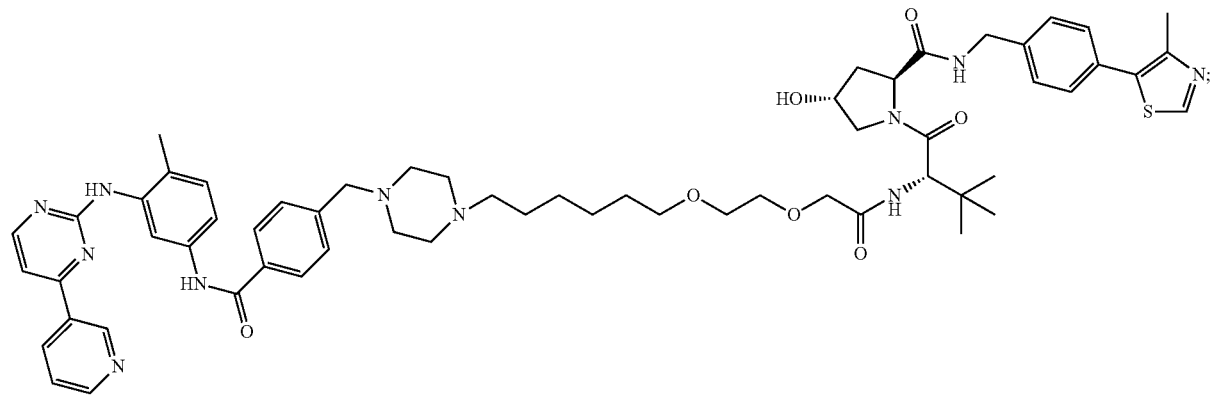 [SMILES: Cc1ccc(NC(=O)c2ccc(CN3CCN(CCCCCCOCCOCC(=O)N[C@H](C(=O)N4C[C@H](O)C[C@H]4C(=O)NCc4ccc(-c5scnc5C)cc4)C(C)(C)C)CC3)cc2)cc1Nc1nccc(-c2cccnc2)n1]

N-(2-chloro-6-methylphenyl)-2-((6-(4-((S)-3-((2S,4R)-4-hydroxy-2-((4-(4-methyl thiazol-5-yl)benzyl)carbamoyl)pyrrolidine-1-carbonyl)-2,2-dimethyl-5-oxo-7,10,13,16,19,22-hexaoxa-4-azaoctacosan-28-yl)piperazin-1-yl)-2-methylpyrimidin-4-yl)amino)thiazole-5-carboxamide (DAS-6-2-2-2-2-2-2-VHL):

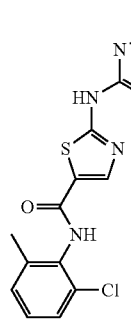
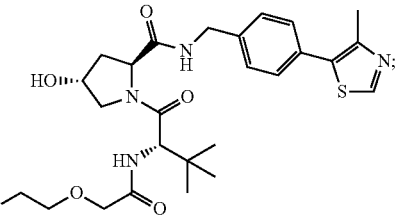

(2S,4R)-1-((S)-2-(tert-butyl)-27-(4-(4-((4-methyl-3-((4-(pyridin-3-yl)pyrimidin-2-yl)amino)phenyl)carbamoyl)benzyl)piperazin-1-yl)-4-oxo-6,9,12,15,18,21-hexaoxa-3-azaheptacosanoyl)-4-hydroxy-N-(4-(4-methylthiazol-5-yl)benzyl)pyrrolidine-2-carboxamide (IMA-6-2-2-2-2-2-2-VHL):

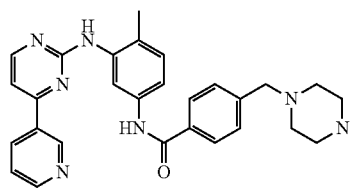
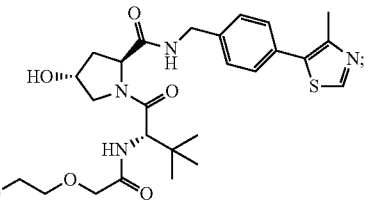

N-(2-chloro-6-methylphenyl)-2-((6-(4-(6-((5-((6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexyl)oxy)pentyl)oxy)hexyl)piperazin-1-yl)-2-methylpyrimidin-4-yl)amino)thiazole-5-carboxamide (DAS-6-5-6-VHL):

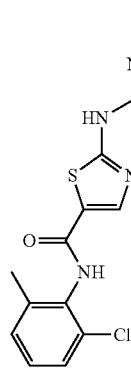
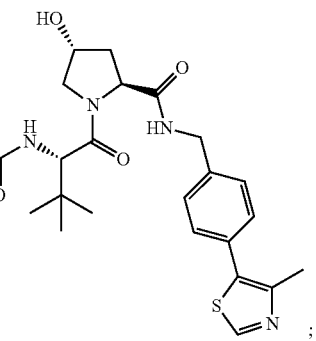

(2S,4R)-1-((S)-3,3-dimethyl-2-(6-((5-((6-(4-(4-((4-methyl-3-((4-(pyridin-3-yl)pyrimidin-2-yl)amino)phenyl)carbamoyl)benzyl)piperazin-1-yl)hexyl)oxy)pentyl)oxy)hexanamido) butanoyl)-4-hydroxy-N-(4-(4-methylthiazol-5-yl)benzyl)pyrrolidine-2-carboxamide (IMA-6-5-6-VHL):

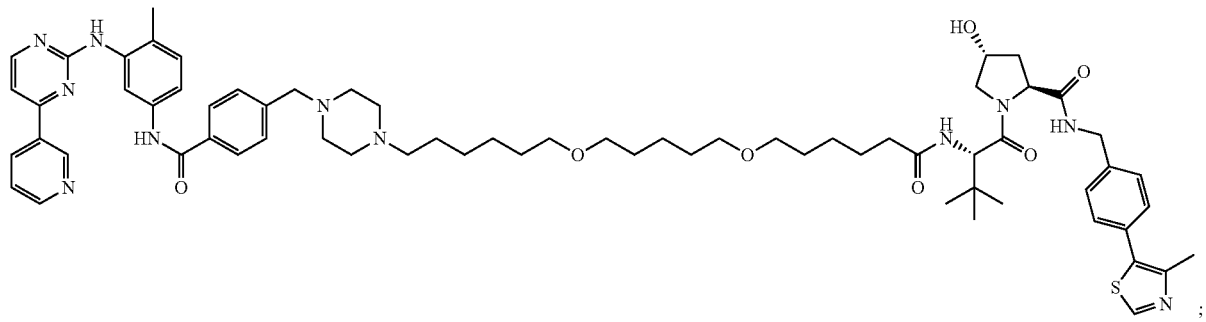 [SMILES: Cc1ccc(NC(=O)c2ccc(CN3CCN(CCCCCCOCCCCCOCCCCCC(=O)N[C@H](C(=O)N4C[C@H](O)C[C@H]4C(=O)NCc4ccc(-c5scnc5C)cc4)C(C)(C)C)CC3)cc2)cc1Nc1nccc(-c2cccnc2)n1]

(2 S,4R)-1-((S)-2-(tert-butyl)-22-(4-(3-((3-cyano-4-((2,4-dichloro-5-methoxyphenyl)amino)-6-methoxyquinolin-7-yl)oxy)propyl)piperazin-1-yl)-4-oxo-10,13,16-trioxa-3-azadocosanoyl)-4-hydroxy-N-(4-(4-methylthiazol-5-yl)benzyl)pyrrolidine-2-carboxamide (BOS-6-2-2-6-VHL):

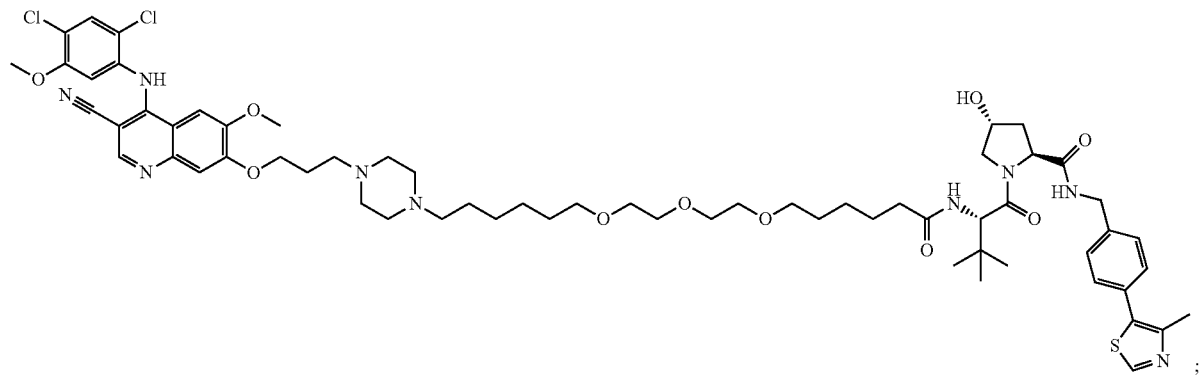

(2S,4R)-1-((S)-2-(2-(2-((6-(4-(3-((3-cyano-4-((2,4-dichloro-5-methoxyphenyl)amino)-6-methoxyquinolin-7-yl)oxy)propyl)piperazin-1-yl)hexyl)oxy)ethoxy)acetamido)-3,3-dimethylbutanoyl)-4-hydroxy-N-(4-(4-methylthiazol-5-yl)benzyl)pyrrolidine-2-carboxamide (BOS-6-2-2-VHL):

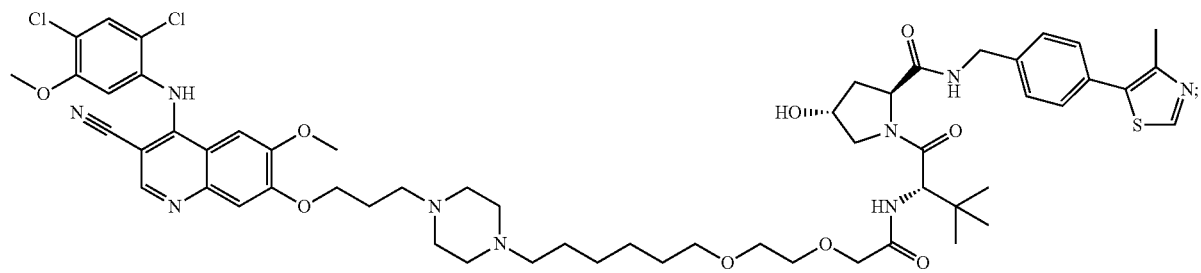 [SMILES: COc1cc(Nc2c(C#N)cnc3cc(OCCCN4CCN(CCCCCCOCCOCC(=O)N[C@H](C(=O)N5C[C@H](O)C[C@H]5C(=O)NCc5ccc(-c6scnc6C)cc5)C(C)(C)C)CC4)c(OC)cc23)c(Cl)cc1Cl]

(2S,4R)-1-((S)-2-(tert-butyl)-27-(4-(3-((3-cyano-4-((2,4-dichloro-5-methoxyphenyl)amino)-6-methoxyquinolin-7-yl)oxy)propyl)piperazin-1-yl)-4-oxo-6,9,12,15,18,21-hexaoxa-3-azaheptacosanoyl)-4-hydroxy-N-(4-(4-methylthiazol-5-yl)benzyl)pyrrolidine-2-carboxamide (BOS-6-2-2-2-2-2-2-VHL):

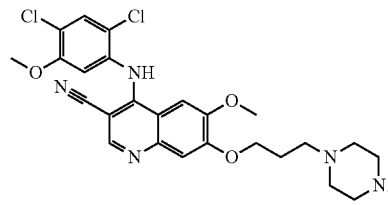
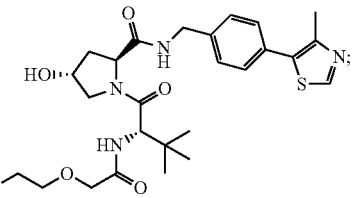

(2 S,4R)-1-((S)-2-(6-((5-((6-(4-(3-((3-cyano-4-((2,4-dichloro-5-methoxyphenyl)amino)-6-methoxyquinolin-7-yl)oxy)propyl)piperazin-1-yl)hexyl)oxy)pentyl)oxy)hexanamido)-3,3-dimethylbutanoyl)-4-hydroxy-N-(4-(4-methylthiazol-5-yl)benzyl)pyrrolidine-2-carboxamide (BOS-6-5-6-VHL):

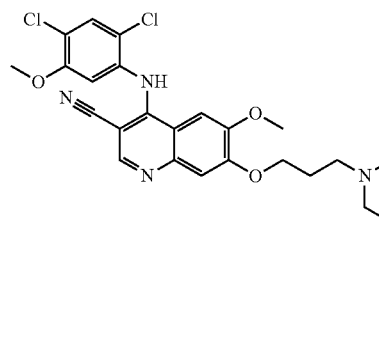
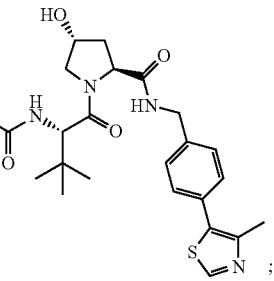

N-(2-chloro-6-methylphenyl)-2-((6-(4-(6-(2-(2-((6-((2-(2,6-dioxopiperidin-3-yl)-1,3-dioxoisoindolin-4-yl)amino)-6-oxohexyl)oxy)ethoxy)ethoxy)hexyl)piperazin-1-yl)-2-methylpyrimidin-4-yl)amino)thiazole-5-carboxamide (DAS-6-2-2-6-CRBN):

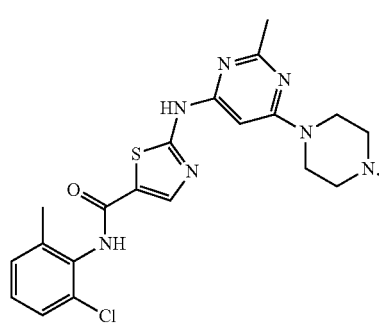
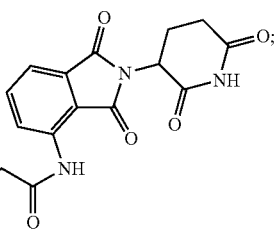

6-(2-(2-((6-(4-(3-((3-cyano-4-((2,4-dichloro-5-methoxyphenyl)amino)-6-methoxyquinolin-7-yl)oxy)propyl)piperazin-1-yl)hexyl)oxy)ethoxy)ethoxy)-N-(2-(2,6-dioxopiperidin-3-yl)-1,3-dioxoisoindolin-4-yl)hexanamide (BOS-6-2-2-6-CRBN):

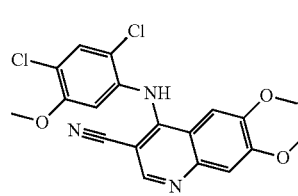 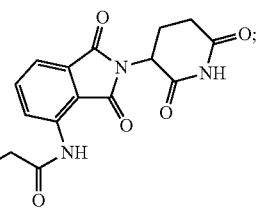

4-((4-(6-(2-(2-((6-((2-(2,6-dioxopiperidin-3-yl)-1,3-dioxoisoindolin-4-yl)amino)-6-oxohexyl) oxy)ethoxy) ethoxy)hexyl)piperazin-1-yl)methyl)-N-(4-methyl-3-((4-(pyridin-3-yl)pyrimidin-2-yl)amino)phenyl) benzamide (IMA-6-2-2-6-CRBN):

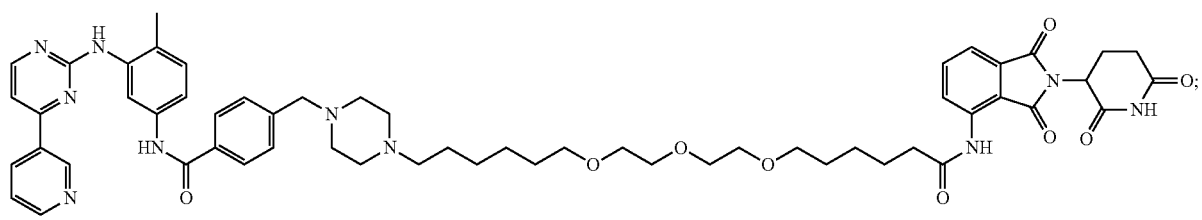 [SMILES: Cc1ccc(NC(=O)c2ccc(CN3CCN(CCCCCCOCCOCCOCCCCCC(=O)Nc4cccc5c4C(=O)N(C4CCC(=O)NC4=O)C5=O)CC3)cc2)cc1Nc1nccc(-c2cccnc2)n1]

N-(2-chloro-6-methylphenyl)-2-((6-(4-(6-(2-(2-((2-(2,6-dioxopiperidin-3-yl)-1,3-dioxoisoindolin-4-yl)amino)-2-oxoethoxy)ethoxy)hexyl)piperazin-1-yl)-2-methylpyrimidin-4-yl)amino)thiazole-5-carboxamide (DAS-6-2-2-CRBN):

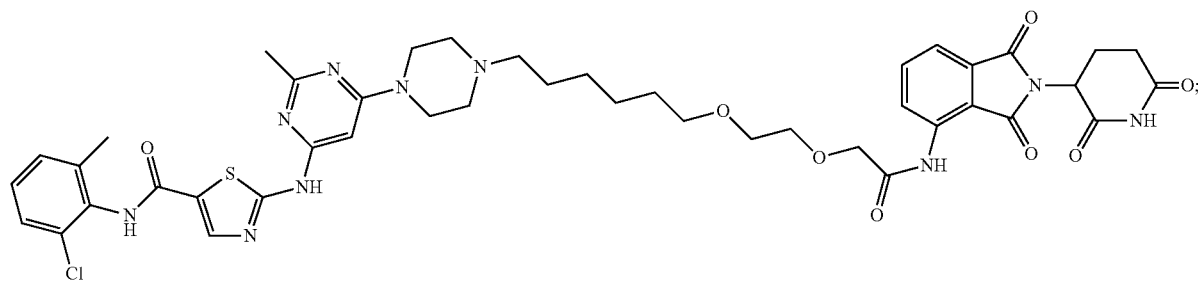 [SMILES: Cc1nc(Nc2ncc(C(=O)Nc3c(C)cccc3Cl)s2)cc(N2CCN(CCCCCCOCCOCC(=O)Nc3cccc4c3C(=O)N(C3CCC(=O)NC3=O)C4=O)CC2)n1]

2-(2-((6-(4-(3-((3-cyano-4-((2,4-dichloro-5-methoxyphenyl)amino)-6-methoxyquinolin-7-yl)oxy)propyl)piperazin-1-yl)hexyl)oxy)ethoxy)-N-(2-(2,6-dioxopiperidin-3-yl)-1,3-dioxoisoindolin-4-yl)acetamide (BOS-6-2-2-CRBN):

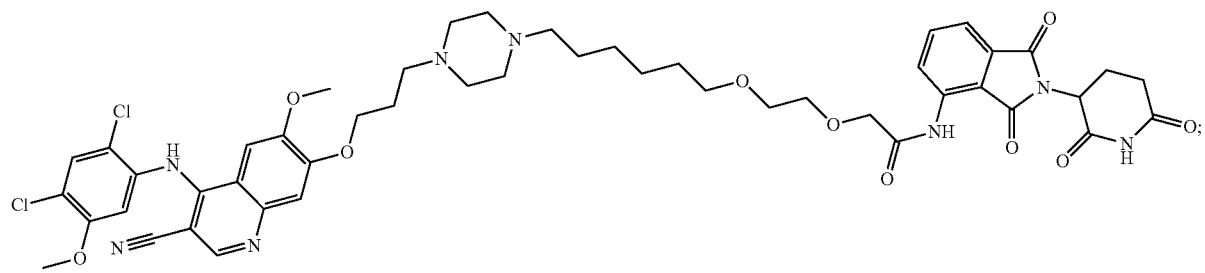 [SMILES: COc1cc(Nc2c(C#N)cnc3cc(OCCCN4CCN(CCCCCCOCCOCC(=O)Nc5cccc6c5C(=O)N(C5CCC(=O)NC5=O)C6=O)CC4)c(OC)cc23)c(Cl)cc1Cl]

4-((4-(6-(2-(2-((2-(2,6-dioxopiperidin-3-yl)-1,3-dioxoisoindolin-4-yl)amino)-2-oxoethoxy)ethoxy)hexyl)piperazin-1-yl)methyl)-N-(4-methyl-3-((4-(pyridin-3-yl)pyrimidin-2-yl)amino)phenyl)benzamide (IMA-6-2-2-CRBN):

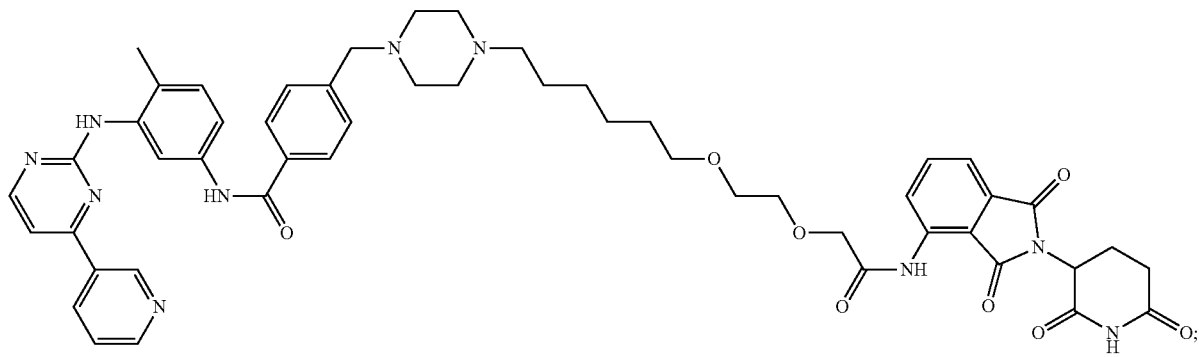 [SMILES: Cc1ccc(NC(=O)c2ccc(CN3CCN(CCCCCCOCCOCC(=O)Nc4cccc5c4C(=O)N(C4CCC(=O)NC4=O)C5=O)CC3)cc2)cc1Nc1nccc(-c2cccnc2)n1]

N-(2-chloro-6-methylphenyl)-2-((6-(4-(1-((2-(2,6-dioxopiperidin-3-yl)-1,3-dioxoisoindolin-4-yl)amino)-1-oxo-3,6,9,12,15,18-hexaoxatetracosan-24-yl)piperazin-1-yl)-2-methylpyrimidin-4-yl)amino)thiazole-5-carboxamide (DAS-6-2-2-2-2-2-2-CRBN):

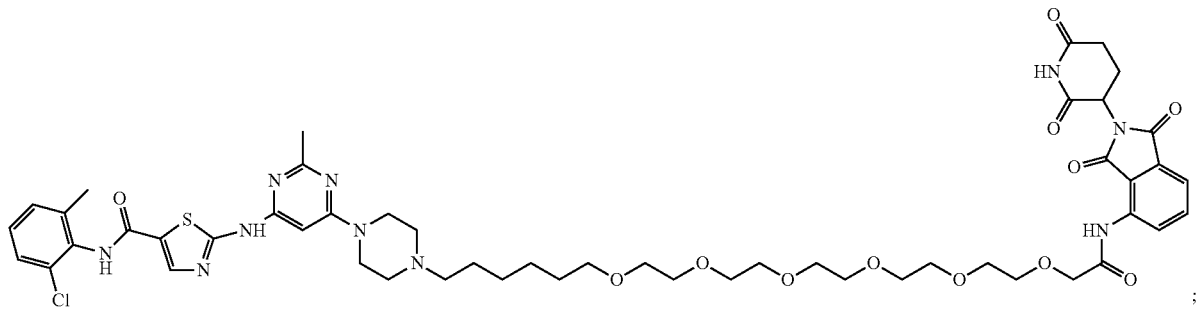

24-(4-(3-((3-cyano-4-((2,4-dichloro-5-methoxyphenyl)amino)-6-methoxyquinolin-7-yl)oxy) propyl)piperazin-1-yl)-N-(2-(2,6-dioxopiperidin-3-yl)-1,3-dioxoisoindolin-4-yl)-3,6,9,12,15,18-hexaoxatetracosanamide (BOS-6-2-2-2-2-2-2-CRBN):

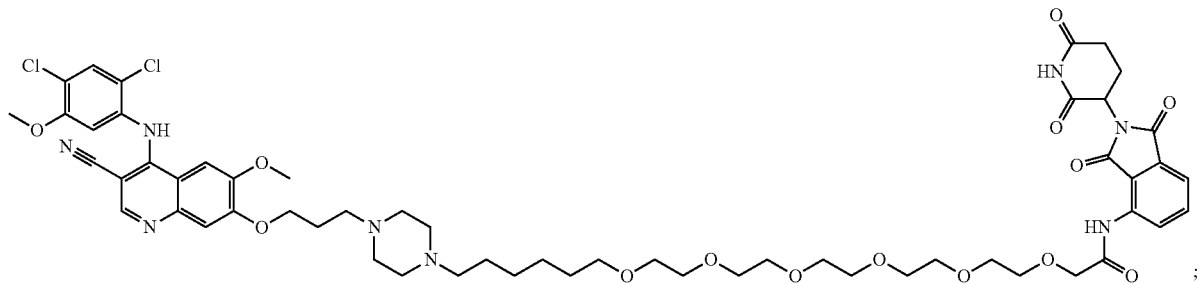 [SMILES: COc1cc(Nc2c(C#N)cnc3cc(OCCCN4CCN(CCCCCCOCCOCCOCCOCCOCCOCC(=O)Nc5cccc6c5C(=O)N(C5CCC(=O)NC5=O)C6=O)CC4)c(OC)cc23)c(Cl)cc1Cl]

N-(2-(2,6-dioxopiperidin-3-yl)-1,3-dioxoisoindolin-4-yl)-24-(4-(4-((4-methyl-3-((4-(pyridin-3-yl)pyrimidin-2-yl)amino)phenyl)carbamoyl)benzyl)piperazin-1-yl)-3,6,9,12,15,18-hexaoxatetracosanamide (IMA-6-2-2-2-2-2-2-CRBN):

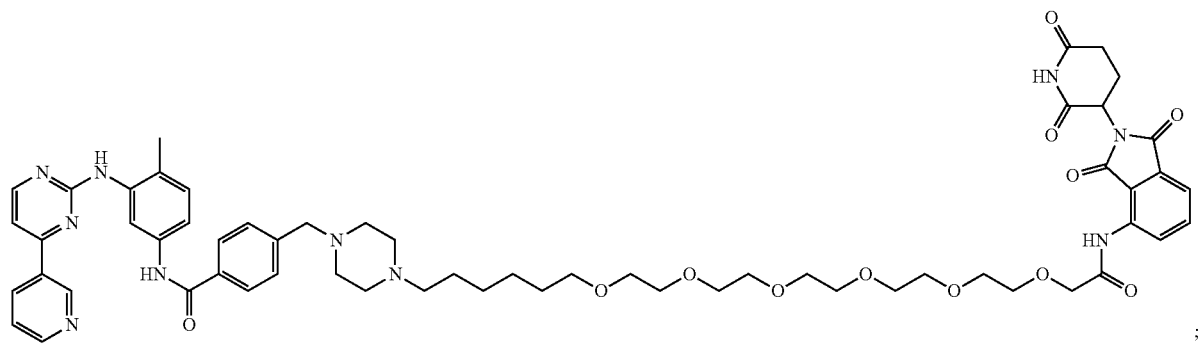 [SMILES: Cc1ccc(NC(=O)c2ccc(CN3CCN(CCCCCCOCCOCCOCCOCCOCCOCC(=O)Nc4cccc5c4C(=O)N(C4CCC(=O)NC4=O)C5=O)CC3)cc2)cc1Nc1nccc(-c2cccnc2)n1]
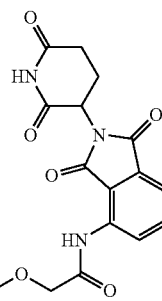

N-(2-chloro-6-methylphenyl)-2-((6-(4-(6-(((5-((6-(((2-(2,6-dioxopiperidin-3-yl)-1,3-dioxoisoindolin-4-yl)amino)-6-oxohexyl)oxy)pentyl)oxy)hexyl)piperazin-1-yl)-2-methylpyrimidin-4-yl)amino)thiazole-5-carboxamide (DAS-6-5-6-CRBN):

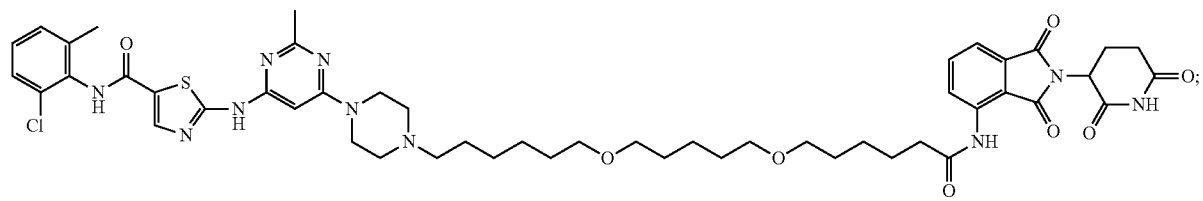 [SMILES: Cc1nc(Nc2ncc(C(=O)Nc3c(C)cccc3Cl)s2)cc(N2CCN(CCCCCCOCCCCCOCCCCCC(=O)Nc3cccc4c3C(=O)N(C3CCC(=O)NC3=O)C4=O)CC2)n1]

6-((5-((6-(4-(3-((3-cyano-4-((2,4-dichloro-5-methoxyphenyl)amino)-6-methoxyquinolin-7-yl)oxy)propyl)piperazin-1-yl)hexyl)oxy)pentyl)oxy)-N-(2-(2,6-dioxopiperidin-3-yl)-1,3-dioxoisoindolin-4-yl)hexanamide (BOS-6-5-6-CRBN):

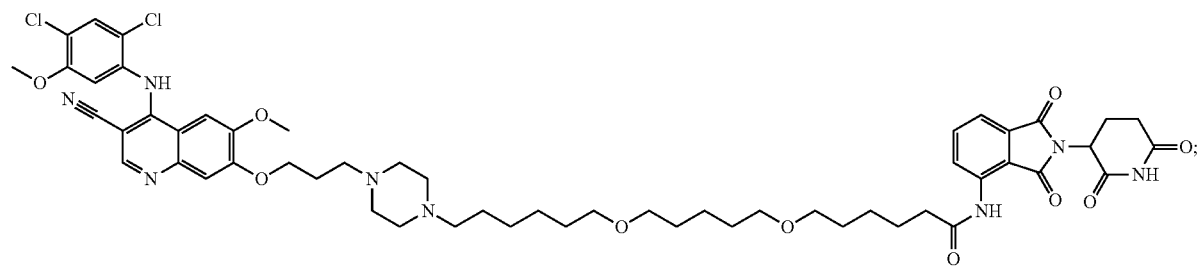 [SMILES: COc1cc(Nc2c(C#N)cnc3cc(OCCCN4CCN(CCCCCCOCCCCCOCCCCCC(=O)Nc5cccc6c5C(=O)N(C5CCC(=O)NC5=O)C6=O)CC4)c(OC)cc23)c(Cl)cc1Cl]

4-((4-(6-((5-((6-(((2-(2,6-dioxopiperidin-3-yl)-1,3-dioxoisoindolin-4-yl)amino)-6-oxohexyl)oxy)pentyl)oxy)hexyl)piperazin-1-yl)methyl)-N-(4-methyl-3-((4-(pyridin-3-yl)pyrimidin-2-yl)amino)phenyl)benzamide (IMA-6-5-6-CRBN):

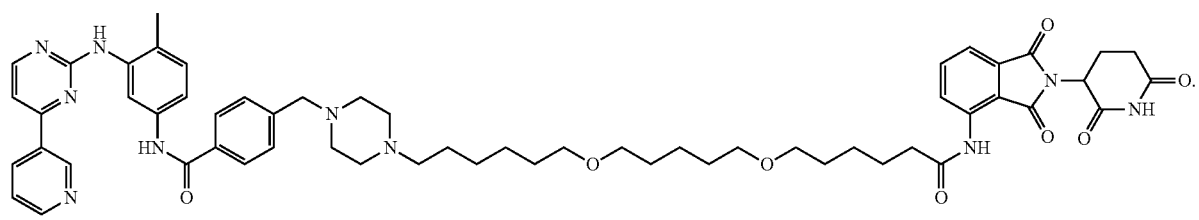 [SMILES: Cc1ccc(NC(=O)c2ccc(CN3CCN(CCCCCCOCCCCCOCCCCCC(=O)Nc4cccc5c4C(=O)N(C4CCC(=O)NC4=O)C5=O)CC3)cc2)cc1Nc1nccc(-c2cccnc2)n1]

19. A pharmaceutical composition comprising at least one compound of claim 1 and at least one pharmaceutically acceptable carrier.

20. The composition of claim 19, further comprising at least one additional therapeutic compound that treats or prevents cancer.

\* \* \* \* \*